US010016448B2

(12) United States Patent
Hodous et al.

(10) Patent No.: US 10,016,448 B2
(45) Date of Patent: Jul. 10, 2018

(54) COMPOSITIONS AND METHODS FOR THE PRODUCTION OF PYRIMIDINE AND PYRIDINE COMPOUNDS WITH BTK INHIBITORY ACTIVITY

(71) Applicant: Merck Patent GmbH, Darmstadt (DE)

(72) Inventors: Brian L. Hodous, Cambridge, MA (US); Lesley Liu-Bujalski, Bedford, MA (US); Reinaldo Jones, Lowell, MA (US); Donald Bankston, Dracut, MA (US); Theresa L. Johnson, Salem, MA (US); Igor Mochalkin, Westford, MA (US); Ngan Nguyen, Arlington, MA (US); Hui Qiu, Acton, MA (US); Andreas Goutopoulos, Boston, MA (US); Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/417,953

(22) Filed: Jan. 27, 2017

(65) Prior Publication Data

US 2017/0136048 A1    May 18, 2017

Related U.S. Application Data

(60) Division of application No. 14/727,050, filed on Jun. 1, 2015, now Pat. No. 9,580,449, which is a continuation of application No. 14/112,428, filed as application No. PCT/US2012/041803 on Jun. 10, 2012, now Pat. No. 9,073,947.

(60) Provisional application No. 61/495,773, filed on Jun. 10, 2011.

(51) Int. Cl.
| | |
|---|---|
| A61K 31/69 | (2006.01) |
| A61K 31/506 | (2006.01) |
| A61K 31/505 | (2006.01) |
| A61K 31/4545 | (2006.01) |
| A61K 31/55 | (2006.01) |
| A61K 31/5377 | (2006.01) |
| A61K 31/44 | (2006.01) |

(52) U.S. Cl.
CPC ............. *A61K 31/69* (2013.01); *A61K 31/44* (2013.01); *A61K 31/4545* (2013.01); *A61K 31/505* (2013.01); *A61K 31/506* (2013.01); *A61K 31/5377* (2013.01); *A61K 31/55* (2013.01)

(58) Field of Classification Search
CPC .......................... A61K 31/506; C07D 401/12
See application file for complete search history.

(56) References Cited

U.S. PATENT DOCUMENTS

| | | | |
|---|---|---|---|
| 5,002,949 A | 3/1991 | Peseckis et al. | |
| 5,753,668 A | 5/1998 | Moschel | |
| 6,007,798 A | 12/1999 | Bohn | |
| 8,575,183 B2 | 11/2013 | Cushing et al. | |
| 8,772,480 B2 | 7/2014 | Andrews et al. | |
| 8,835,420 B2 | 9/2014 | Chang et al. | |
| 9,073,947 B2 | 7/2015 | Hodous et al. | |
| 9,580,449 B2 * | 2/2017 | Hodous | C07D 213/68 |
| 2004/0053908 A1 | 3/2004 | Funahashi | |
| 2005/0171131 A1 | 8/2005 | Kosogof | |
| 2009/0163516 A1 | 6/2009 | Dunkel | |
| 2011/0059118 A1 | 3/2011 | De Vicente Fidalgo | |

FOREIGN PATENT DOCUMENTS

| | | |
|---|---|---|
| EP | 0471297 A1 | 2/1992 |
| EP | 0679645 A1 | 2/1995 |
| EP | 0714896 A1 | 5/1996 |
| EP | 1348706 A1 | 10/2003 |
| EP | 2810939 A1 | 12/2014 |
| GB | 000712595 | 7/1952 |
| JP | 8283246 A | 10/1996 |
| WO | 199919305 A2 | 4/1999 |
| WO | 200127107 A2 | 4/2001 |
| WO | 2003/002525 A1 | 1/2003 |
| WO | 2005073224 A2 | 8/2005 |
| WO | 2006096405 A1 | 9/2006 |
| WO | 2006136442 A1 | 9/2006 |
| WO | 2007056151 A2 | 5/2007 |
| WO | 2007089512 A1 | 8/2007 |
| WO | 2007092531 A2 | 8/2007 |
| WO | 2008033834 A1 | 3/2008 |
| WO | 2008046049 A1 | 4/2008 |
| WO | 2008046216 A1 | 4/2008 |
| WO | 2008058229 A1 | 5/2008 |
| WO | 2008153947 A2 | 12/2008 |
| WO | 2009044162 A1 | 4/2009 |
| WO | 2009051822 A1 | 4/2009 |
| WO | 2009158571 A1 | 12/2009 |
| WO | 2010057126 A1 | 5/2010 |
| WO | 2010144647 A1 | 12/2010 |
| WO | 2011029043 A1 | 3/2011 |
| WO | 2011029046 A1 | 3/2011 |
| WO | 2011099764 A2 | 8/2011 |
| WO | 2011139891 A1 | 11/2011 |
| WO | 2011143365 A1 | 11/2011 |
| WO | 2011143495 A1 | 11/2011 |
| WO | 2012009510 A1 | 1/2012 |
| WO | 2013040044 A1 | 3/2013 |

OTHER PUBLICATIONS

Reider et al., J. Org. Chem., 1987, 52: 3326-3334.

(Continued)

*Primary Examiner* — Golam M Shameem

(74) *Attorney, Agent, or Firm* — Dwight D. Kim; EMD Serono Research and Development Institute

(57) ABSTRACT

The present invention provides novel pyrimidine and pyridine compounds according to Formula (I), Formula (II), Formula (III), Formula (IV) and Formula (V) their manufacture and use for the treatment of hyperproliferative diseases including, but not limited to, cancer, lupus, allergic disorders, Sjogren's disease and rheumatoid arthritis. In preferred embodiments, the present invention describes irreversible kinase inhibitors including, but not limited to, inhibitors of Bruton's tyrosine kinase.

18 Claims, 6 Drawing Sheets

(56) References Cited

OTHER PUBLICATIONS

Schaeffer and Schwartzberg, Curr Op Imm, 2000, 12: 282-288.
Ackermann H et al., Konstitution and Reaktionsfaehigkeit von Trichlor-pyrimidylamino-Verbindungen, Helvetica Chimica ACTA. Verlag Helvetica Chimica Acta, Basel, CH, 1962, 45(5)1683-1698.
Alla Bessmertnykh et al., Efficient Palladium-Catalyzed Synthesis of Aminopyridyl Phosphonates from Bromopyridines and Diethyl Phosphite, Synthesis. 2008, 2008(10).
Atwal K S et al., Synthesis and biological activity of 5-aryl-4-(4-(5-methyl-1H-imidazol-4-yl)piperidin-1-yl)pyrimidine analogs as potent. highly selective. and orally bioavailable NHE-1 inhibitors, Bioorganic & Medicinal Chemistry Letters, Pergamon, Elsevier Science GB, 2006, 16(18):4796-4799.
Barillari C et al., Solid Phase Synthesis of Diamino-Substituted Pyrimidines, Eur. J. Org. Chem, 2001, 4737-4741.
Biressi et al., Su Alcune 5-Fluoro-6-Anilino-Amminopirimidine, Bollettino Chimico Farmaceutico. Societa Editoriale Farmaceutica, Milano, IT, 1966, 105: 660-665.
Buttelmann B et al., 4-(3.4-Dihydro-1H-Isoquinolin-2yl)-Pyridi NES and 4-(3,4-Dihydro-1H-Isoquinolin-2-yl)-Quinol Ines as Potent NR1/2B Subtype Selective NMDA Receptor Antagonists, Bioorganic & Medicinal Chemistry Letters, Pergamon, Elsevier Science. GB, 2003, 13: 1759-1762.
Bongkoch Tarnchompoo et al., Development of 2.4-Diaminopyrimidines as Antimalarials Based on Inhibition of the S108N and C59R+S108N Mutants of Dihydrofolate Reductase from Pyrimethamine-Resistant Plasmodium f alciparum, Journal of Medicinal Chemistry, 2002, 45(6):1244-1252.
Brown D J et al., 120. Pyrimidine Reactions. Part VII. Methylation of substituted 2,4-Diaminopyrimidines, Journal of the Chemical Society (Resumed), 1965, p. 755.
Chang Sung Hong et al., Synthesis of Aromatic Ring Fused Pyrrole Derivatives by Palladium-catalyzed Annulation of o-Iodoarylamines with Allyl Acetate, Heterocycles, Elsevier Science Publishers B.V., Amsterdam, NL, 2004, 63(3) 631-639.
Hurst D T, Application of the Elbs Persulfate Oxidation to the Preparation of 5-hydroxypyrimidines, Australian Journal of Chemistry. CSIRO. AU., 1983, 36:1285-1289.
Iwaki et al., Novel Synthetic Strategy of Carbolines Via Palladium-Catalyzed Amination and Arylation Reaction, Journal of the Chemical Society. Perkin Transactions 1, Chemical Society, 1999, 1505-1510.
Jang M Y et al., Synthesis of novel 5-amino-thiazolo[4.5-d]pyrimidines as *E. coli* and *S. aureus* SecA inhibitors, Bioorganic & Medicinal Chemistry, Pergamon, GB, 2011, 19( 1):702-714.
Kattar S D et al., Parallel medicinal chemistry approaches to selective HDAC1/HDAC2 inhibitor (SHI-1:2) optimization, Bioorganic & Medicinal Chemistry Letters, Pergamon. Elsevier Science. GB, 2009, 19(4)1168-1172.
Kosary J. et al., Preparation of Pyrimidine Derivatives with Potential Cardiotonic Activity, ACTA Pharmaceutica Hungarica. Hungarian Pharmaceutical Association, 1989, 59:241-247.
Lang S A et al., 4-Amino-5-arylpyrimidines as antiinflammatory agents, Journal of Medicinal Chemistry, 1975, 18 (6):623-625.
Large Jonathan et al., Synthesis of Trisubstituted Pyrimidines by Regioselective S N Ar and Suzuki Reactions of Polyhalopyrimidines, Synlett, 2006, 2006(6).
O'Brien D E et al., Pyrimidines, XI, Structural Variations of 2.4-Diamino-6-(halogenoanilino)-5.nitrosopyrimidines, Journal of Medicinal Chemistry, 1963, 6(5):467-471.
Paudler William W et al., Bromination of some pyridine and diazine N-oxides, The Journal of Organic Chemistry, 1983, 48(7):1064-1069.
Pegiadou, The synthesis and characterization of new polymerizable pyrimidines: Immobilization of the monomers onto hydrophilic graft copolymeric supports through radiation-induced copolymerization-grafting, Journal of Applied Polymer Science, 1998, 70(2):211.
Phillips Arthur P et al., Syntheses of 1.3-Diazaphenothiazines.1 I, The Journal of Organic Chemistry, 1963, 28 (6):1488-1490.
Satoshi Mizukami et al., The Ionization Constants of Some 4.5-Substituted 2-Methylpyrimidines, The Journal of Organic Chemistry, 1966, 31(4)1199-1202.
Shigenobu Okuda et al., The Journal of Organic Chemistry, 1959, 24(7) 1008-1011.
Shishoo C J et al., Synthesis of Some 2.4-Diamino-6-substituted-amino-5-arylpyrimidines, Indian Journal of Chemistry, Section B: Organic and Medicinal Chemistry, 1989, 28(1-11) 42-47.
Spivey Alan C et al., Atropisomeric [alpha]-methyl substituted analogues of 4-(dimethylamino)pyridine: synthesis and evaluation as acyl transfer catalysts, Journal of the Chemical Society, Perkin Transactions 1, 2001, 15:1785-1794.
Traverso J. J. et al.., The synthesis and pharmacological activities of amide, sulfamide, and urea derivatives of 1,6-diaminopyrimidines, Journal of Medicinal and Pharmaceutical Chemistry, 1962, 5:808-815.
Vishwakarma J N et al., Reactions of Polarized Keten S,N-Acetals with Guanidine: A Facile General Route to Novel 5.6-Substituted 2-Amino-4-N-alky/aryl/N-azacycloalkylaminopyrimidines, Indian Journal of Chemistry, Section B: Organic and Medicinal Chemistry, 1985, 24:466-471.
Wen Song Yue et al., A Concise Synthesis of All Four Possible Benzo[4.5]furopyridines via Palladium-Mediated Reactions, Organic Letters, 2002, 4(13):2201-2203.
Whitehead C W & Traverso J J, Diuretics. III. 4.6-Diaminopyrimidines, Journal of the American Chemical Society. ACS Publications, US, 1958, 80:2185-2189.
Zhang Y M et al., Synthesis of pyrimido[4,5-b]indoles and benzo[4.5]furo[2,3-d]pyrimidines via Palladium-Catalyzed Intramolecular Arylation, Tetrahedron Letters, Elsevier, Amsterdam, NL, 2002, 43(46):8235-8239.
PCT International Preliminary Report on Patentability, PCT/US2012/041803, dated Dec. 10, 2013, entire report.
Doklady Bolgarskoi Akademii Nauk, 1987, 44(11): 75-78.
Fadda et al., Phosphorus, Sulfur and Silicon, 1999, 155: 59-66.
Guery et al., Bioorg. & Med. Chem. Lett. 2007,17: 6206-6211.
Higashino and Hayashi, Heterocycles, 1981,15(1): 483-487.
Khimiya Geterotsiklicheskikh Soedinenii, 1979, 6: 821-826.
Liu et al., J. Bioorg. & Med. Chem. Lett., 2006,16: 1864-1868.
Peltason et al., Journal of Medicinal Chemistry, 2009, 52(10): 3212-3224.
Chemical Abstracts [STN online], an 85:78077, Prakt. Panelleniou Chem, Synedriou, 4th, 1972, Meeting Date 1970, vol. 64-68.
Foster, Adv. Drug Res., 1985, 14: 1-40.
Garcia-Bustos, et al., EMBO J., 1994, 13: 2352-2361.
Gillette et al, Biochemistry, 1994, 33(10): 2927-2937.
Hanks, S.K., Hunter, T., FASEB J., 1995, 9: 576-596.
Hankzlik et al., J. Org. Chem., 1990, 55: 3992-3997.
Hardie, G. and Hanks, S. (1995) The Protein Kinase Facts Book. I and II, Academic Press, San Diego, CA).
Hiles, et al., Cell, 1992, 70: 419-429.
Jarman et al., Carcinogenesis, 1993, 16(4): 683-688.
Knighton et al., Science, 1991, 253:407-414.
Kunz et al., Cell, 1993, 73:585-596.
Kurosaki, Curr Op Imm, 2000, 12: 276-281.
Pan et al., Chem Med Chem, 2007, 2: 58-61.
CAS Registry No. 1212754-68-1; STN Entry date Mar. 21, 2010.
CAS Registry No. 959566-78-0; STN Entry date Dec. 26, 2007.
CAS Registry No. 959545-79-0; STN Entry date Dec. 26, 2007.
CAS Registry No. 959500-70-0; STN Entry date Dec. 26, 2007.
CAS Registry No. 959492-85-4; STN Entry date Dec. 26, 2007.
CAS Registry No. 1067036-48-9; STN Entry date Oct. 27, 2008.
CAS Registry No. 1060424-73-8; STN Entry date Oct. 13, 2008.
CAS Registry No. 1060515-87-8; STN Entry date Oct. 13, 2008.

\* cited by examiner

ONE-WAY ANOVA
**** P<0.0001 VERSUS VEHICLE CYCLODEXTRIN
% OF INHIBITION

COMPOSITIONS AND METHODS FOR THE PRODUCTION OF PYRIMIDINE AND PYRIDINE COMPOUNDS WITH BTK INHIBITORY ACTIVITY

RELATED APPLICATIONS

This application is a Divisional application of U.S. patent application Ser. No. 14/727,050, filed on Jun. 1, 2015, which is a Continuation application of U.S. patent application Ser. No. 14/112,428 (now U.S. Pat. No. 9,073,947), which is a U.S. national stage application of PCT International application PCT/US12/41803, filed on Jun. 10, 2012, which claims the benefit of U.S. Provisional application No. 61/495,773, filed on Jun. 10, 2011. The contents of the aforementioned are incorporated by reference in their entireties.

FIELD OF THE INVENTION

The invention relates to a series of pyrimidine and pyridine compounds that are useful as therapeutics in the treatment of a variety of pathological conditions including (but not limited to) cancer, auto-immune disease, inflammatory diseases and neurodegenerative diseases in mammals. More particularly, embodiments of the present invention describe irreversible kinase inhibitors including, but not limited to, inhibitors of Bruton's tyrosine kinase (hereinafter referred to as: "BTK"). Methods for the preparation of the aforementioned compounds are disclosed in addition to the incorporation of these compounds into pharmaceutical compositions that include the same. Methods of using these BTK inhibitors are disclosed, alone or in combination with other therapeutic agents, for the treatment of hyperproliferative diseases in mammals, especially humans, as well as pharmaceutical compositions which contain said inhibitors.

SUMMARY OF THE RELATED ART

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

BTK, a member of the Tec family of non-receptor tyrosine kinases, is a signaling enzyme expressed in all hematopoietic cells types except T lymphocytes and natural killer cells. BTK plays a well documented role in the B-cell signaling pathway linking cell surface B-cell receptor stimulation to downstream intracellular responses. BTK is also a regulator of B-cell development, activation, signaling, and survival (Kurosaki, Curr Op Imm, 2000, 276-281; Schaeffer and Schwartzberg, Curr Op Imm 2000, 282-288). In addition, BTK exerts a physiological effect through other hematopoietic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. BTK has an ATP-binding pocket with high similarity to Src-family kinases, such as lymphocyte-specific protein tyrosine kinase (Lck) and Lyn. Comparing BTK to other kinases one finds a conserved cysteine residue, Cys-481, in 11 of 491 kinases, specifically members of the Tec and EGFR (epidermal growth factor receptor) kinase families.

BTK plays important roles in the development, differentiation, activation and proliferation of B cells, as well as their antibody and cytokine generation. In addition, Btk plays a central role in other immunological processes such as cytokine production by neutrophils, mast cells and monocytes, degranulation of neutrophils and mast cells as well as differentiation/activation of osteoclasts. B-cell activation, break of tolerance and auto-antibody production, on one hand and the proinflammatory milieu originated from exacerbated activation of monocytes, neutrophils and mast cells, on the other hand, are crucial in the etiology of autoimmune diseases, including (but not limited to) rheumatoid arthritis and systemic lupus erythematosus.

Reversible kinase inhibitors have been developed into therapeutic compounds. These reversible inhibitors, however, have decided disadvantages. Many reversible inhibitors of kinases interact with the ATP-binding site. Given the structure of the ATP-binding sites are highly conserved among kinases, it has been difficult to develop a reversible inhibitor that selectively inhibits a desired (i.e., target) kinase. Moreover, given that many reversible kinase inhibitors readily dissociate from their target polypeptide(s), maintaining inhibition over extended periods of time can be difficult. When using reversible kinase inhibitors as therapeutics, therefore, often times near toxic dosages and/or frequent dosing is required to achieve the intended biological effect.

What is needed, therefore, are irreversible kinase inhibitors that covalently bind to their target polypeptide(s) without (substantially) binding to off-target polypeptides and, thereby, exerting undesirable off-target effects.

DESCRIPTION OF THE INVENTION

The present invention provides a series of novel pyrimidine and pyridine kinase inhibitors. In some embodiments said kinase inhibitors are irreversible inhibitors of tyrosine kinases. In preferred embodiments, said irreversible kinase inhibitors inhibit BTK. While it is not intended that the compounds described by the present invention be limited to any specific mechanism of action, in some embodiments said irreversible kinase inhibitors exert a physiological effect by forming a covalent bond with Cys 481 in BTK. Significantly, this Cys 481 in BTK finds homologs in other kinases. Embodiments of the present invention also described methods for synthesizing said irreversible inhibitors, methods for using said irreversible inhibitors in the treatment of diseases (including, but not limited to, cancer, auto-immune/inflammatory diseases, and neurodegenerative diseases). Further described are pharmaceutical Formulations that include an irreversible kinase inhibitor including pharmaceutically acceptable salts, solvates or prodrugs thereof, that are kinase inhibitors and useful in the treatment of the above mentioned diseases.

The pyrimidine and pyridine kinase inhibitors of the present invention are defined by Formula (I):

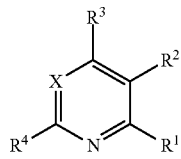

I in which:
X denotes CH or N,
$R^1$ denotes $NH_2$, $CONH_2$ or H,
$R^2$ denotes Hal, $Ar^1$ or $Het^1$,
$R^3$ denotes $NR^5[C(R^5)_2]_nHet^2$, $NR^5[C(R^5)_2]_nCyc$, $Het^2$, $O[C(R^5)_2]_nAr^2$, $NR^5[C(R^5)_2]_nAr^2$, $O[C(R^5)_2]_nHet^2$, $NR^5(CH_2)_nNR^5R^6$, $O(CH_2)_pNR^5R^6$ or $NR^5(CH_2)_p CR^7R^8NR^5R^6$,
$R^4$ denotes H, $CH_3$ or $NH_2$,
$R^5$ denotes H or alkyl having 1, 2, 3 or 4 C atoms,
$R^6$ $N(R^5)_2CH_2CH=CHCONH$, $Het^3CH_2CH=CHCONH$, $CH_2=CHCONH(CH_2)_n$, $Het^4(CH_2)_nCOHet^3$-diyl-$CH_2CH=CHCONH$, $HC\equiv CCO$, $CH_3C\equiv CCO$, $CH_2=CH$—$CO$, $CH_2=C(CH_3)CONH$, $CH_3CH=CHCONH(CH_2)_n$, $N\equiv CCR^7R^8CONH(CH_2)_n$, $Het^4NH(CH_2)_pCOHet^3$-diyl-$CH_2CH=CHCONH$, $Het^4(CH_2)_pCONH(CH_2CH_2O)_p(CH_2)_pCOHet^3$-diyl-$CH_2CH=CHCONH$, $CH_2=CHSO_2$, $ACH=CHCO$, $CH_3CH=CHCO$, $Het^4(CH_2)_pCONH(CH_2)_pHet^3$-diyl-$CH_2CH=CHCONH$, $Ar^3CH=CHSO_2$, $CH_2=CHSO_2NH$ or $N(R^5)CH_2CH=CHCO$,
$R^7$, $R^8$ denote together alkylene having 2, 3, 4, or 5 C atoms,
$Ar^1$ denotes phenyl or naphthyl, each of which is unsubstituted or mono-, di- or trisubstituted by $R^6$, Hal, $(CH_2)_nNH_2$, $CONHAr^3$, $(CH_2)_nNHCOA$, $O(CH_2)_nAr^3$, $OCyc$, A, $COHet^3$, OA and/or $OHet^3$ $(CH_2)$,
$Ar^2$ denotes phenyl, naphthyl or pyridyl each of which is unsubstituted or mono-, di- or trisubstituted by $R^6$, Hal, $OAr^3$, $(CH_2)_nNH_2$, $(CH_2)_nNHCOA$ and/or $Het^3$,
$Ar^3$ denotes phenyl, which is unsubstituted or mono-, di- or trisubstituted by OH, OA, Hal, CN and/or A,
$Het^1$ denotes a mono- or bicyclic saturated, unsaturated or aromatic heterocycle having 1 to 4 N, O and/or S atoms, which may be unsubstituted or mono-, di- or trisubstituted by $R^6$, $O(CH_2)_nAr^3$ and/or $(CH_2)_nAr^3$, $Het^2$ denotes a mono- or bicyclic saturated heterocycle having 1 to 4 N, O and/or S atoms, which may be unsubstituted or mono-, di- or trisubstituted by $R^6$, $Het^3$, $CycSO_2$, OH, Hal, COOH, OA, COA, $COHet^3$, $CycCO$, $SO_2$ and/or =O, $Het^3$ denotes a monocyclic unsaturated, saturated or aromatic heterocycle having 1 to 4 N, O and/or S atoms, which may be unsubstituted or mono-, di- or trisubstituted by Hal, A and/or =O, $Het^4$ denotes a bi- or tricyclic unsaturated, saturated or aromatic heterocycle having 1 to 4 N, O and/or S atoms, which may be unsubstituted or mono-, di-, tri- or tetrasubstituted by A, $NO_2$, Hal and/or =O, Cyc denotes cyclic alkyl having 3, 4, 5 or 6 C atoms, which is unsubstituted, monosubstituted or disubstituted by $R^6$ and/or OH and which may comprise a double bond, A denotes unbranched or branched alkyl having 1-10 C atoms, in which 1-7 H atoms may be replaced by F and/or Cl and/or in which one or two non-adjacent $CH_2$ and/or CH-groups may be replaced by O, NH and/or by N, Hal denotes F, Cl, Br or I,
n denotes 0, 1, 2, 3 or 4,
p denotes 1, 2, 3, 4, 5 or 6,
and pharmaceutically usable salts, tautomers and stereoisomers thereof, including mixtures thereof in all ratios.

In general, all residues which occur more than once may be identical or different, i.e. are independent of one another. In other embodiments, the residues and parameters have the meanings indicated for the Formula (I), unless expressly indicated otherwise.

Further preferred are compounds of Subformulae 1 to 7 of Formula (I), in which the residues not designated in greater detail have the meaning indicated for the preferred group of compounds above, and pharmaceutically acceptable salts, solvates, solvates of salts, or prodrugs thereof, wherein:

In Subformula 1, $Het^1$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by $R^6$, $O(CH_2)_nAr^3$ and/or $(CH_2)_nAr^3$.

In Subformula 2, $Het^1$ denotes pyrazolyl, pyridyl, pyrimidinyl, dihydropyridyl or dihydrobenzodioxinyl, each of which is unsubstituted or mono-, di- or trisubstituted by $R^6$, $O(CH_2)_nAr^3$ and/or $(CH_2)_nAr^3$.

In Subformula 3, $Het^2$ denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-azaspiro[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by $R^6$, $Het^3$, $CycSO_2$, OH, OA, COA, $COHet^3$, $CycCO$, $SO_2$ and/or =O.

In Subformula 4, $Het^3$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O.

In Subformula 5, $Het^3$ denotes piperidinyl, pyrrolidinyl, morpholinyl, furyl, thienyl, pyrrolyl, imidazolyl, pyrazolyl, pyridyl, pyrimidinyl, dihydropyrrolyl, dihydropyrazolyl or dihydropyridyl, each of which may be unsubstituted or mono-, di- or trisubstituted by Hal, A and/or =O.

In Subformula 6, $Het^4$ denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, $NO_2$, Hal and/or =O.

In Subformula 7, selected substituents of Formula I are further defined such that:
X denotes CH or N,
$R^1$ denotes $NH_2$, $CONH_2$ or H,
$R^2$ denotes Hal, $Ar^1$ or $Het^1$,
$R^3$ denotes $NR^5[C(R^5)_2]_nHet^2$, $NR^5[C(R^5)_2]_nCyc$, $Het^2$, $O[C(R^5)_2]_nAr^2$, $NR^5[C(R^5)_2]_nAr^2$, $O[C(R^5)_2]_nHet^2$, $NR^5(CH_2)_pNR^5R^6$, $O(CH_2)_pNR^5R^6$ or $NR^5(CH_2)_pCR^7R^8NR^5R^6$,
$R^4$ denotes H,
$R^5$ denotes H or alkyl having 1, 2, 3 or 4 C atoms,
$R^6$ $N(R^5)_2CH_2CH=CHCONH$, $Het^3CH_2CH=CHCONH$, $CH_2=CHCONH(CH_2)_n$, $Het^4(CH_2)_nCOHet^3$-diyl-$CH_2CH=CHCONH$, HC≡CCO, $CH_3C≡CCO$, $CH_2=CH-CO$, $CH_2=C(CH_3)CONH$, $CH_3CH=CHCONH(CH_2)_n$, N≡CCR$^7$R$^8$CONH(CH$_2$)$_n$, $Het^4NH(CH_2)_pCOHet^3$-diyl-$CH_2CH=CHCONH$, $Het^4(CH_2)_pCONH(CH_2CH_2O)_p(CH_2)_pCOHet^3$-diyl-$CH_2CH=CHCONH$, $CH_2=CHSO_2$, $ACH=CHCO$, $CH_3CH=CHCO$, $Het^4(CH_2)_pCONH(CH_2)_pHet^3$-diyl-$CH_2CH=CHCONH$, $Ar^3CH=CHSO_2$, $CH_2=CHSO_2NH$ or $N(R^5)CH_2CH=CHCO$,
$R^7$, $R^8$ denote together alkylene having 2, 3, 4, or 5 C atoms,
$Ar^1$ denotes phenyl or naphthyl, each of which is unsubstituted or mono-, di- or trisubstituted by $R^6$, Hal, $(CH_2)_nNH_2$, $CONHAr^3$, $(CH_2)_nNHCOA$, $O(CH_2)_nAr^3$, OCyc, A, $COHet^3$, OA and/or $OHet^3$ ($CH_2$),
$Ar^2$ denotes phenyl or naphthyl, each of which is unsubstituted or mono-, di- or trisubstituted by $R^6$, Hal, $OAr^3$, $(CH_2)_nNH_2$, $(CH_2)_nNHCOA$ and/or $Het^3$,
$Ar^3$ denotes phenyl, which is unsubstituted or mono-, di- or trisubstituted by OH, OA, Hal, CN and/or A,
$Het^1$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, aza-bicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by $R^6$, $O(CH_2)_nAr^3$ and/or $(CH_2)_nAr^3$, $Het^2$ denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-azaspiro[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by $R^6$, $Het^3$, $CycSO_2$, OH, OA, COA, $COHet^3$, CycCO, $SO_2$ and/or =O, $Het^3$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O, $Het^4$ denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, $NO_2$, Hal and/or =O, Cyc denotes cyclic alkyl having 3, 4, 5 or 6 C atoms, which is unsubstituted or monosubstituted by $R^6$ and which may comprise a double bond, A denotes unbranched or branched alkyl having 1-10 C atoms, in which 1-7 H atoms may be replaced by F and/or Cl and/or in which one or two non-adjacent $CH_2$ and/or CH-groups may be replaced by O, NH and/or by N, Hal denotes F, Cl, Br or I,
n denotes 0, 1, 2, 3 or 4,
p denotes 1, 2, 3, 4, 5 or 6.

In some embodiments of the present invention, the pyrimidine and pyridine kinase inhibitors of the present invention are also defined by Formula (II):

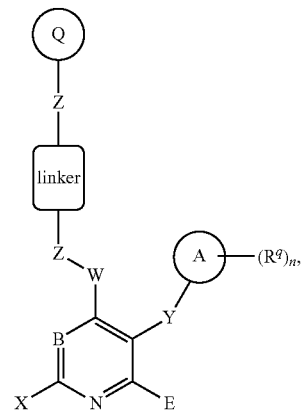

Formula (II)

and pharmaceutically acceptable salts, solvates, solvates of salts, or prodrugs thereof, wherein:
X is H or $CH_3$ or $NH_2$,
Y is H, Hal or is absent,
B is N or CH,
E is $NH_2$ or H, W is NR, O or a cyclic amine, Z is, independently, CH$_2$, CH$_3$, CH$_2$—CH$_2$, CH—CH$_2$, H, NH or is absent, "linker" is (CH$_2$)$_n$, wherein: $_n$ is 1, 2 or 3 or an optionally substituted group selected from a phenyl ring, an aryl ring, heteroaryl ring, branched or unbranched alkyl group, a 5-6 membered monocyclic heteroaryl ring having 1-4 heteroatoms independently selected from nitrogen, or oxygen, a 4-7 membered saturated or partially unsaturated heterocycle having 1-3 heteroatoms independently selected from nitrogen, or oxygen, or a 7-10 membered bicyclic saturated or partially unsaturated heterocyclic ring having 1-5 heteroatoms independently selected from nitrogen, or oxygen, or a 7-10 membered bicyclic saturated or partially unsaturated heterocyclic ring having 1-5 heteroatoms attached to a hetero saturated ring. Linkers may also be cycloalkanes optionally substituted by heteroatoms (independently selected from nitrogen, or oxygen), cycloalkanes optionally substituted with —NH or OH, fused or bridged rings or optionally substituted spirocyclic rings that optionally contain heteroatoms, A is a mono- or bicyclic aromatic homo- or heterocycle having 0, 1, 2, 3 or 4 N, and/or O atoms and 5, 6, 7, 8, 9, or 10 skeleton C atoms, which may be unsubstituted or, independently of one another, mono-, di- or trisubstituted by Hal, OH or OR, Hal is F, Cl, Br or I, R is independently hydrogen, oxygen or an optionally substituted group selected from C$_{1-6}$ linear or cyclic aliphatic, benzyl, phenyl, a phenyl group optionally substituted with 1, 2 or 3 O atoms, a 4-7 membered heterocylic ring having 1-2 heteroatoms independently selected from nitrogen, oxygen, or a 5-6 membered monocyclic heteroaryl ring having 1-4 heteroatoms independently selected from nitrogen, or oxygen or a mono- or bicyclic aromatic homo- or heterocycle having 0, 1, 2, 3 or 4 N, O atoms and 5, 6, 7, or 8 C skeleton atoms, which may be unsubstituted or, independently of one another, mono-, di- or trisubstituted by Hal, A, OH, NH$_2$, nitrile, and/or CH(Hal)$_3$ or is an unbranched or branched linear alkyl having 1, 2, 3, 4, 5, 6, 7 or 8 C atoms, in which one or two CH$_2$ groups may be replaced by an O atom and/or by an —NH—, —CO—, —NHCOO—, —NHCONH—, —CONH—, —NHCO— or —CH=CH— group, and in which 1-3 H atoms may be replaced by Hal, R$^q$ is selected from —R, -A, halogen, —OR, —O(CH$_2$)$_r$OR, —R(NH), —NO$_2$, —C(O)R, —CO$_2$R, —C(O)N(R)$_2$, —NRC(O)R, —NRC(O)NR$_2$, —NRSO$_2$R, or —N(R)$_2$, r is 1-4, n is 0-4, and Q is an electrophilic group such as those listed in Table 1 wherein said electrophilic groups may further comprise a warhead.

As used herein the term "warhead" refers to a part, functional group or substituent of the compounds as claimed in the present invention, wherein, said part, functional group or substituent covalently binds to an amino acid (such as cysteine, lysine, or any other amino acid, either native or modified, that can form said covalent bond) that is present, for example, in the binding region within a given ligand wherein said warhead binds with said ligand, wherein the covalent binding between said warhead and the binding region of said target protein occurs under conditions wherein a physiological function of said protein is irreversibly inhibited.

While it is not intended that the present invention be limited to a specific group for substituent Q, as set out in Formula (II) above, in certain embodiments substituent Q is selected from the groups set out in Table 1. All compounds, in Table 1, appearing within a box are not "warheads" as defined above.

TABLE 1

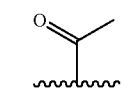

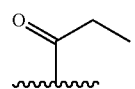 [SMILES: *C(=O)CC]

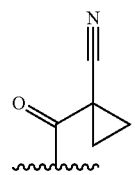 [SMILES: *C(=O)C1(C#N)CC1]

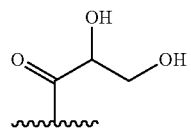 [SMILES: *C(=O)C(O)CO]

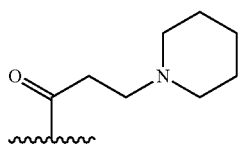 [SMILES: *C(=O)CCN1CCCCC1]

TABLE 1-continued
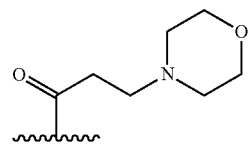 [SMILES: *C(=O)CCN1CCOCC1]
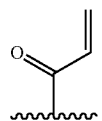
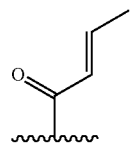 [SMILES: *C(=O)/C=C/C]
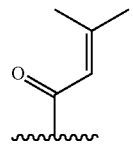 [SMILES: *C(=O)C=C(C)C]
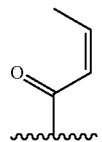 [SMILES: *C(=O)/C=C\C]
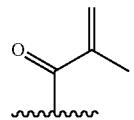 [SMILES: *C(=O)C(=C)C]
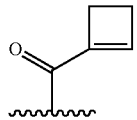 [SMILES: *C(=O)C1=CCC1]
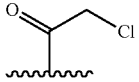
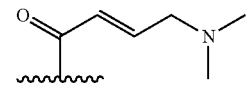 [SMILES: *C(=O)/C=C/CN(C)C]
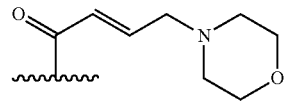 [SMILES: *C(=O)/C=C/CN1CCOCC1]
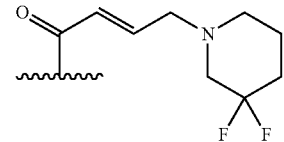 [SMILES: *C(=O)/C=C/CN1CCCC(F)(F)C1]
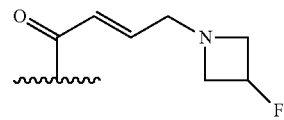 [SMILES: *C(=O)/C=C/CN1CC(F)C1]

TABLE 1-continued
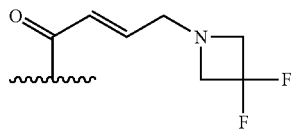 [SMILES: *C(=O)/C=C/CN1CC(F)(F)C1]
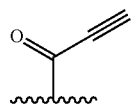 [SMILES: *C(=O)C#C]
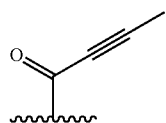 [SMILES: *C(=O)C#CC]
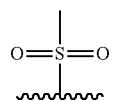
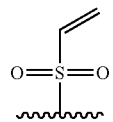
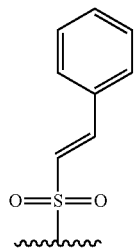 [SMILES: *S(=O)(=O)/C=C/c1ccccc1]
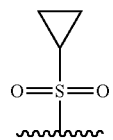
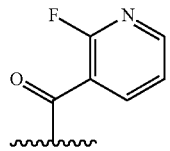
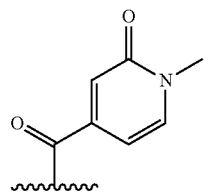 [SMILES: *C(=O)c1ccn(C)c(=O)c1]
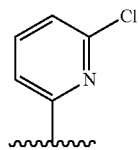 [SMILES: *c1cccc(Cl)n1]

TABLE 1-continued
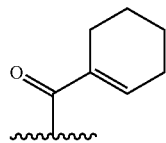
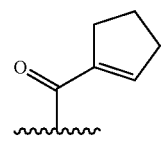 [SMILES: *C(=O)C1=CCCC1]
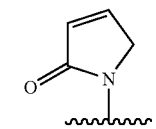 [SMILES: *N1CC=CC1=O]
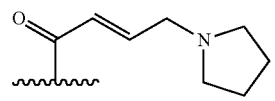 [SMILES: *C(=O)/C=C/CN1CCCC1]
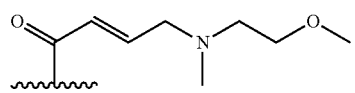 [SMILES: *C(=O)/C=C/CN(C)CCOC]
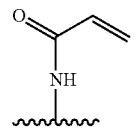 [SMILES: *NC(=O)C=C]
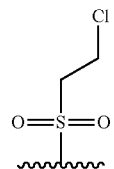
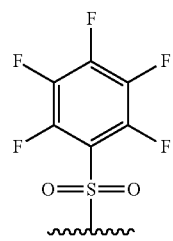
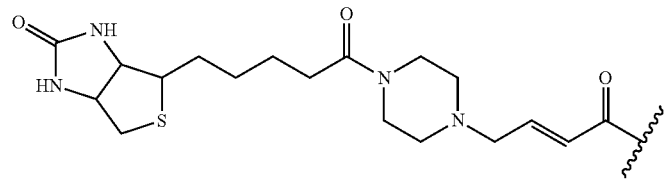 [SMILES: *C(=O)/C=C/CN1CCN(C(=O)CCCCC2SCC3NC(=O)NC32)CC1]
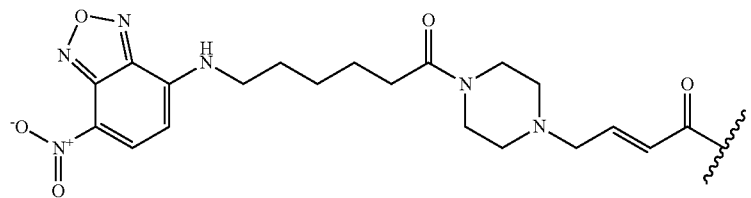

TABLE 1-continued

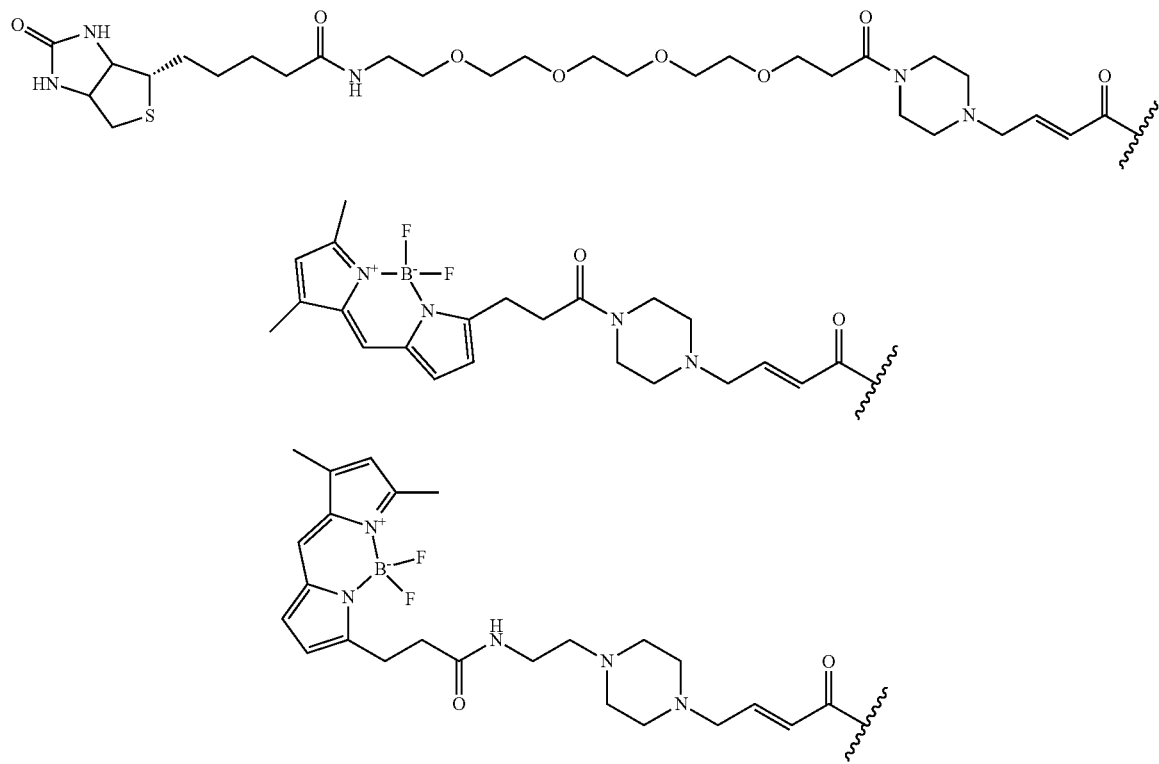

wherein, "⌇⌇⌇" denotes the bonding point of Q to Z in Formula (II).

In other embodiments, the pyrimidine and pyridine kinase inhibitors of the present invention are defined by Formula (III):

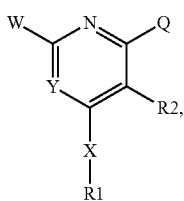

Formula (III)

and pharmaceutically acceptable salts, solvates, solvates of salts, or prodrugs thereof, wherein:
X is O or NH,
Y is N or CH,
W is H, $NH_2$ or $CONH_2$,
Q is H or $NH_2$,
$R^1$ is $L^1$-$R^4$-$L^2$-$R^5$,
$R^2$ is $M^1$-$S^4$-$M^2$-$S^5$
$L^1$ is a single bond, methylene, or cyclic A which may be mono- or disubstituted with N or $NH_2$,
$R^4$ is Ar, A or cyclic A which may be mono- or disubstituted with N, —O— or Hal,
$R^5$ is Ar, A or cyclic A which may be mono- or disubstituted with N, —O— or Hal or is absent. In preferred embodiments, $R^5$ is selected from the group consisting of 2-fluoropyridine, 1-methylpyridin-2(1H)-one and 2-chloropyridine, $L^2$ is H, —O—, substituted or unsubstituted $C_1$-$C_4$alkyl, substituted or unsubstituted $C_1$-$C_4$ heteroalkyl, $C_1$-$C_6$alkoxyalkyl, $C_1$-$C_6$alkylaminoalkyl, substituted or unsubstituted aryl, substituted or unsubstituted heteroaryl, $C_1$-$C_4$alkyl(aryl), $C_1$-$C_4$alkyl(heteroaryl), $C_1$-$C_4$alky($C_3$-$C_8$cycloalkyl), or $C_1$-$C_4$alkyl($C_2$-$C_8$heterocycloalkyl). In some embodiments, $L^2$ is —$CH_2$—O—($C_1$-$C_3$alkyl), —$CH_2$—N($C_1$-$C_3$alkyl)$_2$, $C_1$-$C_4$alkyl(phenyl), or $C_1$-$C_4$alkyl (5- or 6-membered heteroaryl). In some embodiments $L^2$ is -A-. In some embodiments $L^2$ is absent. In preferred embodiments of the present invention $L^2$ is selected from the group consisting of but-3-en-2-one, propan-2-one, (E)-5-(dimethylamino)pent-3-en-2-one, (E)-pent-3-en-2-one, pent-3-yn-2-one, 1-chloropropan-2-one, (methylsulfonyl)ethane, (E)-5-((2-methoxyethyl)(methyl)amino)pent-3-en-2-one or (Z)-pent-3-en-2-one,
$M^1$ is a single bond,
$S^4$ is Ar, A or cyclic A which may be mono- or disubstituted with N, —O— or Hal. In preferred embodiments of the present invention $S^4$ is a heteroaromatic 5 to 6 member ring,
$M^2$ O, NH, $CH_2$ or is absent,
$S^5$ is H, Ar, A or cyclic A which may be mono- or disubstituted with N, —O—, Hal. In certain embodiments of the present invention $S^5$ is selected from the group consisting of but-3-en-2-one, benzene, (E)-5-(dimethylamino)pent-3-en-2-one, ethylbenzene, 1-ethyl-2-methoxybenzene, aniline and (E)-5-morpholinopent-3-en-2-one. In some embodiments of the present invention $S_5$ is absent,
Ar is a mono- or bicyclic aromatic homo- or heterocycle having 0, 1, 2, 3 or 4 N, and/or O atoms and 5, 6, 7, 8, 9, or 10 skeleton atoms, which may be unsubstituted or, independently of one another, mono-, di- or trisubstituted by Hal, A, OH, OA, NH$_2$, NHA, NA$_2$, NO$_2$, CN, OCN, COOH, COOA, CONH$_2$, CONHA, CONA$_2$, NHCOA, NHCONHA, NHCONH, CHO and/or COA, and in which a ring N-atom may be substituted by an O-atom to form an N-oxide group and in which in the case of a bicyclic aromatic cycle on of the two rings may be partly saturated, A is unbranched or branched linear or cyclic alkyl having 1, 2, 3, 4, 5, 6, 7 or 8 C atoms, in which one or two CH$_2$ groups may be replaced by an O atom and/or by an —NH—, —CO—, —NHCOO—, —NHCONH—, —N(LA)-, —CONH—, —NHCO— or CH=CH group, LA is unbranched or branched, linear alkyl having 1, 2, 3 or 4 C atoms, wherein 1, 2 or 3 H atoms may be replaced by Hal, Hal is F, Cl, Br or I.

In some embodiments, the pyrimidine and pyridine kinase inhibitors of the present invention are also defined by Formula (IV):

Formula (IV)

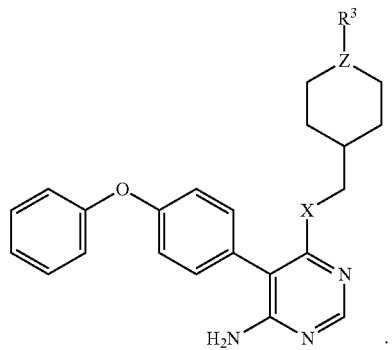

and pharmaceutically acceptable salts, solvates, solvates of salts, or prodrugs thereof, wherein:
Z is N or CH,
X is O or NH, and
R$^3$ is selected from the group consisting of the following structures:

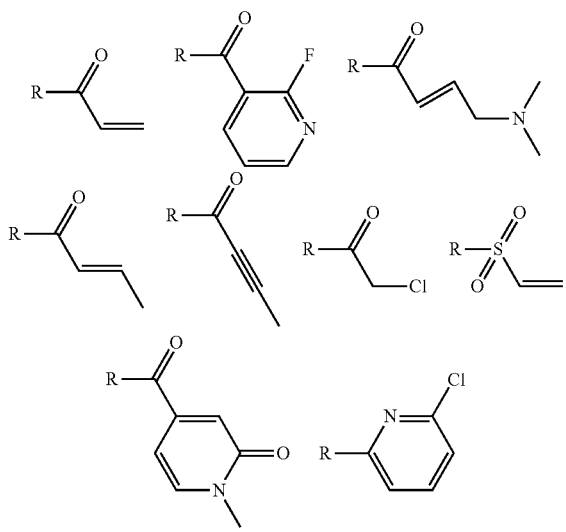

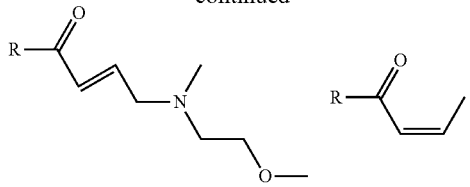

wherein, "R" denotes the bonding point to Z in Formula IV.

In some embodiments, the pyrimidine and pyridine kinase inhibitors of the present invention are also defined by Formula (V):

V

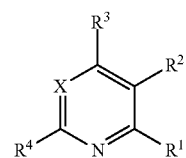

and pharmaceutically acceptable salts, solvates, solvates of salts, or prodrugs thereof,
in which:
X denotes CH or N,
R$^1$ denotes NR$^5$[C(R$^5$)$_2$]$_n$Het$^2$,
R$^2$ denotes Hal, Ar$^1$ or Het$^1$,
R$^3$ denotes NH$_2$,
R$^4$ denotes H, CH$_3$ or NH$_2$,
R$^5$ denotes H or alkyl having 1, 2, 3 or 4 C atoms,
R$^6$ N(R$^5$)$_2$CH$_2$CH=CHCONH, Het$^3$CH$_2$CH=CHCONH, CH$_2$=CHCONH(CH$_2$)$_n$, Het$^4$(CH$_2$)$_n$COHet$^3$-diyl-CH$_2$CH=CHCONH, HC≡CCO, CH$_3$C≡CCO, CH$_2$=CH—CO, CH$_2$=C(CH$_3$)CONH, CH$_3$CH=CHCONH(CH$_2$)$_n$, N≡CCR$^7$R$^8$CONH(CH$_2$)$_n$, Het$^4$NH(CH$_2$)$_p$COHet$^3$-diyl-CH$_2$CH=CHCONH, Het$^4$(CH$_2$)$_p$CONH(CH$_2$CH$_2$O)$_p$(CH$_2$)$_p$COHet$^3$-diyl-CH$_2$CH=CHCONH, CH$_2$=CHSO$_2$, ACH=CHCO, CH$_3$CH=CHCO, Het$^4$(CH$_2$)$_p$CONH(CH$_2$)$_p$Het$^3$-diyl-CH$_2$CH=CHCONH, Ar$^3$CH=CHSO$_2$, CH$_2$=CHSO$_2$NH or N(R$^5$)CH$_2$CH=CHCO,
R$^7$, R$^8$ denote together alkylene having 2, 3, 4, or 5 C atoms,
Ar$^1$ denotes phenyl or naphthyl, each of which is unsubstituted or mono-, di- or trisubstituted by R$^6$, Hal, (CH$_2$)$_n$NH$_2$, CONHAr$^3$, (CH$_2$)$_n$NHCOA, O(CH$_2$)$_n$Ar$^3$, OCyc, A, COHet$^3$, OA and/or OHet$^3$ (CH$_2$),
Ar$^2$ denotes phenyl, naphthyl or pyridyl each of which is unsubstituted or mono-, di- or trisubstituted by R$^6$, Hal, OAr$^3$, (CH$_2$)$_n$NH$_2$, (CH$_2$)$_n$NHCOA and/or Het$^3$,
Ar$^3$ denotes phenyl, which is unsubstituted or mono-, di- or trisubstituted by OH, OA, Hal, CN and/or A,
Het$^1$ denotes a mono- or bicyclic saturated, unsaturated or aromatic heterocycle having 1 to 4 N, O and/or S atoms, which may be unsubstituted or mono-, di- or trisubstituted by R$^6$, O(CH$_2$)$_n$Ar$^3$ and/or (CH$_2$)$_n$Ar$^3$,
Het$^2$ denotes a mono- or bicyclic saturated heterocycle having 1 to 4 N, O and/or S atoms, which may be unsubstituted or mono-, di- or trisubstituted by R$^6$, Het$^3$, CycSO$_2$, OH, Hal, COOH, OA, COA, COHet$^3$, CycCO, SO$_2$ and/or =O,
Het$^3$ denotes a monocyclic unsaturated, saturated or aromatic heterocycle having 1 to 4 N, O and/or S atoms, which may be unsubstituted or mono-, di- or trisubstituted by Hal, A and/or =O, Het$^4$ denotes a bi- or tricyclic unsaturated, saturated or aromatic heterocycle having 1 to 4 N, O and/or S atoms, which may be unsubstituted or mono-, di-, tri- or tetrasubstituted by A, NO$_2$, Hal and/or =O, Cyc denotes cyclic alkyl having 3, 4, 5 or 6 C atoms, which is unsubstituted, monosubstituted or disubstituted by R$^6$ and/or OH and which may comprise a double bond, A denotes unbranched or branched alkyl having 1-10 C atoms, in which 1-7 H atoms may be replaced by F and/or Cl and/or in which one or two non-adjacent CH$_2$ and/or CH-groups may be replaced by O, NH and/or by N, Hal denotes F, Cl, Br or I, n denotes 0, 1, 2, 3 or 4, p denotes 1, 2, 3, 4, 5 or 6, and pharmaceutically usable salts, tautomers and stereoisomers thereof, including mixtures thereof in all ratios.

In general, all residues which occur more than once may be identical or different, i.e. are independent of one another. Above and below, the residues and parameters have the meanings indicated for Formula (I), Formula (II), Formula (III), Formula (IV) and Formula (V) unless expressly indicated otherwise. Accordingly, the invention relates, in particular, to the compounds of Formula (I), Formula (II), Formula (III), Formula (IV) and Formula (V) in which at least one of the said residues has one of the preferred meanings indicated below.

The term "substituted" preferably relates to the substitution by the above-mentioned substituents, where a plurality of different degrees of substitution are possible, unless indicated otherwise.

All physiologically acceptable salts, derivatives, solvates, solvates of salts, and stereoisomers of these compounds, including mixtures thereof in all ratios, are also in accordance with the invention.

The compounds of the Formula (I), (II), (III), (IV) and (V) may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

It is also contemplated that compounds of Formula (I), Formula (II), Formula (III), Formula (IV) and Formula (V) include isotope-labeled forms thereof. An isotope-labeled form of a compound of Formula (I), Formula (II), Formula (III), Formula (IV) and Formula (V) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the Formula I by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. It is also contemplated that a compound of the Formula I, a prodrug, thereof or a pharmaceutically acceptable salt of either which contains one or more of the above-mentioned isotopes and/or other iso-topes of other atoms are embodiments of the present invention. An isotope-labeled compound of the Formula I can be used in a number of beneficial ways. For example, an isotope-labeled compound of the Formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to their ease of preparation and excellent detectability. Incorporation of heavier isotopes, for example deuterium ($^2$H), into a compound of the Formula I may have therapeutic advantages owing to the higher metabolic stability of this isotope-labeled compound. Higher metabolic stability translates directly into an increased in vivo half-life or lower dosages, which under some circumstances would represent a preferred embodiment of the present invention. An isotope-labeled compound of the Formula I can adapted to the procedures disclosed in the synthesis schemes and the related description, in the example part and in the preparation part in the present text, replacing a non-isotope-labeled reactant by a readily available isotope-labeled reactant.

In other embodiments it is contemplated that deuterium ($^2$H) may be incorporated into a compound of Formula (I), Formula (II), Formula (III), Formula (IV) and Formula (V). Such deuterated compounds can modify the oxidative metabolism of said deuterated compound by means the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is observed in any compounds of Formula (I), Formula (II), Formula (III), Formula (IV) and Formula (V) susceptible to oxidation, the profile of this compound, in vivo, can be drastically modified and result in improved pharmacokinetic properties.

When discovering and developing therapeutic agents, the person skilled in the art attempts to optimize pharmacokinetic parameters while retaining desirable in vitro properties. It is reasonable to assume that many compounds with poor pharmacokinetic profiles are susceptible to oxidative metabolism. In vitro liver microsomal assays known in the are may provide valuable information on the course of oxidative metabolism of this type, which in turn permits the rational design of deuterated compounds of Formula (I), Formula (II), Formula (III), Formula (IV) and Formula (V) with improved stability through resistance to said oxidative metabolism. Significant improvements in the pharmacokinetic profiles of compounds of the Formula I may thereby be obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

While it is not intended that the present invention be limited to any deuterated motif, the following is an example. A compound of Formula (I), Formula (II), Formula (III), Formula (IV) and Formula (V) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it can be determined that the half-life of the parent compound may be extended by up to 100% as the result of deuterium-hydrogen exchange of this type.

Deuterium-hydrogen exchange in a compound of Formula (I), Formula (II), Formula (III), Formula (IV) and Formula (V) can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other BTK inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. Preferably, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of BTK as well as diseases modulated by the BTK cascade in mammals, or disorders mediated by aberrant proliferation, such as cancer or hyperactivity of B cells, mast cells, neutrophils and monocytes such in inflammatory conditions.

Figure 1A:
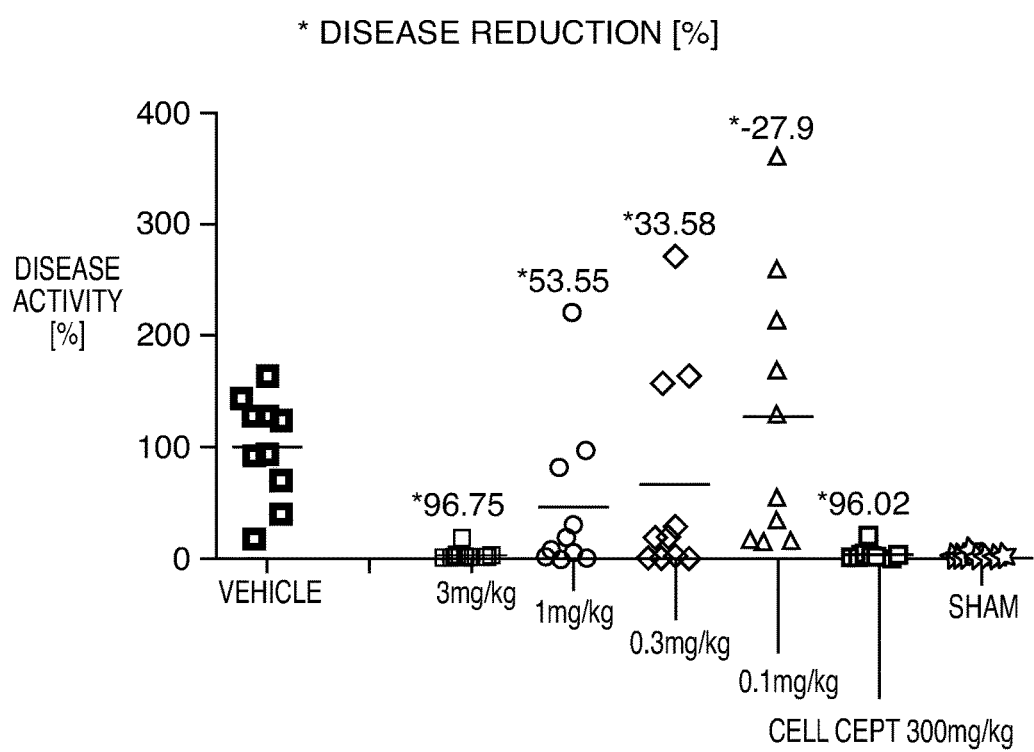
FIGS. 1 A and B present data evaluating a compound described by the present invention [1-(4-(((6-amino-5-(4-phenoxyphenyl)pyrimidin-4-yl)amino)methyl)piperidin-1-yl)prop-2-en-1-one, designated as "CPD. B" in the figure] in an interferon-alpha accelerated systemic lupus erythematosus (SLE) mouse model.
Figure 1B:
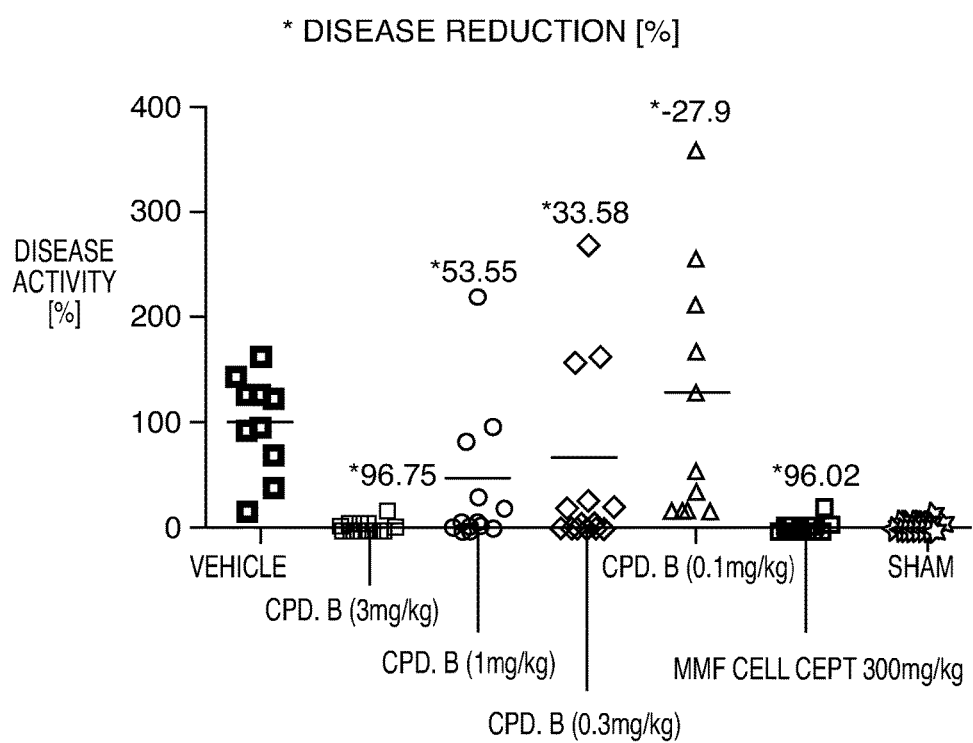

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory diseases such as rheumatoid arthritis, systemic lupus erythematosus, inflammatory bowel disease, Sjögren's Syndrome, atherosclerosis, skin and allegic diseases such as psoriatic arthritis, psoriasis, eczema, and sclerodema, asthma and atopic dermatitis or diseases such as diabetes, diabetic retinopathy, retinopathy of prematurity and age-related macular degeneration.

In one embodiment the treatment of rheumatoid arthritis with BTK inhibitors is preferred given experimental validation which confirms the efficacy of BTK inhibitors in the treatment of collagen antibody induced arthritis and collagen induced arthritis. Pan, Z. et al., Discovery of Selective Irreversible Inhibitors of Brunton's Tyrosine Kinase. ChemMedChem 2, 58-61 (2007). More specifically treatment with BTK inhibitors have been show to reduce the incidence and severity of collagen induced arthritis and K/BxN serum induced arthritis.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

Abbreviations

| Designation | |
|---|---|
| ACN | acetonitrile |
| ATP | Adenosine triphosphate |
| b | Broad peak |
| BOC | tert-butyloxycarbonyl |
| BOP-Cl | Bis(2-oxo-3-oxazolidinyl)phosphinic chloride |
| d | Doublet |
| DBU | 1,8-diazabicyclo[5.4.0]undec-7-ene |
| DCM | dichloromethane |
| dd | doublet of doublets |
| DMSO | dimethylsulfoxide |
| DIEA | N,N-Diisopropylethylamine |
| DIPEA | diisopropylethylamine |
| DMF | dimethylformamide |
| DTT | dithiothreitol |
| EDTA | Ethylenediaminetetraacetic acid |
| equiv. | equivalents |
| Et | ethyl |
| EtOAc | ethyl acetate |
| h | hour |
| HEPES | 4-(2-hydroxyethyl)-1-piperazineethanesulfonic acid |
| $^1$H-NMR | proton NMR |
| HPLC | High pressure/performance liquid chromatography |
| LC | Liquid chromatography |
| LC/MS | Liquid chromatography coupled to mass spectrometry |
| m | multiplet |
| M | Molecular ion |
| m/z | Mass-to-charge ratio |
| MHz | megahertz |
| Me | methyl |
| min | minutes |
| MeOH | methanol |
| MS | Mass spectrometry/spectrum |
| N | Normal (unit of concentration) |
| NMO | 4-methylmorpholine N-oxide |
| NMP | N-methyl-2-pyrrolidone |
| NMR | Nuclear Magnetic Resonance |
| PG | Protecting group |
| psi | Pounds per square inch |

-continued

| Designation | |
|---|---|
| q | Quartette (or quartet) |
| Rf | Retention factor |
| RT/rt | Room temperature |
| Rt./RT | Retention time |
| s | Singlet |
| S-Phos | 2-dicyclohexylphosphino-2',6'-dimethoxybiphenyl triplet |
| t | triplet |
| Tert | Tertiary |
| TEA | Triethylamine |
| TFA | Trifluoroacetic acid |
| THAB | Tetrahexylammonium bromide |
| THF | Tetrahydrofuran |
| T3P | 1-Propanephosphonic Acid Cyclic Anhydride |
| UV | ultraviolet |
| VIS | visible |
| x | times |

The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following schemes and examples. Unless otherwise indicated in the schemes, the variables have the same meaning as described above.

Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of Formula (I), Formula (II), Formula (III), Formula (IV) and Formula (V), as described above, according to the hereinafter described schemes and working examples.

Synthetic Procedures
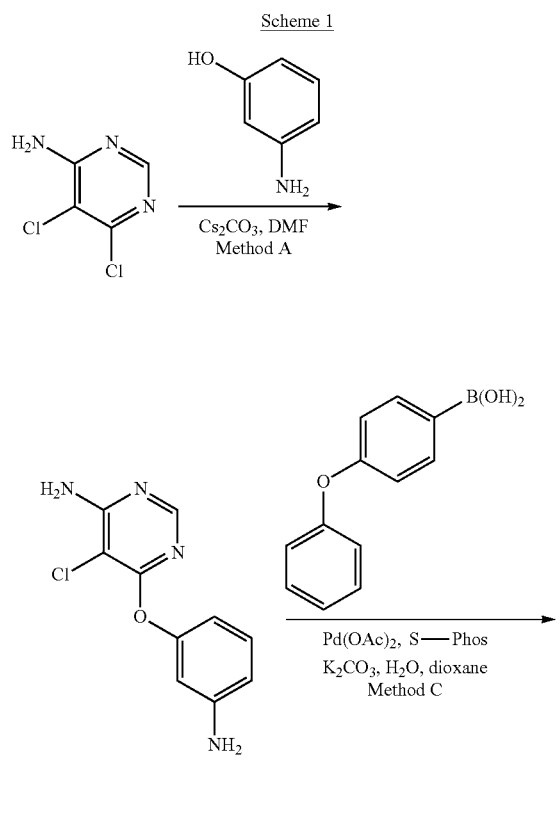
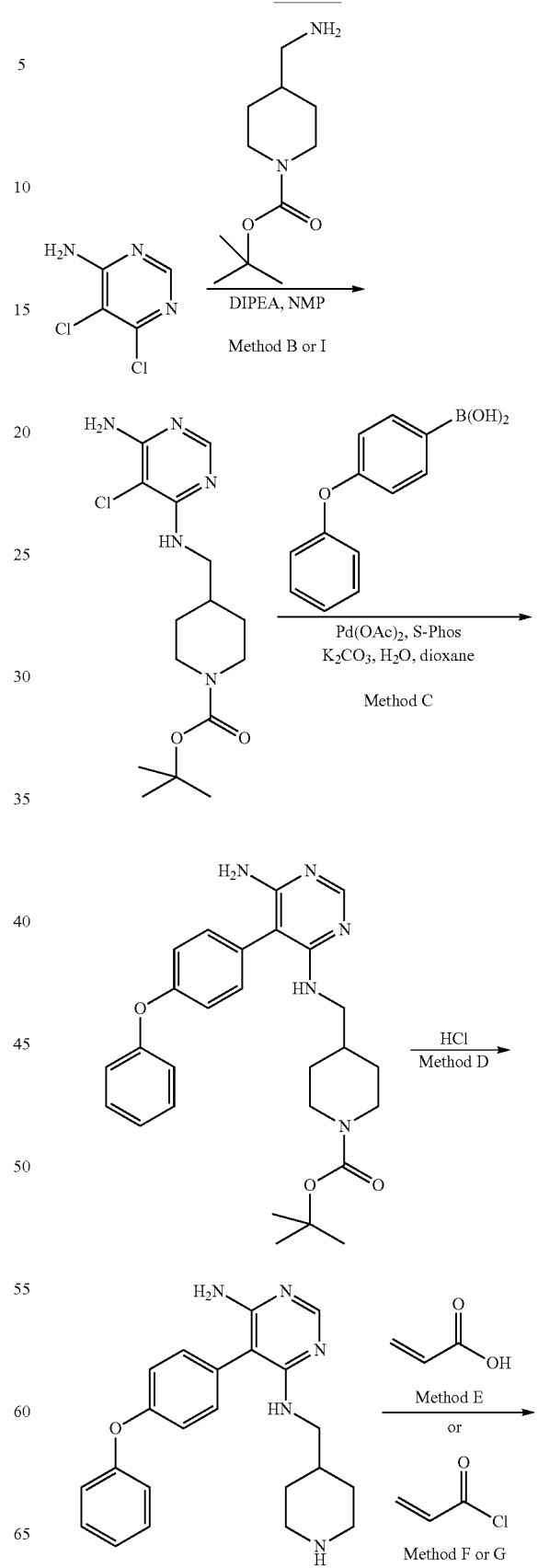

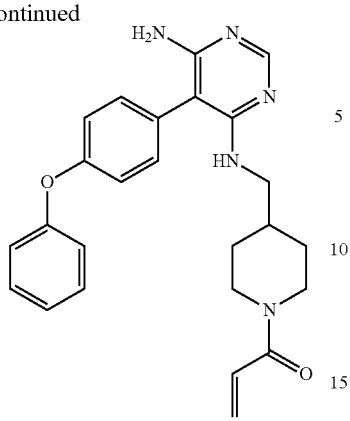

Methods Associated with Reaction Steps in Scheme 1 and Scheme 2

Method A: Nucleophilc Aromatic Substitution Using an Oxygen Nucleophile

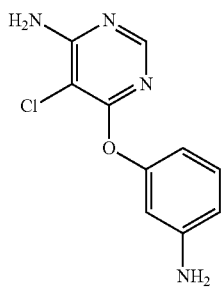 [SMILES: Nc1cccc(Oc2ncnc(N)c2Cl)c1]

6-(3-aminophenoxy)-5-chloropyrimidin-4-amine

Into a 20-mL microwave vial was placed 5,6-dichloropyrimidin-4-amine (500.00 mg; 3.05 mmol), cesium carbonate (1.49 g: 4.57 mmol), and 3-aminophenol (499.08 mg; 4.57 mmol) suspended in DMF (12.00 ml). The reaction mixture was run in the microwave at 160° C. for 2 hours. The reaction mixture was allowed to cool to rt. The mixture was then filtered through a plug of silica gel. The solution was concentrated under reduced pressure and then lyophilized overnight to afford 6-(3-aminophenoxy)-5-chloropyrimidin-4-amine as a black solid crude.

Method B: Nucleophilic Aromatic Substitution Using a Nitrogen Nucleophile

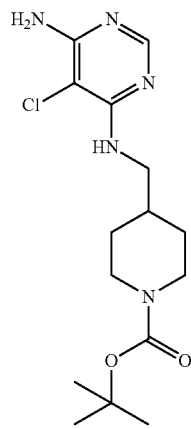 [SMILES: CC(C)(C)OC(=O)N1CCC(CNc2ncnc(N)c2Cl)CC1]

tert-butyl 4-{[(6-amino-5-chloropyrimidin-4-yl)amino]methyl}piperidine-1-carboxylate Into a 10-mL vial was placed 5,6-dichloropyrimidin-4-amine (250.00 mg; 1.52 mmol), tert-butyl 4-(aminomethyl) piperidine-1-carboxylate (653.40 mg; 3.05 mmol), and N,N-diisopropylethylamine (1.01 ml; 6.10 mmol) suspended in NMP (2.50 ml). The reaction mixture was run in the microwave at 150° C. for 2 hours. The reaction mixture was allowed to cool to rt. The mixture was purified using Biotage column chromatography eluting from 50-100% EtOAc/Hexanes. Fractions containing the desired product were combined and concentrated under reduced pressure to afford tert-butyl 4-{[(6-amino-5-chloropyrimidin-4-yl)amino]methyl}piperidine-1-carboxylate as a yellow viscous oil.

Method C: Suzuki Coupling

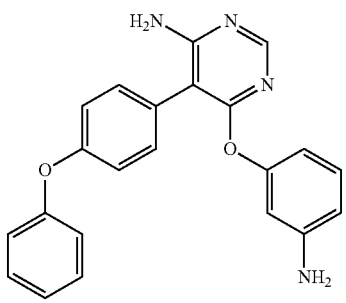 [SMILES: Nc1cccc(Oc2ncnc(N)c2-c2ccc(Oc3ccccc3)cc2)c1]

6-(3-aminophenoxy)-5-(4-phenoxyphenyl)pyrimidin-4-amine

Into a 20-mL microwave vial was placed 6-(3-aminophenoxy)-5-chloropyrimidin-4-amine (400.00 mg; 1.69 mmol.), (4-phenoxyphenyl)boronic acid (542.62 mg; 2.54 mmol), palladium acetate (18.97 mg; 0.08 mmol), 2-dicyclohexylphosphino-2',6'-dimethoxybiphenyl (69.39 mg; 0.17 mmol), potassium carbonate (700.77 mg; 5.07 mmol) suspended in dioxane (8.00 ml) and water (0.80 ml). The reaction mixture was run in the microwave for 20 minutes at 140° C. The reaction mixture was allowed to cool to rt. Na2SO4 was added to the mixture which was subsequently filtered through a plug of silica gel and concentrated under reduced pressure. The crude mixture was purified using Biotage column chromatography eluting from 80-100% EtOAc/hexanes, then 0-100% MeOH/EtOAc. Fractions containing the desired product were combined and concentrated under reduced pressure. The residue was lyophilized overnight to afford 6-(3-aminophenoxy)-5-(4-phenoxyphenyl)pyrimidin-4-amine as a yellow solid (177.00 mg, 74% yield).

Method D: Deprotection of Tert-Butyloxycarbonyl (BOC)-Protected Amine

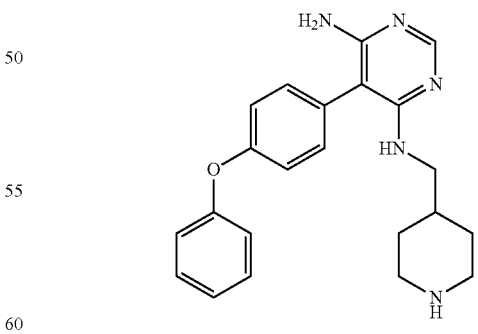

5-(4-phenoxyphenyl)-N-(piperidin-4-ylmethyl)pyrimidine-4,6-diamine

Into a 20-mL vial was placed tert-butyl 4-({[6-amino-5-(4-phenoxyphenyl)pyrimidin-4-yl]amino}methyl)piperidine-1-carboxylate (534.60 mg; 1.12 mmol) dissolved in methanol (4.00 ml). Hydrogen chloride (2.0 M solution in diethyl ether) (5.62 ml) was added to the mixture. The reaction mixture was stirred at rt overnight. The reaction mixture was concentrated under reduced pressured and subsequently lyophilized overnight to afford 5-(4-phenoxyphenyl)-N-(piperidin-4-ylmethyl)pyrimidine-4,6-diamine as a yellow solid crude.

Method E: Amide Formation from Carboxylic Acid

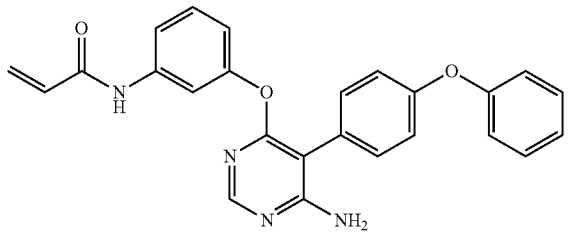 [SMILES: C=CC(=O)Nc1cccc(Oc2ncnc(N)c2-c2ccc(Oc3ccccc3)cc2)c1]

N-(3-{[6-amino-5-(4-phenoxyphenyl)pyrimidin-4-yl]oxy}phenyl)acrylamide

Into a 20 mL reaction vial was added acrylic acid (0.01 ml; 0.12 mmol), and bis(2-oxo-3-oxazolidinyl)phosphinic chloride (42.04 mg; 0.17 mmol), and N,N-diisopropylethylamine (0.07 ml; 0.41 mmol) suspended in dioxane (3.00 ml). The reaction mixture was stirred at rt for 1 h. 6-(3-aminophenoxy)-5-(4-phenoxyphenyl)pyrimidin-4-amine (40.00 mg; 0.08 mmol) was then added. The reaction mixture was stirred at rt overnight. The crude mixture was purified using Biotage column chromatography eluting from 50-100% EtOAc/Hexanes, then 0-40% MeOH/EtOAc. Fractions containing the desired product were combined and concentrated under reduced pressure. The residue was then purified using preparative HPLC eluting from 35-45% $CH_3CN$ in 0.1% TFA in $H_2O$. fractions containing the desired product were combined and lyophilized overnight to afford N-(3-{[6-amino-5-(4-phenoxyphenyl)pyrimidin-4-yl]oxy}phenyl)acrylamide as a white solid (29.00 mg, 25% yield). HPLC purity: 97%, RT=4.264 min. MS: m/z=425 [M+H]$^+$, RT=2.14 min. $^1$H-NMR (DMSO-d$_6$) δ 10.14 (s, 1H), 8.00 (s, 1H), 7.41 (s, 1H), 7.36-7.30 (m, 5H), 7.22 (t, 1H), 7.09 (t, 1H), 7.03-7.01 (m, 4H), 6.71 (d, 1H), 6.53 (broad s, 2H), 6.34 (dd, 1H), 6.18 (d, 1H), 5.69 (d, 1H).

Method F: Amide Formation from Acid Chloride in Presence of Inorganic Base

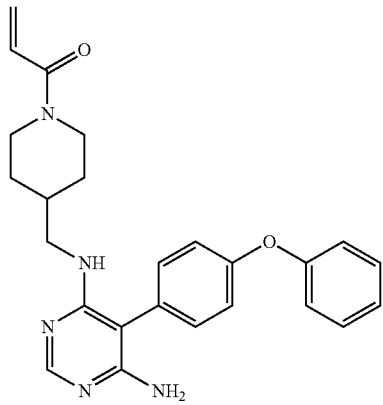 [SMILES: C=CC(=O)N1CCC(CNc2ncnc(N)c2-c2ccc(Oc3ccccc3)cc2)CC1]

N-[(1-acryloylpiperidin-4-yl)methyl]-5-(4-phenoxyphenyl)pyrimidine-4,6-diamine

Into a 20 mL reaction vial was added 5-(4-phenoxyphenyl)-N-(piperidin-4-ylmethyl)pyrimidine-4,6-diamine (70.00 mg; 0.19 mmol), sodium bicarbonate (23.49 mg; 0.28 mmol) suspended in THF (3.00 ml) and water (0.30 ml). The mixture was cooled to 0° C. Acryloyl chloride (0.02 ml; 0.22 mm ol) was added. The ice bath was left to melt. The reaction mixture was then stirred at rt overnight. The crude mixture was purified using Biotage column chromatography eluting 0-50% MeOH/EtOAc. Fractions containing the desired product were combined and concentrated under reduced pressure. The residue was lyophilized overnight to afford N-[(1-acryloylpiperidin-4-yl)methyl]-5-(4-phenoxyphenyl)pyrimidine-4,6-diamine as a white solid (30.00 mg, 37% yield). HPLC purity: 97%, RT=3.665 min. MS: m/z=430 [M+H]$^+$, RT=1.53 min. $^1$H-NMR (DMSO-d$_6$) δ 7.93 (s, 1H), 7.40 (t, 2H), 7.21-7.08 (m, 8H), 6.76 (dd, 1H), 6.04 (d, 1H), 5.61 (d, 1H), 5.43 (s, 2H), 4.34 (d, 1H), 3.98 (d, 1H), 3.12 (t, 2H), 2.95 (t, 1H), 2.56 (t, 1H), 1.81 (m, 1H), 1.59 (m, 2H), 0.92 (m, 2H).

Method G: Amide Formation from Acid Chloride in Presence of Organic Base

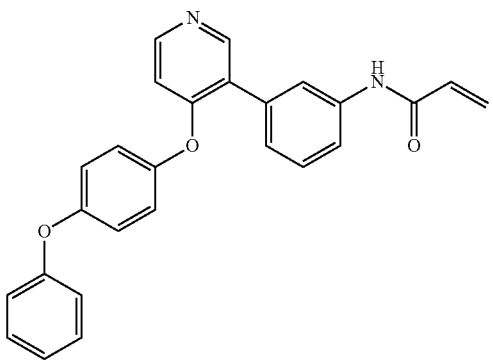 [SMILES: C=CC(=O)Nc1cccc(-c2cnccc2Oc2ccc(Oc3ccccc3)cc2)c1]

N-(3-(4-(4-phenoxyphenoxy)pyridin-3-yl)phenyl)acrylamide

Into a 20 mL vial was placed 3-(4-(4-phenoxyphenoxy)pyridin-3-yl)aniline (30.00 mg, 0.08 mmol), N, N-diethylethanamine (0.02 mL, 0.17 mmol) suspended in 1-methylpyrrolidin-2-one (0.35 mL) and dichloromethane (2.00 mL). The resulting mixture was cooled to 0° C. Added acryloyl chloride (0.02 mL, 0.25 mmol). The ice bath was left to melt and the reaction mixture was stirred at rt overnight. The reaction mixture was purified using Biotage column chromatography eluting 0-40% MeOH in EtOAc. Fractions containing the desired product were combined and concentrated. Purified using prep-HPLC eluting 25-55% $CH_3CN$ in 0.1% TFA in $H_2O$. Fractions containing the desired product were combined and lyophilized overnight to afford N-(3-(4-(4-phenoxyphenoxy)pyridin-3-yl)phenyl)acrylamide as a white solid (12.00 mg, 35% yield). HPLC purity: 100%, RT=4.235 min. MS: m/z=409 [M+H]$^+$, RT=3.38 min. $^1$H-NMR (DMSO-d$_6$) δ 10.23 (s, 1H), 8.52 (s, 1H), 8.43 (d, 1H), 7.95 (s, 1H), 7.71 (d, 1H), 7.44-7.33 (m, 4H), 7.19 (d, 2H), 7.13 (t, 1H), 7.09 (d, 2H), 7.02 (d, 2H), 6.80 (d, 1H), 6.45 (dd, 1H), 6.26 (d, 1H), 5.75 (d, 1H).

Method H: Nucleophilic Aromatic Substitution Using an Aromatic Amine

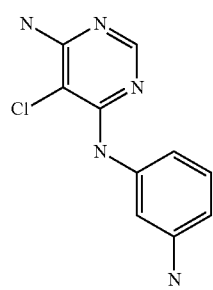 [SMILES: Nc1cccc(Nc2ncnc(N)c2Cl)c1]

N4-(3-aminophenyl)-5-chloropyrimidine-4,6-diamine

Into a 20 mL was placed 5,6-dichloropyrimidin-4-amine (500 mg, 3.05 mmol), benzene-1,3-diamine (329.72 mg, 3.05 mmol) and a pre-made mixture of TFA:TEA (1:1 mol) (347.64 mg: 308.52 mg) dissolved in DMSO (6 mL). The mixture was heated at 90° C. overnight. The reaction mixture was then cooled to rt and the crude mixture was purified using column chromatography eluting 0-40% MeOH in EtOAc. The fractions containing the desired product was concentrated and lyophilized overnight to afford the desired product N4-(3-aminophenyl)-5-chloropyrimidine-4,6-diamine (82% yield) as a brown syrup.

Method I: Nucleophilic Aromatic Substitution Using a Nitrogen Nucleophile

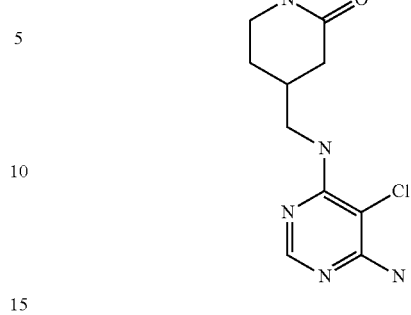

4-(((6-amino-5-chloropyrimidin-4-yl)amino)methyl)piperidin-2-one

Into a 20 mL vial was placed 5,6-dichloropyrimidin-4-amine (100 mg, 0.61 mmol), 4-(((6-amino-5-chloropyrimidin-4-yl)amino)methyl)piperidin-2-one (117.24 mg, 0.91 mmol), and DBU (0.18 mL 1.22 mmol) dissolved in DMF (2 mL). The reaction mixture was stirred at 90° C. overnight. The mixture was then cooled to rt. The crude mixture was purified using column chromatography eluting 0-100% MeOH in EtOAc. Fractions containing the desired product was combined and concentrated and lyophilized overnight to afford the desired product 4-(((6-amino-5-chloropyrimidin-4-yl)amino)methyl)piperidin-2-one (90% yield) as a yellow solid.

Scheme 3

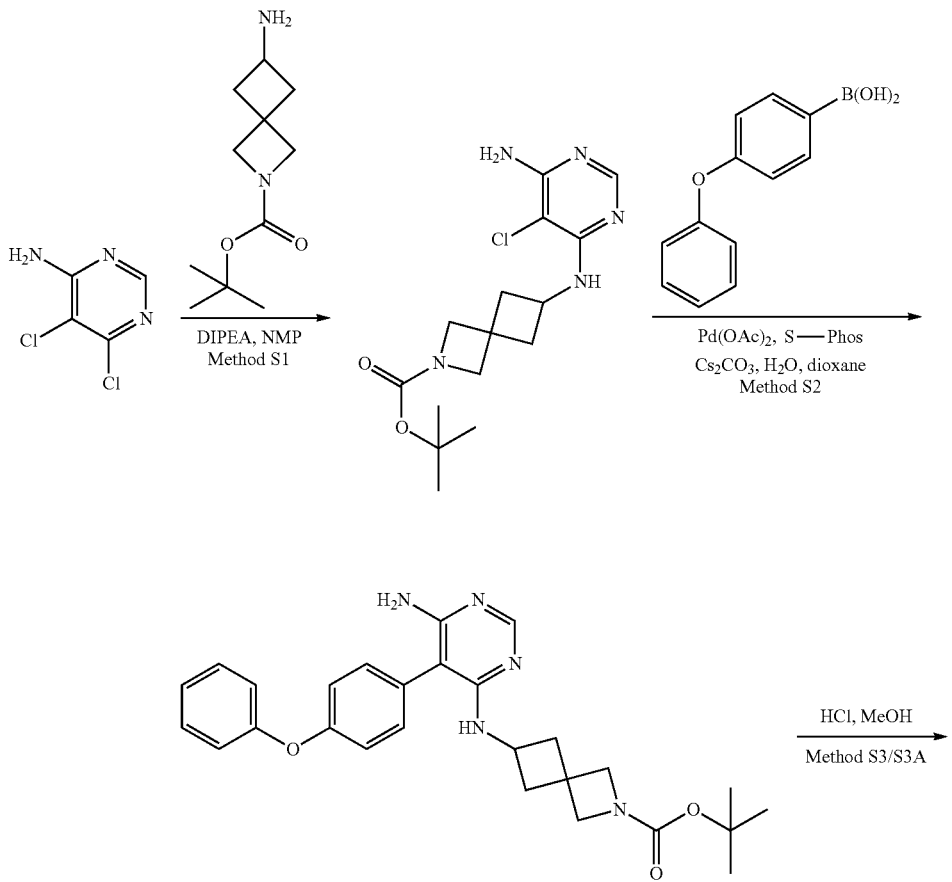

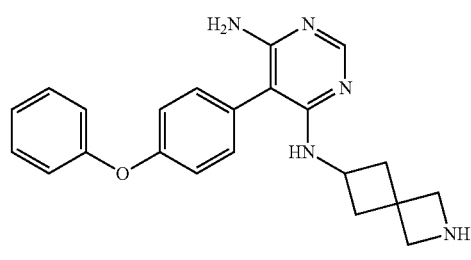 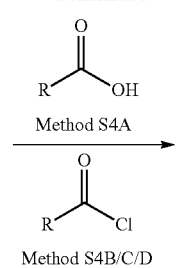 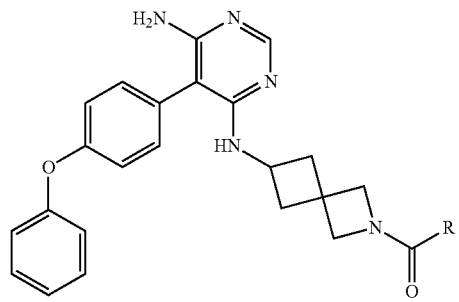

Methods Associated with Reaction Steps in Scheme 3
Method S1: Nucleophilic Aromatic Substitution

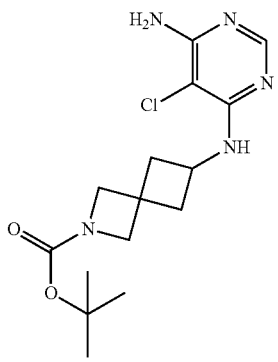 [SMILES: CC(C)(C)OC(=O)N1CC2(CC(Nc3ncnc(N)c3Cl)C2)C1]

tert-butyl 6-((6-amino-5-chloropyrimidin-4-yl)amino)-2-azaspiro[3.3]heptane-2-carboxylate In a round bottom flask containing 5,6-dichloro-pyrimidin-4-ylamine (300.00 mg; 1.83 mmol; 1.00 eq.) and 6-amino-2-aza-spiro[3.3]heptane-2-carboxylic acid tert-butyl ester (466.02 mg; 2.20 mmol; 1.20 eq.) in NMP (1.00 ml) was added DIPEA (0.91 ml; 5.49 mmol; 3.00 eq.). The reaction mixture was stirred at 155° C. for 4 h before it was concentrated.
Method S2: Suzuki Coupling

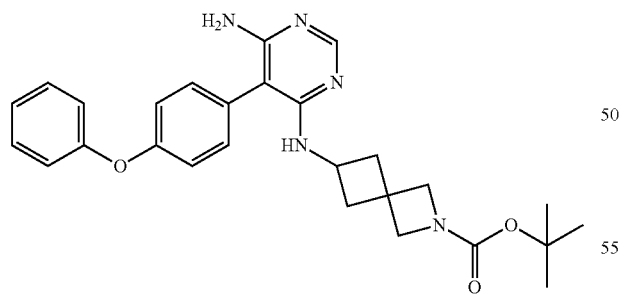

tert-butyl 6-((6-amino-5-(4-phenoxyphenyl)pyrimidin-4-yl)amino)-2-azaspiro[3.3]heptane-2-carboxylate In a microwave vial containing 6-(6-Amino-5-chloropyrimidin-4-ylamino)-2-aza-spiro[3.3]heptane-2-carboxylic acid tert-butyl ester (828.00 mg; 2.44 mmol; 1.00 eq.) in dioxane (4.00 ml; 46.94 mmol; 19.27 eq.) and water (0.40 ml; 22.20 mmol; 9.11 eq.) was added cesium carbonate (1190.86 mg; 3.65 mmol; 1.50 eq.), palladium(II) acetate (27.35 mg; 0.12 mmol; 0.05 eq.), 4-phenoxyphenylboronic acid (651.87 mg; 3.05 mmol; 1.25 eq.) and 2-dicyclohexylphosphino-2',6'-dimethoxybiphenyl (100.03 mg; 0.24 mmol; 0.10 eq.). The reaction mixture was stirred at 140° C. for 16 h before it was concentrated and separated on a 50 g silica gel column with gradient EtOAc/Hexane (0-100%). The fractions were concentrated and carried to the next step.
Method S3: Deprotection of Tert-Butyloxycarbonyl-Protected Amine

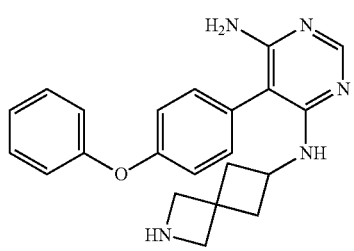 [SMILES: Nc1ncnc(NC2CC3(CNC3)C2)c1-c1ccc(Oc2ccccc2)cc1]

5-(4-phenoxyphenyl)-N'-(2-azaspiro[3.3]heptan-6-yl)pyrimidine-4,6-diamine

In a round bottom flask containing 6-[6-amino-5-(4-phenoxy-phenyl)-pyrimidin-4-ylamino]-2-aza-spiro[3.3]heptane-2-carboxylic acid tert-butyl ester (167.23 mg; 0.35 mmol; 1.00 eq.) in methanol (5.00 ml) was added hydrogen chloride (1.80 ml; 3.53 mmol; 10.00 eq.). The reaction was stirred for 16 h before it was concentrated and carried to the next step.
Method S3A: Deprotection of Tert-Butyloxycarbonyl-Protected Amine 5-(4-phenoxyphenyl)-N'-(2-azaspiro[3.3]heptan-6-yl)pyrimidine-4,6-diamine In a round bottom flask containing 6-[6-amino-5-(4-phenoxy-phenyl)-pyrimidin-4-ylamino]-2-aza-spiro[3.3]heptane-2-carboxylic acid tert-butyl ester (167.23 mg; 0.35 mmol; 1.00 eq.) in methanol (5.00 ml) was added hydrogen chloride (1.80 ml; 3.53 mmol; 10.00 eq.). The reaction was stirred for 16 h before it was concentrated and purified by HPLC. The fractions containing the desired product were lyophilized to afford the title compound as a white solid (50.3 mg, 34%). HPLC purity: 95%. MS: m/z=374[M+H]$^+$. $^1$H NMR (CD$_3$OD) δ 8.25 (s, 1H), 7.10-7.44 (m, 8H), 4.60 (m, 1H), 4.20 (s, 2H), 4.01 (s, 2H), 2.69 (m, 2H), 2.32 (m, 2H).

Method S4A: Amide Formation Using T3P

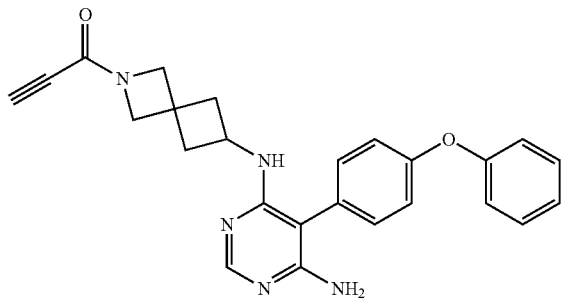 [SMILES: C#CC(=O)N1CC2(CC(Nc3ncnc(N)c3-c3ccc(Oc4ccccc4)cc3)C2)C1]

1-(6-(((6-amino-5-(4-phenoxyphenyl)pyrimidin-4-yl)amino)-2-azaspiro[3.3]heptan-2-yl)prop-2-yn-1-one In a microwave vial containing N-(2-Aza-spiro[3.3]hept-6-yl)-5-(4-phenoxy-phenyl)-pyrimidine-4,6-diamine hydrochloride (80.00 mg; 0.20 mmol; 1.00 eq.) in DCM (1.00 ml) was added DIPEA (0.16 ml; 0.98 mmol; 5.00 eq.) and propiolic acid (24.20 μl; 0.39 mmol; 2.00 eq.) followed by 2,4,6-Tripropyl-[1,3,5,2,4,6]trioxatriphosphinane 2,4,6-trioxide (0.12 ml; 0.29 mmol; 1.50 eq.). The reaction was stirred at rt for 1 h before it was concentrated and purified by preparative HPLC (0.1% TFA-H$_2$O/ACN). Fractions containing the desired product were combined and lyophilized overnight to afford 1-(6-((6-amino-5-(4-phenoxyphenyl)pyrimidin-4-yl)amino)-2-azaspiro[3.3]heptan-2-yl)prop-2-yn-1-one as a white solid (27.8 mg, 26.1%). HPLC purity: 99%. MS: m/z=426 [M+H]$^+$. $^1$H NMR (CD$_3$OD) δ 8.25 (s, 1H), 7.18-7.49 (m, 9H), 4.32 (d, 1H), 4.09 (d, 2H), 3.89 (d, 1H), 2.60 (m, 2H), 2.29 (m, 2H).

Method S4B: Amide Formation Using an Acid Chloride in Pyridine

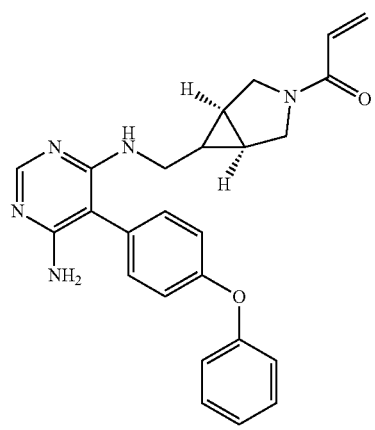 [SMILES: C=CC(=O)N1C[C@@H]2C(CNc3ncnc(N)c3-c3ccc(Oc4ccccc4)cc3)[C@@H]2C1]

1-((1R,5S)-6-(((6-amino-5-(4-phenoxyphenyl)pyrimidin-4-yl)amino)methyl)-3-azabicyclo[3.1.0]hexan-3-yl)prop-2-en-1-one To a round bottom flask containing N-[(1S,5R)-1-(3-Azabicyclo[3.1.0]hex-6-yl)methyl]-5-(4-phenoxy-phenyl)-pyrimidine-4,6-diamine hydrochloride (259.68 mg; 0.63 mmol; 1.00 eq.) in pyridine (1.00 ml; 12.36 mmol; 19.52 eq.) was added acryloyl chloride (0.05 ml; 0.63 mmol; 1.00 eq.) in DCM (3.00 ml; 46.80 mmol; 73.88 eq.) over 1 h at 0° C. The reaction mixture was allowed to warm to room temperature and stirred overnight. It was concentrated and the crude product was subjected to preparative HPLC. Fractions containing the desired product were combined and lyophilized overnight to afford 1-((1R,5S)-6-(((6-amino-5-(4-phenoxyphenyl)pyrimidin-4-yl)amino)methyl)-3-azabicyclo[3.1.0]hexan-3-yl)prop-2-en-1-one as a white solid (2.1 mg, 0.6%). HPLC purity: 99%. MS: m/z=428[M+H]$^+$. $^1$H NMR (CD$_3$OD) δ 8.24 (s, 1H), 7.21-7.46 (m, 9H), 6.53 (m, 1H), 6.22 (m, 1H), 5.74 (m, 1H), 3.77 (m, 2H), 3.69 (m, 1H), 3.41 (m, 2H), 1.70 (m, 2H), 0.93 (m, 2H).

Method S4C: Amide Formation Using an Acid Chloride in THF

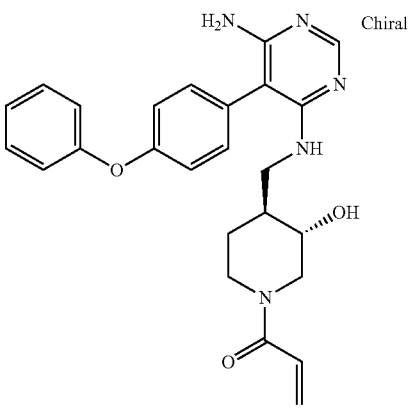 [SMILES: C=CC(=O)N1CC[C@@H](CNc2ncnc(N)c2-c2ccc(Oc3ccccc3)cc2)[C@H](O)C1]

1-((3S,4S)-4-(((6-amino-5-(4-phenoxyphenyl)pyrimidin-4-yl)amino)methyl)-3-hydroxypiperidin-1-yl)prop-2-en-1-one To a round bottom flask containing (3S,4S)-4-{[6-Amino-5-(4-phenoxy-phenyl)-pyrimidin-4-ylamino]-methyl}-piperidin-3-ol hydrochloride (591.95 mg; 1.38 mmol; 1.00 eq.) and DIPEA (0.69 ml; 4.15 mmol; 5.00 eq.) in THF (30.00 ml) was slowly added acryloyl chloride (0.11 ml; 1.38 mmol; 1.00 eq.) in 1 mL THF over 1 h. The reaction mixture was concentrated and purified with using preparative HPLC. Fractions containing the desired product were combined and lyophilized overnight to afford 1-((3S,4S)-4-(((6-amino-5-(4-phenoxyphenyl)pyrimidin-4-yl)amino)methyl)-3-hydroxypiperidin-1-yl)prop-2-en-1-one as a white solid (21.5 mg, 2.7%). HPLC purity: 99%. MS: m/z=446 [M+H]$^+$. $^1$H NMR (CD$_3$OD) δ 8.25 (s, 1H), 7.10-7.45 (m, 9H), 6.73 (dd, 1H), 6.34 (d, 1H), 5.77 (d, 1H), 4.5 (m, 1H), 4.03 (m, 1H), 3.62 (m, 1H), 3.50 (m, 1H), 3.25 (m, 1H), 3.01 (m, 1H), 2.57 (m, 1H), 1.71 (m, 2H), 1.19 (m, 1H).

Method S4D: Amide Formation Using BOP—Cl

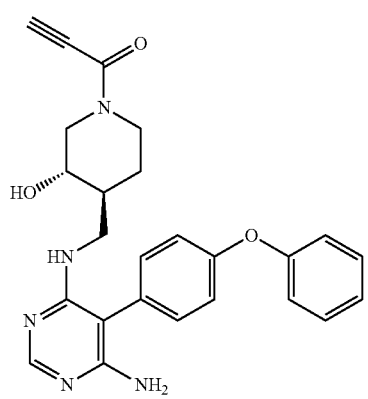 [SMILES: C#CC(=O)N1CC[C@@H](CNc2ncnc(N)c2-c2ccc(Oc3ccccc3)cc2)[C@H](O)C1]

1-((3S,4S)-4-(((6-amino-5-(4-phenoxyphenyl)pyrimidin-4-yl)amino)methyl)-3-hydroxypiperidin-1-yl)prop-2-yn-1-one To a 20 mL reaction vial was added propiolic acid (0.02 ml; 0.37 mmol; 1.10 eq.), bis(2-oxo-3-oxazolidinyl)phosphinic chloride (171.33 mg; 0.67 mmol; 2.00 eq.) and ethyl-diisopropyl-amine (0.28 ml; 1.68 mmol; 5.00 eq.) and 1.0 mL DMF. The reaction was stirred at rt for 1 h. Then (3S,4S)-4-{[6-Amino-5-(4-phenoxy-phenyl)-pyrimidin-4-ylamino]-methyl}-piperidin-3-ol hydrochloride (144.00 mg; 0.34 mmol; 1.00 eq.) in 1.0 mL DMF was added to the reaction mixture. The reaction mixture was stirred at rt overnight and then concentrated. The crude product was subjected to preparative HPLC. Fractions containing the desired product were combined and lyophilized overnight to afford 1-((3S,4S)-4-(((6-amino-5-(4-phenoxyphenyl)pyrimidin-4-yl)amino)methyl)-3-hydroxypiperidin-1-yl)prop-2-yn-1-one as a white solid (35.2 mg, 18.6%). HPLC purity: 99%. MS: m/z=444 [M+H]$^+$. $^1$H NMR (CD$_3$OD) δ 8.24 (s, 1H), 7.10-7.46 (m, 9H), 4.36 (m, 2H), 4.00 (d, 1H), 3.74 (m, 1H), 3.52 (m, 1H), 3.25 (m, 1H), 3.00 (m, 1H), 2.64 (m, 1H), 1.76 (m, 2H), 1.30 (m, 1H).

Scheme 4

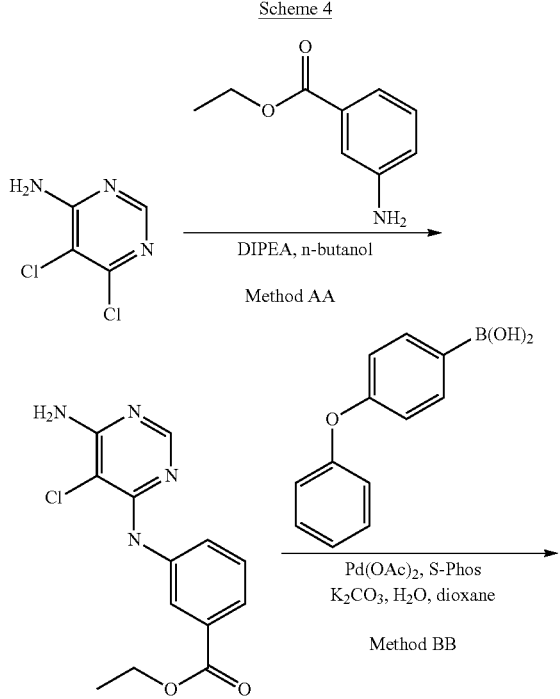

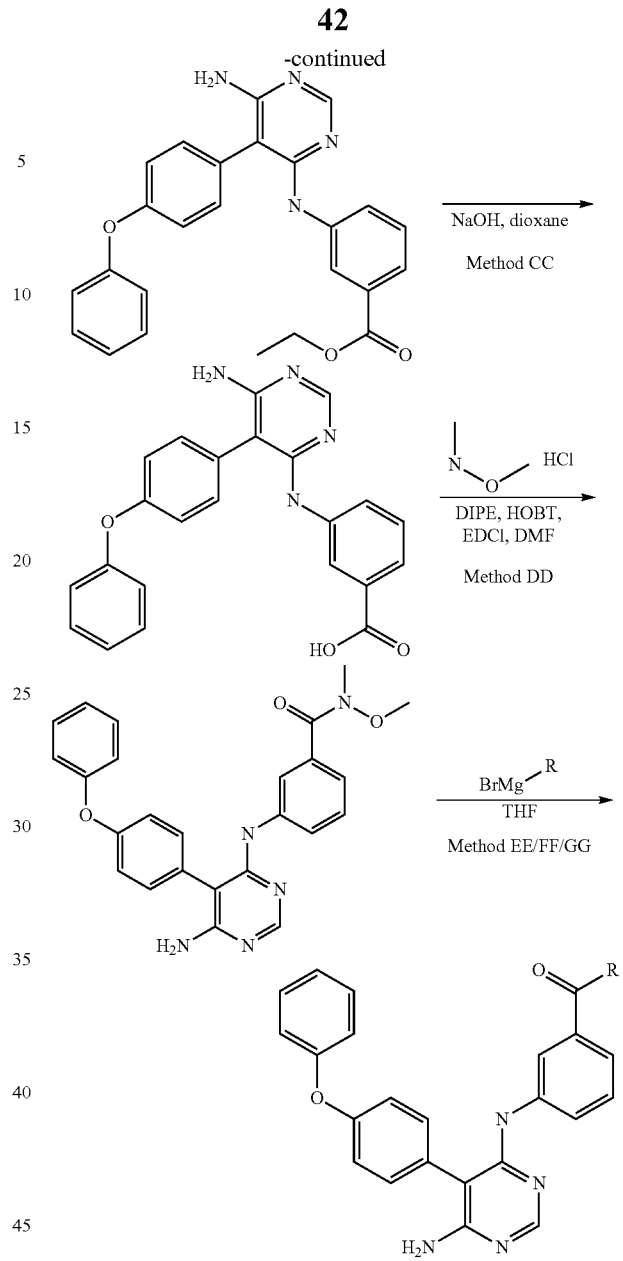

Methods Associated with Reaction Steps in Scheme 4

Method AA: Nucleophilic Aromatic Substitution (4-(6-Amino-5-chloro-pyrimidin-4-ylamino)-phenyl)-acetic acid ethyl ester To a vial with stirbar were added 5,6-dichloro-pyrimidin-4-ylamine (1.4 g, 8.537 mmol, 1.0 eq), (4-amino-phenyl)- acetic acid ethyl ester (4.3 g, 23.993 mmol, 2.8 eq), N,N-diisopropylethylamine (4.5 ml, 25.611 mmol, 3.0 eq), dissolved in n-butanol (100 ml). The reaction suspension was flushed with nitrogen and heated to 115° C. for 8 days. The mixture was concentrated in vacuo, dissolved in EtOAc, washed with water (2×) and brine (1×), dried over sodium sulfate, and concentrated in vacuo. The crude mixture was purified using Biotage column chromatography eluting from 30-70% EtOAc/hexanes. Fractions containing the desired product were combined and concentrated under reduced pressure to afford (4-(6-amino-5-chloro-pyrimidin-4-ylamino)-phenyl)-acetic acid ethyl ester (1.71 g, 49% yield) as white crystals. MS: m/z=307 [M+H]$^+$. $^1$H-NMR (DMSO-d$_6$) δ 8.41 (s, 1H), 7.93 (s, 1H), 7.55 (d, 2H), 7.19 (d, 2H), 6.76 (bs, 2H), 4.11 (q, 2H), 1.21 (t, 3H).

Method BB: Suzuki Coupling

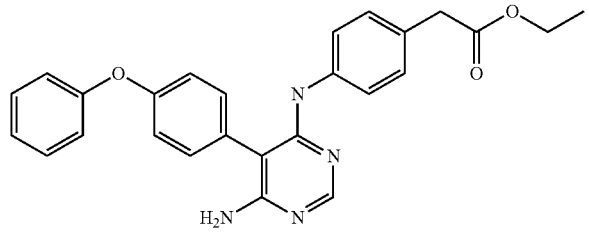 [SMILES: CCOC(=O)Cc1ccc(Nc2ncnc(N)c2-c2ccc(Oc3ccccc3)cc2)cc1]

(4-(6-Amino-5-(4-phenoxyphenyl)-pyrimidin-4-ylamino)-phenyl)-acetic acid ethyl ester Into a microwave vial was placed [4-(6-amino-5-chloro-pyrimidin-4-ylamino)-phenyl]-acetic acid ethyl ester (1.4 g; 3.423 mmol; 1.0 eq.), (4-phenoxyphenyl)boronic acid (1598.9 mg; 7.470 mmol; 2.18 eq.), palladium acetate (38.4 mg; 0.171 mmol; 0.1 eq.), dicyclohexyl-(2',6'-dimethoxy-biphenyl-2-yl)-phosphane (140.5 mg; 0.342 mmol; 0.1 eq.), potassium carbonate (1419.2 mg; 10.269 mmol; 3.0 eq.) suspended in dioxane (15.0 ml) and water (1.5 ml). The vial was flushed with nitrogen. The reaction vial was run in a microwave for 3 hours at 150° C. The mixture was filtered, quenched in water and extracted with EtOAc (3×). The combined organic layer were dried over sodium sulfate, filtered and concentrated in vacuo. The crude compound was purified using Biotage column chromatography (50/50% Hexanes/EtOAc to 100% EtOAc). Fractions containing the desired product were collected and and concentrated to afford (4-(6-amino-5-(4-phenoxyphenyl)-pyrimidin-4-ylamino)-phenyl)-acetic acid ethyl ester (1.43 g, 90% yield) as a yellow foam. MS: m/z=441 [M+H]$^+$. $^1$H-NMR (DMSO-d$_6$) δ 8.06 (s, 1H), 7.45 (t, 4H), 7.34 (d, 2H), 7.16 (dd, 8H), 5.77 (bs, 2H), 4.10 (q, 2H), 3.56 (s, 2H), 1.20 (t, 3H).

Method CC: Ester Hydrolysis

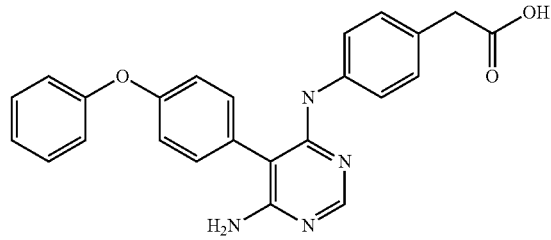 [SMILES: Nc1ncnc(Nc2ccc(CC(=O)O)cc2)c1-c1ccc(Oc2ccccc2)cc1]

(4-(6-Amino-5-(4-phenoxyphenyl)-pyrimidin-4-ylamino)-phenyl)-acetic acid

To a vial with stirbar were added {4-[6-amino-5-(4-phenoxy-phenyl)-pyrimidin-4-ylamino]-phenyl}-acetic acid ethyl ester (1430.0 mg; 3.084 mmol; 1.0 eq.) dissolved in dioxane (15.0 ml; 176.040 mmol; 57.1 eq.), and aqueous sodium hydroxide (2 N, 9.3 ml; 18.504 mmol; 6.0 eq.). The reaction mixture was stirred at room temperature for 1.5 h. The reaction was quenched by the addition of water, and washed once with EtOAc. The aqueous phase was acidified with 1N hydrochloric acid. The precipitate was filtered and dried in vacuo to afford (4-(6-amino-5-(4-phenoxyphenyl)-pyrimidin-4-ylamino)-phenyl)-acetic acid (1.11 g, 85% yield) as white solid. The filtrate was extracted with EtOAc (2×). The organic phase was dried over sodium sulfate, filtered and concentrated in vacuo to afford (4-(6-amino-5-(4-phenoxyphenyl)-pyrimidin-4-ylamino)-phenyl)-acetic acid (265 mg, 19% yield) as white solid. MS: m/z=413 [M+H]$^+$. $^1$H-NMR (DMSO-d$_6$) δ 12.20 (bs, 1H), 8.05 (s, 1H), 7.41-7.39 (m, 4H), 7.34-7.32 (d, 2H), 7.16-7.11 (m, 8H).

Method DD: Weinreb Amide Synthesis

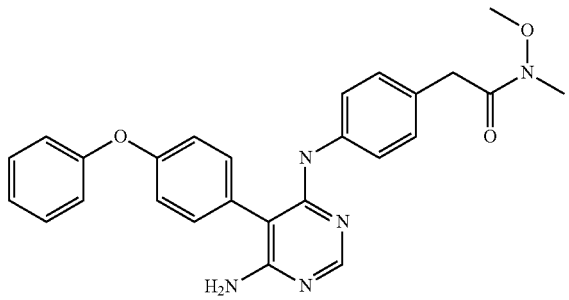 [SMILES: CON(C)C(=O)Cc1ccc(Nc2ncnc(N)c2-c2ccc(Oc3ccccc3)cc2)cc1]

(4-(6-Amino-5-(4-phenoxyphenyl)-pyrimidin-4-ylamino)-phenyl)-N-methoxy-N-methyl-acetamide To a round bottom flask with stirbar were added {4-[6-amino-5-(4-phenoxy-phenyl)-pyrimidin-4-ylamino]-phenyl}-acetic acid (1375 mg; 3.2 mmol; 1 eq.), N,O-dimethylhydroxylamine hydrochloride (344.2 mg; 3.529 mmol; 1.1 eq.), N-(3-dimethylaminopropyl)-N'-ethylcarbodiimide hydrochloride (922.5 mg; 0.005 mol; 1.5 eq.), 1-hydroxybenzotriazole (HOBT) hydrate (225.4 mg; 1.668 mmol; 0.5 eq.), N,N-diisopropylethylamine (0.8 ml; 4.812 mmol; 1.5 eq.), dissolved in DMF (20.0 ml). The reaction mixture was stirred at room temperature overnight.

The reaction was diluted with EtOAc, and washed with water (2×) and brine (1×). The organic phase was dried over sodium sulfate, filtered and concentrated in vacuo. The crude compound was purified using Biotage column chromatography (30-100% EtOAc/hexane). Collected fractions containing the desired product were concentrated. The solid was dissolved in DCM and washed with water (3×). The organic phase was dried over sodium sulfate, filtered and concentrated in vacuo to afford (4-(6-amino-5-(4-phenoxy-phenyl)-pyrimidin-4-ylamino)-phenyl)-N-methoxy-N-methyl-acetamide (751 mg, 51% yield) as white crystals. MS: m/z=456 [M+H]$^+$, $^1$H-NMR (DMSO-d$_6$) δ 7.92 (s, 1H), 7.44 (m, 4H), 7.40 (d, 2H), 7.26 (d, 2H), 7.14 (t, 5H), 6.11 (t, 1H), 5.50 (bs, 2H), 4.52 (d, 2H), 3.50 (s, 3H), 3.23 (s, 3H).

Method EE: Weinreb Ketone Synthesis Using 1-Propenyl-magnesium Bromide

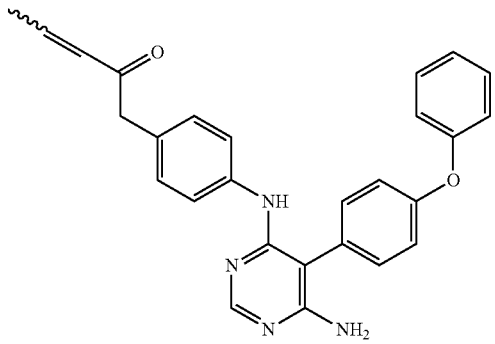

1-(4-(6-Amino-5-(4-phenoxyphenyl)-pyrimidin-4-ylamino)-phenyl)-pent-3-en-2-one

In a round bottom flask with stirbar was added 2-{4-[6-Amino-5-(4-phenoxy-phenyl)-pyrimidin-4-ylamino]-phenyl}-N-methoxy-N-methyl-acetamide (275.0 mg; 0.604 mmol; 1.0 eq.), suspended in THF (2.5 ml; 12.343 mmol; 20.4 eq.). The suspension was cooled to 0° C. At this temperature was added 1-propenylmagnesium bromide (12.1 ml; 6.037 mmol; 10.0 eq.) drop by drop at constant temperature. After complete addition, the reaction mixture was stirred 30 min at room temperature.

The reaction suspension was quenched with aqueous solution of ammonium chloride, and extracted with EtOAc (3×). The combined organic phase were dried over sodium sulfate, filtered and concentrated in vacuo. The crude was dissolved in DMSO and purified by preparative HPLC to afford 1-(4-(6-amino-5-(4-phenoxyphenyl)-pyrimidin-4-ylamino)-phenyl)-pent-3-en-2-one (78 mg, 19%). MS: m/z=437 [M+H]$^+$. $^1$H-NMR (DMSO-d$_6$) 8.50 (bs, 1H), 8.29 (s, 1H), 7.46 (t, 2H), 7.39 (d, 2H), 7.27 (d, 2H), 7.21 (m, 6H), 7.09 (bs, 1H), 7.02 (dd, 1H), 6.20 (ss, 1H), 3.86 (s, 3H), 1.89 (d, 3H).

Method FF: Weinreb Ketone Synthesis Using 1-Propynyl-magnesium Bromide

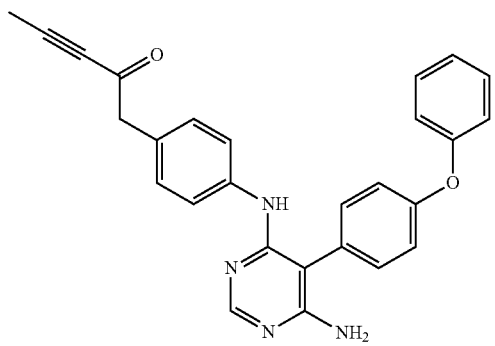

1-(4-(6-Amino-5-(4-phenoxyphenyl)-pyrimidin-4-ylamino)-phenyl)-pent-3-yn-2-one

In a round bottom flask with stirbar was added 2-{4-[6-amino-5-(4-phenoxy-phenyl)-pyrimidin-4-ylamino]-phenyl}-N-methoxy-N-methyl-acetamide (275.0 mg; 0.604 mmol; 1.0 eq.), suspended in THF (2.5 ml; 30.857 mmol; 51.1 eq.). The suspension was cooled to 0° C. At this temperature was added 1-propynylmagnesium bromide (12.1 ml; 6.037 mmol; 10.0 eq.) drop by drop at constant temperature to afford a red solution. After complete addition, the reaction mixture was stirred 30 min at room temperature. The reaction suspension was quenched with aqueous solution of ammonium chloride, and extracted with EtOAc (3×). The combined organic phase were dried over sodium sulfate, filtered and concentrated in vacuo. The crude compound was dissolved in DMSO and purified by preparative HPLC to afford 1-(4-(6-amino-5-(4-phenoxyphenyl)-pyrimidin-4-ylamino)-phenyl)-pent-3-yn-2-one (68 mg, 17% yield) as light yellow solid. MS: m/z=435 [M+H]$^+$. $^1$H-NMR (DMSO-d$_6$) □δ 8.43 (bs, 1H), 8.28 (s, 1H), 7.46 (t, 2H), 7.42 (d, 2 h), 7.37 (d, 2H), 7.31-7.13 (m, 7H), 6.99 (bs, 2H), 3.87 (s, 2H), 2.04 (s, 3H).

Method GG: Weinreb Ketone Synthesis Using Vinylmagnesium Bromide

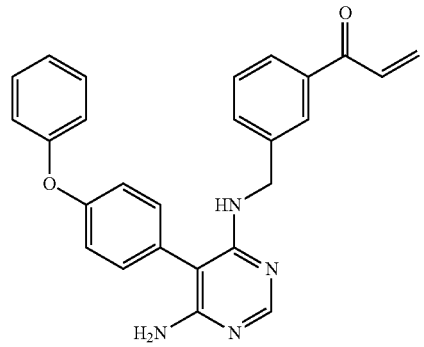 [SMILES: C=CC(=O)c1cccc(CNc2ncnc(N)c2-c2ccc(Oc3ccccc3)cc2)c1]

1-(3-((Amino-5-(4-phenoxyphenyl)-pyrimidin-4-ylamino)-methyl)-phenyl)-propenone

In a round bottom flask with stirbar was added 3-{[6-amino-5-(4-phenoxy-phenyl)-pyrimidin-4-ylamino]-methyl}-N-methoxy-N-methyl-benzamide (140.0 mg; 0.307 mmol; 1.0 eq.), dissolved in THF (2.0 ml; 24.686 mmol; 80.3 eq.). The suspension was cooled to 0° C. At this temperature was added vinylmagnesium bromide 1.0M solution in THF (3.1 ml; 3.073 mmol; 10.0 eq.) drop by drop at constant temperature. After complete addition, the reaction mixture was stirred 30 min at room temperature. The reaction suspension was quenched with aqueous solution of ammonium chloride, and extracted with EtOAc (3×). The combined organic phase were dried over sodium sulfate, filtered and concentrated in vacuo. The crude compound was dissolved in DMSO and purified by preparative HPLC to afford 1-(3-((amino-5-(4-phenoxyphenyl)-pyrimidin-4-ylamino)-methyl)-phenyl)-propenone (20 mg, 10% yield) as white amorphous solid. MS: m/z=484 [M+H]$^+$. $^1$H-NMR (DMSO-d$_6$) δ 8.34 (s, 1H), 7.86 (t, 2H), 7.64 (t, 1H), 7.52 (m, 4H), 7.35 (d, 2H), 7.23 (dd, 3H), 7.14 (d, 2H), 7.02 (bs, 2H), 4.65 (d, 2H), 3.21 (t, 2H), 2.96 (t, 2H).

Analytical Methodology

Analytical LC/MS was Performed Using the Following Three Methods:

Method 1:

A Discovery C$^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (Ill) decrease from 95-15% (B) in a 0.1 min linear gradient (IV) hold for 2.3 min at 15% (B).
Method 2:

A Waters Symmetry C$^{18}$, 3.5 µm, 4.6×75 mm column at a flow rate of 1 mL/min, sample loop 10 µL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).
Method 3:

Gradient: 4.2 min/Flow: 2 ml/min 99:01-0:100 Water+ 0.1% (Vol.) TFA; Acetonitril+0.1% (Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

HPLC Method for Purity Determination

Purity was determined on an Agilent HPLC using UV detection at 254 nm with a Waters Xbridge C8 column (5 µm, 4.6×50 mm). Mobile Phase A: 0.1% TFA in water. Mobile phase B: 0.1% TFA in acetonitrile. The method involved a gradient from 98% mobile phase A/2% mobile phase B to 100% mobile phase B over 8 minutes at a flow rate of 2 mL/min.

General Method for Preparative HPLC

Preparative HPLC was carried out on a Waters preparative HPLC system using a Waters Sunfire C18 column (5 or 10 µm). Mobile phase A: water with 0.1% TFA. Mobile phase B: acetonitrile. Crude compounds were loaded on the column using a minimum volume of methanol or DMSO. A typical gradient used for separation was 0-50% Mobile Phase B over 20-25 minutes with an optional wash step (100% Mobile Phase B).

Examples

The working examples presented below are intended to illustrate particular embodiments of the invention, and are not intended to limit the scope of the specification or the claims in any way. In this section experimental details are provided for a number of Example compounds according to Formula (I), Formula (II), Formula (III), Formula (IV) and Formula (V).

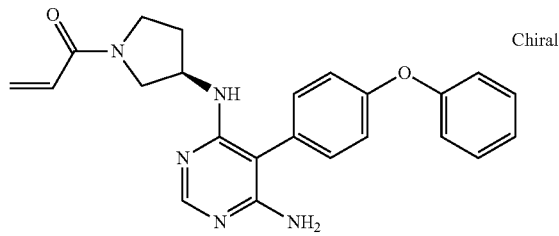 [SMILES: C=CC(=O)N1CC[C@@H](Nc2ncnc(N)c2-c2ccc(Oc3ccccc3)cc2)C1]

(R)-1-(3-((6-amino-5-(4-phenoxyphenyl)pyrimidin-4-yl)amino)pyrrolidin-1-yl)prop-2-en-1-one (A1)

(R)-1-(3-((6-amino-5-(4-phenoxyphenyl)pyrimidin-4-yl) amino)pyrrolidin-1-yl)prop-2-en-1-one was prepared from 5,6-dichloropyrimidin-4-amine, (R)-tert-butyl 3-aminopyrrolidine-1-carboxylate, (4-phenoxyphenyl)boronic acid, and acryloyl chloride using methods B, C, D and F. HPLC purity: 100%. MS: m/z=402 [M+H]$^+$.

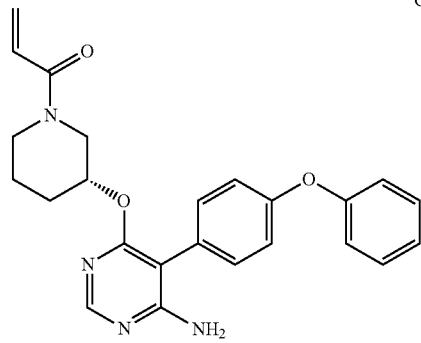

(R)-1-(3-((6-amino-5-(4-phenoxyphenyl)pyrimidin-4-yl)oxy)piperidin-1-yl)prop-2-en-1-one (A2)

(R)-1-(3-((6-amino-5-(4-phenoxyphenyl)pyrimidin-4-yl) oxy)piperidin-1-yl)prop-2-en-1-one was prepared from 5,6-dichloropyrimidin-4-amine, (R)-tert-butyl 3-hydroxypiperidine-1-carboxylate, (4-phenoxyphenyl)boronic acid, and acryloyl chloride using methods A, C, D, and F. HPLC purity: 100%. MS: m/z=417 [M+H]$^+$.

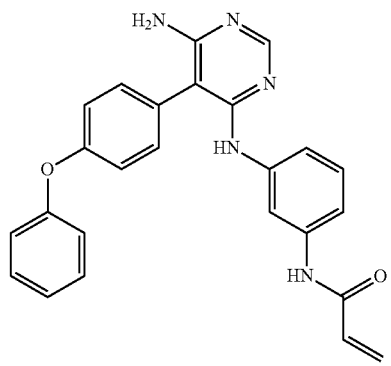 [SMILES: C=CC(=O)Nc1cccc(Nc2ncnc(N)c2-c2ccc(Oc3ccccc3)cc2)c1]

N-(3-((6-amino-5-(4-phenoxyphenyl)pyrimidin-4-yl) amino)phenyl)acrylamide (A3)

N-(3-((6-amino-5-(4-phenoxyphenyl)pyrimidin-4-yl) amino)phenyl)acrylamide was prepared from 5,6-dichloropyrimidin-4-amine, benzene-1,3-diamine, (4-phenoxyphenyl)boronic acid, and acryloyl chloride using methods H, C, and F. HPLC purity: 100%. MS: m/z=424 [M+H]$^+$.
$^1$H-NMR (DMSO-d$_6$), δ 10.11 (s, 1H), 8.47 (broad s, 1H), 8.22 (s, 1H), 7.67 (s, 1H), 7.31-6.97 (m, 14H), 6.37 (dd, 1H), 6.19 (d, 1H), 5.69 (d, 1H).

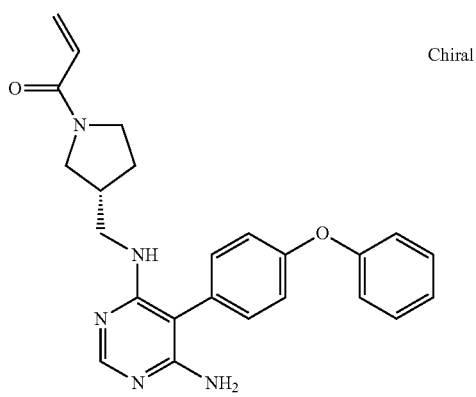 [SMILES: C=CC(=O)N1CC[C@H](CNc2ncnc(N)c2-c2ccc(Oc3ccccc3)cc2)C1]

(R)-1-(3-((((6-amino-5-(4-phenoxyphenyl)pyrimidin-4-yl)amino)methyl)pyrrolidin-1-yl)prop-2-en-1-one (A4)

(R)-1-(3-((((6-amino-5-(4-phenoxyphenyl)pyrimidin-4-yl)amino)methyl)pyrrolidin-1-yl)prop-2-en-1-one was prepared from 5,6-dichloropyrimidin-4-amine, (R)-tert-butyl 3-(aminomethyl)pyrrolidine-1-carboxylate, (4-phenoxyphenyl)boronic acid, and acryloyl chloride using methods B, C, D, and F. HPLC purity: 100%. MS: m/z=416 [M+H]$^+$.

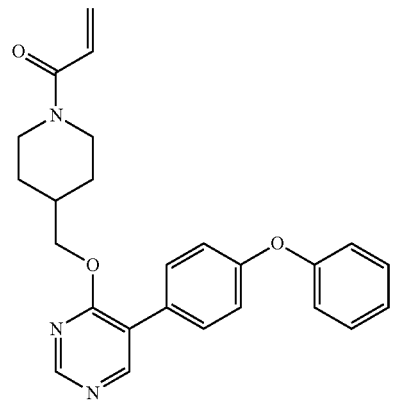

1-(4-(((5-(4-phenoxyphenyl)pyrimidin-4-yl)oxy)methyl)piperidin-1-yl)prop-2-en-1-one (A6)

1-(4-(((5-(4-phenoxyphenyl)pyrimidin-4-yl)oxy)methyl)piperidin-1-yl)prop-2-en-1-one was prepared from 5-bromo-4-chloropyrimidine, tert-butyl 4-(hydroxymethyl)piperidine-1-carboxylate, (4-phenoxyphenyl)boronic acid, and acryloyl chloride using methods A, C, D, and F. HPLC purity: 92%. MS: m/z=416 [M+H]$^+$.

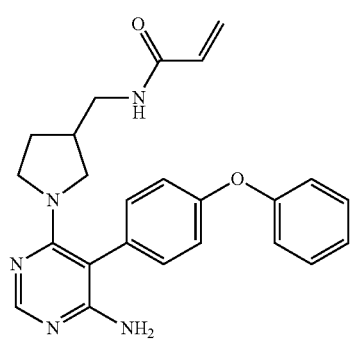 [SMILES: C=CC(=O)NCC1CCN(c2ncnc(N)c2-c2ccc(Oc3ccccc3)cc2)C1]

N-((1-(6-amino-5-(4-phenoxyphenyl)pyrimidin-4-yl)pyrrolidin-3-yl)methyl)acrylamide (A5)

N-((1-(6-amino-5-(4-phenoxyphenyl)pyrimidin-4-yl)pyrrolidin-3-yl)methyl)acrylamide was prepared from 5,6-dichloropyrimidin-4-amine, tert-butyl (pyrrolidin-3-ylmethyl)carbamate, (4-phenoxyphenyl)boronic acid, and acryloyl chloride using methods B, C, D, and F. HPLC purity 97%. MS: m/z=416 [M+H]$^+$.

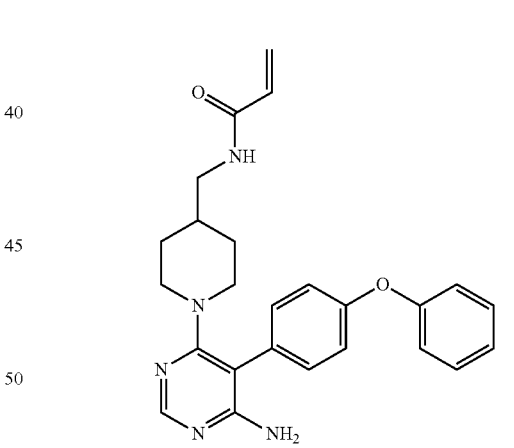

N-((1-(6-amino-5-(4-phenoxyphenyl)pyrimidin-4-yl)piperidin-4-yl)methyl)acrylamide (A7)

N-((1-(6-amino-5-(4-phenoxyphenyl)pyrimidin-4-yl)piperidin-4-yl)methyl)acrylamide was prepared from 5,6-dichloropyrimidin-4-amine, tert-butyl (piperidin-4-ylmethyl)carbamate, (4-phenoxyphenyl)boronic acid, and acryloyl chloride using method B, C, D, and F. HPLC purity: 100%. MS: m/z=430 [M+H]$^+$.

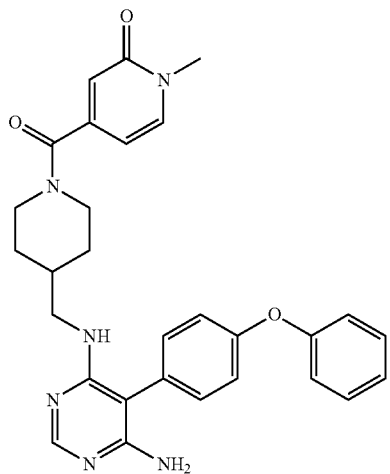 [SMILES: Cn1ccc(C(=O)N2CCC(CNc3ncnc(N)c3-c3ccc(Oc4ccccc4)cc3)CC2)cc1=O]

4-(4-(((6-amino-5-(4-phenoxyphenyl)pyrimidin-4-yl)amino)methyl)piperidine-1-carbonyl)-1-methyl)pyridin-2(1H)-one (A8)

4-(4-(((6-amino-5-(4-phenoxyphenyl)pyrimidin-4-yl)amino)methyl)piperidine-1-carbonyl)-1-methylpyridin-2(1H)-one was prepared from 5,6-dichloropyrimidin-4-amine, tert-butyl 4-(aminomethyl)piperidine-1-carboxylate, (4-phenoxyphenyl)boronic acid, and 1-methyl-2-oxo-1,2-dihydropyridine-4-carboxylic acid using methods B, C, D, and E. HPLC purity: 100%. MS: m/z=511 [M+H]$^+$. $^1$H-NMR (DMSO-d$_6$) δ 8.28 (s, 1H), 7.69 (d, 1H), 7.38 (t, 2H), 7.20 (d, 2H), 7.14-6.90 (m, 8H), 6.19 (s, 1H), 6.06 (d, 1H), 1.28 (d, 1H), 3.47 (d, 1H), 3.35 (s, 3H), 3.18 (s, 2H), 2.90 (t, 1H), 2.61 (t, 1H), 1.76 (s, 1H), 1.58 (d, 1H), 1.48 (d, 1H), 1.04-0.92 (m, 2H).

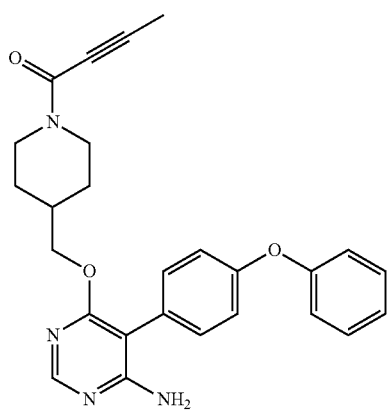 [SMILES: CC#CC(=O)N1CCC(COc2ncnc(N)c2-c2ccc(Oc3ccccc3)cc2)CC1]

1-(4-(((6-amino-5-(4-phenoxyphenyl)pyrimidin-4-yl)oxy)methyl)piperidin-1-yl)but-2-yn-1-one (A9)

1-(4-(((6-amino-5-(4-phenoxyphenyl)pyrimidin-4-yl)oxy)methyl)piperidin-1-yl)but-2-yn-1-one was prepared from 5,6-dichloropyrimidin-4-amine, tert-butyl 4-(hydroxymethyl)piperidine-1-carboxylate, (4-phenoxyphenyl)boronic acid, and but-2-ynoic acid using methods A, C, D, and E. HPLC purity: 100%. MS: m/z=443 [M+H]$^+$.

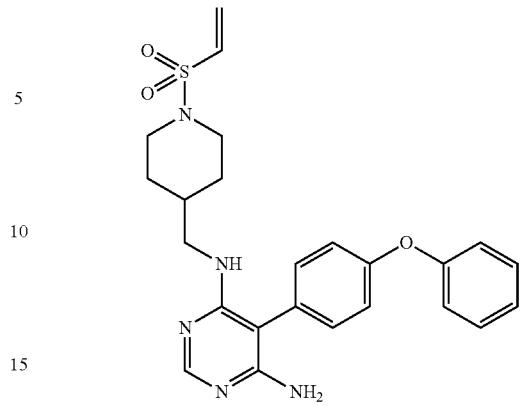

5-(4-phenoxyphenyl)-N4-((1-(vinylsulfonyl)piperidin-4-yl)methyl)pyrimidine-4,6-diamine (A10)

5-(4-phenoxyphenyl)-N4-((1-(vinylsulfonyl)piperidin-4-yl)methyl)pyrimidine-4,6-diamine was prepared from 5,6-dichloropyrimidin-4-amine, tert-butyl 4-(aminomethyl)piperidine-1-carboxylate, (4-phenoxyphenyl)boronic acid and 2-chloroethanesulfonyl chloride using methods B, C, D and G. HPLC purity: 89%. MS: m/z=466 [M+H]$^+$.

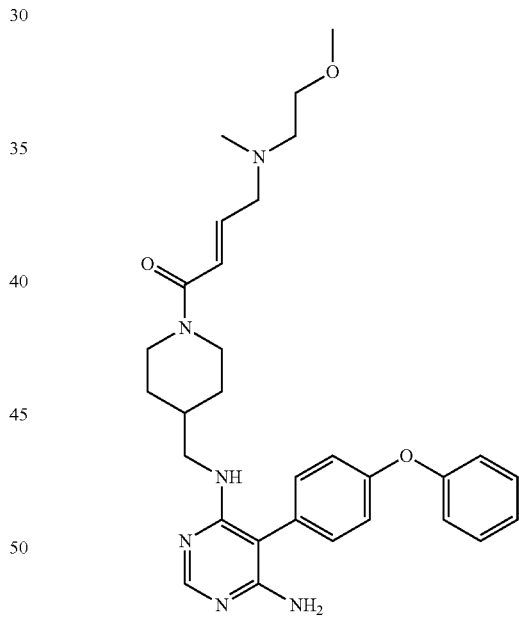

(E)-1-(4-(((6-amino-5-(4-phenoxyphenyl)pyrimidin-4-yl)amino)methyl)piperidin-1-yl)-4-((2-methoxyethyl)(methyl)amino)but-2-en-1-one (A11)

(E)-1-(4-(((6-amino-5-(4-phenoxyphenyl)pyrimidin-4-yl)amino)methyl)piperidin-1-yl)-4-((2-methoxyethyl)(methyl)amino)but-2-en-1-one was prepared from 5,6-dichloropyrimidin-4-amine, tert-butyl 4-(aminomethyl)piperidine-1-carboxylate, (4-phenoxyphenyl)boronic acid and (E)-4-((2-methoxyethyl)(methyl)amino)but-2-enoic acid using methods B, C, D, and E. HPLC purity: 99%. MS: m/z=531 [M+H]$^+$.

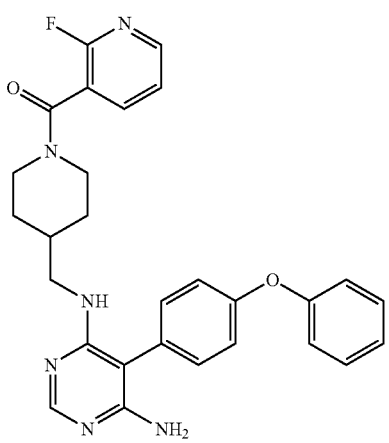 [SMILES: Nc1ncnc(NCC2CCN(C(=O)c3cccnc3F)CC2)c1-c1ccc(Oc2ccccc2)cc1]

(4-(((6-amino-5-(4-phenoxyphenyl)pyrimidin-4-yl)amino)methyl)piperidin-1-yl)(2-fluoropyridin-3-yl)methanone (A12)

(4-(((6-amino-5-(4-phenoxyphenyl)pyrimidin-4-yl)amino)methyl)piperidin-1-yl)(2-fluoropyridin-3-yl)methanone was prepared from 5,6-dichloropyrimidin-4-amine, tert-butyl 4-(aminomethyl)piperidine-1-carboxylate, (4-phenoxyphenyl)boronic acid, and 2-fluoronicotinic acid using methods B, C, D, and E. HPLC purity: 100%. MS: m/z=499 [M+H]$^+$. $^1$H-NMR (DMSO-d$_6$) □ δ 8.28 (s, 1H), 8.25 (d, 1H), 7.92 (t, 1H), 7.39-7.36 (m, 3H), 7.20-6.90 (m, 10H), 4.39 (d, 1H), 3.28 (d, 1H), 3.19 (m, 2H), 2.94 (t, 1H), 2.70 (t, 1H), 1.78 (s, 1H), 1.63 (d, 1H), 1.49 (d, 1H), 1.05-0.92 (m, 2H).

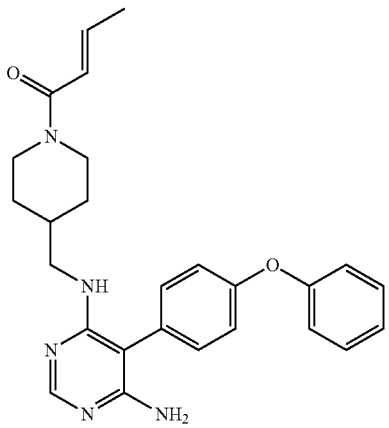 [SMILES: C/C=C/C(=O)N1CCC(CNc2ncnc(N)c2-c2ccc(Oc3ccccc3)cc2)CC1]

(E)-1-(4-(((6-amino-5-(4-phenoxyphenyl)pyrimidin-4-yl)amino)methyl)piperidin-1-yl)but-2-en-1-one (A13)

(E)-1-(4-(((6-amino-5-(4-phenoxyphenyl)pyrimidin-4-yl)amino)methyl)piperidin-1-yl)but-2-en-1-one was prepared from 5,6-dichloropyrimidin-4-amine, tert-butyl 4-(aminomethyl)piperidine-1-carboxylate, (4-phenoxyphenyl)boronic acid, and (E)-but-2-enoic acid using methods B, C, D, and E. HPLC purity: 100%. MS: m/z=444 [M+H]$^+$. $^1$H-NMR (DMSO-d$_6$) □ δ 8.27 (s, 1H), 7.38 (t, 2H), 7.21-6.88 (m, 10H), 6.60-6.52 (m, 1H), 6.40 (d, 1H), 4.27 (m, 1H), 3.96 (m, 1H), 3.16 (m, 3H), 2.87 (m, 1H), 1.75 (d, 4H), 1.53 (m, 2H), 0.88 (m, 2H).

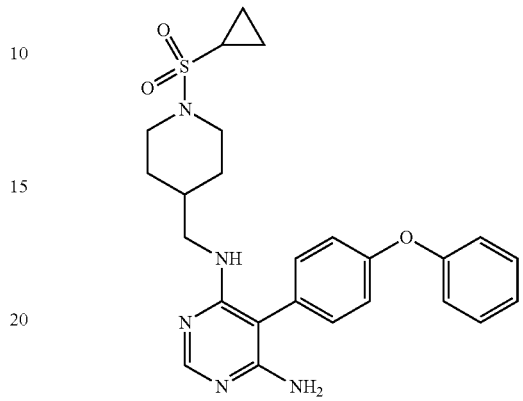

N4-((1-(cyclopropylsulfonyl)piperidin-4-yl)methyl)-5-(4-phenoxyphenyl)pyrimidine-4,6-diamine (A14)

N4-((1-(cyclopropylsulfonyl)piperidin-4-yl)methyl)-5-(4-phenoxyphenyl)pyrimidine-4,6-diamine was prepared from 5,6-dichloropyrimidin-4-amine, tert-butyl 4-(aminomethyl)piperidine-1-carboxylate, (4-phenoxyphenyl)boronic acid, and cyclopropanesulfonyl chloride using methods B, C, D, and G. HPLC purity: 96%. MS: m/z=480 [M+H]$^+$.

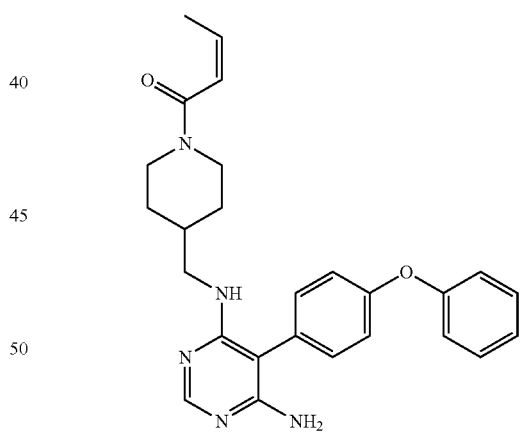

(Z)-1-(4-(((6-amino-5-(4-phenoxyphenyl)pyrimidin-4-yl)amino)methyl)piperidin-1-yl)but-2-en-1-one (A15)

(Z)-1-(4-(((6-amino-5-(4-phenoxyphenyl)pyrimidin-4-yl)amino)methyl)piperidin-1-yl)but-2-en-1-one was prepared from 5,6-dichloropyrimidin-4-amine, tert-butyl 4-(aminomethyl)piperidine-1-carboxylate, (4-phenoxyphenyl)boronic acid, and but-2-ynoic acid using methods B, C, D, E, and hydrogenation using Lindlar's catalyst. HPLC purity: 81%.

MS: m/z=444 [M+H]⁺. ¹H-NMR (DMSO-d₆) □ δ 8.35 (s, 1H), 7.45 (t, 2H), 7.28-6.95 (m, 10H), 6.06 (d, 1H), 5.94-5.86 (m, 1H), 4.35 (d, 1H), 3.83 (d, 1H), 3.24 (m, 2H), 2.94 (t, 1H), 2.55 (t, 1H), 1.82-1.74 (m, 4H), 1.61 (d, 2H), 0.96 (m, 2H).

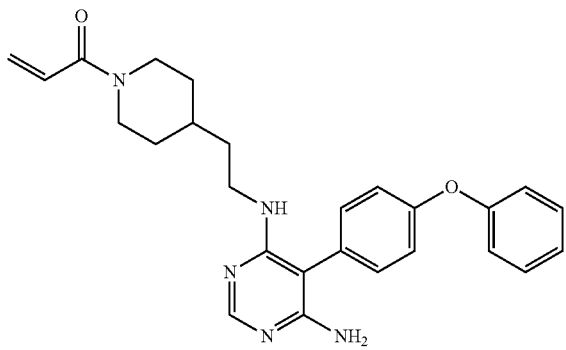 [SMILES: C=CC(=O)N1CCC(CCNc2ncnc(N)c2-c2ccc(Oc3ccccc3)cc2)CC1]

1-(4-(2-((6-amino-5-(4-phenoxyphenyl)pyrimidin-4-yl)amino)ethyl)piperidin-1-yl)prop-2-en-1-one (A16)

1-(4-(2-((6-amino-5-(4-phenoxyphenyl)pyrimidin-4-yl)amino)ethyl)piperidin-1-yl)prop-2-en-1-one was prepared from 5,6-dichloropyrimidin-4-amine, tert-butyl 4-(2-aminoethyl)piperidine-1-carboxylate, (4-phenoxyphenyl)boronic acid, and acryloyl chloride using methods B, C, D, and F. HPLC purity: 98%. MS: m/z=444 [M+H]⁺.

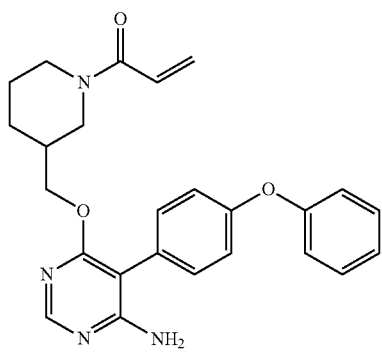 [SMILES: C=CC(=O)N1CCCC(COc2ncnc(N)c2-c2ccc(Oc3ccccc3)cc2)C1]

1-(3-(((6-amino-5-(4-phenoxyphenyl)pyrimidin-4-yl)oxy)methyl)piperidin-1-yl)prop-2-en-1-one (A17)

1-(3-(((6-amino-5-(4-phenoxyphenyl)pyrimidin-4-yl)oxy)methyl)piperidin-1-yl)prop-2-en-1-one was prepared from 5,6-dichloropyrimidin-4-amine, tert-butyl 3-(hydroxymethyl)piperidine-1-carboxylate, (4-phenoxyphenyl)boronic acid, and acryloyl chloride using methods A, C, D, and F. HPLC purity: 100%. MS: m/z=431 [M+H]⁺.

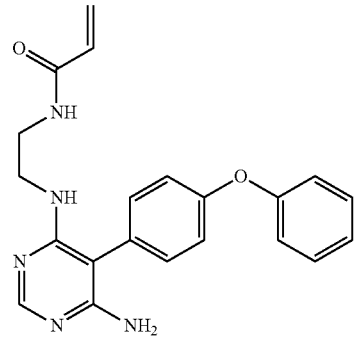 [SMILES: C=CC(=O)NCCNc1ncnc(N)c1-c1ccc(Oc2ccccc2)cc1]

N-(2-((6-amino-5-(4-phenoxyphenyl)pyrimidin-4-yl)amino)ethyl)acrylamide (A18)

N-(2-((6-amino-5-(4-phenoxyphenyl)pyrimidin-4-yl)amino)ethyl)acrylamide was prepared from 5,6-dichloropyrimidin-4-amine, tert-butyl (2-aminoethyl)carbamate, (4-phenoxyphenyl)boronic acid, and acryloyl chloride using methods B, C, D, and F. HPLC purity: 100%. MS: m/z=376 [M+H]⁺.

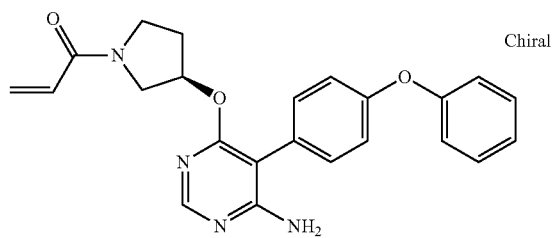 [SMILES: C=CC(=O)N1CC[C@@H](Oc2ncnc(N)c2-c2ccc(Oc3ccccc3)cc2)C1]

(R)-1-(3-(((6-amino-5-(4-phenoxyphenyl)pyrimidin-4-yl)oxy)pyrrolidin-1-yl)prop-2-en-1-one (A19)

(R)-1-(3-(((6-amino-5-(4-phenoxyphenyl)pyrimidin-4-yl)oxy)pyrrolidin-1-yl)prop-2-en-1-one was prepared from 5,6-dichloropyrimidin-4-amine, (R)-tert-butyl 3-hydroxypyrrolidine-1-carboxylate, (4-phenoxyphenyl)boronic acid, and acryloyl chloride using methods A, C, D, and F. HPLC purity: 100%. MS: m/z=403 [M+H]⁺.

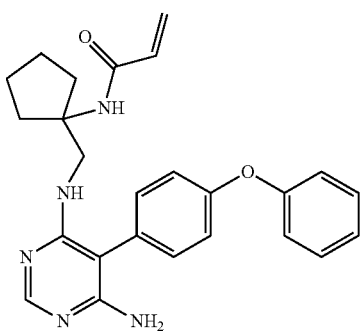 [SMILES: C=CC(=O)NC1(CNc2ncnc(N)c2-c2ccc(Oc3ccccc3)cc2)CCCC1]

N-(1-(((6-amino-5-(4-phenoxyphenyl)pyrimidin-4-yl)amino)methyl)cyclopentyl)acrylamide (A20)

N-(1-((((6-amino-5-(4-phenoxyphenyl)pyrimidin-4-yl)amino)methyl)cyclopentyl)acrylamide was prepared from 5,6-dichloropyrimidin-4-amine, tert-butyl (1-(aminomethyl)cyclopentyl)carbamate, (4-phenoxyphenyl)boronic acid, and acryloyl chloride using methods B, C, D, and F. HPLC purity: 99%. MS: m/z=430 [M+H]$^+$.

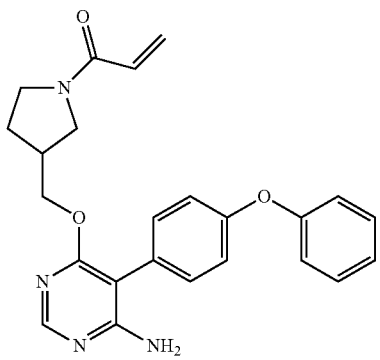 [SMILES: C=CC(=O)N1CCC(COc2ncnc(N)c2-c2ccc(Oc3ccccc3)cc2)C1]

1-(3-(((6-amino-5-(4-phenoxyphenyl)pyrimidin-4-yl)oxy)methyl)pyrrolidin-1-yl)prop-2-en-1-one (A21)

1-(3-(((6-amino-5-(4-phenoxyphenyl)pyrimidin-4-yl)oxy)methyl)pyrrolidin-1-yl)prop-2-en-1-one was prepared from 5,6-dichloropyrimidin-4-amine, tert-butyl 3-(hydroxymethyl)pyrrolidine-1-carboxylate, (4-phenoxyphenyl)boronic acid, and acryloyl chloride using methods A, C, D, and F. HPLC purity: 100%. MS: m/z=417 [M+H]$^+$.

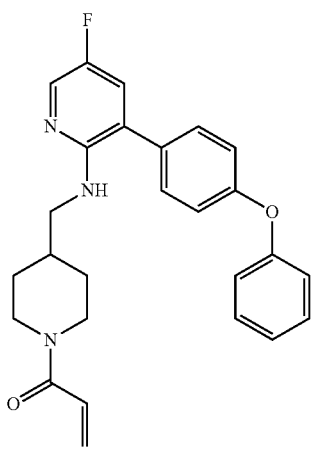 [SMILES: C=CC(=O)N1CCC(CNc2ncc(F)cc2-c2ccc(Oc3ccccc3)cc2)CC1]

1-(4-(((5-fluoro-3-(4-phenoxyphenyl)pyridin-2-yl)amino)methyl)piperidin-1-yl)prop-2-en-1-one (A22)

1-(4-(((5-fluoro-3-(4-phenoxyphenyl)pyridin-2-yl)amino)methyl)piperidin-1-yl)prop-2-en-1-one was prepared from 3-bromo-2-chloro-5-fluoropyridine, tert-butyl 4-(aminomethyl)piperidine-1-carboxylate, (4-phenoxyphenyl)boronic acid, and acryloyl chloride using methods B, C, D, and F. HPLC purity: 99%. MS: m/z=432 [M+H]$^+$. $^1$H-NMR (DMSO-d$_6$) δ 8.01 (s, 1H), 7.47-7.45 (m, 4H), 7.32 (d, 1H), 7.21 (t, 1H), 7.12-7.09 (m, 4H), 6.82-6.75 (m, 1H), 6.07 (d, 1H), 5.82 (broad s, 1H), 5.64 (d, 1H), 4.39 (d, 1H), 4.02 (d, 1H), 3.18 (d, 2H), 2.99 (t, 1H), 2.59 (t, 1H), 1.92 (s, 1H), 1.68 (m, 2H), 1.00 (m, 2H).

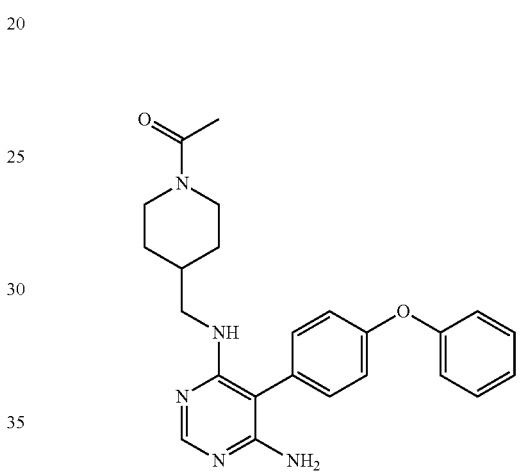

1-(4-(((6-amino-5-(4-phenoxyphenyl)pyrimidin-4-yl)amino)methyl)piperidin-1-yl)ethanone (A23)

1-(4-(((6-amino-5-(4-phenoxyphenyl)pyrimidin-4-yl)amino)methyl)piperidin-1-yl)ethanone was prepared from 5,6-dichloropyrimidin-4-amine, tert-butyl 4-(aminomethyl)piperidine-1-carboxylate, (4-phenoxyphenyl)boronic acid, and acetic acid using methods B, C, D, and E. HPLC purity: 100%. MS: m/z=418 [M+H]$^+$. $^1$H-NMR (DMSO-d$_6$) δ 8.36 (s, 1H), 7.46 (t, 2H), 7.29-7.01 (m, 10H), 4.32 (d, 1H), 3.78 (d, 1H), 3.24 (m, 2H), 2.94 (t, 1H), 2.46 (t, 1H), 1.97 (s, 3H), 1.79 (s, 1H), 1.58 (t, 2H), 1.07-0.87 (m, 2H).

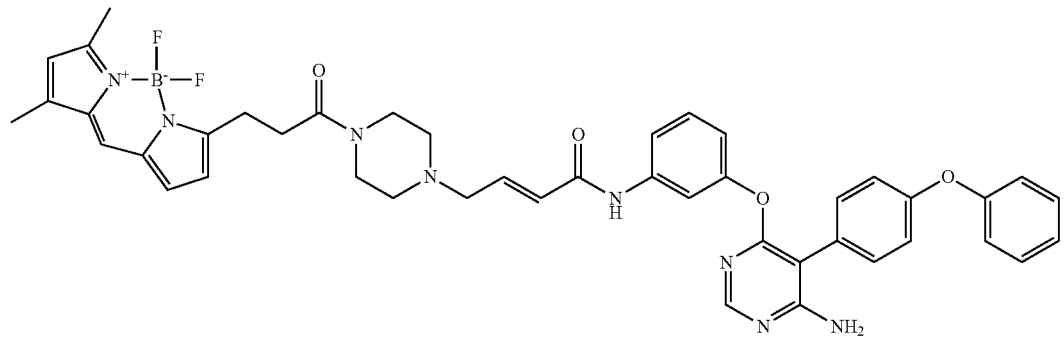 [SMILES: CC1=CC(C)=[N+]2C1=Cc1ccc(CCC(=O)N3CCN(C/C=C/C(=O)Nc4cccc(Oc5ncnc(N)c5-c5ccc(Oc6ccccc6)cc5)c4)CC3)n1[B-]2(F)F]

(E)-7-(3-(4-(4-((3-((6-amino-5-(4-phenoxyphenyl)pyrimidin-4-yl)oxy)phenyl)amino)-4-oxobut-2-en-1-yl)piperazin-1-yl)-3-oxopropyl)-5,5-difluoro-1,3-dimethyl-5H-dipyrrolo[1,2-c:2',1'-f][1,3,2]diazaborinin-4-ium-5-uide (A24)

(E)-7-(3-(4-(4-((3-((6-amino-5-(4-phenoxyphenyl)pyrimidin-4-yl)oxy)phenyl)amino)-4-oxobut-2-en-1-yl)piperazin-1-yl)-3-oxopropyl)-5,5-difluoro-1,3-dimethyl-5H-dipyrrolo[1,2-c:2',1'-f][1,3,2]diazaborinin-4-ium-5-uide was prepared from 5,6-dichloropyrimidin-4-amine, 3-aminophenol, (4-phenoxyphenyl)boronic acid, (E)-4-(4-(tert-butoxycarbonyl)piperazin-1-yl)but-2-enoic acid, and 7-(2-carboxyethyl)-5,5-difluoro-1,3-dimethyl-5H-dipyrrolo[1,2-c:2',1'-f][1,3,2]diazaborinin-4-ium-5-uide using methods A, B, E, D, and E. HPLC purity: 100%. MS: m/z=797 [M+H]+.

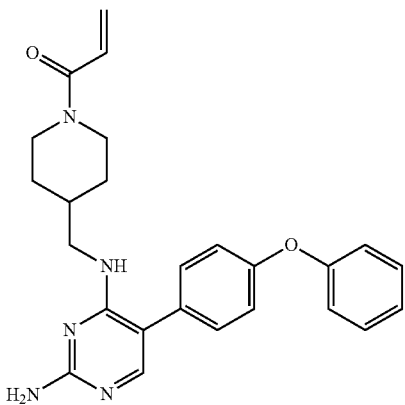 [SMILES: C=CC(=O)N1CCC(CNc2nc(N)ncc2-c2ccc(Oc3ccccc3)cc2)CC1]

1-(4-(((2-amino-5-(4-phenoxyphenyl)pyrimidin-4-yl)amino)methyl)piperidin-1-yl)prop-2-en-1-one (A25)

1-(4-(((2-amino-5-(4-phenoxyphenyl)pyrimidin-4-yl)amino)methyl)piperidin-1-yl)prop-2-en-1-one was prepared from 5-bromo-4-chloropyrimidin-2-amine, tert-butyl 4-(aminomethyl)piperidine-1-carboxylate, (4-phenoxyphenyl)boronic acid, and acryloyl chloride using methods B, C, D, and F. HPLC purity: 100%. MS: m/z=430 [M+H]+.

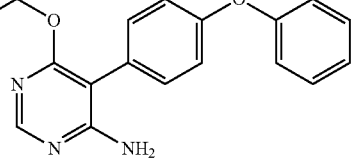

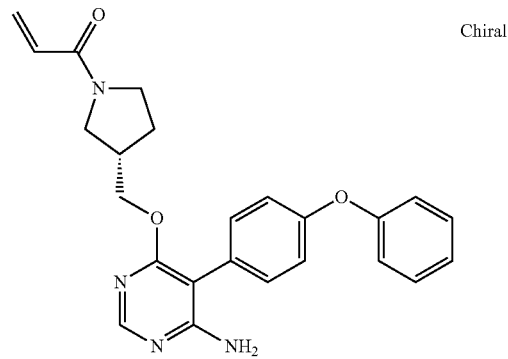 [SMILES: C=CC(=O)N1CC[C@H](COc2ncnc(N)c2-c2ccc(Oc3ccccc3)cc2)C1]

(S)-1-(3-(((6-amino-5-(4-phenoxyphenyl)pyrimidin-4-yl)oxy)methyl)pyrrolidin-1-yl)prop-2-en-1-one (A26)

(S)-1-(3-(((6-amino-5-(4-phenoxyphenyl)pyrimidin-4-yl)oxy)methyl)pyrrolidin-1-yl)prop-2-en-1-one was prepared from 5,6-dichloropyrimidin-4-amine, (S)-tert-butyl 3-(hydroxymethyl)pyrrolidine-1-carboxylate, 4-phenoxyphenyl)boronic acid, and acryloyl chloride using methods A, C, D, and F. HPLC purity: 100%. MS: m/z=417 [M+H]+.

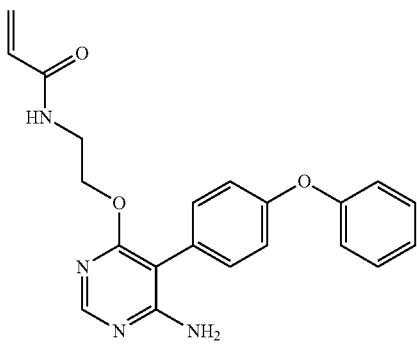 [SMILES: C=CC(=O)NCCOc1ncnc(N)c1-c1ccc(Oc2ccccc2)cc1]

N-(2-((6-amino-5-(4-phenoxyphenyl)pyrimidin-4-yl)oxy)ethyl)acrylamide (A27)

N-(2-(((6-amino-5-(4-phenoxyphenyl)pyrimidin-4-yl)oxy)ethyl)acrylamide was prepared from 5,6-dichloropyrimidin-4-amine, tert-butyl (2-hydroxyethyl)carbamate, 4-phenoxyphenyl)boronic acid, and acryloyl chloride using methods A, C, D, and F. HPLC purity: 100%. MS: m/z=377 [M+H]$^+$. $^1$H-NMR (DMSO-d$_6$) □ δ 8.28 (s, 1H), 8.14 (t, 1H), 7.43 (t, 2H), 7.31 (d, 2H), 7.18 (t, 1H), 7.11 (d, 2H), 7.01 (d, 2H), 6.71 (broad s, 1.5H), 6.16 (dd, 1H), 6.07 (d, 1H), 5.57 (d, 1H), 4.34 (t, 2H), 3.42 (q, 2H).

1-(4-(((6-amino-5-(4-phenoxyphenyl)pyrimidin-4-yl)amino)methyl)piperidin-1-yl)-2-methylprop-2-en-1-one was prepared from 5,6-dichloropyrimidin-4-amine, tert-butyl 4-(aminomethyl)piperidine-1-carboxylate, (4-phenoxyphenyl)boronic acid, and methacrylic acid using methods B, C, D, and E. HPLC purity: 100%. MS: m/z=444 [M+H]$^+$.

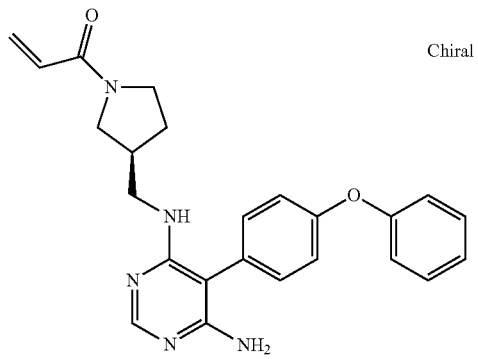 [SMILES: C=CC(=O)N1CC[C@@H](CNc2ncnc(N)c2-c2ccc(Oc3ccccc3)cc2)C1]

Chiral (S)-1-(3-(((6-amino-5-(4-phenoxyphenyl)pyrimidin-4-yl)amino)methyl)pyrrolidin-1-yl)prop-2-en-1-one (A28)

(S)-1-(3-(((6-amino-5-(4-phenoxyphenyl)pyrimidin-4-yl)amino)methyl)pyrrolidin-1-yl)prop-2-en-1-one was prepared from 5,6-dichloropyrimidin-4-amine, (S)-tert-butyl 3-(aminomethyl)pyrrolidine-1-carboxylate, 4-phenoxyphenyl)boronic acid, and acryloyl chloride using methods B, C, D, and F. HPLC purity: 98%. MS: m/z=416 [M+H]$^+$.

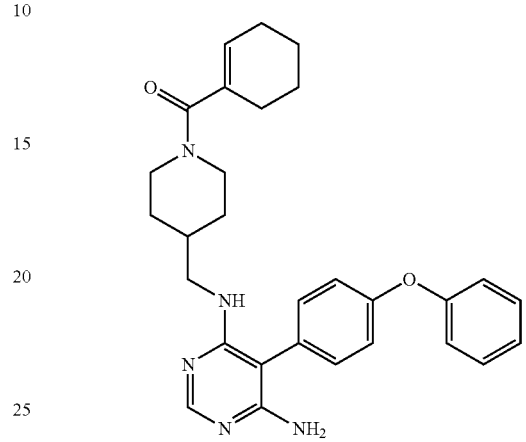

(4-(((6-amino-5-(4-phenoxyphenyl)pyrimidin-4-yl)amino)methyl)piperidin-1-yl)(cyclohex-1-en-1-yl)methanone (A30)

(4-(((6-amino-5-(4-phenoxyphenyl)pyrimidin-4-yl)amino)methyl)piperidin-1-yl)(cyclohex-1-en-1-yl)methanone was prepared from 5,6-dichloropyrimidin-4-amine, tert-butyl 4-(aminomethyl)piperidine-1-carboxylate, (4-phenoxyphenyl)boronic acid, and cyclohex-1-enecarboxylic acid using methods B, C, D, and E. HPLC purity: 100%. MS: m/z=484 [M+H]$^+$.

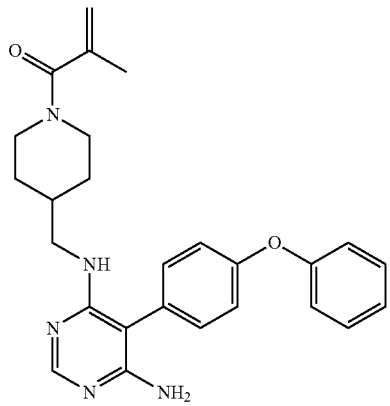 [SMILES: C=C(C)C(=O)N1CCC(CNc2ncnc(N)c2-c2ccc(Oc3ccccc3)cc2)CC1]

1-(4-(((6-amino-5-(4-phenoxyphenyl)pyrimidin-4-yl)amino)methyl)piperidin-1-yl)-2-methylprop-2-en-1-one (A29)

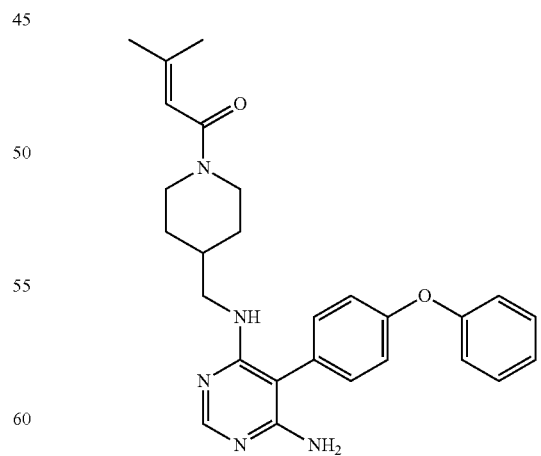

1-(4-(((6-amino-5-(4-phenoxyphenyl)pyrimidin-4-yl)amino)methyl)piperidin-1-yl)-3-methylbut-2-en-1-one (A31)

1-(4-(((6-amino-5-(4-phenoxyphenyl)pyrimidin-4-yl)amino)methyl)piperidin-1-yl)-3-methylbut-2-en-1-one was prepared from 5,6-dichloropyrimidin-4-amine, tert-butyl 4-(aminomethyl)piperidine-1-carboxylate, (4-phenoxyphenyl)boronic acid, and 3-methylbut-2-enoyl chloride using methods B, C, D, and F. HPLC purity: 100%. MS: m/z=458 [M+H]+.

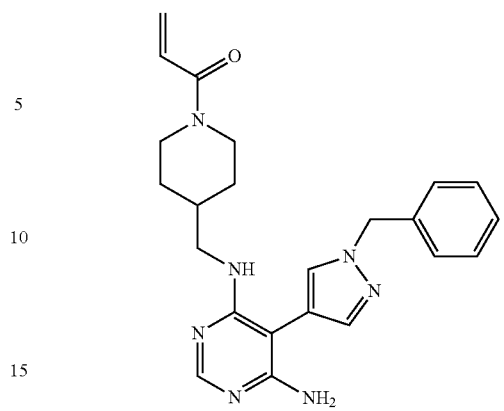

1-(4-(((6-amino-5-(1-benzyl-1H-pyrazol-4-yl)pyrimidin-4-yl)amino)methyl)piperidin-1-yl)prop-2-en-1-one (A33)

1-(4-(((6-amino-5-(1-benzyl-1H-pyrazol-4-yl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (1-benzyl-1H-pyrazol-4-yl)boronic acid, and acryloyl chloride using methods B, C, D, and F. HPLC purity: 100%. MS: m/z=418 [M+H]+.

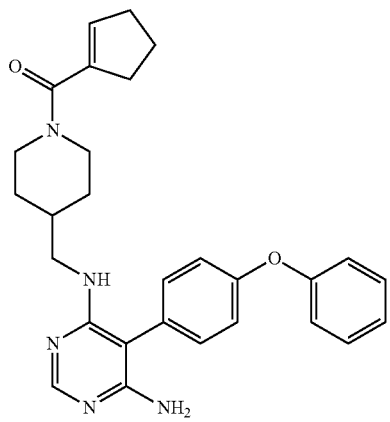 [SMILES: Nc1ncnc(NCC2CCN(C(=O)C3=CCCC3)CC2)c1-c1ccc(Oc2ccccc2)cc1]

(4-(((6-amino-5-(4-phenoxyphenyl)pyrimidin-4-yl)amino)methyl)piperidin-1-yl)(cyclopent-1-en-1-yl)methanone (A32)

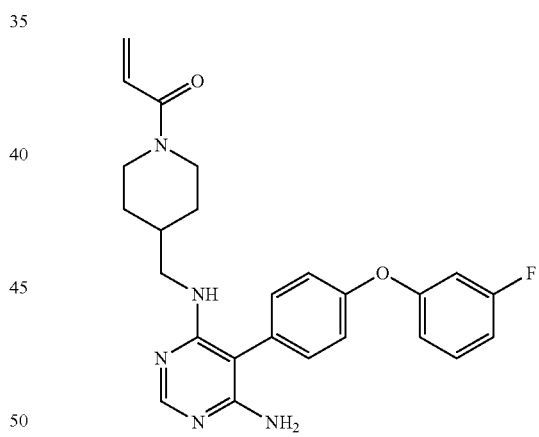

1-(4-(((6-amino-5-(4-(3-fluorophenoxy)phenyl)pyrimidin-4-yl)amino)methyl)piperidin-1-yl)prop-2-en-1-one (A34)

(4-(((6-amino-5-(4-phenoxyphenyl)pyrimidin-4-yl)amino)methyl)piperidin-1-yl)(cyclopent-1-en-1-yl)methanone was prepared from 5,6-dichloropyrimidin-4-amine, tert-butyl 4-(aminomethyl)piperidine-1-carboxylate, (4-phenoxyphenyl)boronic acid, and cyclopent-1-enecarboxylic acid using methods B, C, D, and E. HPLC purity: 99%. MS: m/z=470 [M+H]+.

1-(4-(((6-amino-5-(4-(3-fluorophenoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(3-fluorophenoxy)phenyl)boronic acid, and acryloyl chloride using methods B, C, D, and E. HPLC purity: 100%. MS: m/z=448 [M+H]+.

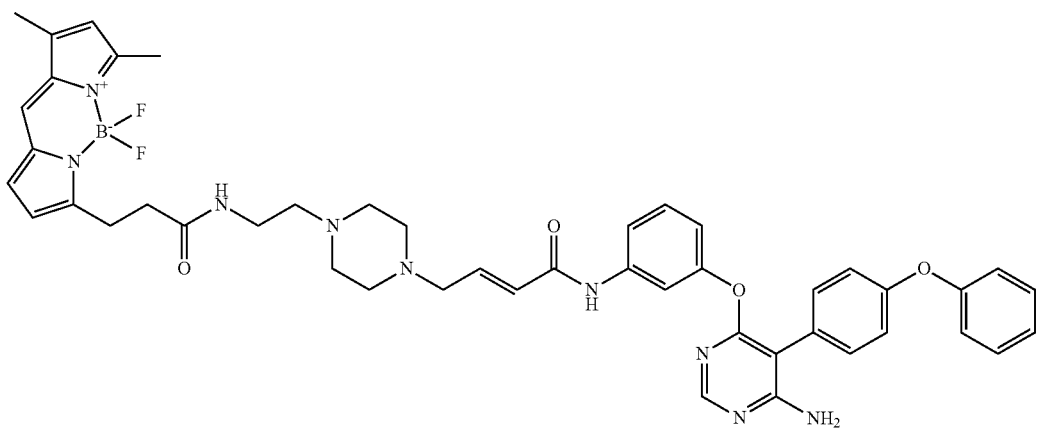 [SMILES: CC1=CC(C)=[N+]2C1=Cc1ccc(CCC(=O)NCCN3CCN(C/C=C/C(=O)Nc4cccc(Oc5ncnc(N)c5-c5ccc(Oc6ccccc6)cc5)c4)CC3)n1[B-]2(F)F]

(E)-7-(3-((2-(4-(4-((3-((6-amino-5-(4-phenoxyphenyl)pyrimidin-4-yl)oxy)phenyl)amino)-4-oxobut-2-en-1-yl)piperazin-1-yl)ethyl)amino)-3-oxopropyl)-5,5-difluoro-1,3-dimethyl-5H-dipyrrolo[1,2-c:2',1'-f][1,3,2]diazaborinin-4-ium-5-uide (A35)

(E)-7-(3-((2-(4-(4-((3-((6-amino-5-(4-phenoxyphenyl)pyrimidin-4-yl)oxy)phenyl)amino)-4-oxobut-2-en-1-yl)piperazin-1-yl)ethyl)amino)-3-oxopropyl)-5,5-difluoro-1,3-dimethyl-5H-dipyrrolo[1,2-c:2',1'-f][1,3,2]diazaborinin-4-ium-5-uide was prepared from 5,6-dichloropyrimidin-4-amine, 3-aminophenol, (4-(3-fluorophenoxy)phenyl)boronic acid, (E)-4-(4-(2-((tert-butoxycarbonyl)amino)ethyl)piperazin-1-yl)but-2-enoic acid, and 7-(2-carboxyethyl)-5,5-difluoro-1,3-dimethyl-5H-dipyrrolo[1,2-c:2',1'-f][1,3,2]diazaborinin-4-ium-5-uide using methods A, C, E, D, and E. HPLC purity: 100%. MS: m/z=840 [M+H]$^+$.

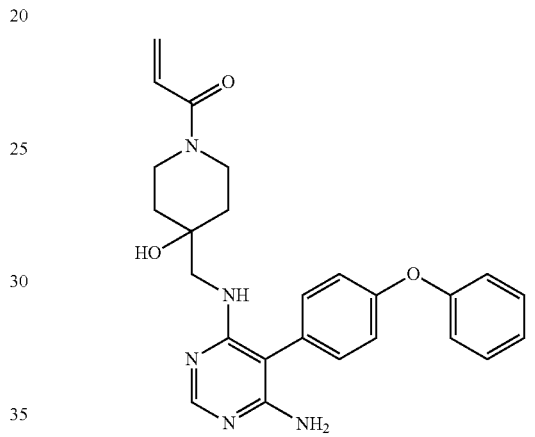

1-(4-(((6-amino-5-(4-phenoxyphenyl)pyrimidin-4-yl)amino)methyl)-4-hydroxypiperidin-1-yl)prop-2-en-1-one (A37)

1-(4-(((6-amino-5-(4-phenoxyphenyl)pyrimidin-4-yl)amino)methyl)-4-hydroxypiperidin-1-yl)prop-2-en-1-one was prepared from 5,6-dichloropyrimidin-4-amine, tert-butyl 4-(aminomethyl)-4-hydroxypiperidine-1-carboxylate, (4-phenoxyphenyl)boronic acid, and acryloyl chloride using methods B, C, D, and F. HPLC purity: 100%. MS: m/z=446 [M+H]$^+$.

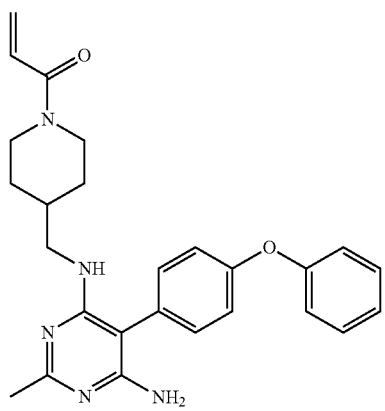 [SMILES: C=CC(=O)N1CCC(CNc2nc(C)nc(N)c2-c2ccc(Oc3ccccc3)cc2)CC1]

1-(4-(((6-amino-2-methyl-5-(4-phenoxyphenyl)pyrimidin-4-yl)amino)methyl)piperidin-1-yl)prop-2-en-1-one (A36)

1-(4-(((6-amino-2-methyl-5-(4-phenoxyphenyl)pyrimidin-4-yl)amino)methyl)piperidin-1-yl)prop-2-en-1-one was prepared from 5,6-dichloro-2-methylpyrimidin-4-amine, tert-butyl 4-(aminomethyl)piperidine-1-carboxylate, (4-phenoxyphenyl)boronic acid, and acryloyl chloride using methods B, C, D, and F. HPLC purity: 100%. MS: m/z=444 [M+H]$^+$.

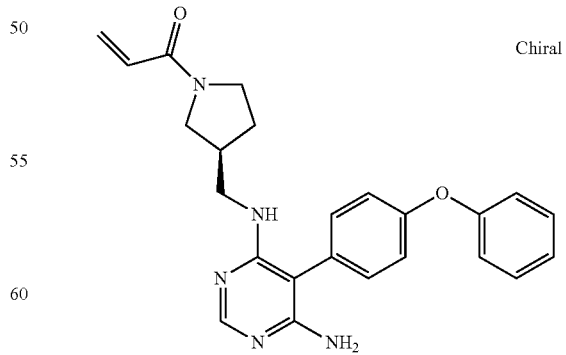

(R)-1-(3-(((6-amino-5-(4-phenoxyphenyl)pyrimidin-4-yl)oxy)methyl)pyrrolidin-1-yl)prop-2-en-1-one (A38)

(R)-1-(3-(((6-amino-5-(4-phenoxyphenyl)pyrimidin-4-yl)oxy)methyl)pyrrolidin-1-yl)prop-2-en-1-one was prepared from 5,6-dichloropyrimidin-4-amine, (R)-tert-butyl 3-(hydroxymethyl)pyrrolidine-1-carboxylate, (4-phenoxyphenyl)boronic acid, and acryloyl chloride using methods A, C, D, and F. HPLC purity: 96%. MS: m/z=417 [M+H]⁺.

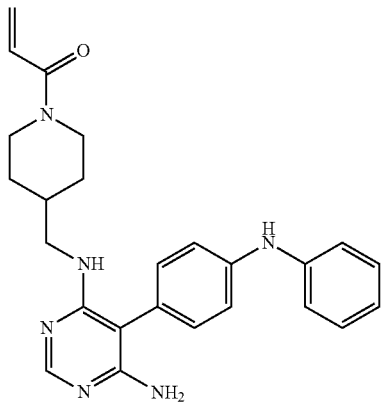

1-(4-(((6-amino-5-(4-(phenylamino)phenyl)pyrimidin-4-yl)amino)methyl)piperidin-1-yl)prop-2-en-1-one (A39)

1-(4-(((6-amino-5-(4-(phenylamino)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, N-phenyl-4-(4,4,5,5-tetramethyl-1,3,2-dioxaborolan-2-yl)aniline, and acryloyl chloride using methods B, C, D, and F. HPLC purity: 98%. MS: m/z=429 [M+H]⁺.

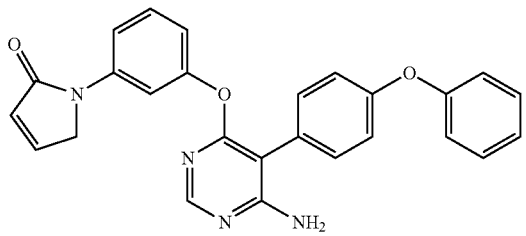 [SMILES: Nc1ncnc(Oc2cccc(N3CC=CC3=O)c2)c1-c1ccc(Oc2ccccc2)cc1]

1-(3-((6-amino-5-(4-phenoxyphenyl)pyrimidin-4-yl)oxy)phenyl)-1H-pyrrol-2(5H)-one (A40)

1-(3-((6-amino-5-(4-phenoxyphenyl)pyrimidin-4-yl)oxy)phenyl)-1H-pyrrol-2(5H)-one was prepared from 5,6-dichloropyrimidin-4-amine, 3-aminophenol, (4-phenoxyphenyl)boronic acid, and 2,5-dimethoxy-2,5-dihydrofuran using methods A, C. HPLC purity: 93%. MS: m/z=437 [M+H]⁺.

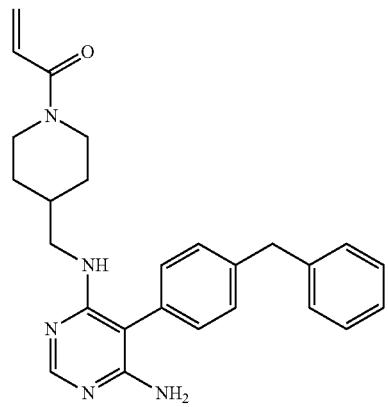 [SMILES: C=CC(=O)N1CCC(CNc2ncnc(N)c2-c2ccc(Cc3ccccc3)cc2)CC1]

1-(4-(((6-amino-5-(4-benzylphenyl)pyrimidin-4-yl)amino)methyl)piperidin-1-yl)prop-2-en-1-one (A41)

1-(4-(((6-amino-5-(4-benzylphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, 2-(4-benzylphenyl)-4,4,5,5-tetramethyl-1,3,2-dioxaborolane, and acryloyl chloride using methods B, C, D, and F. HPLC purity: 100%. MS: m/z=428 [M+H]⁺.

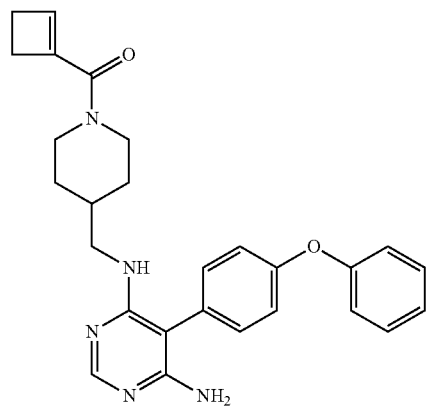 [SMILES: Nc1ncnc(NCC2CCN(C(=O)C3=CCC3)CC2)c1-c1ccc(Oc2ccccc2)cc1]

(4-(((6-amino-5-(4-phenoxyphenyl)pyrimidin-4-yl)amino)methyl)piperidin-1-yl)(cyclobut-1-en-1-yl)methanone (A42)

(4-(((6-amino-5-(4-phenoxyphenyl)pyrimidin-4-yl)amino)methyl)piperidin-1-yl)(cyclobut-1-en-1-yl)methanone was prepared from 5,6-dichloropyrimidin-4-amine, tert-butyl 4-(aminomethyl)piperidine-1-carboxylate, (4-phenoxyphenyl)boronic acid, and cyclobut-1-enecarboxylic acid using methods B, C, D, and E. HPLC purity: 99%. MS: m/z=456 [M+H]⁺.

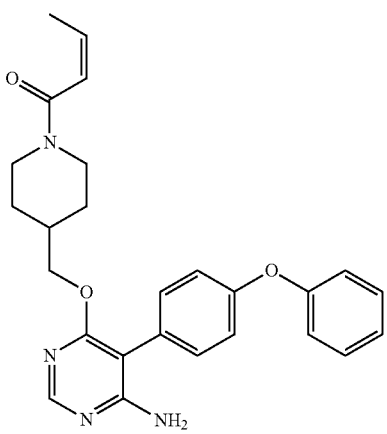 [SMILES: C/C=C\C(=O)N1CCC(COc2ncnc(N)c2-c2ccc(Oc3ccccc3)cc2)CC1]

(Z)-1-(4-(((6-amino-5-(4-phenoxyphenyl)pyrimidin-4-yl)oxy)methyl)piperidin-1-yl)but-2-en-1-one (A43)

(Z)-1-(4-(((6-amino-5-(4-phenoxyphenyl)pyrimidin-4-yl)oxy)methyl)piperidin-1-yl)but-2-en-1-one was prepared from 5,6-dichloropyrimidin-4-amine, tert-butyl 4-(hydroxymethyl)piperidine-1-carboxylate, (4-phenoxyphenyl)boronic acid, and but-2-ynoic acid using methods A, C, D, E, and hydrogenation using Lindlar's catalyst. HPLC purity: 100%. MS: m/z=445 [M+H]$^+$.

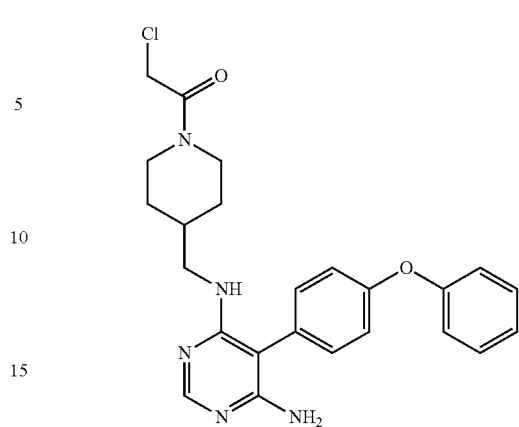

1-(4-(((6-amino-5-(4-phenoxyphenyl)pyrimidin-4-yl)amino)methyl)piperidin-1-yl)-2-chloroethanone (A45)

1-(4-(((6-amino-5-(4-phenoxyphenyl)pyrimidin-4-yl)amino)methyl)piperidin-1-yl)-2-chloroethanone was prepared from 5,6-dichloropyrimidin-4-amine, tert-butyl 4-(aminomethyl)piperidine-1-carboxylate, (4-phenoxyphenyl)boronic acid, and 2-chloroacetyl chloride using methods B, C, D, and G. HPLC purity: 100%. MS: m/z=452 [M+H]$^+$.

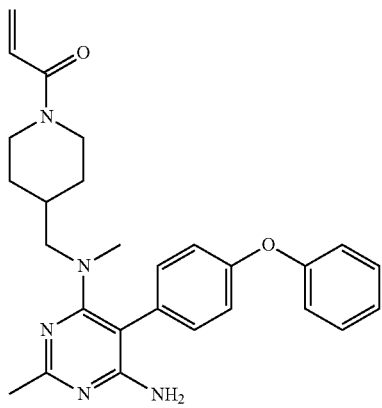 [SMILES: C=CC(=O)N1CCC(CN(C)c2nc(C)nc(N)c2-c2ccc(Oc3ccccc3)cc2)CC1]

1-(4-(((6-amino-2-methyl-5-(4-phenoxyphenyl)pyrimidin-4-yl)(methyl)amino)methyl)piperidin-1-yl)prop-2-en-1-one (A44)

1-(4-(((6-amino-2-methyl-5-(4-phenoxyphenyl)pyrimidin-4-yl)(methyl)amino)methyl)piperidin-1-yl)prop-2-en-1-one was prepared from 5,6-dichloro-2-methylpyrimidin-4-amine, tert-butyl 4-((methylamino)methyl)piperidine-1-carboxylate, (4-phenoxyphenyl)boronic acid, and acryloyl chloride using methods B, C, D, and F. HPLC purity: 100%. MS: m/z=458 [M+H]$^+$.

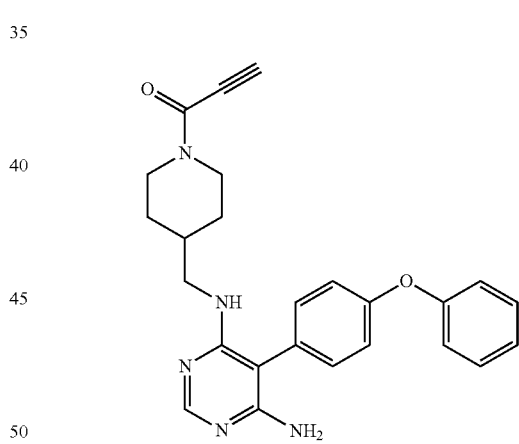

1-(4-(((6-amino-5-(4-phenoxyphenyl)pyrimidin-4-yl)amino)methyl)piperidin-1-yl)prop-2-yn-1-one (A46)

1-(4-(((6-amino-5-(4-phenoxyphenyl)pyrimidin-4-yl)amino)methyl)piperidin-1-yl)prop-2-yn-1-one was prepared from 5,6-dichloropyrimidin-4-amine, tert-butyl 4-(aminomethyl)piperidine-1-carboxylate, (4-phenoxyphenyl)boronic acid, and propiolic acid using methods B, C, D, and E. HPLC purity: 98%. MS: m/z=428 [M+H]$^+$.

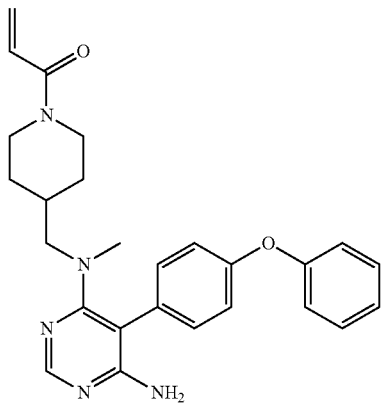 [SMILES: C=CC(=O)N1CCC(CN(C)c2ncnc(N)c2-c2ccc(Oc3ccccc3)cc2)CC1]

1-(4-(((6-amino-5-(4-phenoxyphenyl)pyrimidin-4-yl)(methyl)amino)methyl)piperidin-1-yl)prop-2-en-1-one (A47)

1-(4-(((6-amino-5-(4-phenoxyphenyl)pyrimidin-4-yl)(methyl)amino)methyl)piperidin-1-yl)prop-2-en-1-one was prepared from 5,6-dichloropyrimidin-4-amine, tert-butyl 4-((methylamino)methyl)piperidine-1-carboxylate, (4-phenoxyphenyl)boronic acid, and acryloyl chloride using methods B, C, D, and F. HPLC purity: 100%. MS: m/z=444 [M+H]$^+$. $^1$H-NMR (DMSO-d$_6$) δ 8.32 (s, 1H), 7.45 (t, 2H), 7.33 (d, 2H), 7.20 (t, 1H), 7.12 (t, 4H), 6.95 (broad s, 1.5H), 6.77 (dd, 1H), 6.07 (d, 1H), 5.65 (d, 1H), 4.38 (d, 1H), 4.01 (d, 1H), 3.36 (m, 2H), 2.99 (t, 1H), 2.68 (s, 3H), 2.57 (t, 1H), 1.92 (s, 1H), 1.50 (d, 2H), 0.97 (t, 2H).

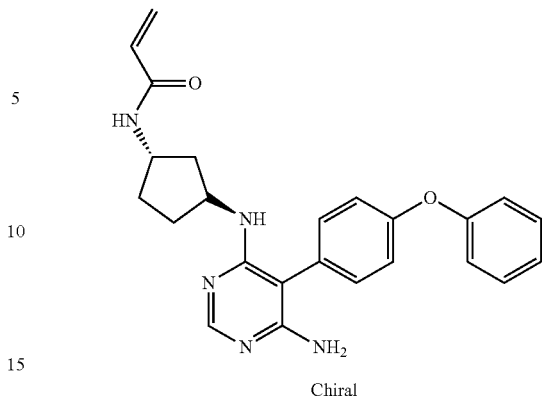

N-((1S,3S)-3-((6-amino-5-(4-phenoxyphenyl)pyrimidin-4-yl)amino)cyclopentyl)acrylamide (A49)

N-((1S,3S)-3-((6-amino-5-(4-phenoxyphenyl)pyrimidin-4-yl)amino)cyclopentyl)acrylamide was prepared from 5,6-dichloropyrimidin-4-amine, tert-butyl-trans-3-aminocyclopentyl)carbamate, (4-phenoxyphenyl)boronic acid, and acryloyl chloride using methods B, C, D, and F. HPLC purity: 100%. MS: m/z=416 [M+H]$^+$. $^1$H-NMR (DMSO-d$_6$) δ 8.35 (s, 1H), 8.12 (d, 1H), 7.46 (t, 2H), 7.28-7.15 (m, 7H), 6.92 (broad s, 1.5H), 6.81 (d, 1H), 6.20 (dd, 1H), 6.06 (d, 1H), 5.57 (d, 1H), 4.64 (s, 1H), 4.21 (q, 1H), 2.05-1.91 (m, 2H), 1.86-1.71 (m, 2H), 1.55-1.34 (m, 2H).

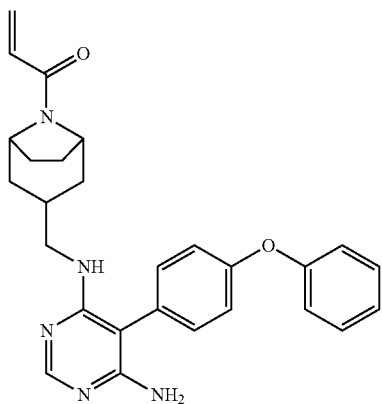 [SMILES: C=CC(=O)N1C2CCC1CC(CNc1ncnc(N)c1-c1ccc(Oc3ccccc3)cc1)C2]

1-(3-(((6-amino-5-(4-phenoxyphenyl)pyrimidin-4-yl)amino)methyl)-8-azabicyclo[3.2.1]octan-8-yl)prop-2-en-1-one (A48)

1-(3-(((6-amino-5-(4-phenoxyphenyl)pyrimidin-4-yl)amino)methyl)-8-azabicyclo[3.2.1]octan-8-yl)prop-2-en-1-one was prepared from 5,6-dichloropyrimidin-4-amine, tert-butyl 3-(aminomethyl)-8-azabicyclo[3.2.1]octane-8-carboxylate, (4-phenoxyphenyl)boronic acid, and acryloyl chloride using methods B, C, D, and F. HPLC purity: 100%. MS: m/z=456 [M+H]$^+$.

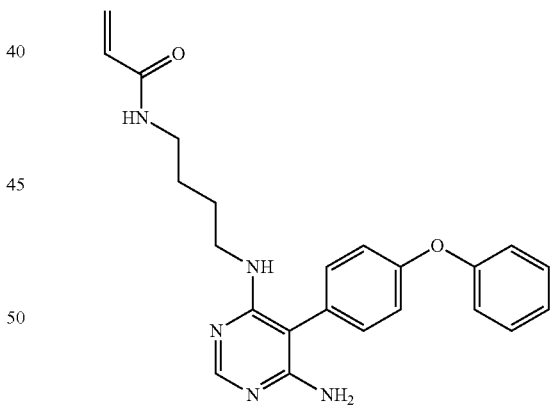

N-(4-((6-amino-5-(4-phenoxyphenyl)pyrimidin-4-yl)amino)butyl)acrylamide (A50)

N-(4-((6-amino-5-(4-phenoxyphenyl)pyrimidin-4-yl)amino)butyl)acrylamide was prepared from 5,6-dichloropyrimidin-4-amine, tert-butyl (4-aminobutyl)carbamate, (4-phenoxyphenyl)boronic acid, and acryloyl chloride using methods B, C, D, and F. HPLC purity: 100%. MS: m/z=404 [M+H]$^+$.

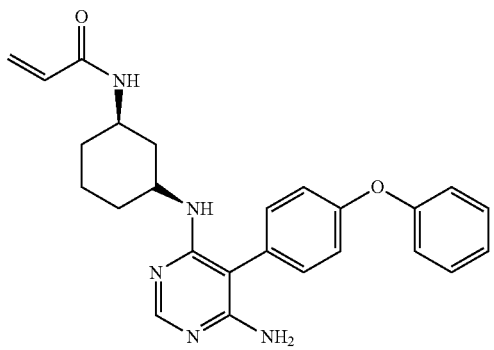

N-(cis-3-((6-amino-5-(4-phenoxyphenyl)pyrimidin-4-yl)amino)cyclohexyl)acrylamide (A51)

N-(cis-3-((6-amino-5-(4-phenoxyphenyl)pyrimidin-4-yl)amino)cyclohexyl)acrylamide was prepared from 5,6-dichloropyrimidin-4-amine, tert-butyl (trans-3-aminocyclohexyl)carbamate, (4-phenoxyphenyl)boronic acid, and acryloyl chloride using methods B, C, D, and F. HPLC purity: 100%. MS: m/z=431 [M+H]+.

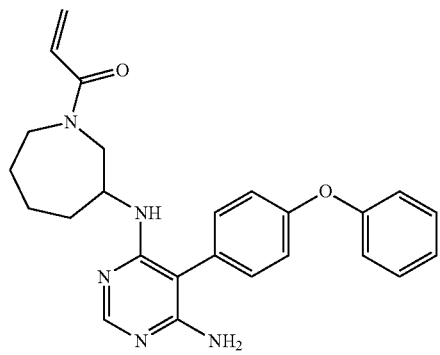 [SMILES: C=CC(=O)N1CCCCC(Nc2ncnc(N)c2-c2ccc(Oc3ccccc3)cc2)C1]

1-(3-((6-amino-5-(4-phenoxyphenyl)pyrimidin-4-yl)amino)azepan-1-yl)prop-2-en-1-one (A52)

1-(3-((6-amino-5-(4-phenoxyphenyl)pyrimidin-4-yl)amino)azepan-1-yl)prop-2-en-1-one was prepared from 5,6-dichloropyrimidin-4-amine, tert-butyl 3-aminoazepane-1-carboxylate, (4-phenoxyphenyl)boronic acid, and acryloyl chloride using methods B, C, D, and F. HPLC purity: 100%. MS: m/z=430 [M+H]+.

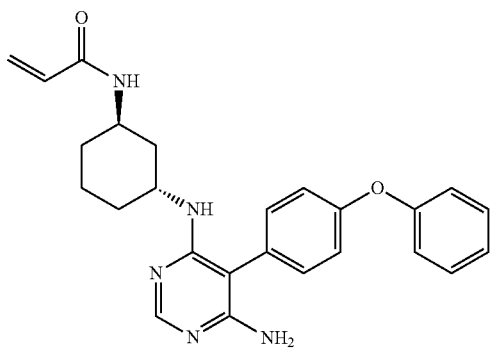 [SMILES: C=CC(=O)N[C@@H]1CCC[C@@H](Nc2ncnc(N)c2-c2ccc(Oc3ccccc3)cc2)C1]

N-(trans-3-((6-amino-5-(4-phenoxyphenyl)pyrimidin-4-yl)amino)cyclohexyl)acrylamide (A53)

N-(trans-3-((6-amino-5-(4-phenoxyphenyl)pyrimidin-4-yl)amino)cyclohexyl)acrylamide was prepared from 5,6-dichloropyrimidin-4-amine, tert-butyl (cis-3-aminocyclohexyl)carbamate, (4-phenoxyphenyl)boronic acid, and acryloyl chloride using methods B, C, D, and F. HPLC purity: 100%. MS: m/z=430 [M+H]+.

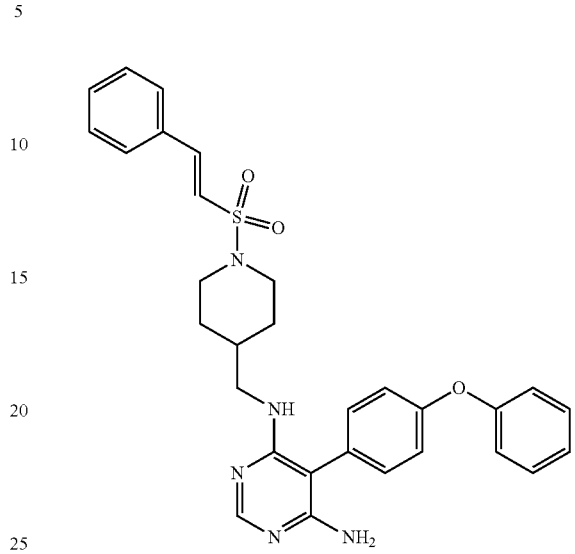

(E)-5-(4-phenoxyphenyl)-N4-((1-(styrylsulfonyl)piperidin-4-yl)methyl)pyrimidine-4,6-diamine (A54)

(E)-5-(4-phenoxyphenyl)-N4-((1-(styrylsulfonyl)piperidin-4-yl)methyl)pyrimidine-4,6-diamine was prepared from 5,6-dichloropyrimidin-4-amine, tert-butyl 4-(aminomethyl)piperidine-1-carboxylate, (4-phenoxyphenyl)boronic acid, and (E)-2-phenylethenesulfonyl chloride using methods B, C, D, G. HPLC purity: 98%. MS: m/z=542 [M+H]+.

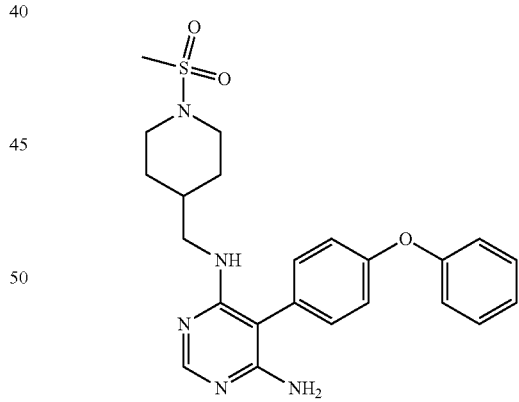

N4-((1-(methylsulfonyl)piperidin-4-yl)methyl)-5-(4-phenoxyphenyl)pyrimidine-4,6-diamine (A55)

N4-((1-(methylsulfonyl)piperidin-4-yl)methyl)-5-(4-phenoxyphenyl)pyrimidine-4,6-diamine was prepared from 5,6-dichloropyrimidin-4-amine, tert-butyl 4-(aminomethyl)piperidine-1-carboxylate, (4-phenoxyphenyl)boronic acid, and methanesulfonyl chloride using methods B, C, D, and G. HPLC purity: 99%. MS: m/z=454 [M+H]+.

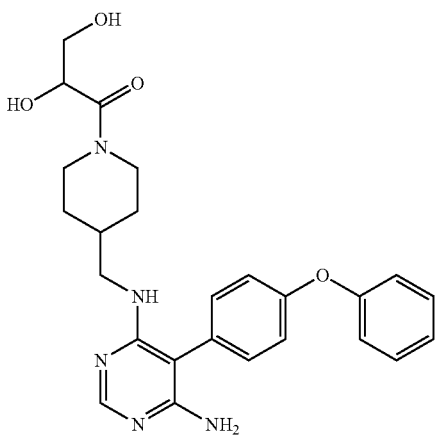 [SMILES: Nc1ncnc(NCC2CCN(C(=O)C(O)CO)CC2)c1-c1ccc(Oc2ccccc2)cc1]

1-(4-(((6-amino-5-(4-phenoxyphenyl)pyrimidin-4-yl)amino)methyl)piperidin-1-yl)-2,3-dihydroxypropan-1-one (A56)

1-(4-(((6-amino-5-(4-phenoxyphenyl)pyrimidin-4-yl)amino)methyl)piperidin-1-yl)-2,3-dihydroxypropan-1-one was prepared from 5,6-dichloropyrimidin-4-amine, tert-butyl 4-(aminomethyl)piperidine-1-carboxylate, (4-phenoxyphenyl)boronic acid, acryloyl chloride using methods B, C, D, F, and dihydroxylation using osmium tetraoxide. HPLC purity: 96%. MS: m/z=464 [M+H]$^+$.

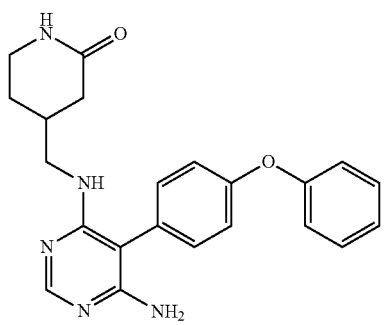 [SMILES: Nc1ncnc(NCC2CCNC(=O)C2)c1-c1ccc(Oc2ccccc2)cc1]

4-(((6-amino-5-(4-phenoxyphenyl)pyrimidin-4-yl)amino)methyl)piperidin-2-one (A57)

4-(((6-amino-5-(4-phenoxyphenyl)pyrimidin-4-yl)amino)methyl)piperidin-2-one was prepared from 5,6-dichloropyrimidin-4-amine, 4-(aminomethyl)piperidin-2-one, (4-phenoxyphenyl)boronic acid using methods I, and C. HPLC purity: 100%. MS: m/z=390 [M+H]$^+$.

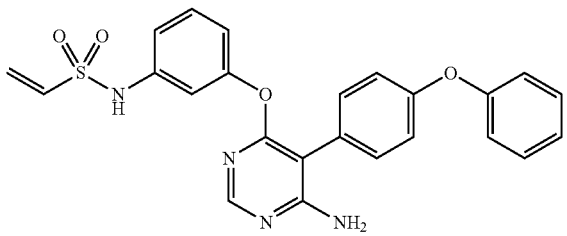 [SMILES: C=CS(=O)(=O)Nc1cccc(Oc2ncnc(N)c2-c2ccc(Oc3ccccc3)cc2)c1]

N-(3-((6-amino-5-(4-phenoxyphenyl)pyrimidin-4-yl)oxy)phenyl)ethenesulfonamide (A58)

N-(3-((6-amino-5-(4-phenoxyphenyl)pyrimidin-4-yl)oxy)phenyl)ethenesulfonamide was prepared from 5,6-dichloropyrimidin-4-amine, 3-aminophenol, (4-phenoxyphenyl)boronic acid, and 2-chloroethanesulfonyl chloride using methods A, C, and G. HPLC purity: 77%. MS: m/z=461 [M+H]$^+$.

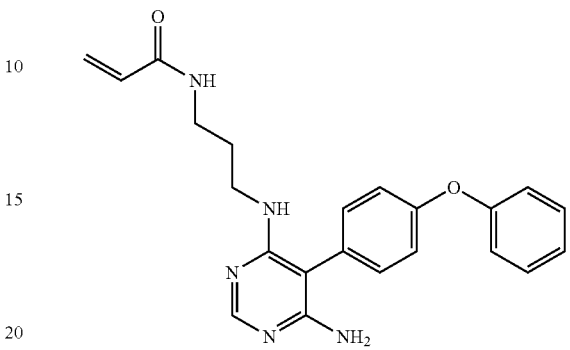

N-(3-((6-amino-5-(4-phenoxyphenyl)pyrimidin-4-yl)amino)propyl)acrylamide (A59)

N-(3-((6-amino-5-(4-phenoxyphenyl)pyrimidin-4-yl)amino)propyl)acrylamide was prepared from 5,6-dichloropyrimidin-4-amine, tert-butyl (3-aminopropyl)carbamate, (4-phenoxyphenyl)boronic acid, and acryloyl chloride using methods B, C, D, and F. HPLC purity: 100%. MS: m/z=390 [M+H]$^+$.

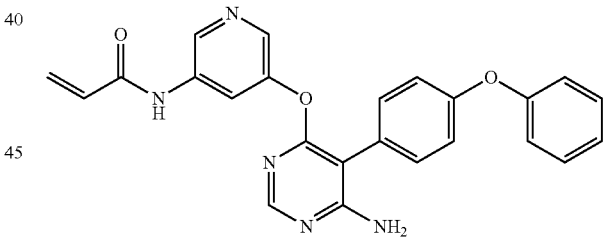

N-(5-((6-amino-5-(4-phenoxyphenyl)pyrimidin-4-yl)oxy)pyridin-3-yl)acrylamide (A60)

N-(5-((6-amino-5-(4-phenoxyphenyl)pyrimidin-4-yl)oxy)pyridin-3-yl)acrylamide was prepared from 6-dichloropyrimidin-4-amine, 5-aminopyridin-3-ol, (4-phenoxyphenyl)boronic acid, and acryloyl chloride using methods A, C, and F. HPLC purity: 97%. MS: m/z=426 [M+H]$^+$. $^1$H-NMR (DMSO-d$_6$) δ 10.49 (s, 1H), 8.58 (s, 1H), 8.13-8.09 (m, 2H), 7.97 (s, 1H), 7.46-7.40 (m, 4H), 7.17 (t, 1H), 7.12-7.09 (m, 4H), 6.64 (broad s, 1.2H), 6.43 (dd, 1H), 6.30 (d, 1H), 5.83 (d, 1H).

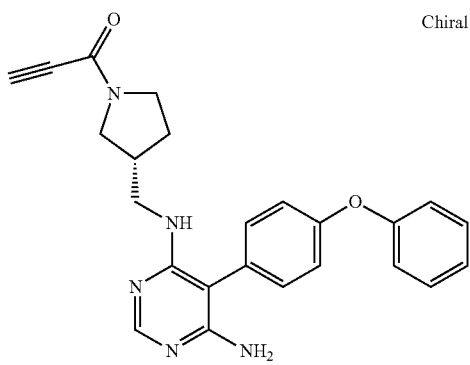 [SMILES: C#CC(=O)N1CC[C@H](CNc2ncnc(N)c2-c2ccc(Oc3ccccc3)cc2)C1]

(R)-1-(3-(((6-amino-5-(4-phenoxyphenyl)pyrimidin-4-yl)amino)methyl)pyrrolidin-1-yl)prop-2-yn-1-one (A61)

(R)-1-(3-(((6-amino-5-(4-phenoxyphenyl)pyrimidin-4-yl)amino)methyl)pyrrolidin-1-yl)prop-2-yn-1-one was prepared from 6-dichloropyrimidin-4-amine, (R)-tert-butyl 3-(aminomethyl)pyrrolidine-1-carboxylate, (4-phenoxyphenyl)boronic acid, and propiolic acid using methods B, C, D and E. HPLC purity: 99%. MS: m/z=414 [M+H]$^+$.

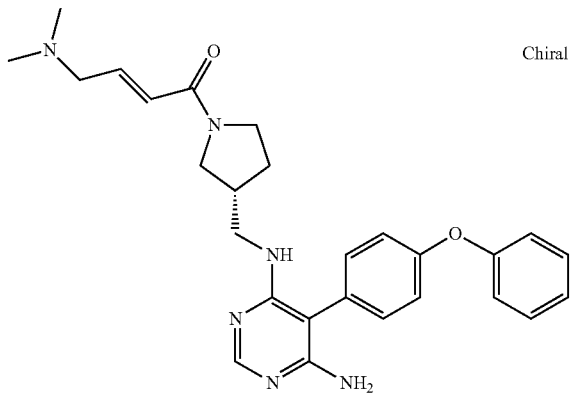 [SMILES: CN(C)C/C=C/C(=O)N1CC[C@H](CNc2ncnc(N)c2-c2ccc(Oc3ccccc3)cc2)C1]

(R,E)-1-(3-(((6-amino-5-(4-phenoxyphenyl)pyrimidin-4-yl)amino)methyl)pyrrolidin-1-yl)-4-(dimethylamino)but-2-en-1-one (A62)

(R,E)-1-(3-(((6-amino-5-(4-phenoxyphenyl)pyrimidin-4-yl)amino)methyl)pyrrolidin-1-yl)-4-(dimethylamino)but-2-en-1-one was prepared from from 6-dichloropyrimidin-4-amine, (R)-tert-butyl 3-(aminomethyl)pyrrolidine-1-carboxylate, (4-phenoxyphenyl)boronic acid, and (E)-4-(dimethylamino)but-2-enoic acid using methods B, C, D, and E. HPLC purity: 100%. MS: m/z=473 [M+H]$^+$.

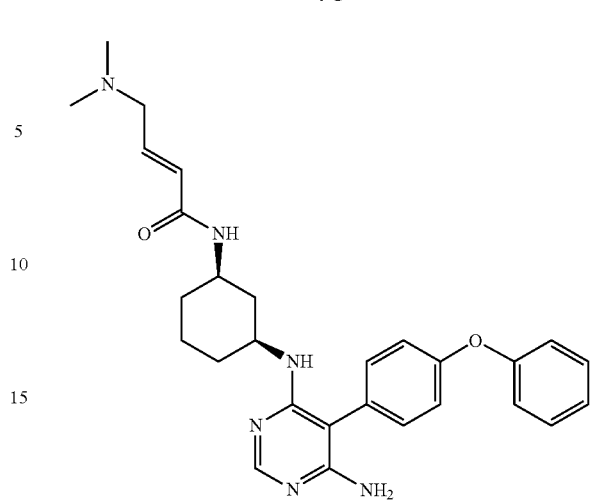

(E)-N-(cis-3-((6-amino-5-(4-phenoxyphenyl)pyrimidin-4-yl)amino)cyclohexyl)-4-(dimethylamino)but-2-enamide (A63)

(E)-N-(cis-3-((6-amino-5-(4-phenoxyphenyl)pyrimidin-4-yl)amino)cyclohexyl)-4-(dimethylamino)but-2-enamide was prepared from 6-dichloropyrimidin-4-amine, tert-butyl (cis-3-aminocyclohexyl)carbamate, (4-phenoxyphenyl)boronic acid, and (E)-4-(dimethylamino)but-2-enoic acid using methods B, C, D, and E. HPLC purity: 99%. MS: m/z=487 [M+H]$^+$.

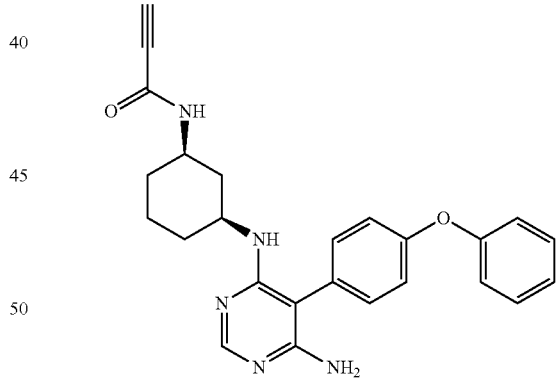

N-(cis-3-((6-amino-5-(4-phenoxyphenyl)pyrimidin-4-yl)amino)cyclohexyl)propiolamide (A64)

N-(cis-3-((6-amino-5-(4-phenoxyphenyl)pyrimidin-4-yl)amino)cyclohexyl)propiolamide was prepared from 6-dichloropyrimidin-4-amine, tert-butyl (cis-3-aminocyclohexyl)carbamate, (4-phenoxyphenyl)boronic acid, and propiolic acid using methods B, C, D, and E. HPLC purity: 100%. MS: m/z=428 [M+H]$^+$.

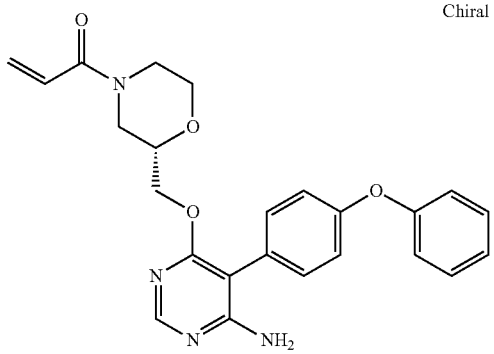 [SMILES: C=CC(=O)N1CCO[C@H](COc2ncnc(N)c2-c2ccc(Oc3ccccc3)cc2)C1]

(S)-1-(2-(((6-amino-5-(4-phenoxyphenyl)pyrimidin-4-yl)oxy)methyl)morpholino)prop-2-en-1-one (A65)

(S)-1-(2-(((6-amino-5-(4-phenoxyphenyl)pyrimidin-4-yl)oxy)methyl)morpholino)prop-2-en-1-one was prepared from 6-dichloropyrimidin-4-amine, (S)-tert-butyl 2-(hydroxymethyl)morpholine-4-carboxylate, (4-phenoxyphenyl)boronic acid, and acryloyl chloride using methods A, C, D, and F. HPLC purity: 99%. MS: m/z=433 [M+H]$^+$.

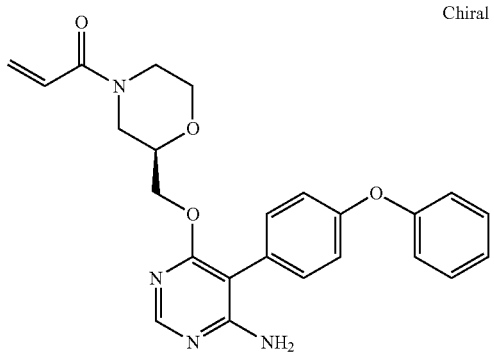 [SMILES: C=CC(=O)N1CCO[C@@H](COc2ncnc(N)c2-c2ccc(Oc3ccccc3)cc2)C1]

(R)-1-(2-(((6-amino-5-(4-phenoxyphenyl)pyrimidin-4-yl)oxy)methyl)morpholino)prop-2-en-1-one (A66)

(R)-1-(2-(((6-amino-5-(4-phenoxyphenyl)pyrimidin-4-yl)oxy)methyl)morpholino)prop-2-en-1-one was prepared from 6-dichloropyrimidin-4-amine, (R)-tert-butyl 2-(hydroxymethyl)morpholine-4-carboxylate, (4-phenoxyphenyl)boronic acid, and acryloyl chloride using methods A, C, D, and F. HPLC purity: 100%. MS: m/z=433 [M+H]$^+$.

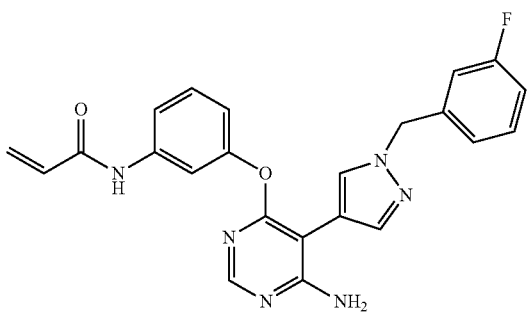 [SMILES: C=CC(=O)Nc1cccc(Oc2ncnc(N)c2-c2cnn(Cc3cccc(F)c3)c2)c1]

N-(3-((6-amino-5-(1-(3-fluorobenzyl)-1H-pyrazol-4-yl)pyrimidin-4-yl)oxy)phenyl)acrylamide (A67)

N-(3-((6-amino-5-(1-(3-fluorobenzyl)-1H-pyrazol-4-yl)pyrimidin-4-yl)oxy)phenyl)acrylamide was prepared from 5,6-dichloropyrimidin-4-amine, 3-aminophenol, 1-(3-fluorobenzyl)-4-(4,4,5,5-tetramethyl-1,3,2-dioxaborolan-2-yl)-1H-pyrazole, and acryloyl chloride using methods A, C, and F. HPLC purity: 100%. MS: m/z=431 [M+H]$^+$. $^1$H-NMR (DMSO-d$_6$) δ 10.21 (s, 1H), 8.16 (s, 1H), 8.03 (s, 1H), 7.74 (s, 1H), 7.51 (s, 1H), 7.42.7.30 (m, 3H), 7.15-7.09 (m, 3H), 7.03-6.61 (m, 2.5H), 6.42 (dd, 1H), 6.25 (d, 1H), 5.57 (d, 1H), 5.40 (s, 2H).

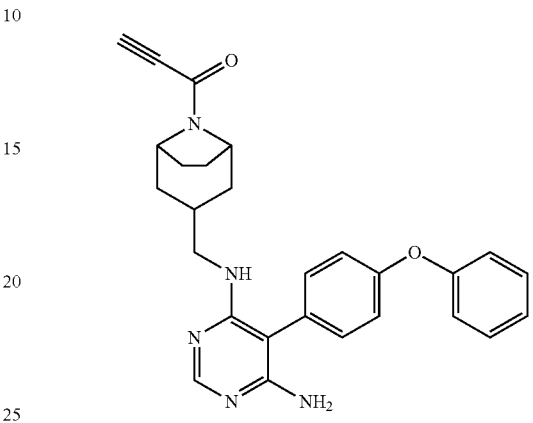

1-(3-(((6-amino-5-(4-phenoxyphenyl)pyrimidin-4-yl)amino)methyl)-8-azabicyclo[3.2.1]octan-8-yl)prop-2-yn-1-one (A68)

1-(3-(((6-amino-5-(4-phenoxyphenyl)pyrimidin-4-yl)amino)methyl)-8-azabicyclo[3.2.1]octan-8-yl)prop-2-yn-1-one was prepared from 5,6-dichloropyrimidin-4-amine, tert-butyl 3-(aminomethyl)-8-azabicyclo[3.2.1]octane-8-carboxylate, (4-phenoxyphenyl)boronic acid, and propiolic acid using methods B, C, D, and E. HPLC purity: 96%. MS: m/z=454 [M+H]$^+$.

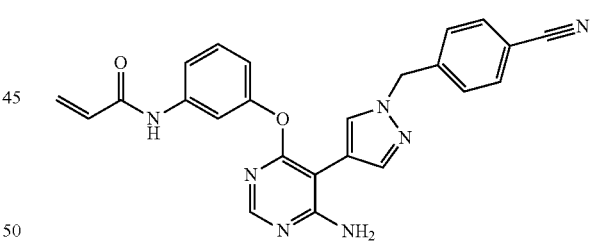

N-(3-((6-amino-5-(1-(4-cyanobenzyl)-1H-pyrazol-4-yl)pyrimidin-4-yl)oxy)phenyl)acrylamide (A69)

N-(3-((6-amino-5-(1-(4-cyanobenzyl)-1H-pyrazol-4-yl)pyrimidin-4-yl)oxy)phenyl)acrylamide was prepared from 5,6-dichloropyrimidin-4-amine, 3-aminophenol, 4-((4-(4,4,5,5-tetramethyl-1,3,2-dioxaborolan-2-yl)-1H-pyrazol-1-yl)methyl)benzonitrile, and acryloyl chloride using methods A, C, and F. HPLC purity: 97%. MS: m/z=438 [M+H]$^+$. $^1$H-NMR (DMSO-d$_6$) δ 10.21 (s, 1H), 8.18 (s, 1H), 8.03 (s, 1H), 7.82 (d, 2H), 7.76 (s, 1H), 7.52 (s, 1H), 7.42 (d, 2H), 7.40 (d, 1H), 7.30 (t, 1H), 6.89-6.67 (m, 2.5H), 6.42 (dd, 1H), 6.25 (d, 1H), 5.77 (d, 1H), 5.49 (s, 2H).

81

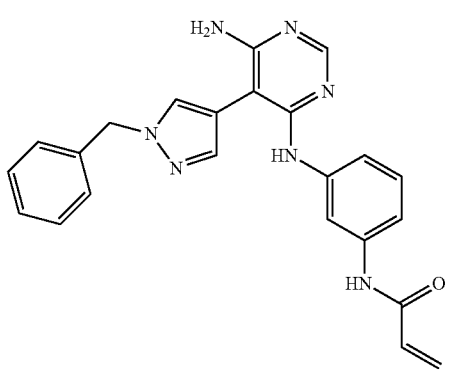 [SMILES: C=CC(=O)Nc1cccc(Nc2ncnc(N)c2-c2cnn(Cc3ccccc3)c2)c1]

N-(3-((6-amino-5-(1-benzyl-1H-pyrazol-4-yl)pyrimidin-4-yl)amino)phenyl)acrylamide (A70)

N-(3-((6-amino-5-(1-benzyl-1H-pyrazol-4-yl)pyrimidin-4-yl)amino)phenyl)acrylamide was prepared from 5,6-dichloropyrimidin-4-amine, benzene-1,3-diamine, 1-benzyl-4-(4,4,5,5-tetramethyl-1,3,2-dioxaborolan-2-yl)-1H-pyrazole, and acryloyl chloride using methods H, C, and F. HPLC purity: 99%. MS: m/z=412 [M+H]$^+$. $^1$H-NMR (DMSO-d$_6$) δ 10.17 (s, 1H), 8.65 (s, 1H), 8.26 (s, 1H), 8.02 (s, 1H), 7.78 (s, 1H), 7.61 (s, 1H), 7.44-7.03 (m, 10H), 6.45 (dd, 1H), 6.26 (d, 1H), 5.76 (d, 1H), 5.39 (s, 2H).

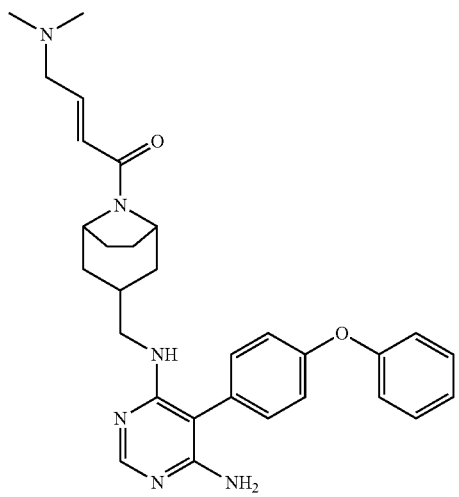 [SMILES: CN(C)C/C=C/C(=O)N1C2CCC1CC(CNc1ncnc(N)c1-c1ccc(Oc3ccccc3)cc1)C2]

(E)-1-(3-(((6-amino-5-(4-phenoxyphenyl)pyrimidin-4-yl)amino)methyl)-8-azabicyclo[3.2.1]octan-8-yl)-4-(dimethylamino)but-2-en-1-one (A71)

(E)-1-(3-(((6-amino-5-(4-phenoxyphenyl)pyrimidin-4-yl)amino)methyl)-8-azabicyclo[3.2.1]octan-8-yl)-4-(dimethylamino)but-2-en-1-one was prepared from 5,6-dichloropyrimidin-4-amine, tert-butyl 3-(aminomethyl)-8-azabicyclo[3.2.1]octane-8-carboxylate, (4-phenoxyphenyl)boronic acid, and (E)-4-(dimethylamino)but-2-enoic acid using methods B, C, D, and E. HPLC purity: 100%. MS: m/z=513 [M+H]$^+$.

82

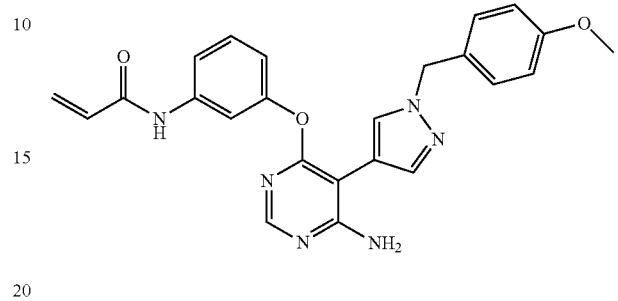

N-(3-((6-amino-5-(1-(4-methoxybenzyl)-1H-pyrazol-4-yl)pyrimidin-4-yl)oxy)phenyl)acrylamide (A72)

N-(3-((6-amino-5-(1-(4-methoxybenzyl)-1H-pyrazol-4-yl)pyrimidin-4-yl)oxy)phenyl)acrylamide was prepared from 5,6-dichloropyrimidin-4-amine, 3-aminophenol, 1-(4-methoxybenzyl)-4-(4,4,5,5-tetramethyl-1,3,2-dioxaborolan-2-yl)-1H-pyrazole, and acryloyl chloride using methods A, C, and F. HPLC purity: 99%. MS: m/z=443 [M+H]$^+$. $^1$H-NMR (DMSO-d$_6$) δ 10.21 (s, 1H), 8.08 (s, 1H), 8.01 (s, 1H), 7.70 (s, 1H), 7.50 (s, 1H), 7.41 (d, 1H), 7.33-7.26 (m, 3H), 6.90 (d, 2H), 6.83-6.58 (m, 2.5H), 6.40 (dd, 1H), 6.25 (d, 1H), 5.76 (d, 1H), 5.28 (s, 2H), 3.73 (s, 3H).

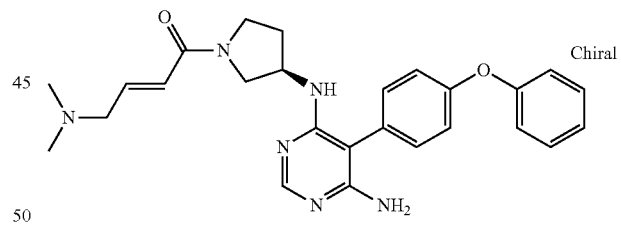

(R,E)-1-(3-((6-amino-5-(4-phenoxyphenyl)pyrimidin-4-yl)amino)pyrrolidin-1-yl)-4-(dimethylamino)but-2-en-1-one (A73)

(R,E)-1-(3-((6-amino-5-(4-phenoxyphenyl)pyrimidin-4-yl)amino)pyrrolidin-1-yl)-4-(dimethylamino)but-2-en-1-one was prepared from 5,6-dichloropyrimidin-4-amine, (R)-tert-butyl 3-aminopyrrolidine-1-carboxylate, (4-phenoxyphenyl)boronic acid, and (E)-4-(dimethylamino)but-2-enoic acid using methods B, C, D and E. HPLC purity: 99%. MS: m/z=459 [M+H]$^+$.

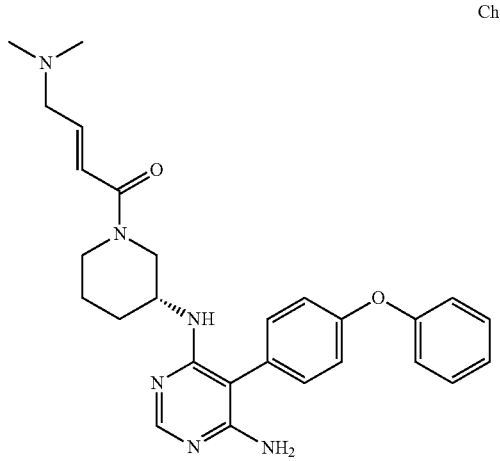

(R,E)-1-(3-((6-amino-5-(4-phenoxyphenyl)pyrimidin-4-yl)amino)piperidin-1-yl)-4-(dimethylamino)but-2-en-1-one (A74)

(R,E)-1-(3-((6-amino-5-(4-phenoxyphenyl)pyrimidin-4-yl)amino)piperidin-1-yl)-4-(dimethylamino)but-2-en-1-one was prepared from 5,6-dichloropyrimidin-4-amine, (R)-tert-butyl 3-aminopiperidine-1-carboxylate, (4-phenoxyphenyl)boronic acid, and (E)-4-(dimethylamino)but-2-enoic acid using methods B, C, D and E. HPLC purity: 100%. MS: m/z=473 [M+H]$^+$.

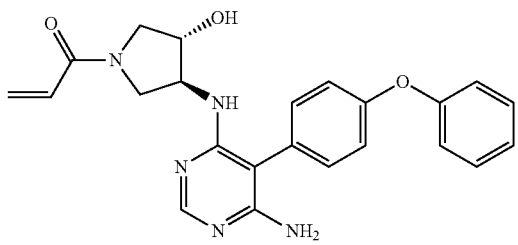 [SMILES: C=CC(=O)N1C[C@H](Nc2ncnc(N)c2-c2ccc(Oc3ccccc3)cc2)[C@@H](O)C1]

1-(trans-3-((6-amino-5-(4-phenoxyphenyl)pyrimidin-4-yl)amino)-4-hydroxypyrrolidin-1-yl)prop-2-en-1-one (A75)

1-(trans-3-((6-amino-5-(4-phenoxyphenyl)pyrimidin-4-yl)amino)-4-hydroxypyrrolidin-1-yl)prop-2-en-1-one was prepared from 5,6-dichloropyrimidin-4-amine, trans-tert-butyl 3-amino-4-hydroxypyrrolidine-1-carboxylate, (4-phenoxyphenyl)boronic acid, and acryloyl chloride using methods B, C, D, and F. HPLC purity: 100%. MS: m/z=418 [M+H]$^+$.

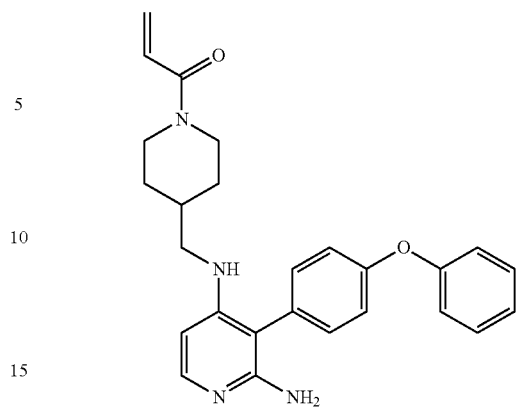

1-(4-(((2-amino-3-(4-phenoxyphenyl)pyridin-4-yl)amino)methyl)piperidin-1-yl)prop-2-en-1-one (A76)

1-(4-(((2-amino-3-(4-phenoxyphenyl)pyridin-4-yl)amino)methyl)piperidin-1-yl)prop-2-en-1-one was prepared from 3,4-dichloropyridin-2-amine, tert-butyl 4-(aminomethyl)piperidine-1-carboxylate, (4-phenoxyphenyl)boronic acid, and acryloyl chloride using methods B, C, D, and F. HPLC purity: 100%. MS: m/z=429 [M+H]$^+$.

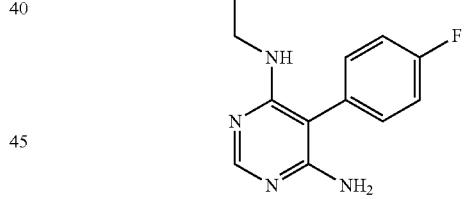

1-(4-(((6-amino-5-(4-fluorophenyl)pyrimidin-4-yl)amino)methyl)piperidin-1-yl)prop-2-en-1-one (A77)

1-(4-(((6-amino-5-(4-fluorophenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-fluorophenyl)boronic acid, and acryloyl chloride in four steps according to general scheme 2, using methods I, C, D and G. MS: m/z=356 [M+H]$^+$. $^1$H-NMR (400 MHz, DMSO-d$_6$) δ 8.35 (s, 1H), 7.40 (t, 2H), 7.32 (dd, 2H), 7.07 (t, 1H), 6.95 (s, 2H), 6.78 (dd, 1H), 6.07 (dd, 1H), 5.65 (dd, 1H), 4.37 (d, 2H), 4.01 (d, 2H), 3.21 (t, 2H), 2.98 (t, 1H), 2.67-2.53 (m, 1H), 1.82 (s, 1H), 1.61 (d, 2H), 0.98 (d, 2H).

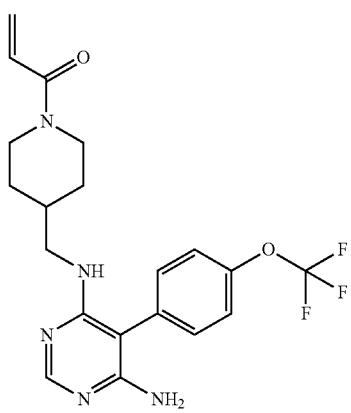 [SMILES: C=CC(=O)N1CCC(CNc2ncnc(N)c2-c2ccc(OC(F)(F)F)cc2)CC1]

1-(4-(((6-amino-5-(4-(trifluoromethoxy)phenyl)pyrimidin-4-yl)amino)methyl)piperidin-1-yl)prop-2-en-1-one (A78)

1-(4-(((6-amino-5-(4-(trifluoromethoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(trifluoromethoxy)phenyl)boronic acid, and acryloyl chloride in four steps according to general scheme 2, using methods I, C, D, and G. MS: m/z=422 [M+H]+. 1H-NMR (400 MHz, DMSO-d6) δ 8.36 (s, 1H), 7.53 (d, 2H), 7.41 (d, 2H), 7.12 (t, 1H), 6.99 (s, 2H), 6.78 (dd, 1H), 6.07 (dd, 1H), 5.65 (dd, 1H), 4.37 (d, 1H), 4.02 (d, 2H), 3.22 (t, 2H), 2.98 (t, 1H), 2.58 (t, 1H), 1.82 (s, 1H), 1.62 (d, 2H), 0.97 (s, 2H).

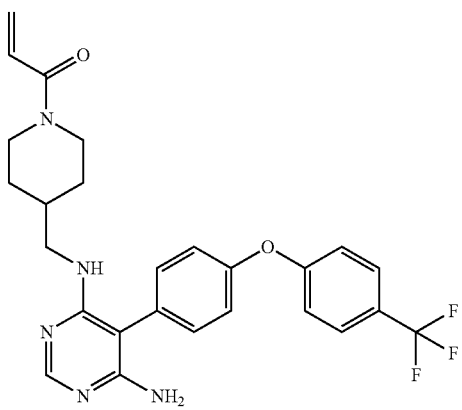 [SMILES: C=CC(=O)N1CCC(CNc2ncnc(N)c2-c2ccc(Oc3ccc(C(F)(F)F)cc3)cc2)CC1]

1-(4-(((6-amino-5-(4-(4-(trifluoromethyl)phenoxy)phenyl)pyrimidin-4-yl)amino)methyl)piperidin-1-yl)prop-2-en-1-one (A79)

1-(4-(((6-amino-5-(4-(4-(trifluoromethyl)phenoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(4-(trifluoromethyl)phenoxy)phenyl)boronic acid, and acryloyl chloride in four steps according to general scheme 2, using methods I, C, D, and G. MS: m/z=498 [M+H]+. 1H-NMR (400 MHz, DMSO-d6) δ 8.37 (s, 1H), 7.79 (d, 2H), 7.31 (m, 4H), 7.10 (bs, 1H), 7.01 (bs, 1H), 6.78 (dd, 1H), 6.07 (dd, 1H), 5.65 (dd, 1H), 4.38 (d, 1H), 4.02 (d, 1H), 3.25 (t, 2H), 3.09-2.90 (m, 1H), 2.59 (t, 1H), 1.84 (m, 1H), 1.63 (d, 2H), 0.99 (m, 2H).

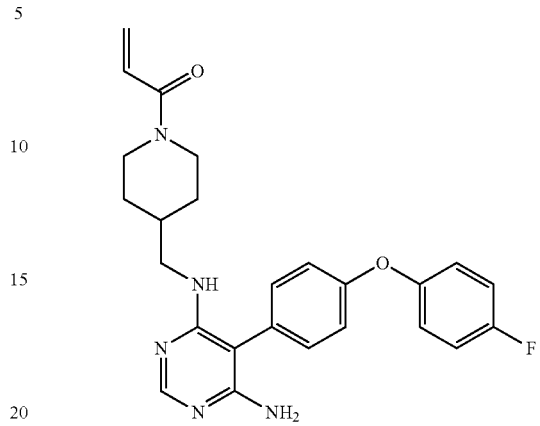

1-(4-(((6-amino-5-(4-(4-(fluorophenoxy)phenyl)pyrimidin-4-yl)amino)methyl)piperidin-1-yl)prop-2-en-1-one (A80)

1-(4-(((6-amino-5-(4-(4-(fluorophenoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(4-fluorophenoxy)phenyl)boronic acid, and acryloyl chloride in four steps according to general scheme 2, using methods I, C, D and G. MS: m/z=448 [M+H]+. 1H-NMR (400 MHz, DMSO-d6) δ 8.35 (s, 1H), 7.37-7.24 (m, 4H), 7.22-7.11 (m, 4H), 7.05 (t, 1H), 6.92 (bs, 2H), 6.78 (dd, 1H), 6.07 (dd, 1H), 5.65 (dd, 1H), 4.37 (d, 1H), 4.02 (d, 1H), 3.23 (t, 2H), 3.00 (t, 1H), 2.58 (t, 1H), 1.83 (m, 1H), 1.62 (d, 2H), 0.97 (m, 2H).

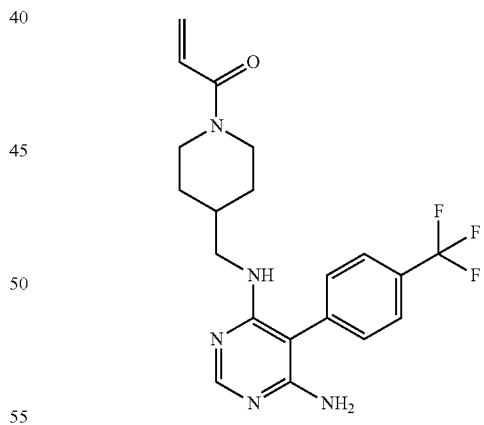

1-(4-(((6-amino-5-(4-(trifluoromethyl)phenyl)pyrimidin-4-yl)amino)methyl)piperidin-1-yl)prop-2-en-1-one (A81)

1-(4-(((6-amino-5-(4-(trifluoromethyl)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(trifluoromethyl)phenyl)boronic acid, and acryloyl chloride in four steps according to general scheme 2, using methods I, C, D and G. MS: m/z=406 [M+H]+. 1H-NMR (400 MHz, DMSO-d6) δ 8.36 (s, 1H), 7.92 (d, 2H), 7.51 (d, 2H), 7.13 (t, 1H), 6.99 (s, 2H), 6.78 (dd, 1H), 6.07 (dd, 1H), 5.65 (dd, 1H), 4.37 (d, 1H), 4.01 (d, 1H), 3.26-3.16 (m, 3H), 3.04-2.91 (m, 1H), 2.65-2.53 (m, 1H), 1.83 (m, H), 1.62 (d, 2H), 1.09-0.86 (m, 2H).

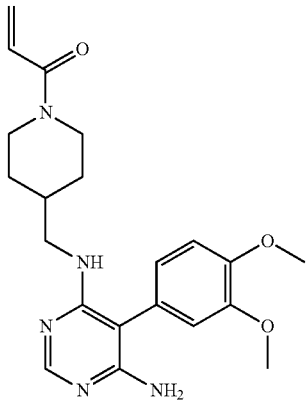 [SMILES: C=CC(=O)N1CCC(CNc2ncnc(N)c2-c2ccc(OC)c(OC)c2)CC1]

1-(4-(((6-amino-5-(3,4-dimethoxyphenyl)pyrimidin-4-yl)amino)methyl)piperidin-1-yl)prop-2-en-1-one (A82)

1-(4-(((6-amino-5-(3,4-dimethoxyphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (3,4-dimethoxyphenyl)boronic acid, and acryloyl chloride in four steps according to general scheme 2, using methods I, C, D and G. MS: m/z=398 [M+H]+. 1H-NMR (400 MHz, CD3OD) δ 8.24 (s, 1H), 7.19 (d, 1H), 6.90 (dd, Hz, 2H), 6.76 (dd, 1H), 6.18 (dd, 1H), 5.73 (dd, 1H), 4.54 (d, 1H), 4.12 (d, 1H), 3.92 (s, 3H), 3.87 (s, 3H), 3.38 (bs, 2H), 3.10 (t, 1H), 2.71 (t, 1H), 2.04-1.85 (m, 1H), 1.75 (bs, 2H), 1.29 (s, 1H), 1.13 (bs, 2H).

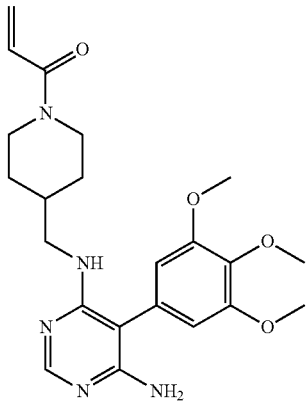 [SMILES: C=CC(=O)N1CCC(CNc2ncnc(N)c2-c2cc(OC)c(OC)c(OC)c2)CC1]

1-(4-(((6-amino-5-(3,4,5-trimethoxyphenyl)pyrimidin-4-yl)amino)methyl)piperidin-1-yl)prop-2-en-1-one (A83)

1-(4-(((6-amino-5-(3,4,5-trimethoxyphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (3,4,5-trimethoxyphenyl)boronic acid, and acryloyl chloride in four steps according to general scheme 2, using methods I, C, D and G. MS: m/z=428 [M+H]+. 1H-NMR (400 MHz, DMSO-d6): δ 8.34 (s, 1H), 7.17 (s, 1H), 6.99 (s, 2H), 6.79 (dd, 1H), 6.57 (s, 2H), 6.07 (dd, 1H), 5.65 (dd, 1H), 4.37 (d, 1H), 4.02 (d, 1H), 3.79 (s, 6H), 3.76 (s, 3H), 3.25 (bs, 2H), 2.99 (t, 1H), 2.59 (t, 1H), 1.85 (bs, 1H), 1.65 (d, 2H), 1.09-0.90 (m, 2H).

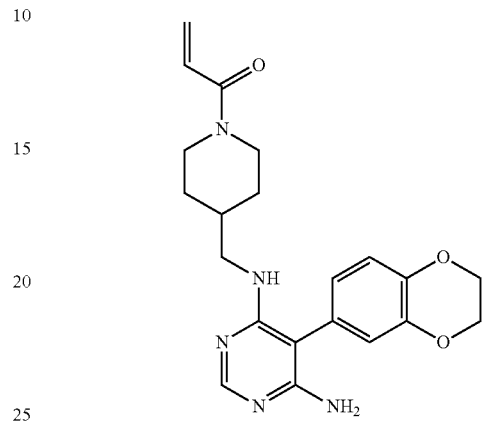

1-(4-(((6-amino-5-(2,3-dihydrobenzo[b][1,4]dioxin-6-yl)pyrimidin-4-yl)amino)methyl)piperidin-1-yl) prop-2-en-1-one (A84)

1-(4-(((6-amino-5-(2,3-dihydrobenzo[b][1,4]dioxin-6-yl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (2,3-dihydrobenzo[b][1,4]dioxin-6-yl)boronic acid, and acryloyl chloride in four steps according to general scheme 2, using methods I, C, D and G. MS: m/z=396 [M+H]+. 1H-NMR (400 MHz, DMSO-d6) δ 8.33 (s, 1H), 7.07 (d, 1H), 7.04 (d, 1H), 6.93 (s, 2H), 6.83-6.73 (m, 2H), 6.70 (dd, 1H), 6.07 (dd, 1H), 5.65 (dd, 1H), 4.36 (d, 1H), 4.30 (s, 3H), 4.01 (d, 1H), 3.22 (s, 3H), 2.98 (t, 1H), 2.66-2.53 (m, 1H), 1.83 (m, 1H), 1.61 (d, 2H), 1.10-0.83 (m, 2H).

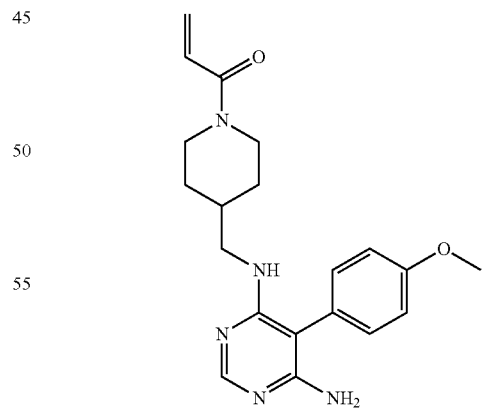

1-(4-(((6-amino-5-(4-methoxyphenyl)pyrimidin-4-yl)amino)methyl)piperidin-1-yl)prop-2-en-1-one (A85)

1-(4-(((6-amino-5-(4-methoxyphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-methoxyphenyl)boronic acid, and acryloyl chloride in four steps according to general scheme 2, using methods I, C, D and G. MS: m/z=368 [M+H]+. 1H-NMR (400 MHz, DMSO-d6) δ 8.34 (s, 1H), 7.17 (dd, 4H), 6.99 (s, 1H), 6.84 (s, 1H), 6.78 (dd, 1H), 6.07 (dd, 1H), 5.65 (dd, 1H), 4.37 (d, 1H), 4.01 (d, 1H), 3.83 (s, 3H), 3.22 (t, 2H), 2.98 (t, 1H), 2.58 (t, 1H), 1.82 (bs, 1H), 1.60 (d, 2H), 1.07-0.86 (m, 2H).

was prepared from 5,6-dichloropyrimidin-4-amine, tert-butyl 4-(aminomethyl)piperidine-1-carboxylate, (2,5-difluoro-4-phenoxyphenyl)boronic acid, and acryloyl chloride in four steps according to general scheme 2, using methods I, C, D and G. MS: m/z=466 [M+H]+. 1H-NMR (400 MHz, DMSO-d6) δ 8.38 (s, 1H), 7.44 (dt, 4H), 7.36-7.12 (m, 5H), 6.79 (dd, 1H), 6.07 (dd, 1H), 5.64 (dd, 1H), 4.38 (d, 1H), 4.03 (d, 1H), 3.31 (bs, 1H), 3.21 (bs, 1H), 2.99 (t, 1H), 2.58 (t, 1H), 1.84 (bs, 1H), 1.64 (d, 2H), 1.00 (bs, 2H).

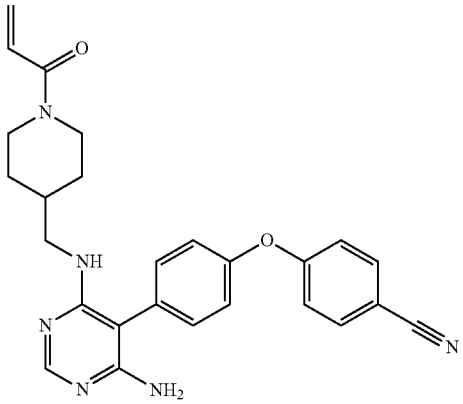 [SMILES: C=CC(=O)N1CCC(CNc2ncnc(N)c2-c2ccc(Oc3ccc(C#N)cc3)cc2)CC1]

4-(4-(4-(((1-acryloylpiperidin-4-yl)methyl)amino)-6-aminopyrimidin-5-yl)phenoxy)benzonitrile (A86)

4-(4-(4-(((1-acryloylpiperidin-4-yl)methyl)amino)-6-aminopyrimidin-5-yl)phenoxy)benzonitrile was prepared from 5,6-dichloropyrimidin-4-amine, tert-butyl 4-(aminomethyl)piperidine-1-carboxylate, (4-cyanophenyl)boronic acid, and acryloyl chloride in four steps according to general scheme 2, using methods I, C, D and G. MS: m/z=455 [M+H]+. 1H-NMR (400 MHz, DMSO-d6) δ 8.27 (s, 1H), 7.77 (d, 2H), 7.48-7.20 (m, 5H), 6.76 (dd, 1H), 6.18 (dd, 1H), 5.73 (dd, 1H), 4.56 (d, 1H), 4.13 (d, 1H), 3.40 (d, 2H), 3.18-3.00 (m, 2H), 2.79-2.63 (m, 1H), 1.96 (bs, 2H), 1.84-1.68 (m, 2H), 1.51 (d, 2H), 1.25-1.04 (m, 2H).

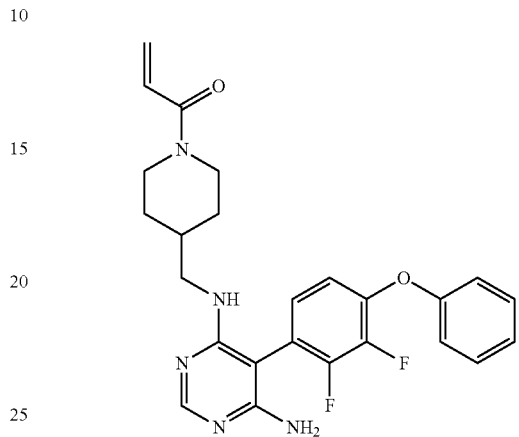

1-(4-(((6-amino-5-(2,3-difluoro-4-phenoxyphenyl)pyrimidin-4-yl)amino)methyl)piperidin-1-yl)prop-2-en-1-one (A88)

1-(4-(((6-amino-5-(2,3-difluoro-4-phenoxyphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (2,3-difluoro-4-phenoxyphenyl)boronic acid, and acryloyl chloride in four steps according to general scheme 2, using methods I, C, D and G. MS: m/z=466 [M+H]+. 1H-NMR (400 MHz, DMSO-d6) δ 8.36 (s, 1H), 7.47 (t, J=8.0 Hz, 2H), 7.35 (bs, 1H), 7.27-7.05 (m, 5H), 6.79 (dd, 1H), 6.07 (dd, 1H), 5.65 (dd, 1H), 4.38 (d, 1H), 4.02 (d, 1H), 3.25 (s, 2H), 3.05-2.92 (t, 1H), 2.60 (t, 1H), 1.84 (bs, 1H), 1.61 (bs, 2H), 1.00 (bs, 2H).

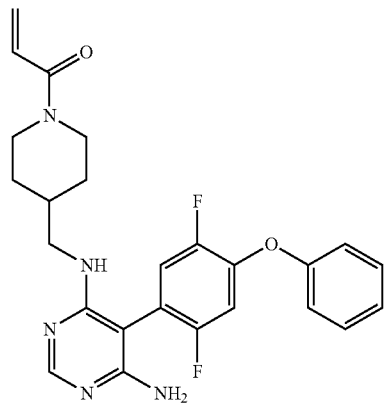 [SMILES: C=CC(=O)N1CCC(CNc2ncnc(N)c2-c2cc(F)c(Oc3ccccc3)cc2F)CC1]

1-(4-(((6-amino-5-(2,5-difluoro-4-phenoxyphenyl)pyrimidin-4-yl)amino)methyl)piperidin-1-yl)prop-2-en-1-one (A87)

1-(4-(((6-amino-5-(2,5-difluoro-4-phenoxyphenyl)pyrimidin-4-yl)amino)methyl)piperidin-1-yl)prop-2-en-1-one

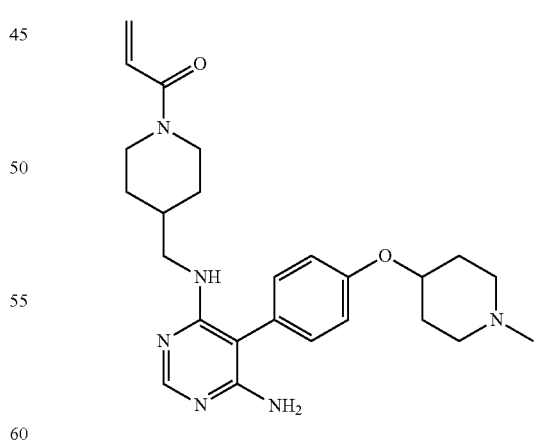

1-(4-(((6-amino-5-(4-((1-methylpiperidin-4-yl)oxy)phenyl)pyrimidin-4-yl)amino)methyl)piperidin-1-yl)prop-2-en-1-one (A89)

1-(4-(((6-amino-5-(4-((1-methylpiperidin-4-yl)oxy)phenyl)pyrimidin-4-yl)amino)methyl)piperidin-1-yl)prop-2-en- 1-one was prepared from 5,6-dichloropyrimidin-4-amine, tert-butyl 4-(aminomethyl)piperidine-1-carboxylate, (4-((1-methylpiperidin-4-yl)oxy)phenyl)boronic acid, and acryloyl chloride in four steps according to general scheme 2, using methods I, C, D and G. MS: m/z=451 [M+H]$^+$. $^1$H-NMR (400 MHz, DMSO-d$_6$) δ 9.79 (s, 1H), 8.35 (s, 1H), 7.19 (m, 5H), 6.93 (m, 3H), 6.78 (dd, 1H), 6.07 (dd, 1H), 5.65 (dd, 1H), 4.81 (s, 1H), 4.60 (s, 1H), 4.37 (d, 1H), 4.01 (d, 1H), 3.19 (d, 5H), 2.98 (t, 1H), 2.85 (d, 4H), 2.65-2.53 (m, 1H), 2.29 (d, 1H), 2.06 (d, 2H), 1.81 (d, 2H), 1.59 (s, 2H), 1.33-1.16 (m, 1H), 1.06-0.82 (m, 2H).

from 5,6-dichloropyrimidin-4-amine, tert-butyl 2,7-diazaspiro[3.5]nonane-7-carboxylate, (4-phenoxyphenyl)boronic acid, and acryloyl chloride in four steps according to general scheme 2, using methods I, C, D and G. MS: m/z=442 [M+H]$^+$. $^1$H-NMR (400 MHz, DMSO-d$_6$) δ 8.31 (s, 1H), 7.43 (t, 2H), 7.34 (d, 2H), 7.18 (t, 1H), 7.11 (d, 4H), 7.04 (bs, 1H), 6.77 (dd, 1H), 6.06 (dd, 1H), 5.65 (dd, 1H), 3.10-3.90 (m, 8H), 1.59 (s, 4H).

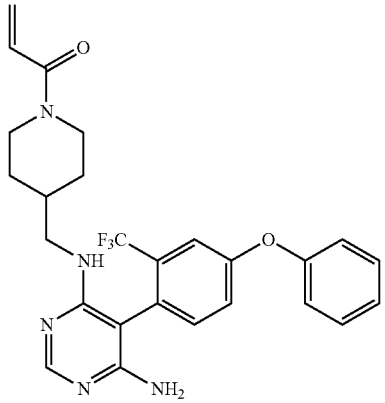 [SMILES: C=CC(=O)N1CCC(CNc2ncnc(N)c2-c2ccc(Oc3ccccc3)cc2C(F)(F)F)CC1]

1-(4-(((6-amino-5-(4-phenoxy-2-(trifluoromethyl)phenyl)pyrimidin-4-yl)amino)methyl)piperidin-1-yl)prop-2-en-1-one (A90)

1-(4-(((6-amino-5-(4-phenoxy-2-(trifluoromethyl)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-phenoxy-2-(trifluoromethyl)phenyl)boronic acid, and acryloyl chloride in four steps according to general scheme 2, using methods I, C, D and G. MS: m/z=498 [M+H]$^+$. $^1$H-NMR (400 MHz, DMSO-d$_6$) δ 8.35 (s, 1H), 7.50 (dd, 2H), 7.39 (m, 2H), 7.28 (t, 1H), 7.19 (d, J=7.8 Hz, 2H), 7.16-7.07 (m, 1H), 7.00 (bs, 1H), 6.78 (dd, 1H), 6.06 (dd, 1H), 5.64 (dd, 1H), 4.36 (d, 1H), 4.01 (d, 1H), 3.16 (m, 2H), 2.97 (t, 1H), 2.65-2.54 (t, 1H), 1.78 (bs, 1H), 1.58 (bs, 2H), 0.97 (bs, 2H).

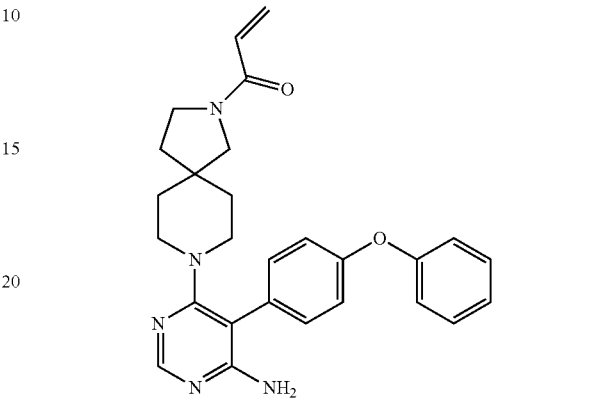

1-(8-(6-amino-5-(4-phenoxyphenyl)pyrimidin-4-yl)-2,8-diazaspiro[4.5]decan-2-yl)prop-2-en-1-one (A92)

1-(8-(6-amino-5-(4-phenoxyphenyl)pyrimidin-4-yl)-2,8-diazaspiro[4.5]decan-2-yl)prop-2-en-1-one was prepared from 5,6-dichloropyrimidin-4-amine, tert-butyl 2,8-diazaspiro[4.5]decane-2-carboxylate, (4-phenoxyphenyl)boronic acid, and acryloyl chloride in four steps according to general scheme 2, using methods I, C, D and G. MS: m/z=456 [M+H]$^+$. $^1$H-NMR (400 MHz, DMSO-d$_6$) δ 8.33 (s, 1H), 7.44 (t, 2H), 7.35 (t, 2H), 7.19 (t, 1H), 7.10 (d, 3H), 6.91 (bs, 2H), 6.53 (m, 1H), 6.13 (d, 1H), 5.72-5.60 (m, 1H), 3.70-3.10 (m, 11H), 1.85 (t, 1H), 1.76 (m, 2H).

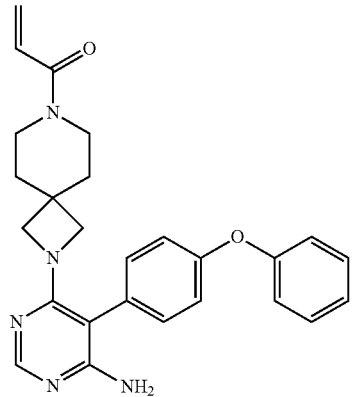 [SMILES: C=CC(=O)N1CCC2(CC1)CN(c1ncnc(N)c1-c1ccc(Oc3ccccc3)cc1)C2]

1-(2-(6-amino-5-(4-phenoxyphenyl)pyrimidin-4-yl)-2,7-diazaspiro[3.5]nonan-7-yl)prop-2-en-1-one (A91)

1-(2-(6-amino-5-(4-phenoxyphenyl)pyrimidin-4-yl)-2,7-diazaspiro[3.5]nonan-7-yl)prop-2-en-1-one was prepared

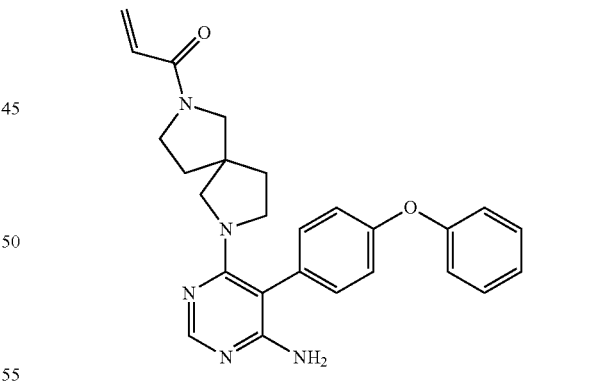

1-(7-(6-amino-5-(4-phenoxyphenyl)pyrimidin-4-yl)-2,7-diazaspiro[4.4]nonan-2-yl)prop-2-en-1-one (A93)

1-(7-(6-amino-5-(4-phenoxyphenyl)pyrimidin-4-yl)-2,7-diazaspiro[4.4]nonan-2-yl)prop-2-en-1-one was prepared from 5,6-dichloropyrimidin-4-amine, tert-butyl 2,7-diazaspiro[4.4]nonane-2-carboxylate, (4-phenoxyphenyl)boronic acid, and acryloyl chloride in four steps according to general scheme 2, using methods I, C, D and G. MS: m/z=442 [M+H]$^+$. $^1$H-NMR (400 MHz, DMSO-d$_6$) δ 8.33

(s, 1H), 7.43 (t, 2H), 7.35 (d, 2H), 7.18 (m, 3H), 7.10 (d, 2H), 6.97 (bs, 2H), 6.54 (ddd, 1H), 6.11 (d, 1H), 5.71-5.60 (m, 1H), 3.70-3.10 (m, 6H), 1.77 (t, 1H), 1.68 (t, 1H), 1.39 (bs, 4H).

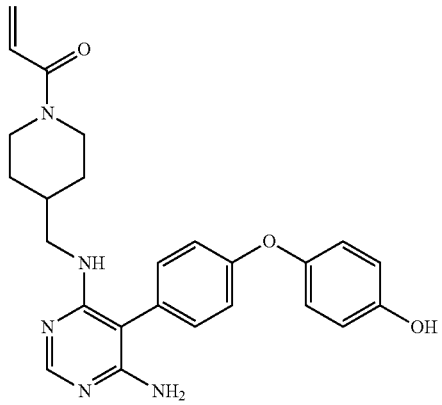 [SMILES: C=CC(=O)N1CCC(CNc2ncnc(N)c2-c2ccc(Oc3ccc(O)cc3)cc2)CC1]

1-(4-(((6-amino-5-(4-(4-hydroxyphenoxy)phenyl)pyrimidin-4-yl)amino)methyl)piperidin-1-yl)prop-2-en-1-one (A94)

1-(4-(((6-amino-5-(4-(4-hydroxyphenoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(4-hydroxyphenoxy)phenyl)boronic acid, and acryloyl chloride in four steps according to general scheme 2, using methods I, C, D and G. MS: m/z=446 [M+H]$^+$. $^1$H-NMR (400 MHz, DMSO-d$_6$) δ 9.39 (bs, 1H), 8.31 (s, 1H), 7.54 (t, 1H), 7.06 (dd, 2H), 7.00 (d, 2H), 6.94 (d, 1H), 6.89 (bs, 1H), 6.79 (d, 2H), 6.72 (bs, 1H), 6.08 (dd, 1H), 5.66 (dd, 1H), 4.38 (d, 1H), 4.01 (d, J 1H), 3.21 (d, 2H), 2.97 (t, 1H), 2.63-2.54 (m, 1H), 1.81 (bs, 1H), 1.58 (d, 2H), 0.96 (bs, 2H).

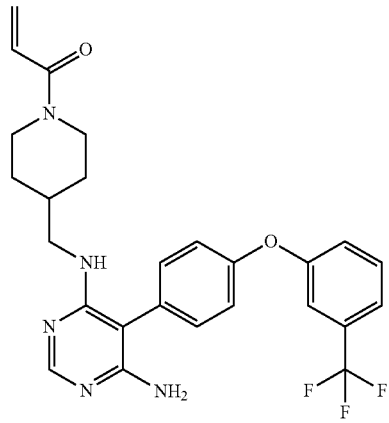 [SMILES: C=CC(=O)N1CCC(CNc2ncnc(N)c2-c2ccc(Oc3cccc(C(F)(F)F)c3)cc2)CC1]

1-(4-(((6-amino-5-(4-(3-(trifluoromethyl)phenoxy)phenyl)pyrimidin-4-yl)amino)methyl)piperidin-1-yl)prop-2-en-1-one (A95)

1-(4-(((6-amino-5-(4-(3-(trifluoromethyl)phenoxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(3-(trifluoromethyl)phenoxy)phenyl)boronic acid, and acryloyl chloride in four steps according to general scheme 2, using methods I, C, D and G. MS: m/z=498 [M+H]$^+$. $^1$H-NMR (400 MHz, DMSO-d$_6$) δ 8.36 (s, 1H), 7.68 (t, 1H), 7.55 (d, 1H), 7.50-7.39 (m, 2H), 7.29 (dd, 4H), 7.08 (bs, 1H), 6.93 (bs, 2H), 6.78 (dd, 1H), 6.07 (dd, 1H), 5.64 (dd, 1H), 4.37 (d, 1H), 4.01 (d, 1H), 3.24 (t, 2H), 3.06-2.91 (m, 1H), 2.60 (t, 1H), 1.83 (bs, 1H), 1.62 (d, 2H), 0.98 (m, 2H).

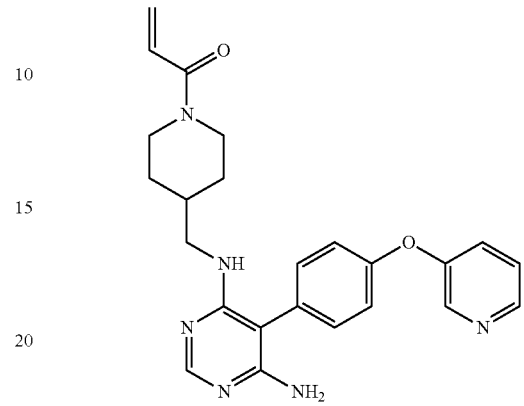

1-(4-(((6-amino-5-(4-(pyridin-3-yloxy)phenyl)pyrimidin-4-yl)amino)methyl)piperidin-1-yl)prop-2-en-1-one (A96)

1-(4-(((6-amino-5-(4-(pyridin-3-yloxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(pyridin-3-yloxy)phenyl)boronic acid, and acryloyl chloride in four steps according to general scheme 2, using methods I, C, D and G. MS: m/z=431 [M+H]$^+$. $^1$H-NMR (400 MHz, DMSO-d$_6$) δ 8.99 (d, 1H), 8.68 (d, 1H), 8.39 (d, 1H), 7.69 (d, 1H), 7.49 (m, 2H), 7.42 (s, 2H), 7.34 (d, 1H), 7.08 (bs, 2H), 6.78 (dd, J=16.6, 10.5 Hz, 1H), 6.07 (dd, J=16.7, 2.3 Hz, 1H), 5.65 (dd, 1H), 4.70 (t, 1H), 4.38 (d, 1H), 4.02 (d, 1H), 3.26 (t, 2H), 3.09-2.92 (m, 2H), 2.59 (t, 1H), 1.84 (bs, 1H), 1.64 (d, 2H), 0.99 (m, 2H).

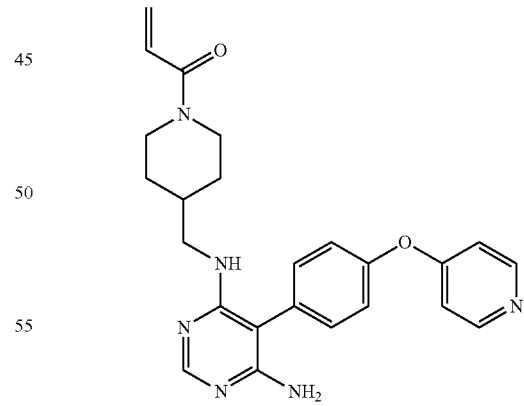

1-(4-(((6-amino-5-(4-(pyridin-4-yloxy)phenyl)pyrimidin-4-yl)amino)methyl)piperidin-1-yl)prop-2-en-1-one (A97)

1-(4-(((6-amino-5-(4-(pyridin-4-yloxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(pyridin-4-yloxy)phenyl)boronic acid, and acryloyl chloride in four steps according to general scheme 2, using methods I, C, D and G. MS: m/z=431 [M+H]+. 1H-NMR (400 MHz, DMSO-d6) δ 9.20 (s, 1H), 8.90 (d, 1H), 8.39 (s, 1H), 8.18 (m, 2H), 7.55-7.36 (m, 4H), 7.03 (s, 2H), 6.78 (dd, 1H), 6.07 (dd, 1H), 5.65 (dd, 1H), 4.85 (t, 2H), 4.38 (d, 1H), 4.02 (d, 1H), 3.25 (t, 2H), 3.14 (t, 2H), 3.06-2.94 (m, 2H), 2.65-2.54 (m, 1H), 1.84 (bs, 1H), 1.62 (d, 2H), 1.00 (m, 2H).

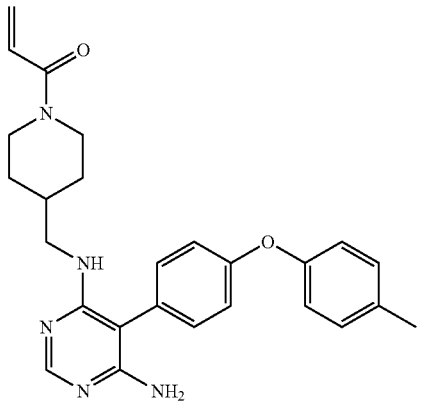 [SMILES: C=CC(=O)N1CCC(CNc2ncnc(N)c2-c2ccc(Oc3ccc(C)cc3)cc2)CC1]

1-(4-(((6-amino-5-(4-(p-tolyloxy)phenyl)pyrimidin-4-yl)amino)methyl)piperidin-1-yl)prop-2-en-1-one (A98)

1-(4-(((6-amino-5-(4-(p-tolyloxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(p-tolyloxy)phenyl)boronic acid, and acryloyl chloride in four steps according to general scheme 2, using methods I, C, D, G. MS: m/z=444 [M+H]+. 1H-NMR (400 MHz, DMSO-d6) δ 8.35 (s, 1H), 7.25 (m, 4H), 7.12 (d, 2H), 7.07 (bs, 1H), 7.04 (t, 2H), 6.93 (bs, 1H), 6.78 (dd, 1H), 6.07 (dd, 1H), 5.64 (dd, 1H), 4.37 (d, 1H), 4.01 (d, 1H), 3.23 (t, 2H), 2.98 (t, 1H), 2.57 (t, 1H), 2.33 (s, 3H), 1.83 (bs, 1H), 1.62 (d, 2H), 0.98 (m, 2H).

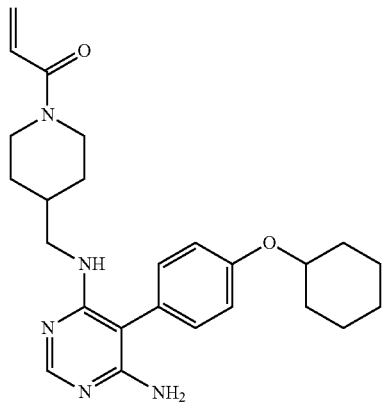 [SMILES: C=CC(=O)N1CCC(CNc2ncnc(N)c2-c2ccc(OC3CCCCC3)cc2)CC1]

1-(4-(((6-amino-5-(4-(cyclohexyloxy)phenyl)pyrimidin-4-yl)amino)methyl)piperidin-1-yl)prop-2-en-1-one (A99)

1-(4-(((6-amino-5-(4-(cyclohexyloxy)phenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-(cyclohexyloxy)phenyl)boronic acid, and acryloyl chloride in four steps according to general scheme 2, using methods I, C, D and G. MS: m/z=436 [M+H]+. 1H-NMR (400 MHz, DMSO-d6) δ 8.34 (s, 1H), 7.13 (dd, 4H), 7.00 (t, 1H), 6.95-6.83 (bs, 2H), 6.78 (dd, 1H), 6.07 (d, 1H), 5.64 (d, 1H), 4.38 (bs, 2H), 4.01 (d, 1H), 3.22 (t, 2H), 2.98 (t, 1H), 2.58 (t, 1H), 1.97 (bs, 2H), 1.91-1.67 (m, 3H), 1.67-1.21 (m, 8H), 1.07-0.86 (m, 2H).

Example Compounds According to Formula (I) Synthesized Using Scheme 3 and Methods S1-S4D

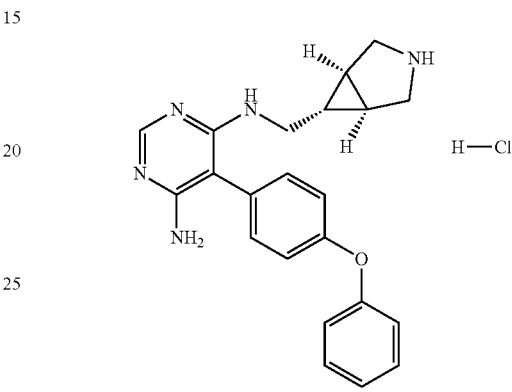

N4-((1R,5S,6r)-3-azabicyclo[3.1.0]hexan-6-ylmethyl)-5-(4-phenoxyphenyl)pyrimidine-4,6-diamine hydrochloride (A100)

N4-((1R,5S,6r)-3-azabicyclo[3.1.0]hexan-6-ylmethyl)-5-(4-phenoxyphenyl)pyrimidine-4,6-diamine hydrochloride was prepared from 5,6-dichloropyrimidin-4-amine, exo-3-Boc-6-aminomethyl-3-azabicyclo[3,1,0]hexane, and (4-phenoxyphenyl) boronic acid according to general scheme 3 using methods S1, S2, and S3.

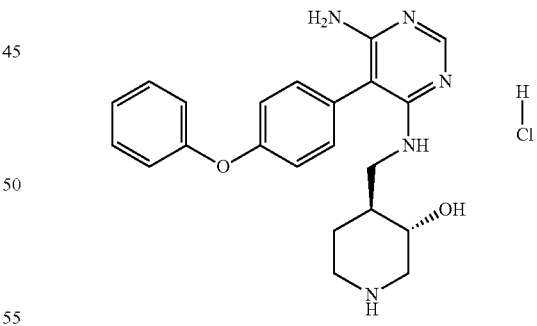

(3S,4S)-4-(((6-amino-5-(4-phenoxyphenyl)pyrimidin-4-yl)amino)methyl)piperidin-3-ol hydrochloride (A101)

(3S,4S)-4-(((6-amino-5-(4-phenoxyphenyl)pyrimidin-4-yl)amino)methyl)piperidin-3-ol hydrochloride was prepared from 5,6-dichloropyrimidin-4-amine, (3S,4S)-tert-butyl 4-(aminomethyl)-3-hydroxypiperidine-1-carboxylate, and (4-phenoxyphenyl) boronic acid according to general scheme 3 using methods S1, S2, and S3.

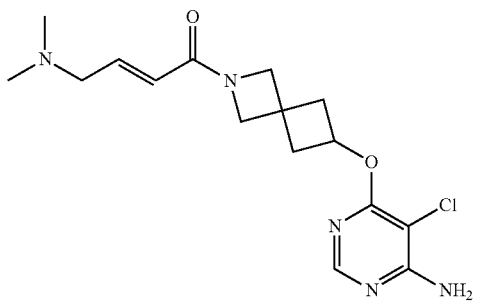 [SMILES: CN(C)C/C=C/C(=O)N1CC2(CC(Oc3ncnc(N)c3Cl)C2)C1]

(E)-1-(6-(((6-amino-5-chloropyrimidin-4-yl)oxy)-2-azaspiro[3.3]heptan-2-yl)-4-(dimethylamino)but-2-en-1-one (A102)

(E)-1-(6-(((6-amino-5-chloropyrimidin-4-yl)oxy)-2-azaspiro[3.3]heptan-2-yl)-4-(dimethylamino)but-2-en-1-one was prepared 5,6-dichloropyrimidin-4-amine, tert-butyl 6-amino-2-azaspiro[3.3]heptane-2-carboxylate and (E)-4-(dimethylamino)but-2-enoic acid hydrochloride in three steps according to general scheme 3 using methods S1, S3, and S4A. HPLC purity: 99%. MS: m/z=352 [M+H]$^+$. $^1$H NMR (CD$_3$OD) δ 8.03 (s, 1H), 6.71 (m, 1H), 6.47 (t, 1H), 5.23 (m, 1H), 4.41 (d, 2H), 4.16 (d, 2H), 3.96 (m, 2H), 2.91 (m, 6H), 2.81 (m, 2H), 2.42 (m, 2H).

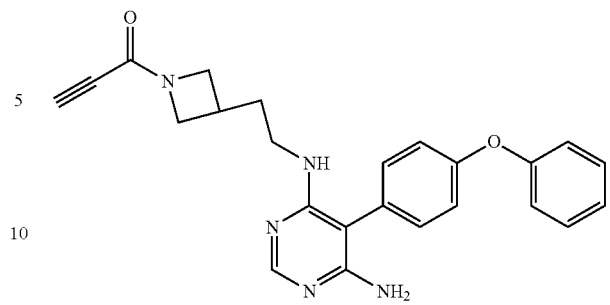

1-(3-(2-(((6-amino-5-(4-phenoxyphenyl)pyrimidin-4-yl)amino)ethyl)azetidin-1-yl)prop-2-yn-1-one (A104)

1-(3-(2-(((6-amino-5-(4-phenoxyphenyl)pyrimidin-4-yl)amino)ethyl)azetidin-1-yl)prop-2-yn-1-one was prepared from 5,6-dichloropyrimidin-4-amine, tert-butyl 3-(2-aminoethyl)azetidine-1-carboxylate, (4-phenoxyphenyl) boronic acid and propiolic acid according to general scheme 3 using methods S1, S2, S3 and S4A. HPLC purity: 99%. MS: m/z=414[M+H]$^+$. $^1$H NMR (CD$_3$OD) δ 8.27 (s, 1H), 7.14-7.45 (m, 9H), 4.33 (t, 1H), 4.09 (dd, 1H), 3.91 (m, 2H), 3.68 (dd, 1H), 3.49 (t, 2H), 2.69 (m, 1H), 1.87 (m, 2H).

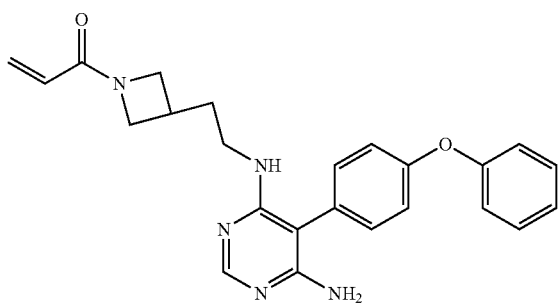 [SMILES: C=CC(=O)N1CC(CCNc2ncnc(N)c2-c2ccc(Oc3ccccc3)cc2)C1]

1-(3-(2-(((6-amino-5-(4-phenoxyphenyl)pyrimidin-4-yl)amino)ethyl)azetidin-1-yl)prop-2-en-1-one (A103)

1-(3-(2-(((6-amino-5-(4-phenoxyphenyl)pyrimidin-4-yl)amino)ethyl)azetidin-1-yl)prop-2-en-1-one was prepared from 5,6-dichloropyrimidin-4-amine, tert-butyl 3-(2-aminoethyl)azetidine-1-carboxylate, (4-phenoxyphenyl) boronic acid and acrylic acid according to general scheme 3 using methods S1, S2, S3 and S4A. HPLC purity: 99%. MS: m/z=416 [M+H]$^+$. $^1$H NMR (CD$_3$OD) δ 8.27 (s, 1H), 7.12-7.45 (m, 9H), 6.25 (m, 2H), 5.73 (d, 1H), 4.37 (t, 1H), 4.12 (dd, 1H), 2.94 (dd, 1H), 3.71 (dd, 1H), 3.49 (t, 2H), 2.69 (m, 1H), 1.88 (m, 2H).

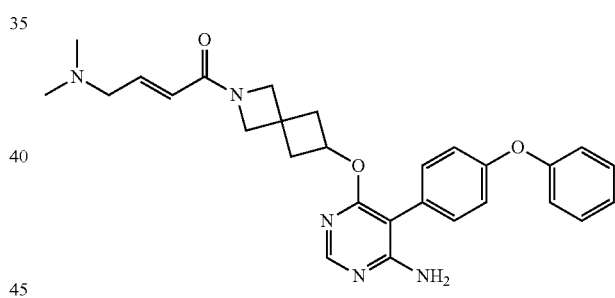

(E)-1-(6-(((6-amino-5-(4-phenoxyphenyl)pyrimidin-4-yl)oxy)-2-azaspiro[3.3]heptan-2-yl)-4-(dimethylamino)but-2-en-1-one (A105)

(E)-1-(6-(((6-amino-5-(4-phenoxyphenyl)pyrimidin-4-yl)oxy)-2-azaspiro[3.3]heptan-2-yl)-4-(dimethylamino)but-2-en-1-one was prepared from 5,6-dichloropyrimidin-4-amine, tert-butyl 6-hydroxyl-2-azaspiro[3.3]heptane-2-carboxylate, (4-phenoxyphenyl) boronic acid and (E)-4-(dimethylamino)but-2-enoic acid hydrochloride according to general scheme 3 using methods S1, S2, S3, and S4A. HPLC purity: 99%. MS: m/z=486 [M+H]$^+$. $^1$H NMR (CD$_3$OD) δ 8.28 (s, 1H), 7.18-7.45 (m, 9H), 6.63 (m, 1H), 6.45 (dd, 1H), 5.25 (m, 1H), 4.32 (d, 2H), 4.13 (d, 2H), 4.92 (t, 2H), 3.81 (m, 6H), 2.74 (m, 2H), 2.23 (m, 2H).

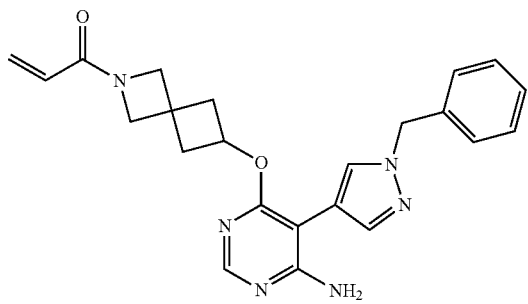 [SMILES: C=CC(=O)N1CC2(CC(Oc3ncnc(N)c3-c3cnn(Cc4ccccc4)c3)C2)C1]

1-(6-(((6-amino-5-(1-benzyl-1H-pyrazol-4-yl)pyrimidin-4-yl)oxy)-2-azaspiro[3.3]heptan-2-yl)prop-2-en-1-one (A106)

1-(6-(((6-amino-5-(1-benzyl-1H-pyrazol-4-yl)pyrimidin-4-yl)oxy)-2-azaspiro[3.3]heptan-2-yl)prop-2-en-1-one was prepared from 5,6-dichloropyrimidin-4-amine, tert-butyl 6-hydroxyl-2-azaspiro[3.3]heptane-2-carboxylate, (1-benzyl-1H-pyrazol-4-yl)boronic acid and acrylic acid according to general scheme 3 using methods S1, S2, S3, and S4A. HPLC purity: 95%. MS: m/z=417 [M+H]$^+$. $^1$H NMR (CD$_3$OD) δ 8.32 (s, 1H), 7.94 (s, 1H), 7.76 (s, 1H), 7.35 (m, 5H), 6.29 (m, 2H), 5.72 (m, 1H), 5.43 (s, 2H), 5.29 (m, 1H), 4.34 (d, 2H), 4.10 (d, 2H), 2.77 (m, 2H), 2.34 (m, 2H).

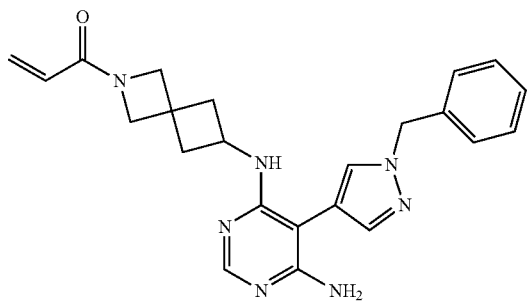 [SMILES: C=CC(=O)N1CC2(CC(Nc3ncnc(N)c3-c3cnn(Cc4ccccc4)c3)C2)C1]

1-(6-(((6-amino-5-(1-benzyl-1H-pyrazol-4-yl)pyrimidin-4-yl)amino)-2-azaspiro[3.3]heptan-2-yl)prop-2-en-1-one (A107)

1-(6-(((6-amino-5-(1-benzyl-1H-pyrazol-4-yl)pyrimidin-4-yl)amino)-2-azaspiro[3.3]heptan-2-yl)prop-2-en-1-one was prepared from 5,6-dichloropyrimidin-4-amine, tert-butyl 6-amino-2-azaspiro[3.3]heptane-2-carboxylate, (1-benzyl-1H-pyrazol-4-yl)boronic acid and acrylic acid according to general scheme 3 using methods S1, S2, S3, and S4A. HPLC purity: 98%. MS: m/z=416 [M+H]$^+$. $^1$H NMR (CD$_3$OD) δ 8.21 (s, 1H), 7.84 (s, 1H), 7.58 (s, 1H), 7.41 (m, 5H), 6.29 (m, 2H), 5.72 (m, 1H), 5.43 (s, 2H), 4.56 (s, 1H), 4.34 (d, 2H), 4.10 (d, 2H), 2.58 (m, 2H), 2.27 (m, 2H).

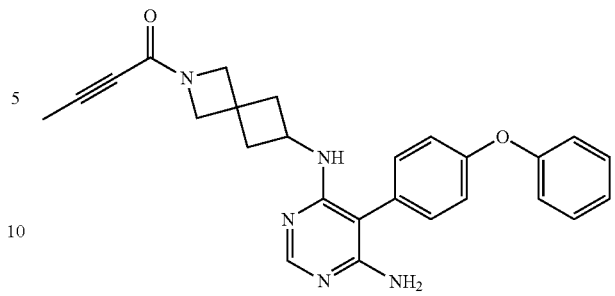

1-(6-(((6-amino-5-(4-phenoxyphenyl)pyrimidin-4-yl)amino)-2-azaspiro[3.3]heptan-2-yl)but-2-yn-1-one (A108)

1-(6-(((6-amino-5-(4-phenoxyphenyl)pyrimidin-4-yl)amino)-2-azaspiro[3.3]heptan-2-yl)but-2-yn-1-one was prepared from 5,6-dichloropyrimidin-4-amine, tert-butyl 6-amino-2-azaspiro[3.3]heptane-2-carboxylate, (4-phenoxyphenyl) boronic acid and but-2-ynoic acid according to general scheme 3 using methods S1, S2, S3, and S4A. HPLC purity: 99%. MS: m/z=440 [M+H]$^+$. $^1$H NMR (CD$_3$OD) δ 8.24 (s, 1H), 7.16-7.45 (m, 9H), 4.57 (s, 1H), 4.27 (d, 2H), 4.05 (d, 2H), 2.61 (m, 2H), 2.27 (m, 2H), 2.00 (m, 3H).

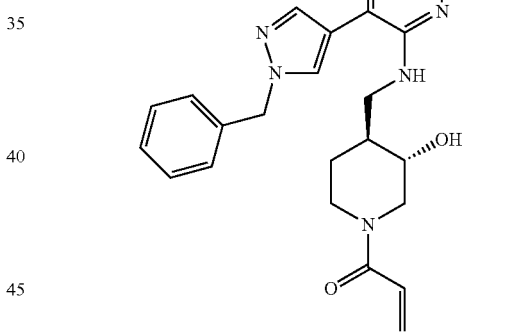

1-((3S,4S)-4-(((6-amino-5-(1-benzyl-1H-pyrazol-4-yl)pyrimidin-4-yl)amino)methyl)-3-hydroxypiperidin-1-yl)prop-2-en-1-one (A109)

1-((3S,4S)-4-(((6-amino-5-(1-benzyl-1H-pyrazol-4-yl)pyrimidin-4-yl)amino)methyl)-3-hydroxypiperidin-1-yl)prop-2-en-1-one was prepared from 5,6-dichloropyrimidin-4-amine, (3S,4S)-tert-butyl 4-(aminomethyl)-3-hydroxypiperidine-1-carboxylate, (1-benzyl-1H-pyrazol-4-yl)boronic acid and acrylic acid according to general scheme 3 using methods S1, S2, S3, and S4A. HPLC purity: 99%. MS: m/z=434 [M+H]$^+$. $^1$H NMR (CD$_3$OD) δ 8.22 (s, 1H), 7.84 (s, 1H), 7.60 (s, 1H), 7.40 (m, 5H), 6.76 (m, 1H), 6.21 (d, 1H), 5.74 (d, 1H), 5.43 (s, 2H), 4.53 (m, 1H), 4.08 (m, 1H), 3.61 (m, 2H), 3.03 (m, 1H), 2.72 (m, 1H), 1.89 (m, 1H), 1.72 (m, 2H), 1.21 (m, 1H), 1.01 (m, 1H).

101

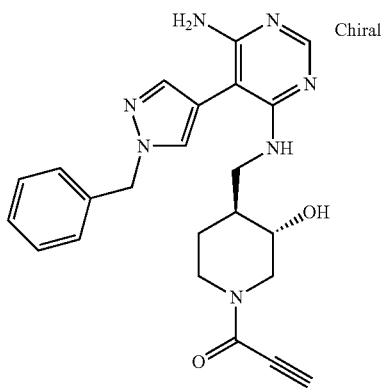 [SMILES: C#CC(=O)N1CC[C@@H](CNc2ncnc(N)c2-c2cnn(Cc3ccccc3)c2)[C@H](O)C1]

1-((3S,4S)-4-((((6-amino-5-(1-benzyl-1H-pyrazol-4-yl)pyrimidin-4-yl)amino)methyl)-3-hydroxypiperidin-1-yl)prop-2-yn-1-one (A110)

1-((3S,4S)-4-((((6-amino-5-(1-benzyl-1H-pyrazol-4-yl)pyrimidin-4-yl)amino)methyl)-3-hydroxypiperidin-1-yl)prop-2-yn-1-one was prepared from 5,6-dichloropyrimidin-4-amine, (1-benzyl-1H-pyrazol-4-yl)boronic acid, (3S,4S)-tert-butyl 4-(aminomethyl)-3-hydroxypiperidine-1-carboxylate and propiolic acid according to general scheme 3 using methods S1, S2, S3, and S4A. HPLC purity: 99%. MS: m/z=432 [M+H]$^+$. $^1$H NMR (CD$_3$OD) δ 8.22 (s, 1H), 7.84 (s, 1H), 7.69 (s, 1H), 7.40 (m, 5H), 4.43 (m, 2H), 4.01 (d, 1H), 3.62 (m, 1H), 3.61 (m, 1H), 3.29 (m, 1H), 3.03 (m, 1H), 2.60 (m, 1H), 1.76 (m, 3H), 1.24 (m, 1H), 1.21 (m, 1H).

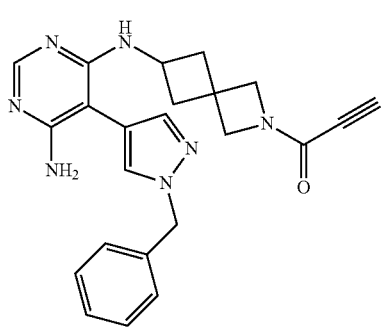 [SMILES: C#CC(=O)N1CC2(CC(Nc3ncnc(N)c3-c3cnn(Cc4ccccc4)c3)C2)C1]

1-(6-(((6-amino-5-(1-benzyl-1H-pyrazol-4-yl)pyrimidin-4-yl)amino)-2-azaspiro[3.3]heptan-2-yl)prop-2-yn-1-one (A111)

1-(6-(((6-amino-5-(1-benzyl-1H-pyrazol-4-yl)pyrimidin-4-yl)amino)-2-azaspiro[3.3]heptan-2-yl)prop-2-yn-1-one was prepared from 5,6-dichloropyrimidin-4-amine, (1-benzyl-1H-pyrazol-4-yl)boronic acid, tert-butyl 6-amino-2-azaspiro[3.3]heptane-2-carboxylate and propiolic acid according to general scheme 3 using methods S1, S2, S3, and S4A. HPLC purity: 95%. MS: m/z=414 [M+H]$^+$. $^1$H NMR (CD$_3$OD) δ 8.21 (s, 1H), 7.83 (s, 1H), 7.57 (s, 1H), 7.41 (m, 5H), 5.42 (s, 2H), 4.54 (s, 1H), 4.31 (d, 2H), 4.08 (d, 2H), 3.88 (d, 1H), 2.61 (m, 2H), 2.30 (m, 2H).

102

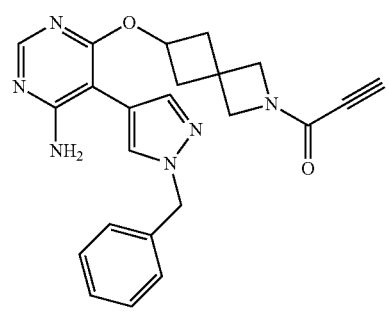 [SMILES: C#CC(=O)N1CC2(CC(Oc3ncnc(N)c3-c3cnn(Cc4ccccc4)c3)C2)C1]

1-(6-(((6-amino-5-(1-benzyl-1H-pyrazol-4-yl)pyrimidin-4-yl)oxy)-2-azaspiro[3.3]heptan-2-yl)prop-2-yn-1-one (A112)

1-(6-(((6-amino-5-(1-benzyl-1H-pyrazol-4-yl)pyrimidin-4-yl)oxy)-2-azaspiro[3.3]heptan-2-yl)prop-2-yn-1-one was prepared from 5,6-dichloropyrimidin-4-amine, (1-benzyl-1H-pyrazol-4-yl)boronic acid, tert-butyl 6-hydroxyl-2-azaspiro[3.3]heptane-2-carboxylate and propiolic acid according to general scheme 3 using methods S1, S2, S3, and S4A. HPLC purity: 95%. MS: m/z=415 [M+H]$^+$. $^1$H NMR (CD$_3$OD) δ 8.26 (s, 1H), 7.94 (s, 1H), 7.74 (s, 1H), 7.35 (m, 5H), 5.42 (s, 2H), 5.22 (m, 1H), 4.31 (d, 2H), 4.08 (d, 2H), 3.88 (d, 1H), 2.76 (m, 2H), 2.39 (m, 2H).

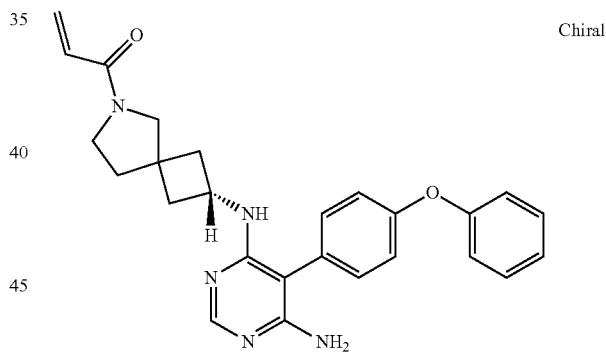

1-(2-(((6-amino-5-(4-phenoxyphenyl)pyrimidin-4-yl)amino)-6-azaspiro[3.4]octan-6-yl)prop-2-en-1-one (A113)

1-(2-(((6-amino-5-(4-phenoxyphenyl)pyrimidin-4-yl)amino)-6-azaspiro[3.4]octan-6-yl)prop-2-en-1-one was prepared from 5,6-dichloropyrimidin-4-amine, tert-butyl 2-amino-6-azaspiro[3.4]octane-6-carboxylate, (4-phenoxyphenyl) boronic acid and acrylic acid according to general scheme 3 using methods S1, S2, S3 and S4A. HPLC purity: 99%. MS: m/z=442 [M+H]$^+$. $^1$H NMR (CD$_3$OD) δ 8.25 (s, 1H), 7.16-7.47 (m, 9H), 6.50 (m, 1H), 6.24 (m, 1H), 5.73 (m, 1H), 4.71 (m, 1H), 3.60 (t, 1H), 3.52 (m, 2H), 3.41 (s, 1H), 2.34 (m, 1H), 2.11 (m, 3H), 1.97 (m, 1H).

103

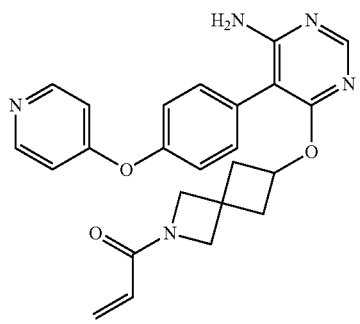 [SMILES: C=CC(=O)N1CC2(CC(Oc3ncnc(N)c3-c3ccc(Oc4ccncc4)cc3)C2)C1]

1-(6-((6-amino-5-(4-(pyridin-4-yloxy)phenyl)pyrimidin-4-yl)oxy)-2-azaspiro[3.3]heptan-2-yl)prop-2-en-1-one (A114)

1-(6-((6-amino-5-(4-(pyridin-4-yloxy)phenyl)pyrimidin-4-yl)oxy)-2-azaspiro[3.3]heptan-2-yl)prop-2-en-1-one was prepared from 5,6-dichloropyrimidin-4-amine, tert-butyl 6-hydroxyl-2-azaspiro[3.3]heptane-2-carboxylate, (4-(pyridin-4-yloxy)phenyl)boronic acid and acrylic acid according to general scheme 3 using methods S1, S2, S3, and S4A. HPLC purity: 99%. MS: m/z=430 [M+H]$^+$. $^1$H NMR (CD$_3$OD) δ 8.75 (m, 2H), 8.31 (m, 1H), 7.56 (m, 4H), 7.44 (m, 2H), 6.27 (m, 1H), 5.73 (m, 1H), 5.24 (m, 1H), 4.26 (d, 2H), 4.01 (d, 2H), 2.73 (m, 2H), 2.25 (m, 2H).

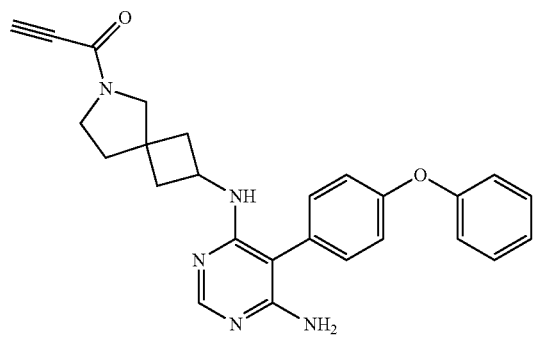 [SMILES: C#CC(=O)N1CCC2(CC(Nc3ncnc(N)c3-c3ccc(Oc4ccccc4)cc3)C2)C1]

1-(2-((6-amino-5-(4-phenoxyphenyl)pyrimidin-4-yl)amino)-6-azaspiro[3.4]octan-6-yl)prop-2-yn-1-one (A115)

1-(2-((6-amino-5-(4-phenoxyphenyl)pyrimidin-4-yl)amino)-6-azaspiro[3.4]octan-6-yl)prop-2-yn-1-one was prepared from 5,6-dichloropyrimidin-4-amine, tert-butyl 2-amino-6-azaspiro[3.4]octane-6-carboxylate, (4-phenoxyphenyl) boronic acid and propiolic acid according to general scheme 3 using methods S1, S2, S3, and S4A. HPLC purity: 99%. MS: m/z=440 [M+H]$^+$. $^1$H NMR (CD$_3$OD) δ 8.01 (s, 1H), 7.12-7.48 (m, 9H), 4.52 (t, 1H), 3.71 (t, 1H), 3.58 (s, 1H), 3.50 (dd, 1H), 2.33 (m, 2H), 2.05 (m, 2H), 1.96 (m, 2H), 1.47 (s, 2H).

104

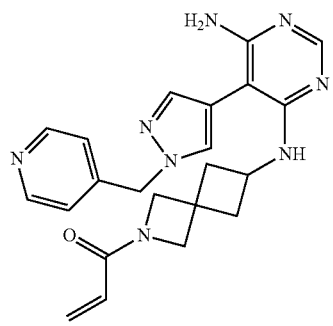 [SMILES: C=CC(=O)N1CC2(CC(Nc3ncnc(N)c3-c3cnn(Cc4ccncc4)c3)C2)C1]

1-(6-((6-amino-5-(1-(pyridin-4-ylmethyl)-1H-pyrazol-4-yl)pyrimidin-4-yl)amino)-2-azaspiro[3.3]heptan-2-yl)prop-2-en-1-one (A116)

1-(6-((6-amino-5-(1-(pyridin-4-ylmethyl)-1H-pyrazol-4-yl)pyrimidin-4-yl)amino)-2-azaspiro[3.3]heptan-2-yl)prop-2-en-1-one was prepared from 5,6-dichloropyrimidin-4-amine, tert-butyl 6-amino-2-azaspiro[3.3]heptane-2-carboxylate, (1-(pyridin-4-ylmethyl)-1H-pyrazol-4-yl) boronic acid and acrylic acid according to general scheme 3 using methods S1, S2, S3, and S4A. HPLC purity: 99%. MS: m/z=416 [M+H]$^+$. $^1$H NMR (CD$_3$OD) δ 8.77 (m, 2H), 8.23 (s, 1H), 8.00 (s, 1H), 7.88 (m, 2H), 7.68 (s, 1H), 6.26 (m, 2H), 5.75 (m, 3H), 4.54 (m, 1H), 4.27 (d, 2H), 4.11 (d, 2H), 2.59 (m, 2H), 2.26 (m, 2H).

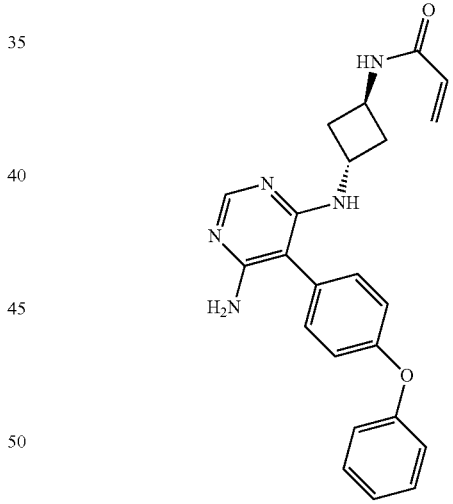

N-(1,3-trans-3-((6-amino-5-(4-phenoxyphenyl)pyrimidin-4-yl)amino)cyclobutyl)acrylamide (A117)

N-(1,3-trans-3-((6-amino-5-(4-phenoxyphenyl)pyrimidin-4-yl)amino)cyclobutyl)acrylamide was prepared from 5,6-dichloropyrimidin-4-amine, tert-butyl cis-3-aminocyclobutyl carbamate, (4-phenoxyphenyl) boronic acid and acrylic acid according to scheme 3 using methods S1, S2, S3, and S4A. HPLC purity: 99%. MS: m/z=402 [M+H]$^+$. $^1$H NMR (CD$_3$OD) δ 8.25 (s, 1H), 7.10-7.46 (m, 9H), 6.26 (m, 2H), 5.63 (d, 1H), 4.77 (m, 1H), 4.24 (m, 1H), 2.42 (m, 2H), 2.27 (m, 2H).

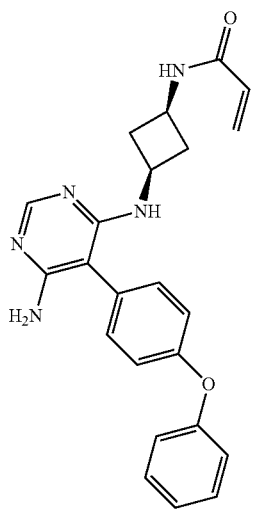 [SMILES: C=CC(=O)N[C@H]1C[C@@H](Nc2ncnc(N)c2-c2ccc(Oc3ccccc3)cc2)C1]

N-((1,3-cis-3-((6-amino-5-(4-phenoxyphenyl)py-
rimidin-4-yl)amino)cyclobutyl)acrylamide (A118)

N-((1,3-cis-3-((6-amino-5-(4-phenoxyphenyl)pyrimidin-4-yl)amino)cyclobutyl)acrylamide was prepared from 5,6-dichloropyrimidin-4-amine, tert-butyl trans-3-aminocyclobutyl carbamate, (4-phenoxyphenyl) boronic acid and acrylic acid according to general scheme 3 using methods S1, S2, S3, and S4A. HPLC purity 99%. MS: m/=402 [M+H]+. 1H NMR (CD3OD) δ 8.23 (s, 1H), 7.10-7.46 (m, 9H), 6.26 (m, 2H), 5.60 (d, 1H), 4.31 (m, 1H), 4.03 (m, 1H), 2.76 (m, 2H), 1.98 (m, 2H).

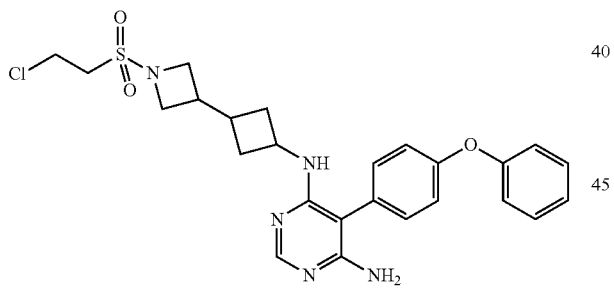

N'-(2-((2-chloroethyl)sulfonyl)-2-azaspiro[3.3]heptan-6-yl)-5-(4-phenoxyphenyl)pyrimidine-4,6-diamine (A119)

N'-(2-((2-chloroethyl)sulfonyl)-2-azaspiro[3.3]heptan-6-yl)-5-(4-phenoxyphenyl)pyrimidine-4,6-diamine (10.5 mg, 11.2%) was prepared from 5,6-dichloropyrimidin-4-amine, 6-amino-2-aza-spiro[3.3]heptane-2-carboxylic acid tert-butyl ester, (4-phenoxyphenyl)boronic acid and 2-chloro-ethanesulfonyl chloride according to general scheme 3 using methods S1, S2, S3, and S4C. HPLC purity 95%. MS: m/z=501 [M+H]+. 1H NMR (CD3OD) δ 8.24 (s, 1H), 7.10-7.47 (m, 9H), 6.70 (m, 1H), 6.19 (d, 1H), 6.01 (d, 1H), 4.62 (m, 1H), 3.58 (s, 2H), 3.13 (s, 2H), 2.37 (m, 2H), 1.81 (m, 2H).

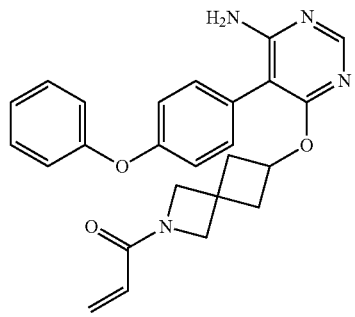 [SMILES: C=CC(=O)N1CC2(CC(Oc3ncnc(N)c3-c3ccc(Oc4ccccc4)cc3)C2)C1]

1-(6-((6-amino-5-(4-phenoxyphenyl)pyrimidin-4-yl)
oxy)-2-azaspiro[3.3]heptan-2-yl) prop-2-en-1-one
(A120)

1-(6-((6-amino-5-(4-phenoxyphenyl)pyrimidin-4-yl)oxy)-2-azaspiro[3.3]heptan-2-yl)prop-2-en-1-one was prepared from 5,6-dichloropyrimidin-4-amine, 6-hydroxyl-2-aza-spiro[3.3]heptane-2-carboxylic acid tert-butyl ester, (4-phenoxyphenyl) boronic acid and acryloyl chloride according to general scheme 3 using methods S1, S2, S3, and S4C. HPLC purity: 99%. MS: m/z=429 [M+H]+. 1H NMR (CD3OD) δ 8.36 (s, 1H), 7.09-7.45 (m, 9H), 6.25 (m, 2H), 5.74 (m, 1H), 5.28 (m, 1H), 4.33 (d, 2H), 4.09 (d, 2H), 2.74 (m, 2H), 2.32 (m, 2H).

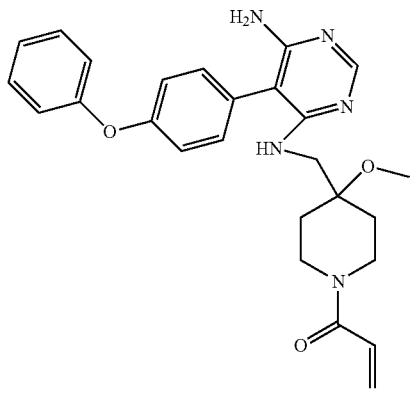 [SMILES: C=CC(=O)N1CCC(CNc2ncnc(N)c2-c2ccc(Oc3ccccc3)cc2)(OC)CC1]

1-(4-(((6-amino-5-(4-phenoxyphenyl)pyrimidin-4-yl)amino)methyl)-4-methoxypiperidin-1-yl)prop-2-en-1-one (A121)

1-(4-(((6-amino-5-(4-phenoxyphenyl)pyrimidin-4-yl)amino)methyl)-4-methoxypiperidin-1-yl)prop-2-en-1-one was prepared from 5,6-dichloropyrimidin-4-amine, 4-aminomethyl-4-methoxy-piperidine-1-carboxylic acid tert-butyl ester, (4-phenoxyphenyl) boronic acid and acryloyl chloride according to general scheme 3 using with method S1, S2, S3, and S4C. HPLC purity: 99%. MS: m/z=460 [M+H]+. 1H NMR (CD3OD) δ 8.28 (s, 1H), 7.13-7.43 (m, 9H), 6.77 (m, 1H), 6.17 (d, 1H), 5.75 (d, 1H), 4.27 (d, 1H), 3.85 (d, 1H), 3.62 (s, 2H), 3.83 (m, 1H), 3.22 (s, 3H), 3.04 (m, 1H), 1.79 (m, 2H), 1.44 (m, 2H).

107

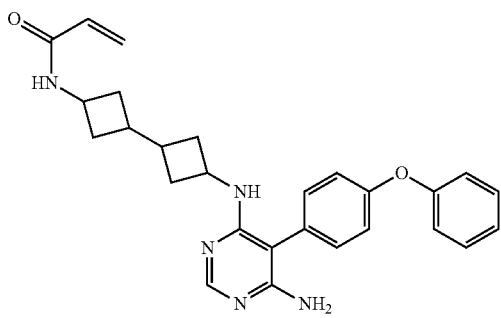 [SMILES: C=CC(=O)NC1CC(C2CC(Nc3ncnc(N)c3-c3ccc(Oc4ccccc4)cc3)C2)C1]

N-(6-(((6-amino-5-(4-phenoxyphenyl)pyrimidin-4-yl)
amino)spiro[3.3]heptan-2-yl)acrylamide (A122)

N-(6-(((6-amino-5-(4-phenoxyphenyl)pyrimidin-4-yl)
amino)spiro[3.3]heptan-2-yl)acrylamide was prepared from
5,6-dichloropyrimidin-4-amine, tert-butyl (6-aminospiro
[3.3]heptan-2-yl)carbamate, (4-phenoxyphenyl) boronic
acid and acryloyl chloride according to general scheme 3
using methods S1, S2, S3, and S4C. HPLC purity: 95%. MS:
m/z=442 [M+H]$^+$. $^1$H NMR (CD$_3$OD) δ 8.23 (s, 1H),
7.10-7.46 (m, 9H), 6.23 (m, 1H), 5.66 (m, 1H), 4.59 (m, 1H),
3.69 (m, 1H), 3.19 (d, 1H), 2.54 (m, 2H), 2.08-2.34 (m, 6H).

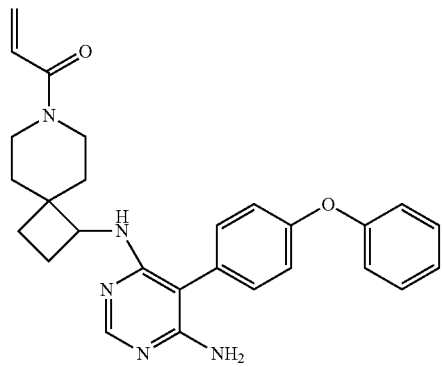 [SMILES: C=CC(=O)N1CCC2(CCC2Nc2ncnc(N)c2-c2ccc(Oc3ccccc3)cc2)CC1]

1-(1-(((6-amino-5-(4-phenoxyphenyl)pyrimidin-4-yl)
amino)-7-azaspiro[3.5]nonan-7-yl)prop-2-en-1-one
(A123)

1-(1-(((6-amino-5-(4-phenoxyphenyl)pyrimidin-4-yl)
amino)-7-azaspiro[3.5]nonan-7-yl)prop-2-en-1-one was
prepared from 5,6-dichloropyrimidin-4-amine, tert-butyl
1-amino-7-azaspiro[3.5]nonane-7-carboxylate, (4-phenoxy-
phenyl) boronic acid and acryloyl chloride according to
general scheme 3 using methods S1, S2, S3, and S4C. HPLC
purity: 99%. MS: m/z=456 [M+H]$^+$. $^1$H NMR (CD$_3$OD) δ
8.24 (s, 1H), 7.11-7.50 (m, 9H), 6.73 (m, 1H), 6.18 (d, 1H),
5.71 (d, 1H), 4.53 (m, 1H), 4.21 (m, 1H), 3.83 (m, 1H), 3.18
(m, 1H), 2.95 (m, 1H), 2.27 (m, 2H), 2.06 (m, 1H), 1.86 (m,
2H), 1.68 (m, 3H), 1.37 (m, 1H).

108

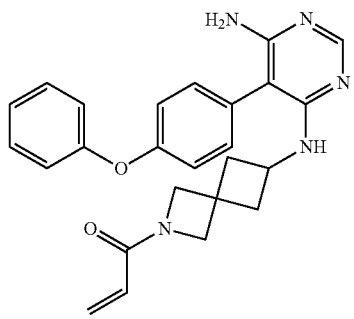 [SMILES: C=CC(=O)N1CC2(CC(Nc3ncnc(N)c3-c3ccc(Oc4ccccc4)cc3)C2)C1]

1-(6-(((6-amino-5-(4-phenoxyphenyl)pyrimidin-4-yl)
amino)-2-azaspiro[3.3]heptan-2-yl)prop-2-en-1-one
(A124)

1-(6-(((6-amino-5-(4-phenoxyphenyl)pyrimidin-4-yl)
amino)-2-azaspiro[3.3]heptan-2-yl)prop-2-en-1-one was
prepared from 5,6-dichloropyrimidin-4-amine, tert-butyl
6-amino-2-azaspiro[3.3]heptane-2-carboxylate, (4-phe-
noxyphenyl) boronic acid and acryloyl chloride according to
general scheme 3 using methods S1, S2, S3, and S4C. HPLC
purity: 99%. MS: m/z=428 [M+H]$^+$. $^1$H NMR (CD$_3$OD) δ
8.24 (s, 1H), 7.13-7.50 (m, 9H), 6.25 (m, 2H), 5.71 (m, 1H),
4.59 (m, 1H), 4.35 (d, 2H), 4.11 (d, 2H), 2.61 (m, 2H), 2.29
(m, 2H).

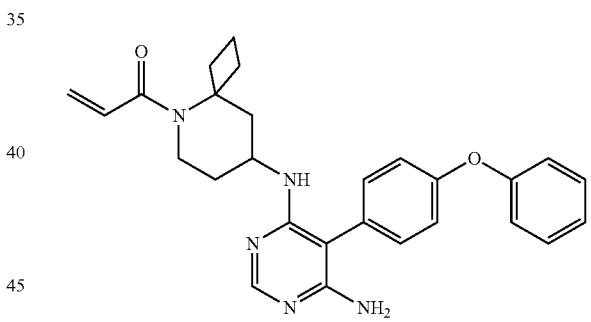

1-(84(6-amino-5-(4-phenoxyphenyl)pyrimidin-4-yl)
amino)-5-azaspiro[3.5]nonan-5-yl)prop-2-en-1-one
(A125)

1-(8-(((6-amino-5-(4-phenoxyphenyl)pyrimidin-4-yl)
amino)-5-azaspiro[3.5]nonan-5-yl)prop-2-en-1-one was
prepared from 5,6-dichloropyrimidin-4-amine, tert-butyl
8-amino-5-azaspiro[3.5]nonane-5-carboxylate, (4-phenoxy-
phenyl) boronic acid and acryloyl chloride according to
general scheme 3 using methods S1, S2, S3, and S4C. HPLC
purity: 95%. MS: m/z=456 [M+H]$^+$. $^1$H NMR (CD$_3$OD) δ
8.28 (s, 1H), 7.15-7.43 (m, 9H), 6.61 (m, 1H), 6.13 (d, 1H),
5.67 (d, 1H), 4.64 (m, 1H), 3.95 (m, 1H), 3.03 (m, 1H), 2.66
(m, 1H), 2.30 (m, 1H), 2.19 (m, 2H), 2.07 (m, 1H), 1.80 (m,
4H), 1.30 (m, 1H).

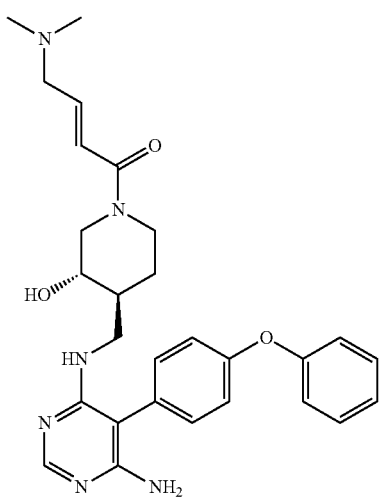 [SMILES: CN(C)C/C=C/C(=O)N1CC[C@@H](CNc2ncnc(N)c2-c2ccc(Oc3ccccc3)cc2)[C@H](O)C1]

(E)-1-((3S,4S)-4-(((6-amino-5-(4-phenoxyphenyl)pyrimidin-4-yl)amino)methyl)-3-hydroxypiperidin-1-yl)-4-(dimethylamino)but-2-en-1-one (A126)

(E)-1-((3S,4S)-4-(((6-amino-5-(4-phenoxyphenyl)pyrimidin-4-yl)amino)methyl)-3-hydroxypiperidin-1-yl)-4-(dimethylamino)but-2-en-1-one was prepared from 5,6-dichloropyrimidin-4-amine, (3S,4S)-tert-butyl 4-(aminomethyl)-3-hydroxypiperidine-1-carboxylate, (4-phenoxyphenyl) boronic acid and (E)-4-(dimethylamino)but-2-enoic acid hydrochloride according to general scheme 3 using methods S1, S2, S3, and S4D. HPLC purity: 99%. MS: m/z=503 [M+H]$^+$. $^1$H NMR (CD$_3$OD) δ 8.26 (s, 1H), 7.10-7.45 (m, 9H), 6.91 (d, 1H), 6.67 (m, 1H), 4.54 (m, 1H), 4.02 (m, 1H), 3.97 (m, 2H), 3.74 (m, 1H), 3.51 (m, 1H), 3.00 (m, 1H), 2.62 (m, 1H), 1.76 (m, 2H), 1.23 (m, 1H).

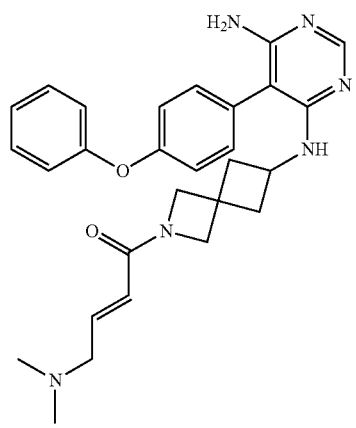 [SMILES: CN(C)C/C=C/C(=O)N1CC2(CC(Nc3ncnc(N)c3-c3ccc(Oc4ccccc4)cc3)C2)C1]

(E)-1-(6-(((6-amino-5-(4-phenoxyphenyl)pyrimidin-4-yl)amino)-2-azaspiro[3.3]heptan-2-yl)-4-(dimethylamino)but-2-en-1-one (A127)

(E)-1-(6-(((6-amino-5-(4-phenoxyphenyl)pyrimidin-4-yl)amino)-2-azaspiro[3.3]heptan-2-yl)-4-(dimethylamino)but-2-en-1-one was prepared from 5,6-dichloropyrimidin-4-amine, tert-butyl 6-amino-2-azaspiro[3.3]heptane-2-carboxylate, (4-phenoxyphenyl) boronic acid and (E)-4-(dimethylamino)but-2-enoic acid hydrochloride according to general scheme 3 using methods S1, S2, S3, and S4D. HPLC purity: 99%. MS: m/z=485 [M+H]$^+$. $^1$H NMR (CD$_3$OD) δ 8.24 (s, 1H), 7.13-7.50 (m, 9H), 6.75 (m, 1H), 6.46 (dd, 1H), 4.59 (m, 1H), 4.35 (d, 2H), 4.11 (d, 2H), 3.91 (m, 2H), 2.82 (d, 6H), 2.61 (m, 2H), 2.29 (m, 2H).

Example Compounds According to Formula (I) Synthesized Using Scheme 4 and Methods AA-GG

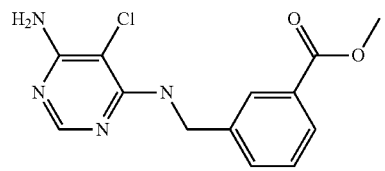 [SMILES: COC(=O)c1cccc(CNc2ncnc(N)c2Cl)c1]

3-((6-Amino-5-chloro-pyrimidin-4-ylamino)-methyl)-benzoic acid methyl ester (A128)

3-((6-Amino-5-chloro-pyrimidin-4-ylamino)-methyl)-benzoic acid methyl ester was prepared from 3-aminomethyl-benzoic acid methyl ester using Method AA (59% yield), MS: m/z=293 [M+H]$^+$. $^1$H-NMR (DMSO-d$_6$) δ 7.90 (s, 1H), 7.83 (d, 2H), 7.58 (d, 1H), 7.48 (t, 1H), 7.38 (t, 1H), 6.52 (bs, 2H), 4.62 (d, 2H), 3.85 (s, 3H).

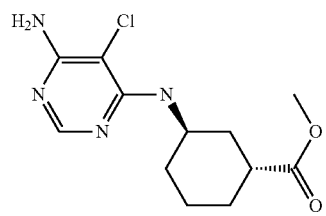 [SMILES: COC(=O)[C@@H]1CCC[C@@H](Nc2ncnc(N)c2Cl)C1]

Trans-3-(6-Amino-5-chloro-pyrimidin-4-ylamino)-cyclohexanecarboxylic acid methyl ester (A129)

Trans-3-(6-amino-5-chloro-pyrimidin-4-ylamino)-cyclohexanecarboxylic acid methyl ester was prepared from trans-methyl-3-aminocyclohexanecarboxylate hydrochloride using Method AA (53% yield). MS: m/z=285 [M+H]$^+$. $^1$H-NMR (DMSO-d$_6$) δ 7.86 (s, 1H), 6.46 (bs, 2H), 5.98 (d, 1H), 4.07-3.98 (s, 3H), 2.00-1.43 (bm, 9H).

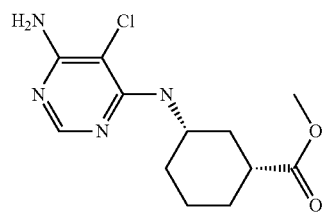 [SMILES: COC(=O)[C@@H]1CCC[C@H](Nc2ncnc(N)c2Cl)C1]

(1R,3S)-3-(6-Amino-5-chloro-pyrimidin-4-ylamino)-cyclohexanecarboxylic acid methyl ester (A130)

(1R,3S)-3-(6-amino-5-chloro-pyrimidin-4-ylamino)-cyclohexanecarboxylic acid methyl ester was prepared from (1R,3S)-3-amino-cyclohexanecarboxylic acid methyl ester hydrochloride using Method AA (42% yield). MS: m/z=285 [M+H]+. ¹H-NMR (DMSO-d₆) δ 7.86 (s, 1H), 6.45 (bs, 2H), 6.24 (d, 1H), 4.05-3.92 (bm, 1H), 3.59 (s, 3H), 2.47-2.41 (bm, 1H), 2.01-2.00 (bm, 1H), 1.83-1.77 (bm, 3H), 1.45-1.17 (bm, 4H).

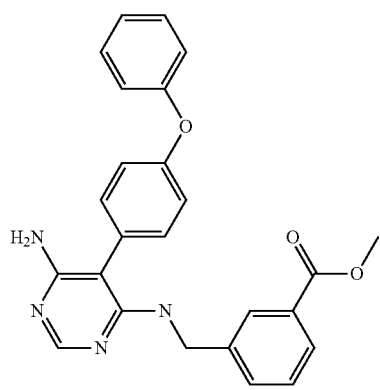 [SMILES: COC(=O)c1cccc(CNc2ncnc(N)c2-c2ccc(Oc3ccccc3)cc2)c1]

3-((6-Amino-5-(4-phenoxy-phenyl)-pyrimidin-4-ylamino)-methyl)-benzoic acid methyl ester (A131)

3-((6-amino-5-(4-phenoxy-phenyl)-pyrimidin-4-ylamino)-methyl)-benzoic acid methyl ester was prepared from 3-((6-amino-5-chloro-pyrimidin-4-ylamino)-methyl)-benzoic acid methyl ester using Method BB (63% yield). MS: m/z=427 [M+H]+. ¹H-NMR (DMSO-d₆) δ 7.92 (s, 1H), 7.85 (s, 1H), 7.79 (d, 1H), 7.53 (d, 1H), 7.45-7.40 (m, 3H), 7.29 (d, 2H), 7.19-7.11 (m, 5H), 6.17 (t, 1H), 5.52 (bs, 2H), 4.54 (d, 2H), 3.84 (s, 3H).

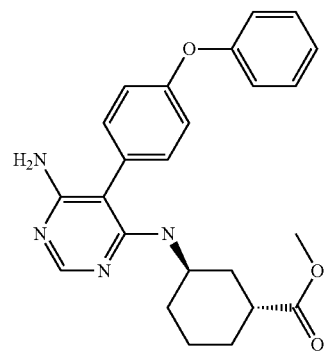 [SMILES: COC(=O)[C@@H]1CCC[C@@H](Nc2ncnc(N)c2-c2ccc(Oc3ccccc3)cc2)C1]

Trans-3-(6-amino-5-(4-phenoxyphenyl)-pyrimidin-4-ylamino)-cyclohexanecarboxylic acid methyl ester (A132)

Trans-3-(6-amino-5-(4-phenoxyphenyl)-pyrimidin-4-ylamino)-cyclohexanecarboxylic acid methyl ester was prepared from trans-3-(6-amino-5-chloro-pyrimidin-4-ylamino)-cyclohexanecarboxylic acid methyl ester using Method BB (63% yield). MS: m/z=419 [M+H]+. ¹H-NMR (DMSO-d₆) δ 7.97 (s, 1H), 7.45 (dd, 2H), 7.28 (d, 2H), 7.26 (m, 5H), 5.54 (bs, 1H), 4.60 (d, 1H), 4.11 (bd, 1H), 3.60 (s, 3H), 1.77-1.39 (bm, 9H).

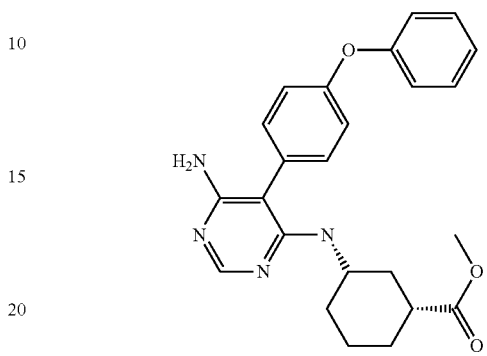

(1R,3S)-3-(6-Amino-5-(4-phenoxyphenyl)-pyrimidin-4-ylamino)-cyclohexanecarboxylic acid methyl ester (A133)

(1R,3S)-3-(6-amino-5-(4-phenoxyphenyl)-pyrimidin-4-ylamino)-cyclohexanecarboxylic acid methyl ester was prepared from (1R,3S)-3-(6-amino-5-chloro-pyrimidin-4-ylamino)-cyclohexanecarboxylic acid methyl ester using Method BB (85% yield), MS: m/z=419 [M+H]+.

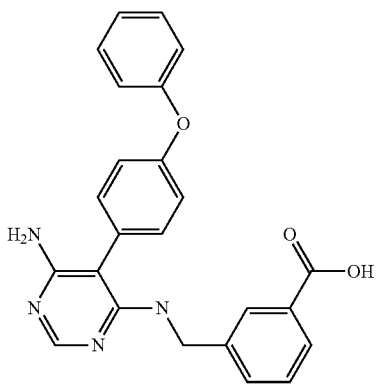

3-((6-Amino-5-(4-phenoxy-phenyl)-pyrimidin-4-ylamino)-methyl)-benzoic acid (134)

3-((6-amino-5-(4-phenoxy-phenyl)-pyrimidin-4-ylamino)-methyl)-benzoic acid was prepared from 3-((6-amino-5-(4-phenoxy-phenyl)-pyrimidin-4-ylamino)-methyl)-benzoic acid methyl ester using Method CC (104% yield). MS: m/z=413 [M+H]+. ¹H-NMR (DMSO-d₆) δ 12.35 (bs, 1H), 7.92 (s, 1H), 7.83 (s, 1H), 7.77 (d, 1H), 7.49 (d, 1H), 7.44 (dd, 3H), 7.29 (d, 2H), 7.18 (m, 5H), 6.15 (t, 3H), 5.51 (bs, 2H), 4.53 (d, 2H).

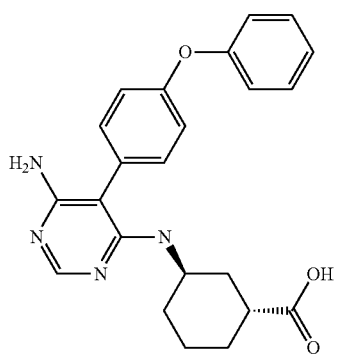 [SMILES: Nc1ncnc(N[C@@H]2CCC[C@@H](C(=O)O)C2)c1-c1ccc(Oc2ccccc2)cc1]

(1S,3S)-3-(6-Amino-5-(4-phenoxyphenyl)-pyrimidin-4-ylamino)-cyclohexanecarboxylic acid (A135)

(1S,3S)-3-(6-amino-5-(4-phenoxyphenyl)-pyrimidin-4-ylamino)-cyclohexanecarboxylic acid was prepared from (1S,3S)-3-(6-amino-5-(4-phenoxyphenyl)-pyrimidin-4-ylamino)-cyclohexanecarboxylic acid methyl ester using Method CC (83% yield). MS: m/z=405 [M+H]$^+$. $^1$H-NMR (DMSO-d$_6$) δ12.06 (bs, 1H), 7.97 (s, 1H), 7.44 (t, 2H), 7.28 (d, 2H), 7.19 (m, 5H), 5.54 (bs, 2H), 4.57 (d, 1H), 4.12 (bs, 1H), 2.40 (bs, 1H), 1.77-1.30 (bm, 8H).

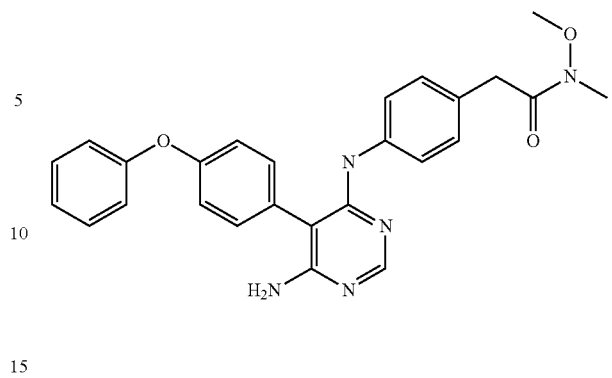

(4-(6-Amino-5-(4-phenoxyphenyl)-pyrimidin-4-ylamino)-phenyl)-N-methoxy-N-methyl-acetamide (A137)

(4-(6-Amino-5-(4-phenoxyphenyl)-pyrimidin-4-ylamino)-phenyl)-N-methoxy-N-methyl-acetamide was prepared from (4-(6-Amino-5-(4-phenoxyphenyl)-pyrimidin-4-ylamino)-phenyl)-acetic acid using Method DD (51% yield). MS: m/z=456 [M+H]$^+$. $^1$H-NMR (DMSO-d$_6$) δ 8.05 (s, 1H), 7.45 (t, 4H), 7.34 (d, 2H), 7.19 (s, 1H), 7.16 (d, 5H), 7.09 (d, 2H), 5.76 (bs, 2H), 3.66 (s, 3H), 3.64 (s, 2H), 3.10 (s, 3H).

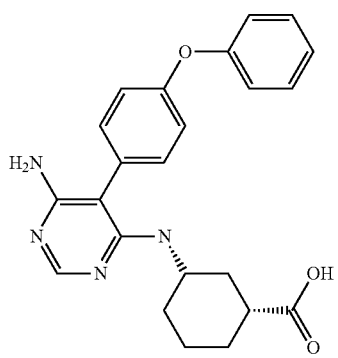

(1R,3S)-3-(6-Amino-5-(4-phenoxyphenyl)-pyrimidin-4-ylamino)-cyclohexanecarboxylic acid (A136)

(1R,3S)-3-(6-amino-5-(4-phenoxyphenyl)-pyrimidin-4-ylamino)-cyclohexanecarboxylic acid was prepared from (1R,3S)-3-(6-amino-5-(4-phenoxyphenyl)-pyrimidin-4-ylamino)-cyclohexanecarboxylic acid methyl ester using Method CC (71% yield). MS: m/z=405 [M+H]$^+$. $^1$H-NMR (DMSO-d$_6$) δ 11.99 (bs, 1H), 8.24 (s, 1H), 7.47 (t, 2H), 7.26-7.13 (bm, 6H), 6.48 (bs, 2H), 6.10 (bs, 1H), 4.07-4.01 (bm, 1H), 2.32-2.26 (bm, 1H), 1.84-1.71 (bm, 3H), 1.40-1.10 (bm, 5H).

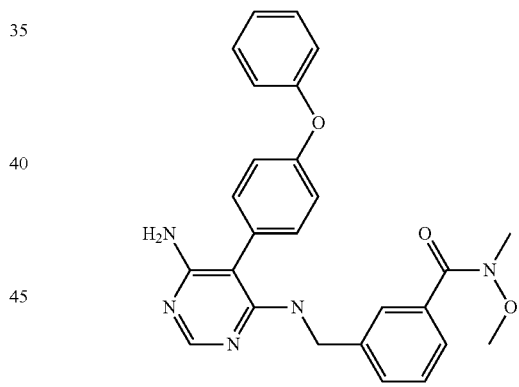

3-((6-Amino-5-(4-phenoxy-phenyl)-pyrimidin-4-ylamino)-methyl)-N-methoxy-N-methyl-benzamide (A138)

3-((6-amino-5-(4-phenoxy-phenyl)-pyrimidin-4-ylamino)-methyl)-N-methoxy-N-methyl-benzamide was prepared from 3-((6-amino-5-(4-phenoxy-phenyl)-pyrimidin-4-ylamino)-methyl)-benzoic acid using Method DD (50% yield). MS: m/z=456 [M+H]$^+$. $^1$H-NMR (DMSO-d$_6$) δ 7.96 (s, 1H), 7.44 (m, 4H), 7.36 (d, 2H), 7.26 (d, 2H), 7.14 (m, 5H), 6.11 (t, 1H), 5.50 (bs, 1H), 4.52 (d, 2H), 3.50 (s, 3H), 3.23 (s, 3H).

115

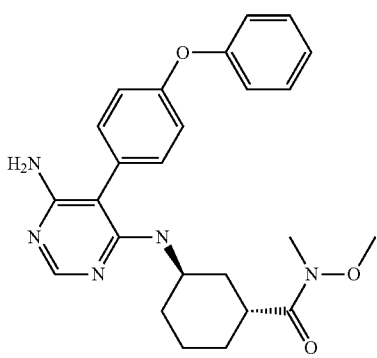 [SMILES: CON(C)C(=O)[C@@H]1CCC[C@@H](Nc2ncnc(N)c2-c2ccc(Oc3ccccc3)cc2)C1]

(1S,3S)-3-(6-Amino-5-(4-phenoxyphenyl)-pyrimidin-4-ylamino)-cyclohexanecarboxylic acid methoxy-methyl-amide (A139)

(1S,3S)-3-(6-amino-5-(4-phenoxyphenyl)-pyrimidin-4-ylamino)-cyclohexanecarboxylic acid methoxy-methyl-amide was prepared from (1S,3S)-3-(6-amino-5-(4-phenoxyphenyl)-pyrimidin-4-ylamino)-cyclohexanecarboxylic acid using Method DD (43% yield). MS: m/z=448 [M+H]⁺. ¹H-NMR (DMSO-d₆) □δ 7.98 (s, 1H), 7.45 (t, 2H), 7.31 (d, 2H), 7.20 (t, 3H), 7.11 (d, 2H), 5.76 (s, 1H), 5.61 (bs, 2H), 3.50 (s, 3H), 3.04 (s, 3H), 1.74-1.19 (bm, 10H).

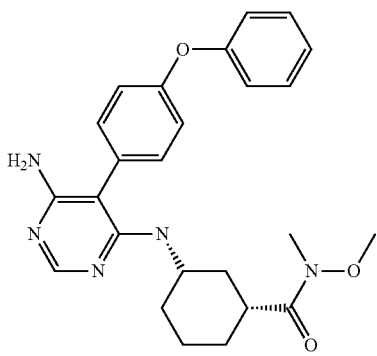

(1R,3S)-3-(6-Amino-5-(4-phenoxyphenyl)-pyrimidin-4-ylamino)-cyclohexanecarboxylic acid methoxy-methyl-amide (A140)

(1R,3S)-3-(6-amino-5-(4-phenoxyphenyl)-pyrimidin-4-ylamino)-cyclohexanecarboxylic acid methoxy-methyl-amide was prepared from (1R,3S)-3-(6-amino-5-(4-phenoxyphenyl)-pyrimidin-4-ylamino)-cyclohexanecarboxylic acid using Method DD (84% yield). MS: m/z=448 [M+H]⁺. ¹H-NMR (DMSO-d₆) □δ 7.96 (s, 4H), 7.45 (t, 2H), 7.22-7.09 (m, 5H), 5.46 (bs, 2H), 3.99 (bs, 2H), 3.68 (s, 3H), 3.31 (s, 3H), 1.80-1.64 (bm, 3H), 1.61 (bd, 1H), 1.38-1.09 (bm, 4H).

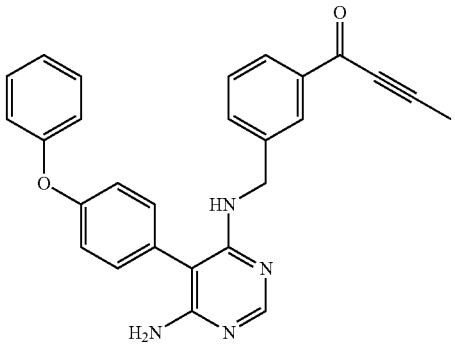 [SMILES: CC#CC(=O)c1cccc(CNc2ncnc(N)c2-c2ccc(Oc3ccccc3)cc2)c1]

1-(3-((6-Amino-5-(4-phenoxyphenyl)-pyrimidin-4-ylamino)-methyl)-phenyl)-but-2-yn-1-one (A141)

1-(3-((6-amino-5-(4-phenoxyphenyl)-pyrimidin-4-ylamino)-methyl)-phenyl)-but-2-yn-1-one was prepared from using 3-((6-amino-5-(4-phenoxy-phenyl)-pyrimidin-4-ylamino)-methyl)-N-methoxy-N-methyl-benzamide Method FF (13% yield). MS: m/z=435 [M+H]⁺. ¹H-NMR (DMSO-d₆) □δ 8.34 (s, 1H), 7.97 (t, 2H), 7.60 (d, 2H), 7.55 (t, 1H), 7.47 (t, 2H), 7.34 (d, 2H), 7.22 (t, 3H), 7.14 (d, 2H), 7.00 (bs, 2H), 4.46 (d, 2H), 2.20 (s, 3H). ccc

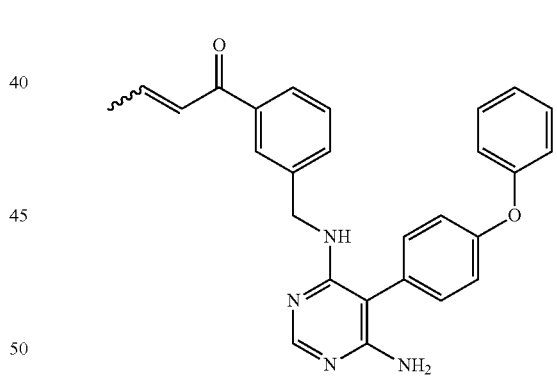

1-(3-((6-Amino-5-(4-phenoxyphenyl)-pyrimidin-4-ylamino)-methyl)-phenyl)-but-2-en-1-one (A142)

1-(3-((6-amino-5-(4-phenoxyphenyl)-pyrimidin-4-ylamino)-methyl)-phenyl)-but-2-en-1-one was prepared from 3-((6-amino-5-(4-phenoxy-phenyl)-pyrimidin-4-ylamino)-methyl)-N-methoxy-N-methyl-benzamide using Method EE (20% yield). MS: m/z=437 [M+H]⁺. ¹H-NMR (DMSO-d₆) □δ 8.33 (s, 1H), 7.86 (bt, 2H), 7.56-7.43 (m, 5H), 7.34 (d, 2H), 7.22-7.08 (m, 6H), 7.01 (m, 3H), 4.65 (d, 2H), 1.98 (d, 3H).

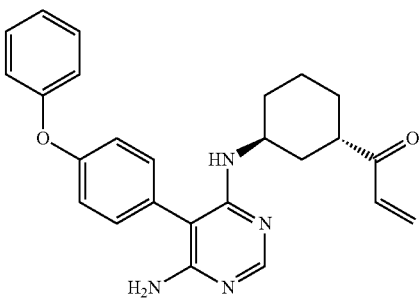 [SMILES: C=CC(=O)[C@H]1CCC[C@H](Nc2ncnc(N)c2-c2ccc(Oc3ccccc3)cc2)C1]

1-((1S,3S)-3-(6-Amino-5-(4-phenoxyphenyl)-pyrimidin-4-ylamino)-cyclohexyl)-propenone (A143)

1-((1S,3S)-3-(6-Amino-5-(4-phenoxyphenyl)-pyrimidin-4-ylamino)-cyclohexyl)-propenone was prepared from (1S,3S)-3-(6-Amino-5-(4-phenoxyphenyl)-pyrimidin-4-ylamino)-cyclohexanecarboxylic acid methoxy-methyl-amide using Method GG (24 yield). MS: m/z=415 [M+H]$^+$. $^1$H-NMR (DMSO-d$_6$) □δ 8.35 (s, 1H), 7.47 (t, 2H), 7.32 (d, 2H), 7.21-7.13 (m, 5H), 6.91 (bs, 2H), 6.56 (dd, 1H), 6.21 (d, 1H), 5.83 (d, 1H), 4.28 (bs, 1H), 3.00 (t, 1H), 1.85-1.38 (bm, 9H).

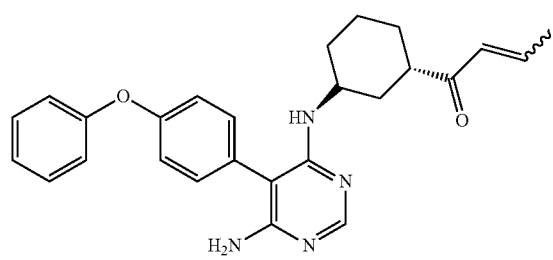

1-((1S,3S)-3-(6-Amino-5-(4-phenoxyphenyl)-pyrimidin-4-ylamino)-cyclohexyl)-but-2-en-1-one (A144)

1-((1S,3S)-3-(6-amino-5-(4-phenoxyphenyl)-pyrimidin-4-ylamino)-cyclohexyl)-but-2-en-1-one was prepared from (1S,3S)-3-(6-amino-5-(4-phenoxyphenyl)-pyrimidin-4-ylamino)-cyclohexanecarboxylic acid methoxy-methyl-amide using Method EE (35% yield). MS: m/z=429 [M+H]$^+$. $^1$H-NMR (DMSO-d$_6$) δ 8.35 (s, 1H), 7.47 (t, 2H), 7.32 (d, 2H), 7.23-7.13 (m, 5H), 6.94 (bs, 2H), 6.84 (m, 1H), 6.28/6.32 (s, 1H), 6.24 (bs, 1H), 4.29 (bs, 1H), 2.90 (t, 1H), 1.87 (d, 3H), 1.49-1.35 (m, 8H).

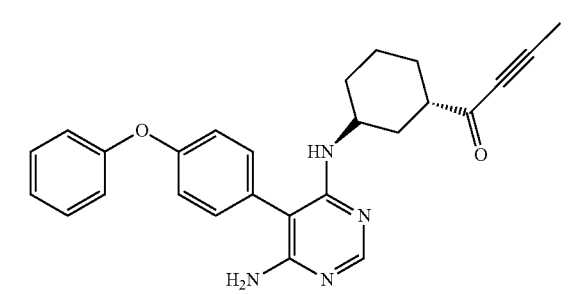

1-((1S,3S)-3-(6-Amino-5-(4-phenoxyphenyl)-pyrimidin-4-ylamino)-cyclohexyl)-but-2-yn-1-one (A145)

1-((1S,3S)-3-(6-amino-5-(4-phenoxyphenyl)-pyrimidin-4-ylamino)-cyclohexyl)-but-2-yn-1-one was prepared from (1S,3S)-3-(6-A=amino-5-(4-phenoxyphenyl)-pyrimidin-4-ylamino)-cyclohexanecarboxylic acid methoxy-methyl-amide using Method FF (44% yield). MS: m/z=427 [M+H]$^+$. $^1$H-NMR (DMSO-d$_6$) □δ 8.35 (s, 1H), 7.48 (t, 2H), 7.30 (d, 2H), 7.23-7.13 (bm, 5H), 6.91 (bs, 2H), 6.36 (bs, 1H), 4.16 (bs, 1H), 2.75 (t, 1H), 2.08-1.25 (bm, 12H).

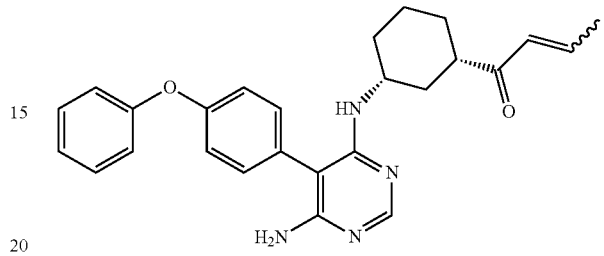

1-((1S,3R)-3-(6-Amino-5-(4-phenoxyphenyl)-pyrimidin-4-ylamino)-cyclohexyl)-but-2-en-1-one (A146)

1-((1S,3R)-3-(6-amino-5-(4-phenoxyphenyl)-pyrimidin-4-ylamino)-cyclohexyl)-but-2-en-1-one was prepared from (1S,3R)-3-(6-amino-5-(4-phenoxyphenyl)-pyrimidin-4-ylamino)-cyclohexanecarboxylic acid methoxy-methyl-amide using Method EE (23% yield). MS: m/z=429 [M+H]$^+$. $^1$H-NMR (DMSO-d$_6$) □δ 8.35 (s, 1H), 7.47 (t, 2H), 7.47-7.13 (m, 6H), 6.90-6.85 (bm, 3H), 6.68 (bd, 1H), 6.22 (ss, 1H), 4.11 (bs, 1H), 2.79 (bm, 1H), 1.88 (d, 3H), 1.74 (bs, 4H), 1.46-1.00 (bm, 5H).

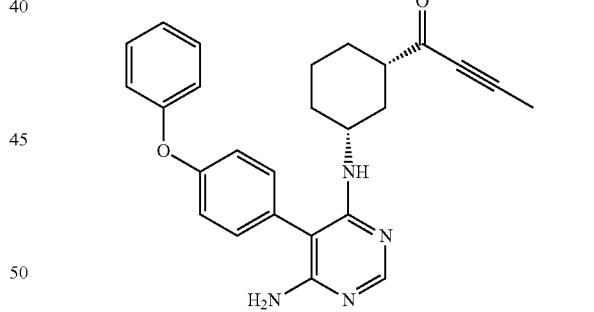

1-((1S,3R)-3-(6-amino-5-(4-phenoxyphenyl)-pyrimidin-4-ylamino)-cyclohexyl)-but-2-yn-1-one (A147)

1-((1S,3R)-3-(6-amino-5-(4-phenoxyphenyl)-pyrimidin-4-ylamino)-cyclohexyl)-but-2-yn-1-one was prepared from (1S,3R)-3-(6-amino-5-(4-phenoxyphenyl)-pyrimidin-4-ylamino)-cyclohexanecarboxylic acid methoxy-methyl-amide using Method FF (31% yield). MS: m/z=427 [M+H]$^+$. $^1$H-NMR (DMSO-d$_6$) δ 8.35 (s, 1H), 7.47 (t, 2H), 7.27 (d, 2H), 7.22 (t, 3H), 7.17 (m, 4H), 6.92 (bs, 2H), 6.67 (d, 1H), 4.09 (bs, 2H), 2.07 (s, 3H), 1.95 (bm, 2H), 1.79-1.70 (bm, 2H), 1.44-1.25 (bm, 3H), 1.08-1.14 (bm, 1H).

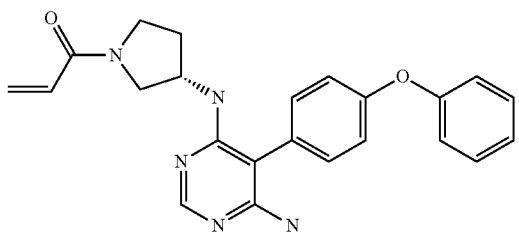 [SMILES: C=CC(=O)N1CC[C@H](Nc2ncnc(N)c2-c2ccc(Oc3ccccc3)cc2)C1]

(S)-1-(3-((6-amino-5-(4-phenoxyphenyl)pyrimidin-4-yl)amino)pyrrolidin-1-yl)prop-2-en-1-one (A148)

(S)-1-(3-((6-amino-5-(4-phenoxyphenyl)pyrimidin-4-yl)amino)pyrrolidin-1-yl)prop-2-en-1-one was prepared from 5,6-dichloropyrimidin-4-amine, (S)-tert-butyl 3-aminopyrrolidine-1-carboxylate, (4-phenoxyphenyl)boronic acid, and acryloyl chloride using methods B, C, D and F. HPLC: 100%. MS: m/z=402 [M+H]$^+$.

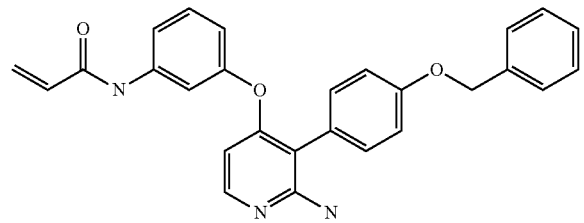 [SMILES: C=CC(=O)Nc1cccc(Oc2ccnc(N)c2-c2ccc(OCc3ccccc3)cc2)c1]

N-(3-((2-amino-3-(4-(benzyloxy)phenyl)pyridin-4-yl)oxy)phenyl)acrylamide (A149)

N-(3-((2-amino-3-(4-(benzyloxy)phenyl)pyridin-4-yl)oxy)phenyl)acrylamide was prepared from 4-chloro-3-iodopyridin-2-amine, 3-aminophenol, (4-(benzyloxy)phenyl)boronic acid, and acryloyl chloride using methods A, C, and F. HPLC: 100%. MS: m/z=438 [M+H]$^+$. $^1$H-NMR (DMSO-D6) δ 10.36 (s, 1H), 7.92 (d, 1H), 7.64 (s, 1H), 7.47-7.32 (m, 11H), 7.16 (d, 2H), 6.86 (m, 1H), 6.40 (dd, 1H), 6.33 (d, 1H), 6.24 (d, 1H), 5.77 (d, 1H), 5.13 (s, 2H).

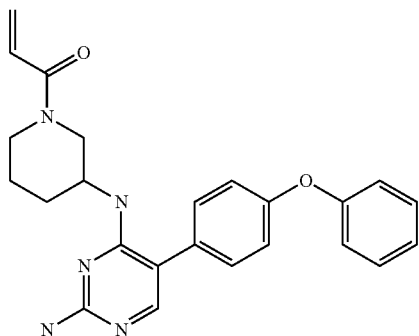 [SMILES: C=CC(=O)N1CCCC(Nc2nc(N)ncc2-c2ccc(Oc3ccccc3)cc2)C1]

1-(3-((2-amino-5-(4-phenoxyphenyl)pyrimidin-4-yl)amino)piperidin-1-yl)prop-2-en-1-one (A150)

1-(3-((2-amino-5-(4-phenoxyphenyl)pyrimidin-4-yl)amino)piperidin-1-yl)prop-2-en-1-one was prepared from 5-bromo-4-chloropyrimidin-2-amine, tert-butyl 3-aminopiperidine-1-carboxylate, (4-phenoxyphenyl)boronic acid, and acryloyl chloride using methods B, C, D and F. HPLC: 97%. MS: m/z=416 [M+H]$^+$.

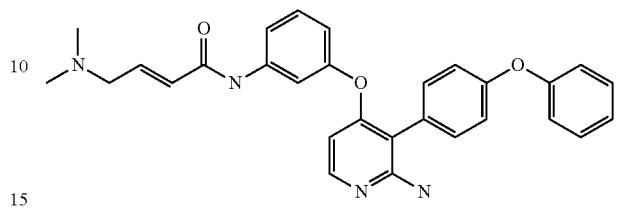

(E)-N-(3-((2-amino-3-(4-phenoxyphenyl)pyridin-4-yl)oxy)phenyl)-4-(dimethylamino)but-2-enamide (A151)

(E)-N-(3-((2-amino-3-(4-phenoxyphenyl)pyridin-4-yl)oxy)phenyl)-4-(dimethylamino)but-2-enamide was prepared from 4-chloro-3-iodopyridin-2-amine, 3-aminophenol, (4-phenoxyphenyl)boronic acid, and (E)-4-(dimethylamino)but-2-enoic acid hydrochloride using methods A, C, and E. HPLC: 100%. MS: m/z=481 [M+H]$^+$. $^1$H-NMR (DMSO-D6) δ 10.51 (s, 1H), 9.88 (broad s, 1H), 7.95 (d, 1H), 7.61 (s, 1H), 7.43-7.32 (m, 8H), 7.17 (t, 1H), 7.12-7.08 (m, 4H), 6.89 (s, 1H), 6.72 (m, 1H), 6.42 (d, 1H), 6.32 (d, 1H), 3.93 (d, 2H), 2.79 (s, 6H).

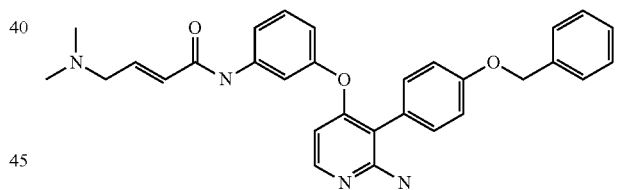

(E)-N-(3-((2-amino-3-(4-(benzyloxy)phenyl)pyridin-4-yl)oxy)phenyl)-4-(dimethylamino)but-2-enamide (A152)

(E)-N-(3-((2-amino-3-(4-(benzyloxy)phenyl)pyridin-4-yl)oxy)phenyl)-4-(dimethylamino)but-2-enamide was prepared from 4-chloro-3-iodopyridin-2-amine, 3-aminophenol, (4-(benzyloxy)phenyl)boronic acid, and (E)-4-(dimethylamino)but-2-enoic acid hydrochloride using methods A, C, and E. HPLC: 100%. MS: m/z=495 [M+H]$^+$. $^1$H-NMR (DMSO-D6) δ 10.51 (s, 1H), 9.90 (broad s, 1H), 7.92 (d, 1H), 7.59 (s, 1H), 7.47-7.27 (m, 11H), 7.16 (d, 2H), 6.88 (s, 1H), 6.72 (m, 1H), 6.42 (d, 1H), 6.30 (d, 1H), 5.13 (s, 2H), 3.93 (d, 2H), 2.79 (s, 6H).

121

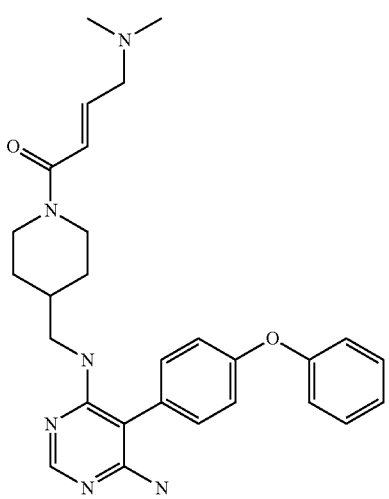 [SMILES: CN(C)C/C=C/C(=O)N1CCC(CNc2ncnc(N)c2-c2ccc(Oc3ccccc3)cc2)CC1]

(E)-1-(4-(((6-amino-5-(4-phenoxyphenyl)pyrimidin-4-yl)amino)methyl)piperidin-1-yl)-4-(dimethylamino)but-2-en-1-one (A153)

(E)-1-(4-(((6-amino-5-(4-phenoxyphenyl)pyrimidin-4-yl)amino)methyl)piperidin-1-yl)-4-(dimethylamino)but-2-en-1-one was prepared from 5,6-dichloropyrimidin-4-amine, tert-butyl 4-(aminomethyl)piperidine-1-carboxylate, (4-phenoxyphenyl)boronic acid, and (E)-4-(dimethylamino)but-2-enoic acid hydrochloride using methods B, C, D, and E. HPLC: 100%. MS: m/z=487 [M+H]$^+$.

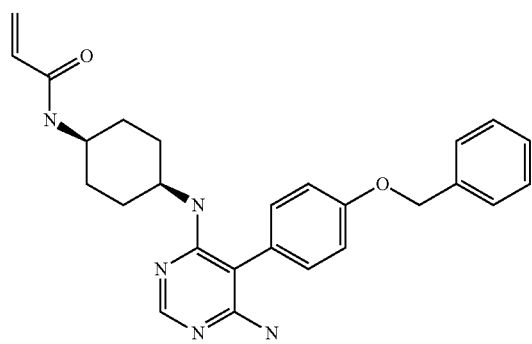 [SMILES: C=CC(=O)N[C@H]1CC[C@@H](Nc2ncnc(N)c2-c2ccc(OCc3ccccc3)cc2)CC1]

N-cis-4-((6-amino-5-(4-(benzyloxy)phenyl)pyrimidin-4-yl)amino)cyclohexyl)acrylamide (A154)

N-cis-4-((6-amino-5-(4-(benzyloxy)phenyl)pyrimidin-4-yl)amino)cyclohexyl)acrylamide was prepared from 5,6-dichloropyrimidin-4-amine, tert-butyl-(cis-4-aminocyclohexyl)carbamate, (4-(benzyloxy)phenyl)boronic acid, and acryloyl chloride using method B, C, D, and F. HPLC: 99%. MS: m/z=444 [M+H]$^+$. $^1$H-NMR (DMSO-D6) δ 8.33 (s, 1H), 7.78 (d, 1H), 7.51 (d, 2H), 7.43 (t, 2H), 7.37 (t, 1H),

122

7.25 (s, 4H), 6.81 (broad s, 2H), 6.27 (dd, 1H), 6.06 (d, 1H), 5.79 (broad s, 1H), 5.55 (d, 1H), 5.16 (s, 2H), 4.00 (s, 1H), 3.81 (s, 1H), 1.56 (s, 8H).

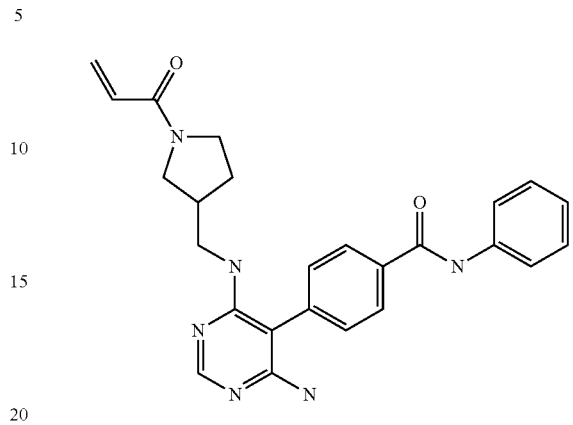

4-(4-(((1-acryloylpyrolidin-3-yl)methyl)amino)-6-aminopyrimidin-5-yl)-N-phenylbenzamide (A155)

4-(4-(((1-acryloylpyrrolidin-3-yl)methyl)amino)-6-aminopyrimidin-5-yl)-N-phenylbenzamide was prepared from 5,6-dichloropyrimidin-4-amine, tert-butyl 3-(aminomethyl)pyrrolidine-1-carboxylate, N-phenyl-4-(4,4,5,5-tetramethyl-1,3,2-dioxaborolan-2-yl)benzamide, and acryloyl chloride using methods B, C, D, and F. HPLC: 100%. MS: m/z=443 [M+H]$^+$.

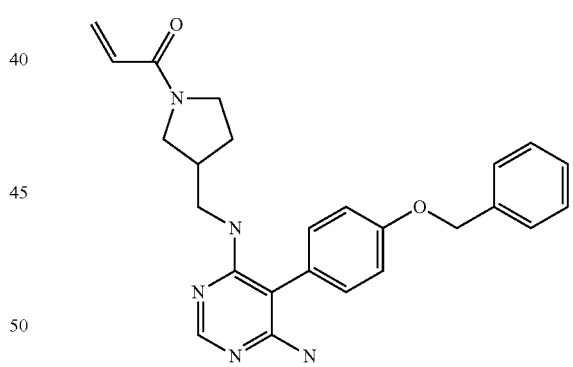

1-(3-(((6-amino-5-(4-(benzyloxy)phenyl)pyrimidin-4-yl)amino)methyl)pyrrolidin-1-yl)prop-2-en-1-one (A156)

1-(3-(((6-amino-5-(4-(benzyloxy)phenyl)pyrimidin-4-yl)amino)methyl)pyrrolidin-1-yl)prop-2-en-1-one was prepared from 5,6-dichloropyrimidin-4-amine, tert-butyl 3-(aminomethyl)pyrrolidine-1-carboxylate, (4-(benzyloxy)phenyl)boronic acid, and acryloyl chloride using methods B, C, D, and F. HPLC: 97%. MS: m/z=430 [M+H]$^+$.

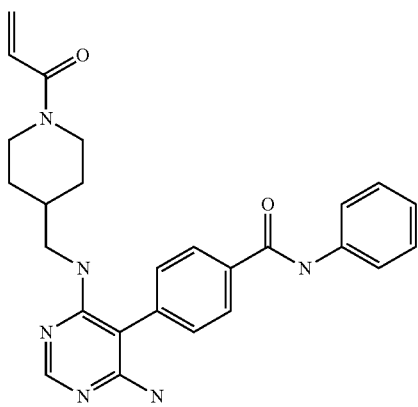 [SMILES: C=CC(=O)N1CCC(CNc2ncnc(N)c2-c2ccc(C(=O)Nc3ccccc3)cc2)CC1]

4-(4-(((1-acryloylpiperidin-4-yl)methyl)amino)-6-aminopyrimidin-5-yl)-N-phenylbenzamide (A157)

4-(4-(((1-acryloylpiperidin-4-yl)methyl)amino)-6-aminopyrimidin-5-yl)-N-phenylbenzamide was prepared from 5,6-dichloropyrimidin-4-amine, tert-butyl 4-(aminomethyl)piperidine-1-carboxylate, N-phenyl-4-(4,4,5,5-tetramethyl-1,3,2-dioxaborolan-2-yl)benzamide and acryloylchloride using methods B, C, D and F. HPLC: 99%. MS: m/z=457 [M+H]$^+$.

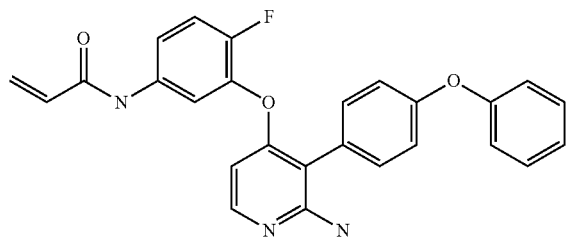 [SMILES: C=CC(=O)Nc1ccc(F)c(Oc2ccnc(N)c2-c2ccc(Oc3ccccc3)cc2)c1]

N-(3-((2-amino-3-(4-phenoxyphenyl)pyridin-4-yl)oxy)-4-fluorophenyl)acrylamide (A158)

N-(3-((2-amino-3-(4-phenoxyphenyl)pyridin-4-yl)oxy)-4-fluorophenyl)acrylamide was prepared from 4-chloro-3-iodopyridin-2-amine, 5-amino-2-fluorophenol, (4-phenoxyphenyl)boronic acid and acryloyl chloride using methods A, C, and F. HPLC: 100%. MS: m/z=442 [M+H]$^+$. $^1$H-NMR (DMSO-D6) δ 10.35 (s, 1H), 7.96 (d, 1H), 7.79 (d, 1H), 7.45-7.38 (m, 6H), 7.21-7.10 (m, 6H), 6.41-6.36 (m, 2H), 6.26 (d, 1H), 5.79 (d, 1H).

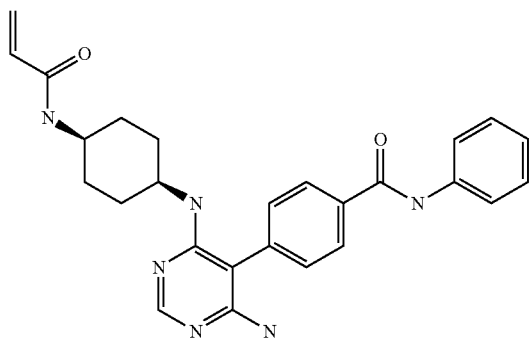 [SMILES: C=CC(=O)N[C@H]1CC[C@@H](Nc2ncnc(N)c2-c2ccc(C(=O)Nc3ccccc3)cc2)CC1]

4-(4-((cis-4-acrylamidocyclohexyl)amino)-6-aminopyrimidin-5-yl)-N-phenylbenzamide (A159)

4-(4-((cis-4-acrylamidocyclohexyl)amino)-6-aminopyrimidin-5-yl)-N-phenylbenzamide was prepared from 5,6-dichloropyrimidin-4-amine, tert-butyl-(cis-4-aminocyclohexyl)carbamate, N-phenyl-4-(4,4,5,5-tetramethyl-1,3,2-dioxaborolan-2-yl)benzamide, and acryloyl chloride using methods B, C, D, and E. HPLC: 100%. MS: m/z=457 [M+H]$^+$.

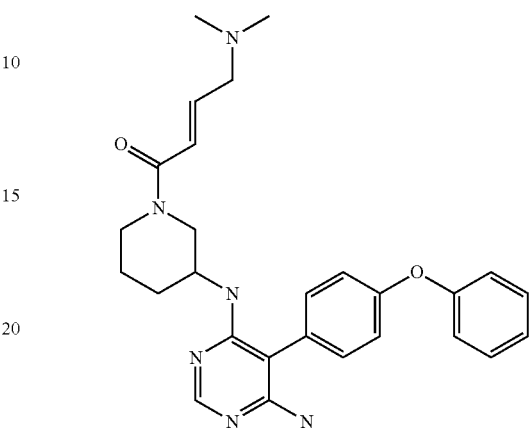

(E)-1-(3-((6-amino-5-(4-phenoxyphenyl)pyrimidin-4-yl)amino)piperidin-1-yl)-4-(dimethylamino)but-2-en-1-one (A160)

(E)-1-(3-((6-amino-5-(4-phenoxyphenyl)pyrimidin-4-yl)amino)piperidin-1-yl)-4-(dimethylamino)but-2-en-1-one was prepared from 5,6-dichloropyrimidin-4-amine, tert-butyl 3-aminopiperidine-1-carboxylate, (4-phenoxyphenyl)boronic acid, and (E)-4-(dimethylamino)but-2-enoic acid hydrochloride using methods B, C, D, and E. HPLC: 100%. MS: m/z=473 [M+H]$^+$.

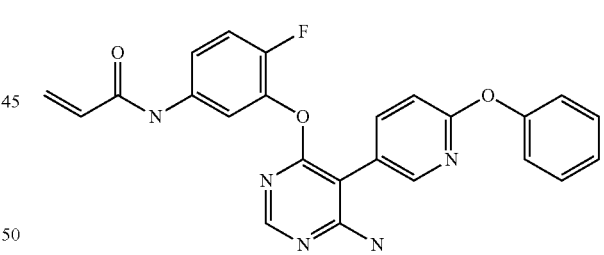

N-(3-((6-amino-5-(6-phenoxypyridin-3-yl)pyrimidin-4-yl)oxy)-4-fluorophenyl)acrylamide (A161)

N-(3-((6-amino-5-(6-phenoxypyridin-3-yl)pyrimidin-4-yl)oxy)-4-fluorophenyl)acrylamide was prepared from 5,6-dichloropyrimidin-4-amine, 5-amino-2-fluorophenol, 2-phenoxy-5-(4,4,5,5-tetramethyl-1,3,2-dioxaborolan-2-yl)pyridine, and acryloyl chloride using methods A, C, and F. HPLC: 100%. MS: m/z=444 [M+H]$^+$. $^1$H-NMR (DMSO-D6) δ 10.16 (s, 1H), 8.09 (s, 1H), 7.99 (s, 1H), 7.80 (d, 1H), 7.59 (d, 1H), 7.38-7.32 (m, 3H), 7.21-6.91 (m, 5H), 6.70 (broad s, 2H), 6.31 (dd, 1H), 6.18 (d, 1H), 5.69 (d, 1H).

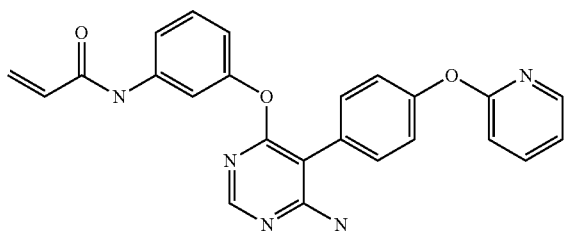 [SMILES: C=CC(=O)Nc1cccc(Oc2ncnc(N)c2-c2ccc(Oc3ccccn3)cc2)c1]

N-(3-((6-amino-5-(4-(pyridin-2-yloxy)phenyl)pyrimidin-4-yl)oxy)phenyl)acrylamide (A162)

N-(3-((6-amino-5-(4-(pyridin-2-yloxy)phenyl)pyrimidin-4-yl)oxy)phenyl)acrylamide was prepared from 5,6-dichloropyrimidin-4-amine, 3-aminophenol, 2-(4-(4,4,5,5-tetramethyl-1,3,2-dioxaborolan-2-yl)phenoxy)pyridine, and acryloyl chloride using methods A, C, and F. HPLC: 100%. MS: m/z=426 [M+H]$^+$. $^1$H-NMR (DMSO-D6) δ 10.22 (s, 1H), 8.20 (d, 1H), 8.08 (s, 1H), 7.87 (t, 1H), 7.50 (s, 1H), 7.46 (d, 2H), 7.39 (d, 1H), 7.30 (t, 1H), 7.23 (d, 2H), 7.16 (m, 1H), 7.07 (d, 1H), 6.80 (d, 1H), 6.58 (broad s, 2H), 6.41 (dd, 1H), 6.25 (d, 1H), 5.76 (d, 1H).

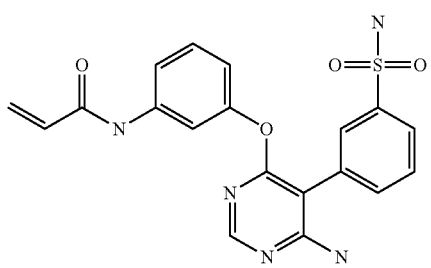 [SMILES: C=CC(=O)Nc1cccc(Oc2ncnc(N)c2-c2cccc(S(N)(=O)=O)c2)c1]

N-(3-((6-amino-5-(3-sulfamoylphenyl)pyrimidin-4-yl)oxy)phenyl)acrylamide (A163)

N-(3-((6-amino-5-(3-sulfamoylphenyl)pyrimidin-4-yl)oxy)phenyl)acrylamide was prepared from 5,6-dichloropyrimidin-4-amine, 3-aminophenol, 3-(4,4,5,5-tetramethyl-1,3,2-dioxaborolan-2-yl)benzenesulfonamide, and acryloyl chloride using methods A, C, and F. HPLC: 98%. MS: m/z=412 [M+H]$^+$. $^1$H-NMR (DMSO-D6) δ 10.17 (s, 1H), 8.04 (s, 1H), 7.79-7.75 (m, 2H), 7.61-7.58 (m, 2H), 7.43 (s, 1H), 7.32-7.30 (m, 3H), 7.23 (t, 1H), 6.77-6.52 (m, 3H), 6.34 (dd, 1H), 6.18 (d, 1H), 5.70 (d, 1H).

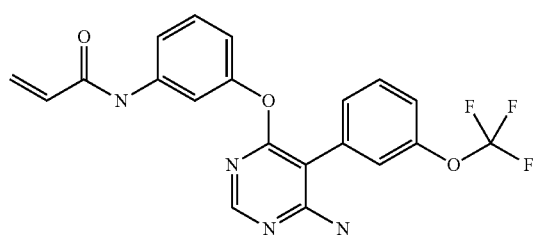 [SMILES: C=CC(=O)Nc1cccc(Oc2ncnc(N)c2-c2cccc(OC(F)(F)F)c2)c1]

N-(3-((6-amino-5-(3-(trifluoromethoxy)phenyl)pyrimidin-4-yl)oxy)phenyl)acrylamide (A164)

N-(3-((6-amino-5-(3-(trifluoromethoxy)phenyl)pyrimidin-4-yl)oxy)phenyl)acrylamide was prepared from 5,6-dichloropyrimidin-4-amine, 3-aminophenol, (3-(trifluoromethoxy)phenyl)boronic acid, and acryloyl chloride using methods A, C, and F. HPLC: 100%. MS: m/z=417 [M+H]$^+$. $^1$H-NMR (DMSO-D6) δ 10.22 (s, 1H), 8.09 (s, 1H), 7.59 (t, 1H), 7.48-7.44 (m, 2H), 7.39-7.36 (m, 3H), 7.28 (t, 1H), 6.95-6.55 (m, 3H), 6.39 (dd, 1H), 6.23 (d, 1H), 5.75 (d, 1H).

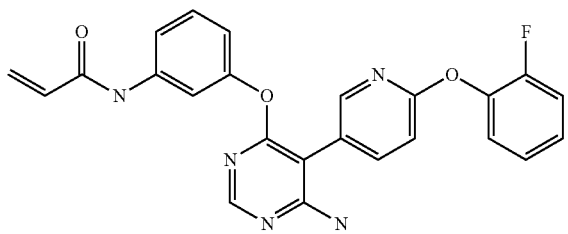 [SMILES: C=CC(=O)Nc1cccc(Oc2ncnc(N)c2-c2ccc(Oc3ccccc3F)nc2)c1]

N-(3-((6-amino-5-(6-(2-fluorophenoxy)pyridin-3-yl)pyrimidin-4-yl)oxy)phenyl)acrylamide (A165)

N-(3-((6-amino-5-(6-(2-fluorophenoxy)pyridin-3-yl)pyrimidin-4-yl)oxy)phenyl)acrylamide was prepared from 5,6-dichloropyrimidin-4-amine, 3-aminophenol, 2-(2-fluorophenoxy)-5-(4,4,5,5-tetramethyl-1,3,2-dioxaborolan-2-yl)pyridine, and acryloyl chloride using methods A, C, and F. HPLC: 99%. MS: m/z=444 [M+H]$^+$. $^1$H-NMR (DMSO-D6) δ 10.16 (s, 1H), 8.07 (s, 1H), 8.02 (s, 1H), 7.84 (d, 1H), 7.42 (s, 1H), 7.32-7.15 (m, 7H), 6.86-6.60 (m, 3H), 6.34 (dd, 1H), 6.18 (d, 1H), 5.69 (d, 1H).

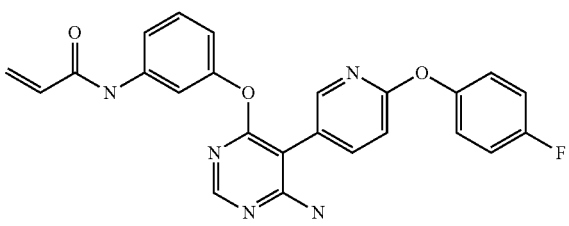 [SMILES: C=CC(=O)Nc1cccc(Oc2ncnc(N)c2-c2ccc(Oc3ccc(F)cc3)nc2)c1]

N-(3-((6-amino-5-(6-(4-fluorophenoxy)pyridin-3-yl)pyrimidin-4-yl)oxy)phenyl)acrylamide (A166)

N-(3-((6-amino-5-(6-(4-fluorophenoxy)pyridin-3-yl)pyrimidin-4-yl)oxy)phenyl)acrylamide was prepared from 5,6-dichloropyrimidin-4-amine, 3-aminophenol, 2-(4-fluorophenoxy)-5-(4,4,5,5-tetramethyl-1,3,2-dioxaborolan-2-yl)pyridine, and acryloyl chloride using methods A, C, and F. HPLC: 99%. MS: m/z=444 [M+H]$^+$. $^1$H-NMR (DMSO-D6) δ 10.17 (s, 1H), 8.09 (d, 1H), 8.03 (s, 1H), 7.82 (d, 1H), 7.43 (s, 1H), 7.30 (d, 1H), 7.25-7.15 (m, 6H), 7.07 (d, 1H), 6.92-6.58 (m, 3H), 6.34 (dd, 1H), 6.18 (d, 1H), 5.70 (d, 1H).

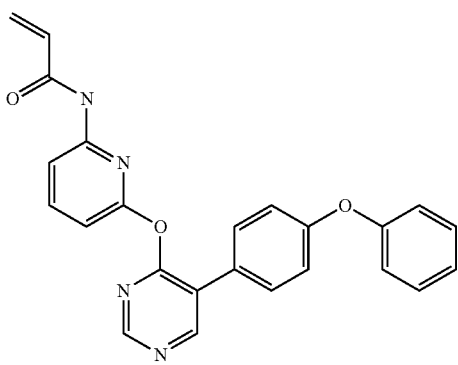 [SMILES: C=CC(=O)Nc1cccc(Oc2ncncc2-c2ccc(Oc3ccccc3)cc2)n1]

N-(6-((5-(4-phenoxyphenyl)pyrimidin-4-yl)amino)pyridin-2-yl)acrylamide MSC2375022 (A167)

N-(6-((5-(4-phenoxyphenyl)pyrimidin-4-yl)amino)pyridin-2-yl)acrylamide was prepared from 5-bromo-4-chloropyrimidine, pyridine-2,6-diamine, (4-phenoxyphenyl)boronic acid, and acryloyl chloride using methods H, C, and F. HPLC: 97%. MS: m/z=410 [M+H]$^+$. $^1$H-NMR (DMSO-D6) δ 10.43 (s, 1H), 8.75 (s, 1H), 8.33 (s, 1H), 8.04 (broad s, 1H), 7.85-7.73 (m, 3H), 7.48 (d, 2H), 7.39 (t, 2H), 7.15 (t, 1H), 7.07 (d, 2H), 7.03 (d, 2H), 6.47 (dd, 1H), 6.22 (d, 1H), 5.70 (d, 1H).

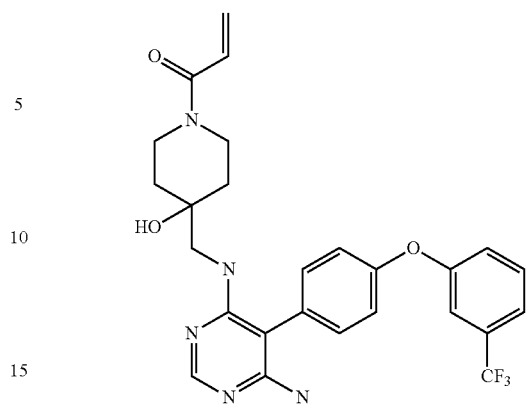

1-(4-(((6-amino-5-(4-(3-(trifluoromethyl)phenoxy)phenyl)pyrimidin-4-yl)amino)methyl)-4-hydroxypiperidin-1-yl)prop-2-en-1-one (A169)

1-(4-(((6-amino-5-(4-(3-(trifluoromethyl)phenoxy)phenyl)pyrimidin-4-yl)amino)methyl)-4-hydroxypiperidin-1-yl)prop-2-en-1-one was prepared from 5,6-dichloropyrimidin-4-amine, tert-butyl 4-(aminomethyl)-4-hydroxypiperidine-1-carboxylate, (4-(3-(trifluoromethyl)phenoxy)phenyl)boronic acid, and acryloyl chloride using methods B, C, D, and F. HPLC: 99%. MS: m/z=514 [M+H]$^+$. $^1$H NMR (500 MHz, dmso) δ 7.88 (s, 1H), 7.57 (t, J. 7.9 Hz, 1H), 7.44 (d, J. 7.8 Hz, 1H), 7.38 (s, 1H), 7.32 (dd, J. 8.2, 2.3 Hz, 1H), 7.22 (dd, J. 6.5, 4.6 Hz, 2H), 7.14 (t, 2H), 6.71 (dd, 10.5 Hz, 1H), 5.99 (dd, 1H), 5.63-5.52 (m, 3H), 5.15 (t, 1H), 5.09 (s, 1H), 3.94 (d, 1H), 3.66 (d, 1H), 2.96 (t, 1H), 1.40-1.20 (m, 5H), 0.79 (t, 1H).

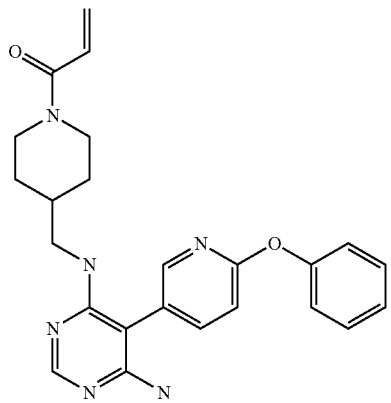 [SMILES: C=CC(=O)N1CCC(CNc2ncnc(N)c2-c2ccc(Oc3ccccc3)nc2)CC1]

1-(4-(((6-amino-5-(6-phenoxypyridin-3-yl)pyrimidin-4-yl)amino)methyl)piperidin-1-yl)prop-2-en-1-one (A168)

1-(4-(((6-amino-5-(6-phenoxypyridin-3-yl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, 2-phenoxy-5-(4,4,5,5-tetramethyl-1,3,2-dioxaborolan-2-yl)pyridine, and acryloyl chloride using methods B, C, D, and F. HPLC: 100%. MS: m/z=431 [M+H]$^+$.

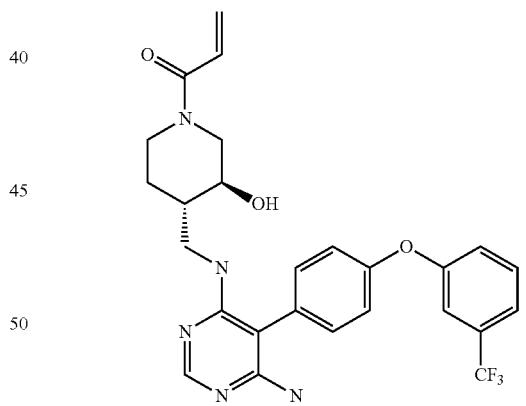

1-((3S,4S)-4-(((6-amino-5-(4-(3-(trifluoromethyl)phenoxy)phenyl)pyrimidin-4-yl)amino)methyl)-3-hydroxypiperidin-1-yl)prop-2-en-1-one (A170)

1-((3S,4S)-4-(((6-amino-5-(4-(3-(trifluoromethyl)phenoxy)phenyl)pyrimidin-4-yl)amino)methyl)-3-hydroxypiperidin-1-yl)prop-2-en-1-one was prepared from 5,6-dichloropyrimidin-4-amine, (3S,4S)-tert-butyl 4-(aminomethyl)-3-hydroxypiperidine-1-carboxylate, (4-(3-(trifluoromethyl)phenoxy)phenyl)boronic acid, and acryloyl chloride using methods B, C, D, and F. HPLC: 100%. MS: m/z=514 [M+H]$^+$. $^1$H NMR (400 MHz, DMSO) δ 7.95 (d, J. 5.4 Hz, 1H), 7.64 (t, J. 8.0 Hz, 1H), 7.51 (d, J. 7.8 Hz, 1H), 7.45 (s, 1H), 7.38 (dd, 1H), 7.31-7.24 (m, 2H), 7.19 (d, 2H), 6.79-6.69 (m, 1H), 6.06 (d, 1H), 5.69-5.57 (m, 2H), 5.54 (s, 2H), 5.39 (bs, 1H), 4.41 (d, 1H), 4.22 (d, 1H), 3.93 (t, 1H), 3.49-3.35 (m, 2H), 3.16-2.99 (m, 1H), 2.86 (dt, 1H), 2.61 (t, 1H), 2.34 (t, 1H), 1.60 (bs, 2H), 1.13-0.96 (m, 1H).

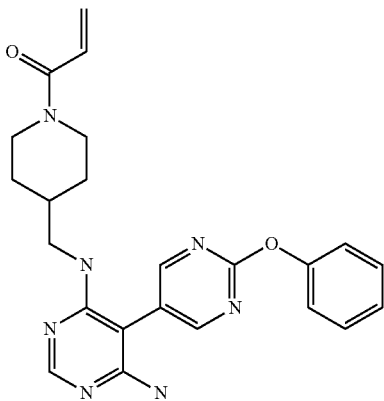 [SMILES: C=CC(=O)N1CCC(CNc2ncnc(N)c2-c2cnc(Oc3ccccc3)nc2)CC1]

1-(4-(((6-amino-2'-phenoxy-[5,5'-bipyrimidin]-4-yl)amino)methyl)piperidin-1-yl)prop-2-en-1-one (A171)

1-(4-(((6-amino-2'-phenoxy-[5,5'-bipyrimidin]-4-yl)amino)methyl)piperidin-1-yl)prop-2-en-1-one was prepared from 5,6-dichloropyrimidin-4-amine, tert-butyl 4-(aminomethyl)piperidine-1-carboxylate, 2-phenoxy-5-(4,4,5,5-tetramethyl-1,3,2-dioxaborolan-2-yl)pyrimidine, and acryloyl chloride using methods B, C, D, and F. MS: m/z=432 [M+H]$^+$. $^1$H NMR (400 MHz, DMSO) δ 8.37 (s, 2H), 7.96 (s, 1H), 7.47 (t, 2H), 7.30-7.20 (m, 3H), 6.76 (dd, 1H), 6.10-5.97 (m, 2H), 5.80 (s, 2H), 5.62 (dd, 1H), 4.35 (d, 1H), 3.99 (d, 1H), 3.10 (t, 2H), 3.02-2.89 (m, 1H), 2.56 (m, 1H), 1.81 (m, 1H), 1.63 (d, 2H), 1.02-0.83 (m, 2H).

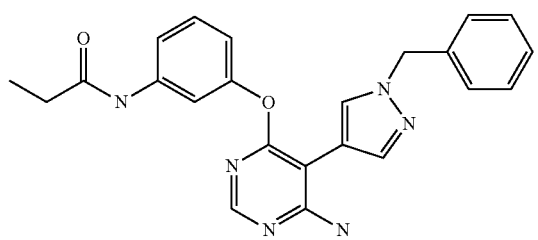 [SMILES: CCC(=O)Nc1cccc(Oc2ncnc(N)c2-c2cnn(Cc3ccccc3)c2)c1]

N-(3-((6-amino-5-(1-benzyl-1H-pyrazol-4-yl)pyrimidin-4-yl)oxy)phenyl)acrylamide (A172)

N-(3-((6-amino-5-(1-benzyl-1H-pyrazol-4-yl)pyrimidin-4-yl)oxy)phenyl)acrylamide was prepared from 5,6-dichloropyrimidin-4-amine, 3-aminophenol, 1-benzyl-4-(4,4,5,5-tetramethyl-1,3,2-dioxaborolan-2-yl)-1H-pyrazole, and acryloyl chloride using methods A, C, and F. HPLC: 100%. MS: m/z= 413 [M+H]$^+$. $^1$H-NMR (DMSO-D6) δ 10.18 (s, 1H), 8.08 (s, 1H), 7.98 (s, 1H), 7.66 (s, 1H), 7.45 (s, 1H), 7.33 (t, 1H), 7.29-7.20 (m, 6H), 6.99-6.64 (m, 3H), 6.34 (dd, 1H), 6.18 (d, 1H), 5.70 (d, 1H), 5.30 (s, 2H).

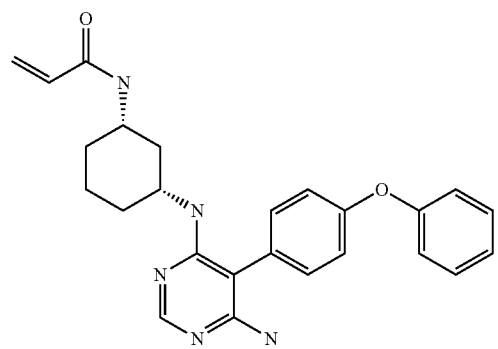 [SMILES: C=CC(=O)N[C@H]1CCC[C@@H](Nc2ncnc(N)c2-c2ccc(Oc3ccccc3)cc2)C1]

N-((1S,3R)-3-((6-amino-5-(4-phenoxyphenyl)pyrimidin-4-yl)amino)cyclohexyl)acrylamide (A173)

N-((1S,3R)-3-((6-amino-5-(4-phenoxyphenyl)pyrimidin-4-yl)amino)cyclohexyl)acrylamide was prepared from 5,6-dichloropyrimidin-4-amine, tert-butyl (cis-3-aminocyclohexyl)carbamate, (4-phenoxyphenyl)boronic acid, and acryloyl chloride using methods B, C, D, F and chiral separation. HPLC: 95%. MS: m/z=430 [M+H]$^+$.

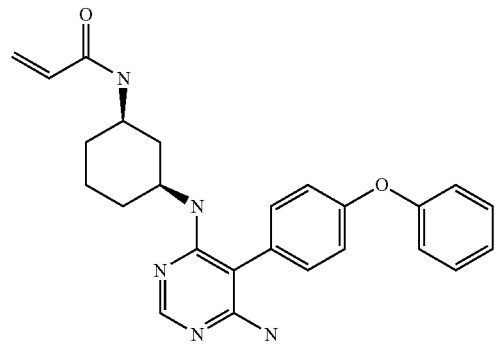 [SMILES: C=CC(=O)N[C@@H]1CCC[C@H](Nc2ncnc(N)c2-c2ccc(Oc3ccccc3)cc2)C1]

N-((1R,3S)-3-((6-amino-5-(4-phenoxyphenyl)pyrimidin-4-yl)amino)cyclohexyl)acrylamide (A174)

N-((1R,3S)-3-((6-amino-5-(4-phenoxyphenyl)pyrimidin-4-yl)amino)cyclohexyl)acrylamide was prepared from 5,6-dichloropyrimidin-4-amine, tert-butyl (cis-3-aminocyclohexyl)carbamate, (4-phenoxyphenyl)boronic acid, and acryloyl chloride using methods B, C, D, F and chiral separation. HPLC: 98%. MS: m/z=430 [M+H]$^+$.

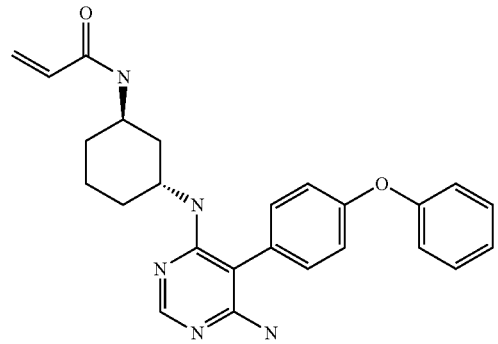 [SMILES: C=CC(=O)N[C@@H]1CCC[C@@H](Nc2ncnc(N)c2-c2ccc(Oc3ccccc3)cc2)C1]

N-((1R,3R)-3-((6-amino-5-(4-phenoxyphenyl)pyrimidin-4-yl)amino)cyclohexyl)acrylamide (A175)

N-((1R,3R)-3-((6-amino-5-(4-phenoxyphenyl)pyrimidin-4-yl)amino)cyclohexyl)acrylamide was prepared from 5,6- dichloropyrimidin-4-amine, tert-butyl (trans-3-aminocyclohexyl)carbamate, (4-phenoxyphenyl)boronic acid, and acryloyl chloride using methods B, C, D, F and chiral separation. HPLC: 98%. MS: m/z=430 [M+H]⁺.

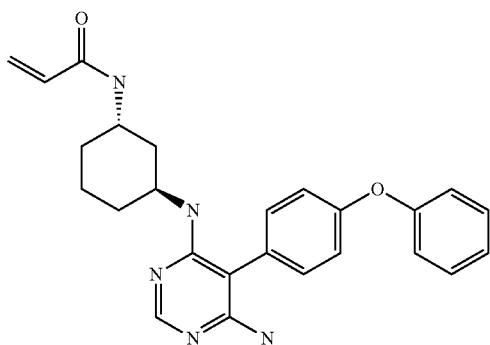 [SMILES: C=CC(=O)N[C@H]1CCC[C@H](Nc2ncnc(N)c2-c2ccc(Oc3ccccc3)cc2)C1]

N-((1S,3S)-3-((6-amino-5-(4-phenoxyphenyl)pyrimidin-4-yl)amino)cyclohexyl)acrylamide (A176)

N-((1S,3S)-3-((6-amino-5-(4-phenoxyphenyl)pyrimidin-4-yl)amino)cyclohexyl)acrylamide was prepared from 5,6-dichloropyrimidin-4-amine, tert-butyl (trans-3-aminocyclohexyl)carbamate, (4-phenoxyphenyl)boronic acid, and acryloyl chloride using methods B, C, D, F and chiral separation. HPLC: 97%. MS: m/z=430 [M+H]⁺.

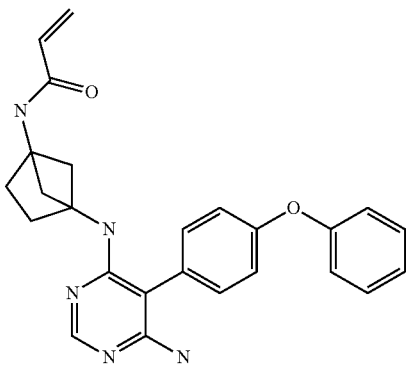 [SMILES: C=CC(=O)NC12CCC(Nc3ncnc(N)c3-c3ccc(Oc4ccccc4)cc3)(C1)C2]

N-(4-((6-amino-5-(4-phenoxyphenyl)pyrimidin-4-yl)amino)bicyclo[2.1.1]hexan-1-yl)acrylamide (A177)

N-(4-((6-amino-5-(4-phenoxyphenyl)pyrimidin-4-yl)amino)bicyclo[2.1.1]hexan-1-yl)acrylamide was prepared from 5,6-dichloropyrimidin-4-amine, benzyl (4-aminobicyclo[2.1.1]hexan-1-yl)carbamate hydrochloride, (4-phenoxyphenyl)boronic acid, and acryloyl chloride using methods B, C, hydrogenation, and F. HPLC: 100%. MS: m/z=428 [M+H]⁺. ¹H-NMR (DMSO-d₆) δ 8.46 (s, 1H), 8.32 (s, 1H), 7.44 (t, 2H), 7.27-7.12 (m, 8H), 6.85 (broad s, 2H), 6.18 (dd, 1H), 6.04 (d, 1H), 5.54 (d, 1H), 1.99-1.94 (m, 4H), 1.85-1.81 (m, 4H).

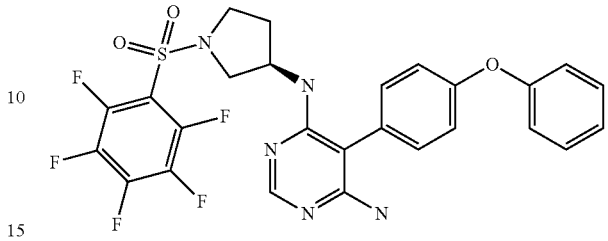

(R)—N4-(1-((perfluorophenyl)sulfonyl)pyrrolidin-3-yl)-5-(4-phenoxyphenyl)pyrimidine-4,6-diamine (A178)

(R)—N4-(1-((perfluorophenyl)sulfonyl)pyrrolidin-3-yl)-5-(4-phenoxyphenyl)pyrimidine-4,6-diamine was prepared from 5,6-dichloropyrimidin-4-amine, (R)-tert-butyl 3-aminopyrrolidine-1-carboxylate, (4-phenoxyphenyl)boronic acid, and 2,3,4,5,6-pentafluorobenzene-1-sulfonyl chloride using methods B, C, D, and addition using pyridine in final step. HPLC: 99%. MS: m/z=578 [M+H]⁺.

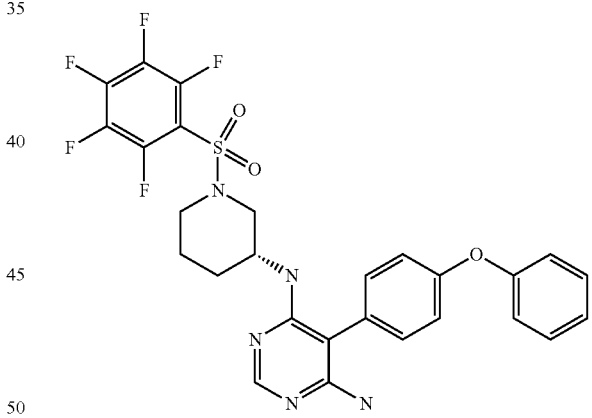

(R)—N4-(1-((perfluorophenyl)sulfonyl)piperidin-3-yl)-5-(4-phenoxyphenyl)pyrimidine-4,6-diamine (A179)

(R)—N4-(1-((perfluorophenyl)sulfonyl)piperidin-3-yl)-5-(4-phenoxyphenyl)pyrimidine-4,6-diamine was prepared from 5,6-dichloropyrimidin-4-amine, (R)-tert-butyl 3-aminopiperidine-1-carboxylate, (4-phenoxyphenyl)boronic acid, and 2,3,4,5,6-pentafluorobenzene-1-sulfonyl chloride using methods B, C, D, and addition using pyridine in final step. HPLC: 96%. MS: m/z=592 [M+H]⁺.

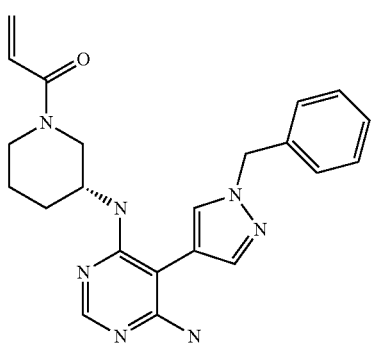 [SMILES: C=CC(=O)N1CCC[C@@H](Nc2ncnc(N)c2-c2cnn(Cc3ccccc3)c2)C1]

(R)-1-(3-(((6-amino-5-(1-benzyl-1H-pyrazol-4-yl)pyrimidin-4-yl)amino)piperidin-1-yl)prop-2-en-1-one (A180)

(R)-1-(3-(((6-amino-5-(1-benzyl-1H-pyrazol-4-yl)pyrimidin-4-yl)amino)piperidin-1-yl)prop-2-en-1-one was prepared from 5,6-dichloropyrimidin-4-amine, (R)-tert-butyl 3-aminopiperidine-1-carboxylate, 1-benzyl-4-(4,4,5,5-tetramethyl-1,3,2-dioxaborolan-2-yl)-1H-pyrazole, and acryloyl chloride using methods B, C, D, and F. HPLC: 100%. MS: m/z=404 [M+H]$^+$.

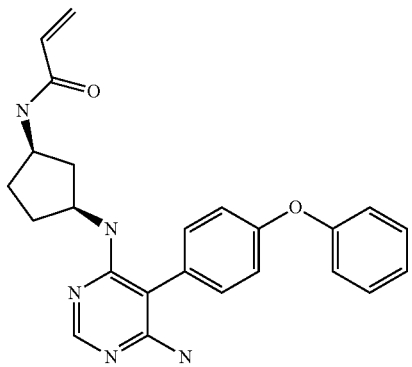 [SMILES: C=CC(=O)N[C@@H]1CC[C@H](Nc2ncnc(N)c2-c2ccc(Oc3ccccc3)cc2)C1]

N-(cis-3-((6-amino-5-(4-phenoxyphenyl)pyrimidin-4-yl)amino)cyclopentyl)acrylamide (A181)

N-(cis-3-((6-amino-5-(4-phenoxyphenyl)pyrimidin-4-yl)amino)cyclopentyl)acrylamide was prepared from 5,6-dichloropyrimidin-4-amine, tert-butyl (cis-3-aminocyclopentyl)carbamate, (4-phenoxyphenyl)boronic acid, and acryloyl chloride using methods B, C, D, and F. HPLC: 98%. MS: m/z=416 [M+H]$^+$. $^1$H-NMR (DMSO-d6) δ 8.36 (s, 1H), 8.11 (d, 1H), 7.45 (t, 2H), 7.28-7.12 (m, 7H), 7.07-6.82 (m, 3H), 6.15 (dd, 1H), 6.04 (d, 1H), 5.56 (d, 1H), 4.43 (broad s, 1H), 3.96 (sextet, 1H), 2.22 (m, 1H), 1.90-1.80 (m, 2H), 1.68-1.43 (m, 3H).

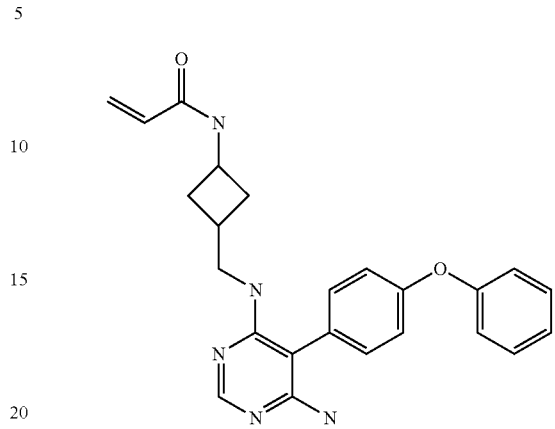

N-(3-(((6-amino-5-(4-phenoxyphenyl)pyrimidin-4-yl)amino)methyl)cyclobutyl)acrylamide (A182)

N-(3-(((6-amino-5-(4-phenoxyphenyl)pyrimidin-4-yl)amino)methyl)cyclobutyl)acrylamide was prepared from 5,6-dichloropyrimidin-4-amine, tert-butyl (3-(aminomethyl)cyclobutyl)carbamate, (4-phenoxyphenyl)boronic acid, and acryloyl chloride using methods B, C, D, and F. HPLC: 100%. MS: m/z=416 [M+H]$^+$.

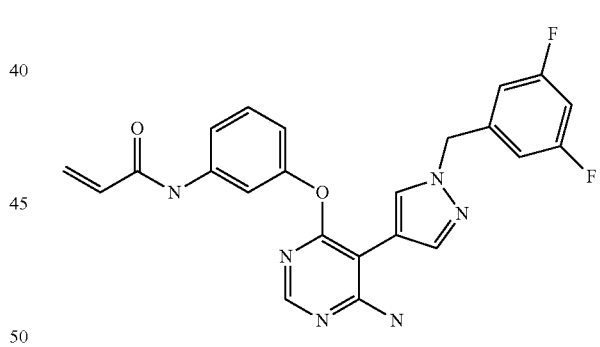

N-(3-((6-amino-5-(1-(3,5-difluorobenzyl)-1H-pyrazol-4-yl)pyrimidin-4-yl)oxy)phenyl)acrylamide (A183)

N-(3-((6-amino-5-(1-(3,5-difluorobenzyl)-1H-pyrazol-4-yl)pyrimidin-4-yl)oxy)phenyl)acrylamide was prepared from 5,6-dichloropyrimidin-4-amine, 3-aminophenol, 1-(3,5-difluorobenzyl)-4-(4,4,5,5-tetramethyl-1,3,2-dioxaborolan-2-yl)-1H-pyrazole, and acryloyl chloride using methods A, C, and F. HPLC: 100%. MS: m/z=449 [M+H]$^+$. $^1$H-NMR (DMSO-d$_6$) δ 10.23 (s, 1H), 8.19 (s, 1H), 8.09 (s, 1H), 7.77

(s, 1H), 7.54 (s, 1H), 7.41 (d, 1H), 7.32 (t, 1H), 7.16 (t, 1H), 7.14-6.78 (m, 5H), 6.42 (dd, 1H), 6.25 (d, 1H), 5.76 (d, 1H), 5.42 (s, 2H).

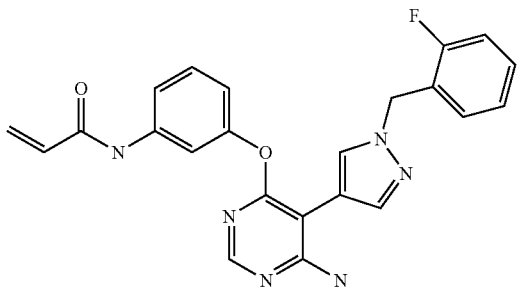 [SMILES: C=CC(=O)Nc1cccc(Oc2ncnc(N)c2-c2cnn(Cc3ccccc3F)c2)c1]

N-(3-((6-amino-5-(1-(2-fluorobenzyl)-1H-pyrazol-4-yl)pyrimidin-4-yl)oxy)phenyl)acrylamide (A184)

N-(3-((6-amino-5-(1-(2-fluorobenzyl)-1H-pyrazol-4-yl)pyrimidin-4-yl)oxy)phenyl)acrylamide was prepared from 5,6-dichloropyrimidin-4-amine, 3-aminophenol, 1-(2-fluorobenzyl)-4-(4,4,5,5-tetramethyl-1,3,2-dioxaborolan-2-yl)-1H-pyrazole, and acryloyl chloride using methods A, C, and F. HPLC: 100%. MS: m/z=431 [M+H]$^+$. $^1$H-NMR (DMSO-d$_6$) δ 10.21 (s, 1H), 8.12 (s, 1H), 8.01 (s, 1H), 7.73 (s, 1H), 7.50 (s, 1H), 7.40-7.17 (m, 6H), 6.82-6.65 (m, 3H), 6.42 (dd, 1H), 6.25 (d, 1H), 5.77 (d, 1H), 5.43 (s, 2H).

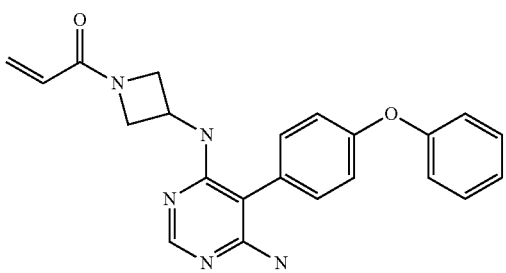 [SMILES: C=CC(=O)N1CC(Nc2ncnc(N)c2-c2ccc(Oc3ccccc3)cc2)C1]

1-(3-((6-amino-5-(4-phenoxyphenyl)pyrimidin-4-yl)amino)azetidin-1-yl)prop-2-en-1-one (A185)

1-(3-((6-amino-5-(4-phenoxyphenyl)pyrimidin-4-yl)amino)azetidin-1-yl)prop-2-en-1-one was prepared from 5,6-dichloropyrimidin-4-amine, tert-butyl 3-aminoazetidine-1-carboxylate, (4-phenoxyphenyl)boronic acid, and acryloyl chloride using methods B, C, D, and F. HPLC: 100%. MS: m/z=388 [M+H]$^+$. $^1$H-NMR (DMSO-d$_6$) δ 8.33 (s, 1H), 7.45 (t, 2H), 7.30-7.13 (m, 8H), 6.83 (broad s, 1.5H), 6.28 (dd, 1H), 6.08 (d, 1H), 5.66 (d, 1H), 4.90 (m, 1H), 4.44 (t, 1H), 1.12 (q, 2H), 3.87 (m, 1H).

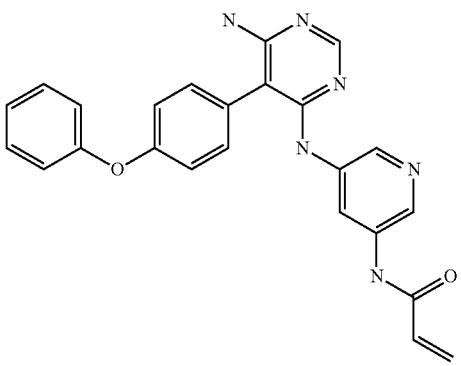 [SMILES: C=CC(=O)Nc1cncc(Nc2ncnc(N)c2-c2ccc(Oc3ccccc3)cc2)c1]

N-(5-((6-amino-5-(4-phenoxyphenyl)pyrimidin-4-yl)amino)pyridin-3-yl)acrylamide (A186)

N-(5-((6-amino-5-(4-phenoxyphenyl)pyrimidin-4-yl)amino)pyridin-3-yl)acrylamide was prepared from 5,6-dichloropyrimidin-4-amine, pyridine-3,5-diamine, (4-phenoxyphenyl)boronic acid, and acryloyl chloride using methods J, C, and F. HPLC: 100%. MS: m/z=425 [M+H]$^+$.

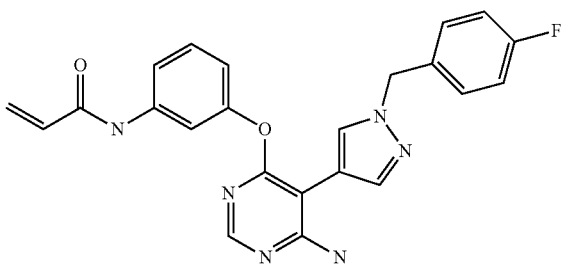 [SMILES: C=CC(=O)Nc1cccc(Oc2ncnc(N)c2-c2cnn(Cc3ccc(F)cc3)c2)c1]

N-(3-((6-amino-5-(1-(4-fluorobenzyl)-1H-pyrazol-4-yl)pyrimidin-4-yl)oxy)phenyl)acrylamide (A187)

N-(3-((6-amino-5-(1-(4-fluorobenzyl)-1H-pyrazol-4-yl)pyrimidin-4-yl)oxy)phenyl)acrylamide was prepared from 5,6-dichloropyrimidin-4-amine, 3-aminophenol, 1-(4-fluorobenzyl)-4-(4,4,5,5-tetramethyl-1,3,2-dioxaborolan-2-yl)-1H-pyrazole, and acryloyl chloride using methods A, C, and F. HPLC: 99%. MS: m/z=431 [M+H]$^+$. $^1$H-NMR (DMSO-d$_6$) δ 10.22 (s, 1H), 8.14 (s, 1H), 8.04 (s, 1H), 7.73 (s, 1H), 7.52 (s, 1H), 7.39-7.32 (m, 4H), 7.17 (t, 2H), 6.95-6.68 (m, 2.5H), 6.42 (dd, 1H), 6.25 (d, 1H), 5.77 (d, 1H), 5.36 (s, 2H).

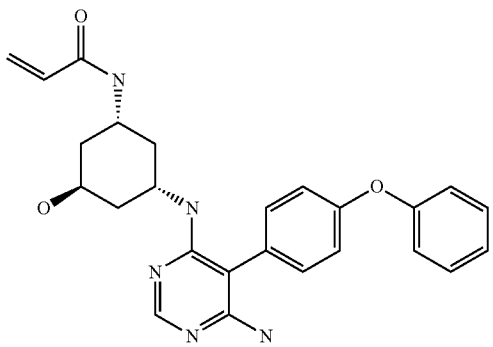 [SMILES: C=CC(=O)N[C@H]1C[C@H](O)C[C@@H](Nc2ncnc(N)c2-c2ccc(Oc3ccccc3)cc2)C1]

N-((1R,3S,5R)-3-((6-amino-5-(4-phenoxyphenyl)pyrimidin-4-yl)amino)-5-hydroxycyclohexyl)acrylamide (racemic) (A188)

N-((1R,3S,5R)-3-((6-amino-5-(4-phenoxyphenyl)pyrimidin-4-yl)amino)-5-hydroxycyclohexyl)acrylamide (racemic) was prepared from 5,6-dichloropyrimidin-4-amine, (1R,3S,5r)-5-((tert-butyldimethylsilyl)oxy)cyclohexane-1,3-diamine dihydrochloride (racemic), (4-phenoxyphenyl)boronic acid, and acryloyl chloride using methods B, C, deprotection with TBAF, and F. HPLC: 97%. MS: m/z=446 [M+H]⁺.

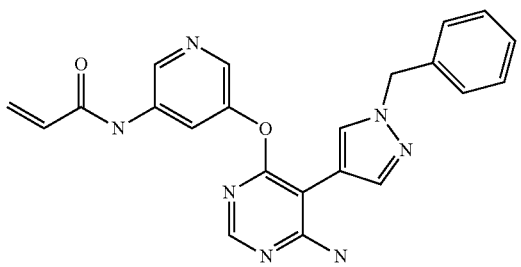 [SMILES: C=CC(=O)Nc1cncc(Oc2ncnc(N)c2-c2cnn(Cc3ccccc3)c2)c1]

N-(5-(((6-amino-5-(1-benzyl-1H-pyrazol-4-yl)py-rimidin-4-yl)oxy)pyridin-3-yl)acrylamide (A189)

N-(5-(((6-amino-5-(1-benzyl-1H-pyrazol-4-yl)pyrimidin-4-yl)oxy)pyridin-3-yl)acrylamide was prepared from 5,6-dichloropyrimidin-4-amine, 5-aminopyridin-3-ol dihydrochloride, 1-benzyl-4-(4,4,5,5-tetramethyl-1,3,2-dioxaborolan-2-yl)-1H-pyrazole, and acryloyl chloride using methods A, C, and F. HPLC: 77%. MS: m/z=414 [M+H]⁺.

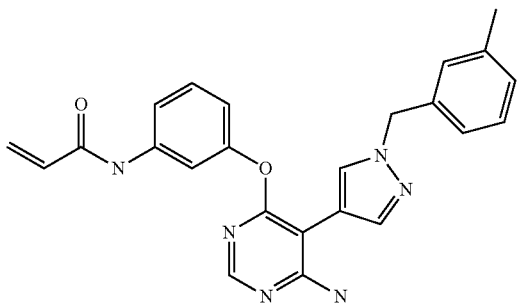 [SMILES: C=CC(=O)Nc1cccc(Oc2ncnc(N)c2-c2cnn(Cc3cccc(C)c3)c2)c1]

N-(3-(((6-amino-5-(1-(3-methylbenzyl)-1H-pyrazol-4-yl)pyrimidin-4-yl)oxy)phenyl)acrylamide (A190)

N-(3-(((6-amino-5-(1-(3-methylbenzyl)-1H-pyrazol-4-yl)pyrimidin-4-yl)oxy)phenyl)acrylamide was prepared from 5,6-dichloropyrimidin-4-amine, 3-aminophenol, 1-(3-methylbenzyl)-4-(4,4,5,5-tetramethyl-1,3,2-dioxaborolan-2-yl)-1H-pyrazole, and acryloyl chloride using methods A, C, and F. HPLC: 100%. MS: m/z=427 [M+H]⁺. ¹H-NMR (DMSO-d₆) δ 10.21 (s, 1H), 8.12 (s, 1H), 8.02 (s, 1H), 7.72 (s, 1H), 7.51 (s, 1H), 7.40 (d, 1H), 7.31 (t, 1H), 7.22 (t, 1H), 7.11 (m, 3H), 6.82-6.63 (m, 2.7H), 6.42 (dd, 1H), 6.25 (d, 1H), 5.76 (d, 1H), 5.32 (s, 2H), 2.27 (s, 3H).

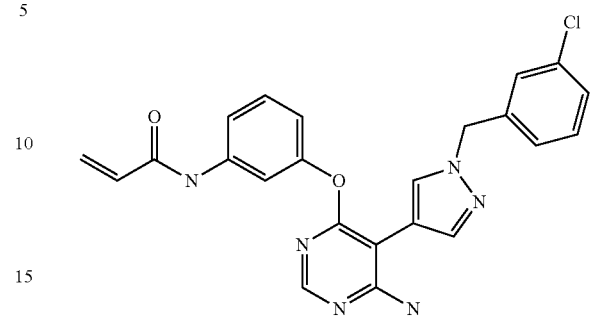

N-(3-(((6-amino-5-(1-(3-chlorobenzyl)-1H-pyrazol-4-yl)pyrimidin-4-yl)oxy)phenyl)acrylamide (A191)

N-(3-(((6-amino-5-(1-(3-chlorobenzyl)-1H-pyrazol-4-yl)pyrimidin-4-yl)oxy)phenyl)acrylamide was prepared from 5,6-dichloropyrimidin-4-amine, 3-aminophenol, 1-(3-chlorobenzyl)-4-(4,4,5,5-tetramethyl-1,3,2-dioxaborolan-2-yl)-1H-pyrazole, and acryloyl chloride using methods A, C, and F. HPLC: 99%. MS: m/z=447 [M+H]⁺. ¹H-NMR (DMSO-d₆) δ 10.21 (s, 1H), 8.18 (s, 1H), 8.03 (s, 1H), 7.75 (s, 1H), 7.52 (s, 1H), 7.42-7.26 (m, 6H), 6.96-6.65 (m, 2.6H), 6.42 (dd, 1H), 6.25 (d, 1H), 5.76 (d, 1H), 5.39 (s, 2H).

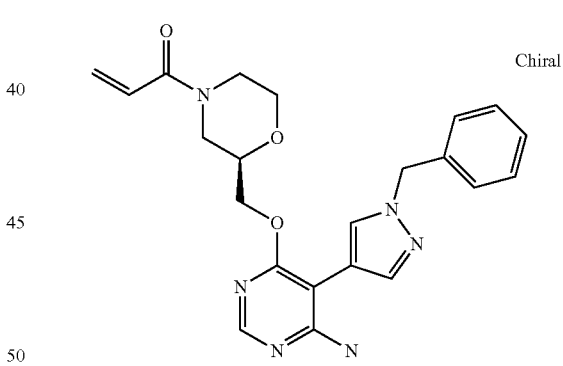

(R)-1-(2-(((6-amino-5-(1-benzyl-1H-pyrazol-4-yl)pyrimidin-4-yl)oxy)methyl)morpholino)prop-2-en-1-one (A192)

(R)-1-(2-(((6-amino-5-(1-benzyl-1H-pyrazol-4-yl)pyrimidin-4-yl)oxy)methyl)morpholino)prop-2-en-1-one was prepared from 5,6-dichloropyrimidin-4-amine, (R)-tert-butyl 2-(hydroxymethyl)morpholine-4-carboxylate, 1-benzyl-4-(4,4,5,5-tetramethyl-1,3,2-dioxaborolan-2-yl)-1H-pyrazole, and acryloyl chloride using methods A, C, D, and F. HPLC: 99%. MS: m/z=421 [M+H]⁺.

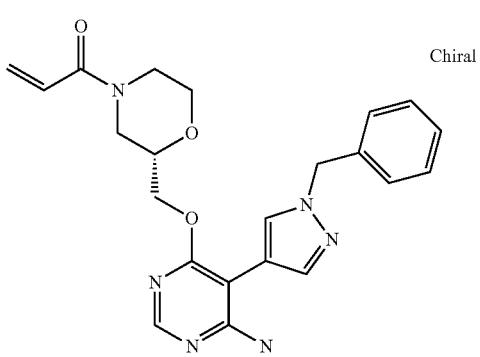 [SMILES: C=CC(=O)N1CCO[C@H](COc2ncnc(N)c2-c2cnn(Cc3ccccc3)c2)C1]

(S)-1-(2-(((6-amino-5-(1-benzyl-1H-pyrazol-4-yl)pyrimidin-4-yl)oxy)methyl)morpholino)prop-2-en-1-one (A193)

(S)-1-(2-(((6-amino-5-(1-benzyl-1H-pyrazol-4-yl)pyrimidin-4-yl)oxy)methyl)morpholino)prop-2-en-1-one was prepared from 5,6-dichloropyrimidin-4-amine, (S)-tert-butyl 2-(hydroxymethyl)morpholine-4-carboxylate, 1-benzyl-4-(4,4,5,5-tetramethyl-1,3,2-dioxaborolan-2-yl)-1H-pyrazole, and acryloyl chloride using methods A, C, D, and F. HPLC: 100%. MS: m/z=421 [M+H]$^+$.

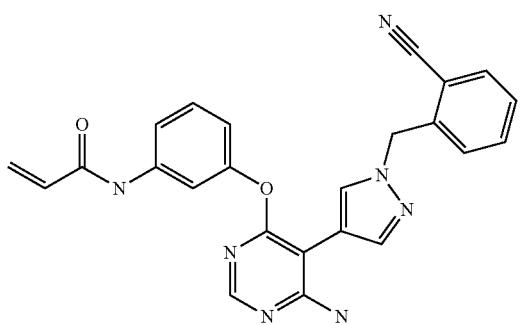 [SMILES: C=CC(=O)Nc1cccc(Oc2ncnc(N)c2-c2cnn(Cc3ccccc3C#N)c2)c1]

N-(3-((6-amino-5-(1-(2-cyanobenzyl)-1H-pyrazol-4-yl)pyrimidin-4-yl)oxy)phenyl)acrylamide (A194)

N-(3-((6-amino-5-(1-(2-cyanobenzyl)-1H-pyrazol-4-yl)pyrimidin-4-yl)oxy)phenyl)acrylamide was prepared from 5,6-dichloropyrimidin-4-amine, 3-aminophenol, 2-((4-(4,4,5,5-tetramethyl-1,3,2-dioxaborolan-2-yl)-1H-pyrazol-1-yl)methyl)benzonitrile, and acryloyl chloride using methods A, C, and F. HPLC: 96%. MS: m/z=438 [M+H]$^+$. $^1$H-NMR (DMSO-d$_6$) δ 10.21 (s, 1H), 8.21 (s, 1H), 8.01 (s, 1H), 7.88 (d, 1H), 7.75 (s, 1H), 7.69 (t, 1H), 7.54-7.29 (m, 5H), 6.81 (d, 1H), 6.66 (broad s, 2H), 6.42 (dd, 1H), 6.25 (d, 1H), 5.77 (d, 1H), 5.59 (s, 2H).

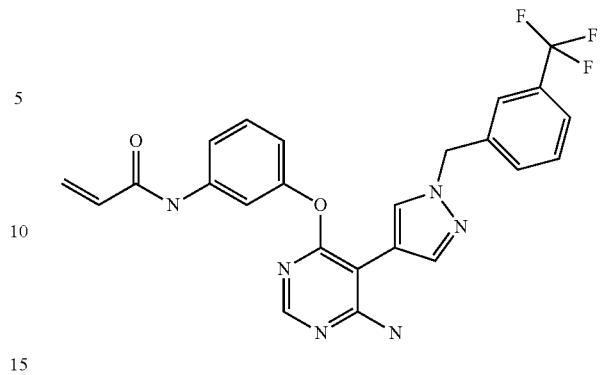

N-(3-((6-amino-5-(1-(3-(trifluoromethyl)benzyl)-1H-pyrazol-4-yl)pyrimidin-4-yl)oxy)phenyl)acrylamide (A195)

N-(3-((6-amino-5-(1-(3-(trifluoromethyl)benzyl)-1H-pyrazol-4-yl)pyrimidin-4-yl)oxy)phenyl)acrylamide was prepared from 5,6-dichloropyrimidin-4-amine, 3-aminophenol, 4-(4,4,5,5-tetramethyl-1,3,2-dioxaborolan-2-yl)-1-(3-(trifluoromethyl)benzyl)-1H-pyrazole, and acryloyl chloride using methods A, C, and F. HPLC: 98%. MS: m/z=481 [M+H]$^+$. $^1$H-NMR (DMSO-d$_6$) δ 10.20 (s, 1H), 8.20 (s, 1H), 8.00 (s, 1H), 7.75-7.29 (m, 8H), 6.93-6.58 (m, 3H), 6.42 (dd, 1H), 6.25 (d, 1H), 5.77 (d, 1H), 5.49 (s, 2H).

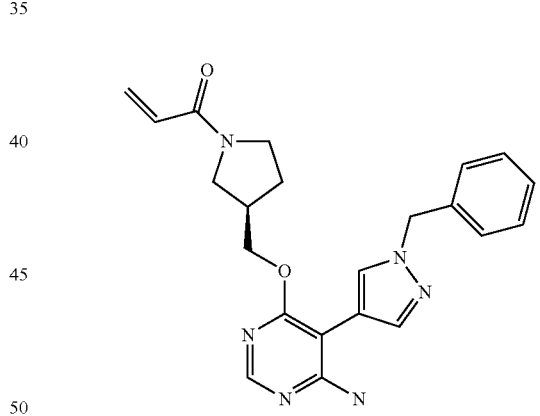

(R)-1-(3-(((6-amino-5-(1-benzyl-1H-pyrazol-4-yl)pyrimidin-4-yl)oxy)methyl)pyrolidin-1-yl)prop-2-en-1-one (A196)

(R)-1-(3-(((6-amino-5-(1-benzyl-1H-pyrazol-4-yl)pyrimidin-4-yl)oxy)methyl)pyrrolidin-1-yl)prop-2-en-1-one was prepared from 5-bromo-6-chloropyrimidin-4-amine, (R)-tert-butyl 3-(hydroxymethyl)pyrrolidine-1-carboxylate, 1-benzyl-4-(4,4,5,5-tetramethyl-1,3,2-dioxaborolan-2-yl)-1H-pyrazole, and acryloyl chloride using methods A, C, D, and F. HPLC: 99%. MS: m/z=405 [M+H]$^+$.

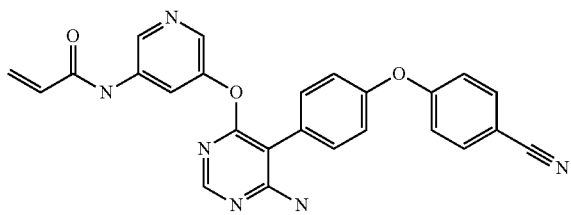 [SMILES: C=CC(=O)Nc1cncc(Oc2ncnc(N)c2-c2ccc(Oc3ccc(C#N)cc3)cc2)c1]

N-(5-((6-amino-5-(4-(4-cyanophenoxy)phenyl)pyrimidin-4-yl)oxy)pyridin-3-yl)acrylamide (A197)

N-(5-((6-amino-5-(4-(4-cyanophenoxy)phenyl)pyrimidin-4-yl)oxy)pyridin-3-yl)acrylamide was prepared from 5,6-dichloropyrimidin-4-amine, 5-aminopyridin-3-ol dihydrochloride, 4-(4-(4,4,5,5-tetramethyl-1,3,2-dioxaborolan-2-yl)phenoxy)benzonitrile, and acryloyl chloride using methods A, C, and F. HPLC: 98%. MS: m/z=452 [M+H]+. 1H-NMR (DMSO-d6) δ 10.48 (s, 1H), 8.57 (s, 1H), 8.12-8.09 (m, 2H), 7.97 (t, 1H), 7.86 (d, 2H), 7.52 (d, 2H), 7.23 (t, 4H), 6.43 (dd, 1H), 6.29 (d, 1H), 5.83 (d, 1H).

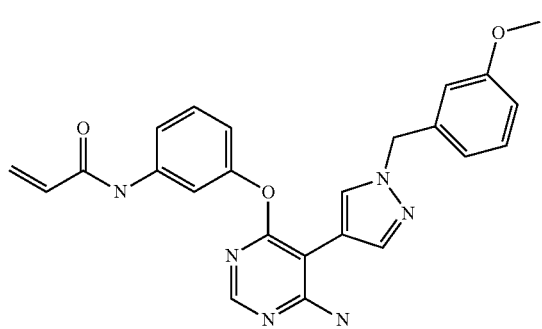 [SMILES: C=CC(=O)Nc1cccc(Oc2ncnc(N)c2-c2cnn(Cc3cccc(OC)c3)c2)c1]

N-(3-((6-amino-5-(1-(3-methoxybenzyl)-1H-pyrazol-4-yl)pyrimidin-4-yl)oxy)phenyl)acrylamide (A198)

N-(3-((6-amino-5-(1-(3-methoxybenzyl)-1H-pyrazol-4-yl)pyrimidin-4-yl)oxy)phenyl)acrylamide was prepared from 5,6-dichloropyrimidin-4-amine, 3-aminophenol, 1-(3-methoxybenzyl)-4-(4,4,5,5-tetramethyl-1,3,2-dioxaborolan-2-yl)-1H-pyrazole, and acryloyl chloride using methods A, C, and F. HPLC: 99%. MS: m/z=443 [M+H]+. 1H-NMR (DMSO-d6) δ 10.20 (s, 1H), 8.13 (s, 1H), 7.99 (s, 1H), 7.72 (s, 1H), 7.49 (s, 1H), 7.41 (d, 1H), 7.33-7.23 (m, 2H), 6.87-6.79 (m, 4H), 6.63 (broad s, 2H), 6.42 (dd, 1H), 6.25 (d, 1H), 5.76 (d, 1H), 5.33 (s, 2H), 3.70 (s, 3H).

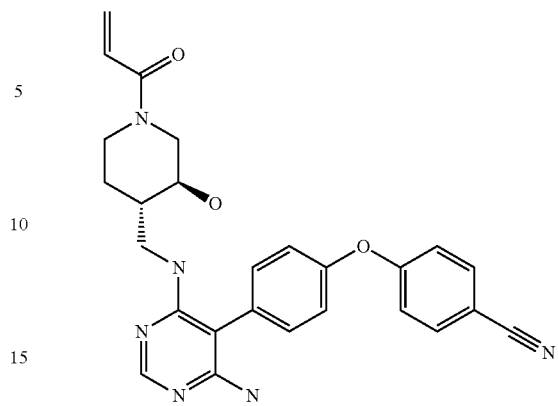

4-(4-(4-(((((3S,4S)-1-acryloyl-3-hydroxypiperidin-4-yl)methyl)amino)-6-aminopyrimidin-5-yl)phenoxy)benzonitrile (A199)

4-(4-(4-(((((3S,4S)-1-acryloyl-3-hydroxypiperidin-4-yl)methyl)amino)-6-aminopyrimidin-5-yl)phenoxy)benzonitrile (racemic) was prepared from 5,6-dichloropyrimidin-4-amine, (3S,4S)-tert-butyl 4-(aminomethyl)-3-hydroxypiperidine-1-carboxylate (racemic), 4-(4-(4,4,5,5-tetramethyl-1,3,2-dioxaborolan-2-yl)phenoxy)benzonitrile, and acryloyl chloride using methods B, C, D, and F. HPLC: 100%. MS: m/z=471 [M+H]+.

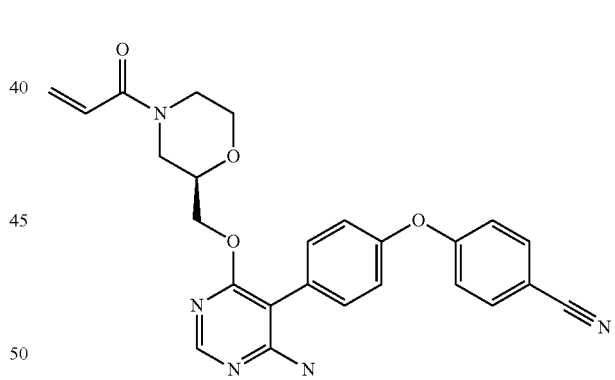

(R)-4-(4-(4-((4-acryloylmorpholin-2-yl)methoxy)-6-aminopyrimidin-5-yl)phenoxy)benzonitrile (A200)

(R)-4-(4-(4-((4-acryloylmorpholin-2-yl)methoxy)-6-aminopyrimidin-5-yl)phenoxy)benzonitrile was prepared from 5,6-dichloropyrimidin-4-amine, (R)-tert-butyl 2-(hydroxymethyl)morpholine-4-carboxylate, 4-(4-(4,4,5,5-tetramethyl-1,3,2-dioxaborolan-2-yl)phenoxy)benzonitrile, and acryloyl chloride using methods A, C, D, and F. HPLC: 99%. MS: m/z=458 [M+H]+.

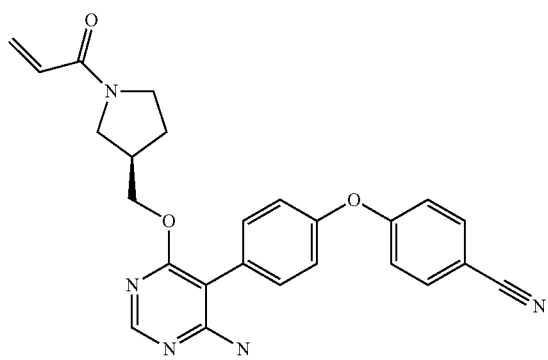 [SMILES: C=CC(=O)N1CC[C@@H](COc2ncnc(N)c2-c2ccc(Oc3ccc(C#N)cc3)cc2)C1]

(R)-4-(4-(4-((1-acryloylpyrrolidin-3-yl)methoxy)-6-aminopyrimidin-5-yl)phenoxy)benzonitrile (A201)

(R)-4-(4-(4-((1-acryloylpyrrolidin-3-yl)methoxy)-6-aminopyrimidin-5-yl)phenoxy)benzonitrile was prepared from 5,6-dichloropyrimidin-4-amine, (R)-tert-butyl 3-(hydroxymethyl)pyrrolidine-1-carboxylate, 4-(4-(4,4,5,5-tetramethyl-1,3,2-dioxaborolan-2-yl)phenoxy)benzonitrile, and acryloyl chloride using methods A, C, D, and F. HPLC: 99%. MS: m/z=442 [M+H]$^+$.

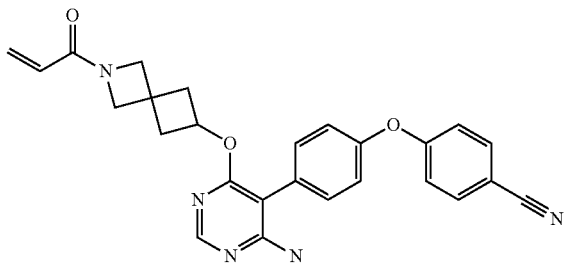 [SMILES: C=CC(=O)N1CC2(CC(Oc3ncnc(N)c3-c3ccc(Oc4ccc(C#N)cc4)cc3)C2)C1]

4-(4-(4-((2-acryloyl-2-azaspiro[3.3]heptan-6-yl)oxy)-6-aminopyrimidin-5-yl)phenoxy)benzonitrile (A202)

4-(4-(4-((2-acryloyl-2-azaspiro[3.3]heptan-6-yl)oxy)-6-aminopyrimidin-5-yl)phenoxy)benzonitrile was prepared from 5,6-dichloropyrimidin-4-amine, tert-butyl 6-hydroxy-2-azaspiro[3.3]heptane-2-carboxylate, 4-(4-(4,4,5,5-tetramethyl-1,3,2-dioxaborolan-2-yl)phenoxy)benzonitrile, and acryloyl chloride using methods A, C, D, and F. HPLC: 100%. MS: m/z=454 [M+H]$^+$.

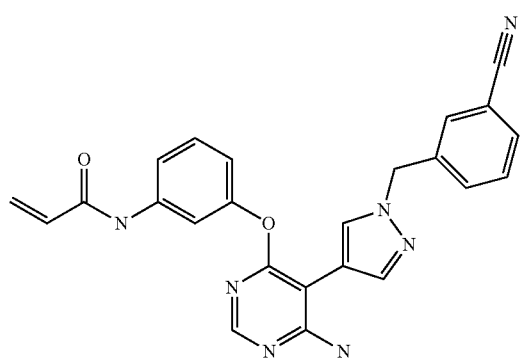 [SMILES: C=CC(=O)Nc1cccc(Oc2ncnc(N)c2-c2cnn(Cc3cccc(C#N)c3)c2)c1]

N-(3-((6-amino-5-(1-(3-cyanobenzyl)-1H-pyrazol-4-yl)pyrimidin-4-yl)oxy)phenyl)acrylamide (A203)

N-(3-((6-amino-5-(1-(3-cyanobenzyl)-1H-pyrazol-4-yl)pyrimidin-4-yl)oxy)phenyl)acrylamide was prepared from 5,6-dichloropyrimidin-4-amine, 3-aminophenol, 3-((4-(4,4,5,5-tetramethyl-1,3,2-dioxaborolan-2-yl)-1H-pyrazol-1-yl)methyl)benzonitrile, and acryloyl chloride using methods A, C, and F. HPLC: 100%. MS: m/z=438 [M+H]$^+$. $^1$H-NMR (DMSO-d$_6$) δ 10.20 (s, 1H), 8.18 (s, 1H), 8.00 (s, 1H), 7.79-7.74 (m, 3H), 7.65-7.50 (m, 3H), 7.41 (d, 1H), 7.31 (t, 1H), 6.81 (d, 1H), 6.69 (broad s, 2H), 6.42 (dd, 1H), 6.25 (d, 1H), 5.77 (d, 1H), 5.44 (s, 2H).

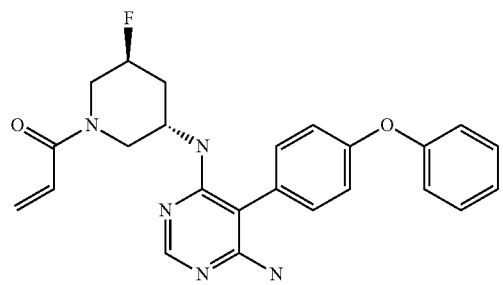 [SMILES: C=CC(=O)N1C[C@@H](F)C[C@H](Nc2ncnc(N)c2-c2ccc(Oc3ccccc3)cc2)C1]

1-((3S,5S)-3-((6-amino-5-(4-phenoxyphenyl)pyrimidin-4-yl)amino)-5-fluoropiperidin-1-yl)prop-2-en-1-one (A204)

1-((3S,5S)-3-((6-amino-5-(4-phenoxyphenyl)pyrimidin-4-yl)amino)-5-fluoropiperidin-1-yl)prop-2-en-1-one was prepared from 5,6-dichloropyrimidin-4-amine, (3S,5S)-5-fluoro-1-(4-methoxybenzyl)piperidin-3-amine, (4-phenoxyphenyl)boronic acid, and acryloyl chloride using methods B, C, hydrogenation, and F. HPLC: 97%. MS: m/z=434 [M+H]$^+$.

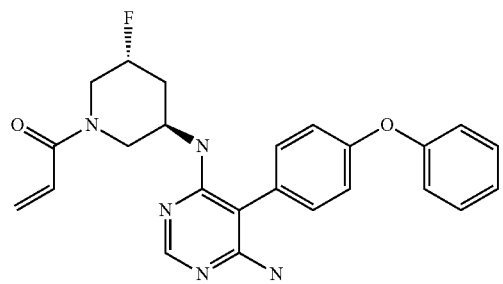 [SMILES: C=CC(=O)N1C[C@H](F)C[C@@H](Nc2ncnc(N)c2-c2ccc(Oc3ccccc3)cc2)C1]

1-((3R,5R)-3-((6-amino-5-(4-phenoxyphenyl)pyrimidin-4-yl)amino)-5-fluoropiperidin-1-yl)prop-2-en-1-one (A205)

1-((3R,5R)-3-((6-amino-5-(4-phenoxyphenyl)pyrimidin-4-yl)amino)-5-fluoropiperidin-1-yl)prop-2-en-1-one was prepared from 5,6-dichloropyrimidin-4-amine, (3R,5R)-5-fluoro-1-(4-methoxybenzyl)piperidin-3-amine, (4-phenoxyphenyl)boronic acid, and acryloyl chloride using methods B, C, hydrogenation, and F. HPLC: 99%. MS: m/z=434 [M+H]$^+$.

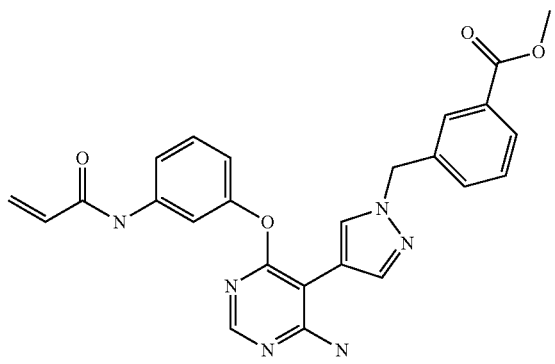 [SMILES: C=CC(=O)Nc1cccc(Oc2ncnc(N)c2-c2cnn(Cc3cccc(C(=O)OC)c3)c2)c1]

methyl 3-((4-(4-(3-acrylamidophenoxy)-6-aminopyrimidin-5-yl)-1H-pyrazol-1-yl)methyl)benzoate (A206)

methyl 3-((4-(4-(3-acrylamidophenoxy)-6-aminopyrimidin-5-yl)-1H-pyrazol-1-yl)methyl)benzoate was prepared from 5,6-dichloropyrimidin-4-amine, 3-aminophenol, methyl 3-((4-(4,4,5,5-tetramethyl-1,3,2-dioxaborolan-2-yl)-1H-pyrazol-1-yl)methyl)benzoate, and acryloyl chloride using methods A, C, and F. HPLC: 94%. MS: m/z=471 [M+H]$^+$. $^1$H-NMR (DMSO-d$_6$) δ 10.20 (s, 1H), 8.18 (s, 1H), 7.99 (s, 1H), 7.94 (s, 1H), 7.89 (d, 1H), 7.74 (s, 1H), 7.59 (d, 1H), 7.53-7.49 (m, 2H), 7.41 (d, 1H), 7.31 (t, 1H), 6.81 (d, 1H), 6.65 (broad s, 2H), 6.42 (dd, 1H), 6.25 (d, 1H), 5.77 (d, 1H), 5.46 (s, 2H), 3.83 (s, 3H).

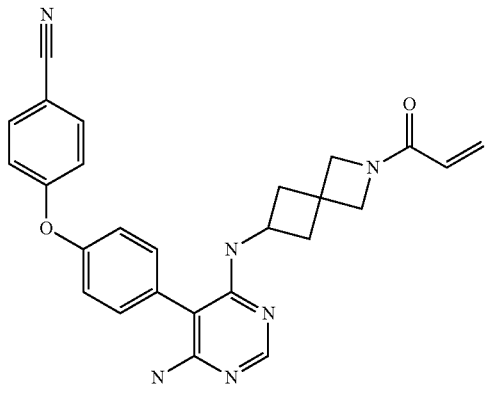 [SMILES: C=CC(=O)N1CC2(CC(Nc3ncnc(N)c3-c3ccc(Oc4ccc(C#N)cc4)cc3)C2)C1]

4-(4-(4-((2-acryloyl-2-azaspiro[3.3]heptan-6-yl)amino)-6-aminopyrimidin-5-yl)phenoxy)benzonitrile (A207)

4-(4-(4-((2-acryloyl-2-azaspiro[3.3]heptan-6-yl)amino)-6-aminopyrimidin-5-yl)phenoxy)benzonitrile was prepared from 5,6-dichloropyrimidin-4-amine, tert-butyl 6-amino-2-azaspiro[3.3]heptane-2-carboxylate, 4-(4-(4,4,5,5-tetramethyl-1,3,2-dioxaborolan-2-yl)phenoxy)benzonitrile, and acryloyl chloride using methods B, C, D, and E. HPLC: 98%. MS: m/z=453 [M+H]$^+$. $^1$H-NMR (DMSO-d$_6$) δ 7.96 (s, 1H), 7.87 (d, 2H), 7.29-7.23 (m, 6H), 6.31-6.22 (m, 1H), 6.07 (d, 1H), 5.67-5.46 (m, 4H), 4.40 (q, 1H), 4.25 (s, 1H), 4.08 (s, 1H), 3.96 (s, 1H), 3.79 (s, 1H), 2.47-2.40 (m, 2H), 2.14-2.09 (m, 2H).

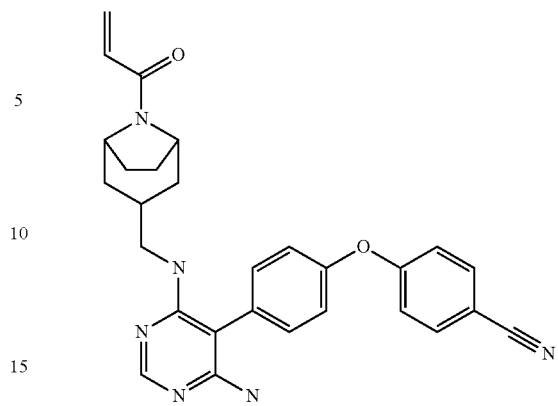

4-(4-(4-(((8-acryloyl-8-azabicyclo[3.2.1]octan-3-yl)methyl)amino)-6-aminopyrimidin-5-yl)phenoxy)benzonitrile (A208)

4-(4-(4-(((8-acryloyl-8-azabicyclo[3.2.1]octan-3-yl)methyl)amino)-6-aminopyrimidin-5-yl)phenoxy)benzonitrile was prepared from 5-bromo-6-chloropyrimidin-4-amine, tert-butyl 3-(aminomethyl)-8-azabicyclo[3.2.1]octane-8-carboxylate, 4-(4-(4,4,5,5-tetramethyl-1,3,2-dioxaborolan-2-yl)phenoxy)benzonitrile, and acryloyl chloride using methods B, C, D, and F. HPLC: 98%. MS: m/z=481 [M+H]$^+$.

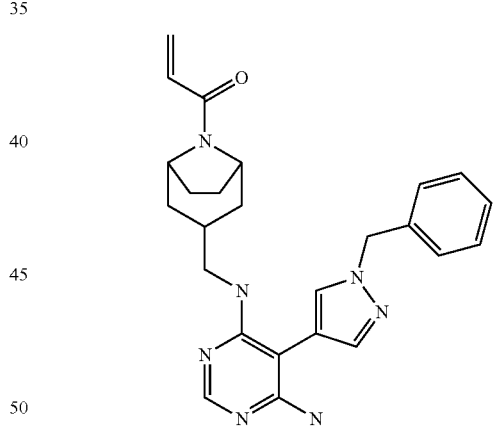

1-(3-(((6-amino-5-(1-benzyl-1H-pyrazol-4-yl)pyrimidin-4-yl)amino)methyl)-8-azabicyclo[3.2.1]octan-8-yl)prop-2-en-1-one (A209)

1-(3-(((6-amino-5-(1-benzyl-1H-pyrazol-4-yl)pyrimidin-4-yl)amino)methyl)-8-azabicyclo[3.2.1]octan-8-yl)prop-2-en-1-one was prepared from 5-bromo-6-chloropyrimidin-4-amine, tert-butyl 3-(aminomethyl)-8-azabicyclo[3.2.1]octane-8-carboxylate, 1-benzyl-4-(4,4,5,5-tetramethyl-1,3,2-dioxaborolan-2-yl)-1H-pyrazole, and acryloyl chloride using methods B, C, D, and F. HPLC: 99%. MS: m/z=444 [M+H]$^+$.

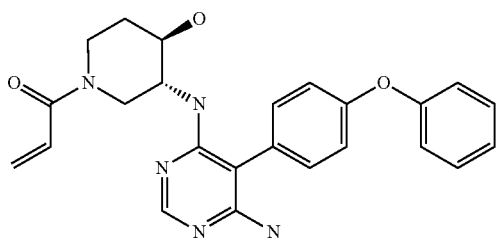 [SMILES: C=CC(=O)N1CC[C@@H](O)[C@H](Nc2ncnc(N)c2-c2ccc(Oc3ccccc3)cc2)C1]

1-((3R,4R)-3-((6-amino-5-(4-phenoxyphenyl)pyrimidin-4-yl)amino)-4-hydroxypiperidin-1-yl)prop-2-en-1-one (racemic) (A210)

1-((3R,4R)-3-((6-amino-5-(4-phenoxyphenyl)pyrimidin-4-yl)amino)-4-hydroxypiperidin-1-yl)prop-2-en-1-one (racemic) was prepared from 5,6-dichloropyrimidin-4-amine, (3R,4R)-benzyl 3-amino-4-hydroxypiperidine-1-carboxylate (racemic), (4-phenoxyphenyl)boronic acid, and acryloyl chloride using methods B, C, hydrogenation, and F. HPLC: 100%. MS: m/z=432 [M+H]+.

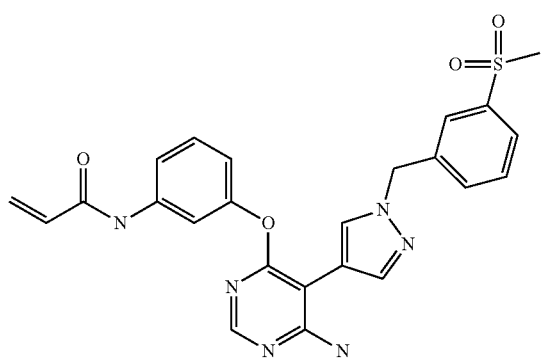 [SMILES: C=CC(=O)Nc1cccc(Oc2ncnc(N)c2-c2cnn(Cc3cccc(S(C)(=O)=O)c3)c2)c1]

N-(3-((6-amino-5-(1-(3-(methylsulfonyl)benzyl)-1H-pyrazol-4-yl)pyrimidin-4-yl)oxy)phenyl)acrylamide (A211)

N-(3-((6-amino-5-(1-(3-(methylsulfonyl)benzyl)-1H-pyrazol-4-yl)pyrimidin-4-yl)oxy)phenyl)acrylamide was prepared from 5,6-dichloropyrimidin-4-amine, 3-aminophenol, 1-(3-(methylsulfonyl)benzyl)-4-(4,4,5,5-tetramethyl-1,3,2-dioxaborolan-2-yl)-1H-pyrazole, and acryloyl chloride using methods A, C, and F. HPLC: 83%. MS: m/z=456 [M+H]+.

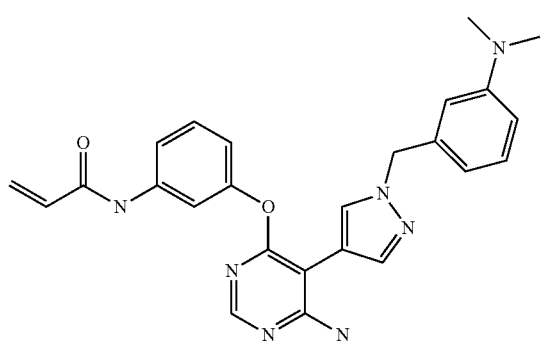 [SMILES: C=CC(=O)Nc1cccc(Oc2ncnc(N)c2-c2cnn(Cc3cccc(N(C)C)c3)c2)c1]

N-(3-((6-amino-5-(1-(3-(dimethylamino)benzyl)-1H-pyrazol-4-yl)pyrimidin-4-yl)oxy)phenyl)acrylamide (A212)

N-(3-((6-amino-5-(1-(3-(dimethylamino)benzyl)-1H-pyrazol-4-yl)pyrimidin-4-yl)oxy)phenyl)acrylamide was prepared from from 5,6-dichloropyrimidin-4-amine, 3-aminophenol, N,N-dimethyl-3-((4-(4,4,5,5-tetramethyl-1,3,2-dioxaborolan-2-yl)-1H-pyrazol-1-yl)methyl)aniline, and acryloyl chloride using methods A, C, and F. HPLC: 100%. MS: m/z=456 [M+H]+. 1H-NMR (DMSO-d6) δ 10.20 (s, 1H), 8.11 (s, 1H), 7.99 (s, 1H), 7.71 (s, 1H), 7.49 (s, 1H), 7.41 (d, 1H), 7.31 (t, 1H), 7.12 (t, 1H), 6.80 (d, 1H), 6.64-6.56 (m, 5H), 6.42 (dd, 1H), 6.25 (d, 1H), 5.76 (d, 1H), 5.28 (s, 2H), 2.83 (s, 6H).

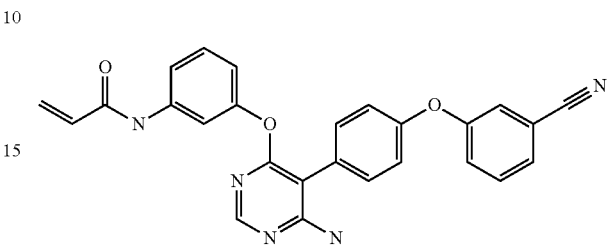

N-(3-((6-amino-5-(4-(3-cyanophenoxy)phenyl)pyrimidin-4-yl)oxy)phenyl)acrylamide (A213)

N-(3-((6-amino-5-(4-(3-cyanophenoxy)phenyl)pyrimidin-4-yl)oxy)phenyl)acrylamide was prepared from 5,6-dichloropyrimidin-4-amine, 3-aminophenol, 3-(4-(4,4,5,5-tetramethyl-1,3,2-dioxaborolan-2-yl)phenoxy)benzonitrile, and acryloyl chloride using methods A, C, and F. HPLC: 98%. MS: m/z=450 [M+H]+. 1H-NMR (DMSO-d6) δ 10.21 (s, 1H), 8.07 (s, 0.5H), 7.61-7.57 (m, 3.5H), 7.49-7.43 (m, 4H), 7.38 (d, 1H), 7.30 (t, 1H), 7.19 (d, 2H), 6.79 (d, 1H), 6.57 (broad s, 1.5H), 6.41 (dd, 1H), 6.25 (d, 1H), 5.76 (d, 1H).

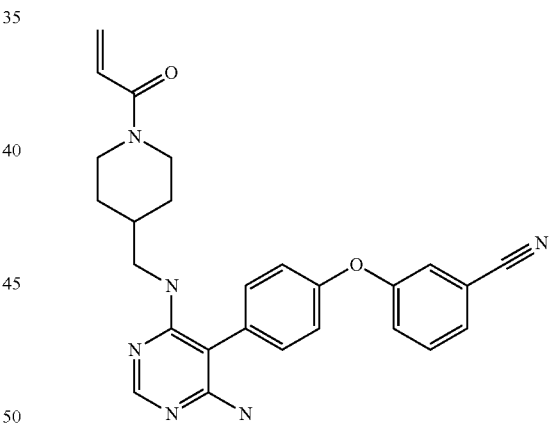

3-(4-(4-(((1-acryloylpiperidin-4-yl)methyl)amino)-6-aminopyrimidin-5-yl)phenoxy)benzonitrile (A214)

3-(4-(4-(((1-acryloylpiperidin-4-yl)methyl)amino)-6-aminopyrimidin-5-yl)phenoxy)benzonitrile was prepared from 5,6-dichloropyrimidin-4-amine, tert-butyl 4-(aminomethyl)piperidine-1-carboxylate, 3-(4-(4,4,5,5-tetramethyl-1,3,2-dioxaborolan-2-yl)phenoxy)benzonitrile, and acryloyl chloride using methods B, C, D, and F. HPLC: 100%. MS: m/z=455 [M+H]+. 1H-NMR (DMSO-d6) δ 7.96 (s, 1H), 7.63-7.56 (m, 3H), 7.50-7.45 (m, 1H), 7.29-7.19 (m, 4H), 6.78 (dd, 1H), 6.06 (d, 1H), 5.63 (d, 1H), 5.58-5.42 (m, 3H), 4.36 (d, 1H), 4.00 (d, 1H), 3.15 (t, 2H), 2.96 (t, 1H), 2.58 (t, 1H), 1.90-1.78 (m, 1H), 1.69-1.55 (m, 2H), 1.04-0.87 (m, 2H).

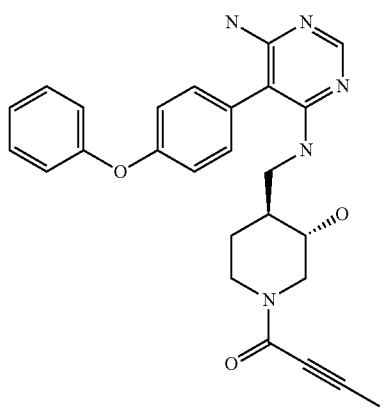 [SMILES: CC#CC(=O)N1CC[C@@H](CNc2ncnc(N)c2-c2ccc(Oc3ccccc3)cc2)[C@H](O)C1]

1-((3S,4S)-4-(((6-amino-5-(4-phenoxyphenyl)pyrimidin-4-yl)amino)methyl)-3-hydroxypiperidin-1-yl)but-2-yn-1-one (A215)

1-((3S,4S)-4-(((6-amino-5-(4-phenoxyphenyl)pyrimidin-4-yl)amino)methyl)-3-hydroxypiperidin-1-yl)but-2-yn-1-one was prepared 5,6-dichloropyrimidin-4-amine, 4-phenoxyphenylboronic acid, (3S,4S)-tert-butyl 4-(aminomethyl)-3-hydroxypiperidine-1-carboxylate and but-2-ynoic acid with method S1, S2, S3, S4A. Yield 41.3%. $^1$H NMR (CD$_3$OD) δ 8.26 (s, 1H), 7.14-7.40 (m, 9H), 4.28-4.48 (m, 2H), 3.66 (m, 1H), 3.52 (m, 1H), 3.01 (m, 1H), 2.60 (m, 1H), 2.0 (m, 3H), 1.75 (m, 2H), 1.20 (m, 1H). HPLC PURITY: 99%, MS: m/z=458[M+H]+

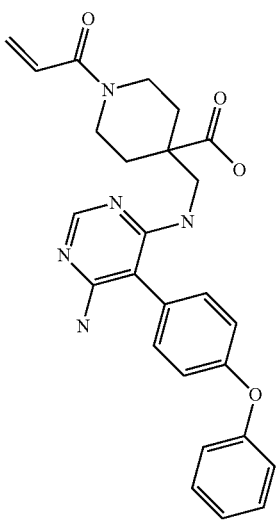 [SMILES: C=CC(=O)N1CCC(CNc2ncnc(N)c2-c2ccc(Oc3ccccc3)cc2)(C(=O)O)CC1]

1-acryloyl-4-(((6-amino-5-(4-phenoxyphenyl)pyrimidin-4-yl)amino)methyl)piperidine-4-carboxylic acid (A216)

1-acryloyl-4-(((6-amino-5-(4-phenoxyphenyl)pyrimidin-4-yl)amino)methyl)piperidine-4-carboxylic acid was prepared 5,6-dichloropyrimidin-4-amine, 4-phenoxyphenylboronic acid 4-(aminomethyl)-1-(tert-butoxycarbonyl)piperidine-4-carboxylic acid carboxylate and acrylic acid with method S1, S2, S3, S4A. Yield 35.9%. $^1$H NMR (CD$_3$OD) δ 8.26 (s, 1H), 7.14-7.40 (m, 9H), 6.73 (m, 1H), 6.21 (d, 1H), 5.73 (d, 1H), 4.25 (d, 1H), 3.89 (d, 1H), 3.73 (s, 2H), 3.02 (t, 1H), 2.08 (t, 2H), 1.45 (m, 2H). HPLC PURITY: 94%, MS: m/z=474[M+H]+

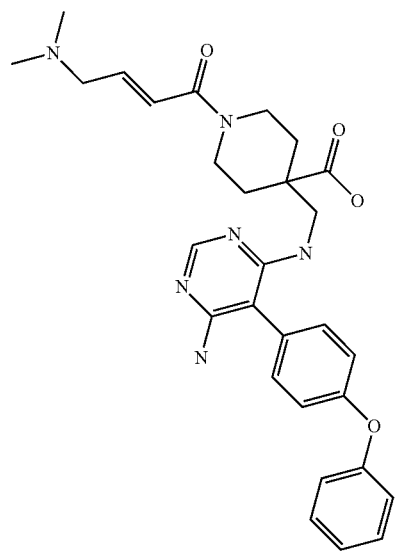 [SMILES: CN(C)C/C=C/C(=O)N1CCC(CNc2ncnc(N)c2-c2ccc(Oc3ccccc3)cc2)(C(=O)O)CC1]

(E)-4-(((6-amino-5-(4-phenoxyphenyl)pyrimidin-4-yl)amino)methyl)-1-(4-(dimethylamino)but-2-enoyl)piperidine-4-carboxylic acid (A217)

(E)-4-(((6-amino-5-(4-phenoxyphenyl)pyrimidin-4-yl)amino)methyl)-1-(4-(dimethylamino)but-2-enoyl)piperidine-4-carboxylic acid was prepared 5,6-dichloropyrimidin-4-amine, 4-phenoxyphenylboronic acid 4-(aminomethyl)-1-(tert-butoxycarbonyl)piperidine-4-carboxylic acid carboxylate and (E)-4-(dimethylamino)but-2-enoic acid hydrochloride with method S1, S2, S3, S4A. Yield 15.6%. $^1$H NMR (CD$_3$OD) δ 8.26 (s, 1H), 7.14-7.40 (m, 9H), 6.94 (d, 1H), 6.66 (m, 1H), 4.25 (d, 1H), 3.97 (m, 3H), 3.73 (s, 2H), 3.31 (m, 1H), 3.08 (t, 1H), 2.08 (t, 2H), 1.49 (m, 2H). HPLC PURITY: 94%, MS: m/z=531[M+H]+

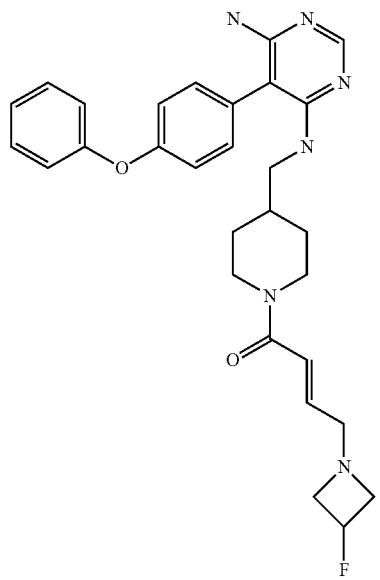 [SMILES: Nc1ncnc(NCC2CCN(C(=O)/C=C/CN3CC(F)C3)CC2)c1-c1ccc(Oc2ccccc2)cc1]

(E)-1-(4-(((6-amino-5-(4-phenoxyphenyl)pyrimidin-4-yl)amino)methyl)piperidin-1-yl)-4-(3-fluoroazetidin-1-yl)but-2-en-1-one (A218)

(E)-1-(4-(((6-amino-5-(4-phenoxyphenyl)pyrimidin-4-yl)amino)methyl)piperidin-1-yl)-4-(3-fluoroazetidin-1-yl)but-2-en-1-one was prepared 5,6-dichloropyrimidin-4-amine, 4-phenoxyphenylboronic acid, tert-butyl 4-(aminomethyl)piperidine-1-carboxylate and (E)-4-(3-fluoroazetidin-1-yl)but-2-enoic acid with method S1, S2, S3, S4A. Yield 6.0%. $^1$H NMR (CD$_3$OD) δ 8.04 (s, 1H), 7.19-7.47 (m, 9H), 6.57 (m, 2H), 5.22 (m, 1H), 4.50 (d, 1H), 4.10 (d, 1H), 3.79 (m, 2H), 3.50 (m, 3H), 3.13 (m, 1H), 2.63 (t, 1H), 1.87 (m, 1H), 1.76 (t, 2H), 1.15 (m, 2H). HPLC PURITY: 99%, MS: m/z=517[M+H]+

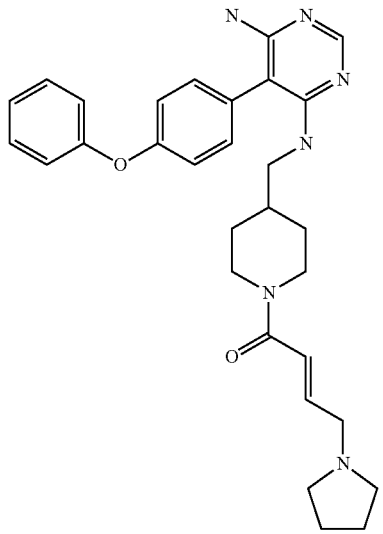

(E)-1-(4-(((6-amino-5-(4-phenoxyphenyl)pyrimidin-4-yl)amino)methyl)piperidin-1-yl)-4-(pyrrolidin-1-yl)but-2-en-1-one (A220)

(E)-1-(4-(((6-amino-5-(4-phenoxyphenyl)pyrimidin-4-yl)amino)methyl)piperidin-1-yl)-4-(pyrrolidin-1-yl)but-2-en-1-one was prepared 5,6-dichloropyrimidin-4-amine, 4-phenoxyphenylboronic acid, tert-butyl 4-(aminomethyl)piperidine-1-carboxylate and (E)-4-(pyrrolidin-1-yl)but-2-enoic acid with method S1, S2, S3, S4A. Yield 9.1%. $^1$H NMR (CD$_3$OD) δ 8.31 (m, 2H), 7.19-7.47 (m, 9H), 6.92 (d, 1H), 6.63 (m, 1H), 4.54 (d, 1H), 4.07 (d, 1H), 4.01 (d, 2H), 3.64 (s, 1H), 3.12 (t, 2H), 2.75 (t, 1H), 2.20 (s, 1H), 2.03 (s, 1H), 1.75 (t, 2H), 1.11 (t, 2H). HPLC PURITY: 91%, MS: m/z=513[M+H]+

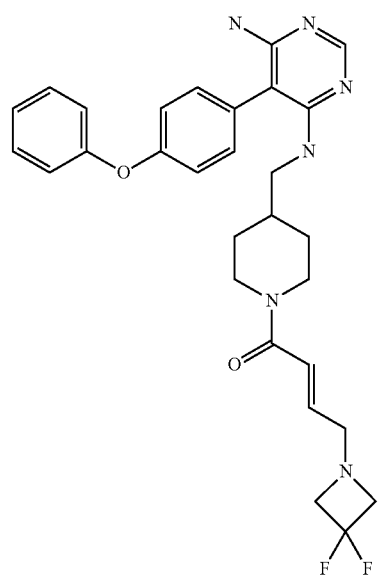 [SMILES: Nc1ncnc(NCC2CCN(C(=O)/C=C/CN3CC(F)(F)C3)CC2)c1-c1ccc(Oc2ccccc2)cc1]

(E)-1-(4-(((6-amino-5-(4-phenoxyphenyl)pyrimidin-4-yl)amino)methyl)piperidin-1-yl)-4-(3,3-difluoroazetidin-1-yl)but-2-en-1-one (A219)

(E)-1-(4-(((6-amino-5-(4-phenoxyphenyl)pyrimidin-4-yl)amino)methyl)piperidin-1-yl)-4-(3,3-difluoroazetidin-1-yl)but-2-en-1-one was prepared 5,6-dichloropyrimidin-4-amine, 4-phenoxyphenylboronic acid, tert-butyl 4-(aminomethyl)piperidine-1-carboxylate and (E)-4-(3,3-difluoroazetidin-1-yl)but-2-enoic acid with method S1, S2, S3, S4A. Yield 19.3%. $^1$H NMR (CD$_3$OD) δ 8.26 (s, 1H), 7.19-7.47 (m, 9H), 6.78 (d, 1H), 6.14 (m, 1H), 4.50 (d, 1H), 4.41 (t, 3H), 4.09 (d, 1H), 3.89 (d, 1H), 3.38 (m, 2H), 3.13 (m, 1H), 2.72 (t, 1H), 1.91 (m, 1H), 1.76 (t, 2H), 1.28 (m, 2H). HPLC PURITY: 99%, MS: m/z=535[M+H]+

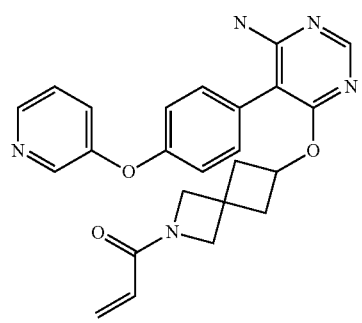 [SMILES: C=CC(=O)N1CC2(CC(Oc3ncnc(N)c3-c3ccc(Oc4cccnc4)cc3)C2)C1]

1-(6-((6-amino-5-(4-(pyridin-3-yloxy)phenyl)pyrimidin-4-yl)oxy)-2-azaspiro[3.3]heptan-2-yl)prop-2-en-1-one (A221)

1-(6-((6-amino-5-(4-(pyridin-3-yloxy)phenyl)pyrimidin-4-yl)oxy)-2-azaspiro[3.3]heptan-2-yl)prop-2-en-1-one was prepared 5,6-dichloropyrimidin-4-amine, (4-(pyridin-3-yloxy)phenyl)boronic acid, tert-butyl 6-hydroxy-2-azaspiro[3.3]heptane-2-carboxylate and acrylic acid with method S1, S2, S3, S4A. Yield 21.2%. $^1$H NMR (CD$_3$OD) δ 8.31 (m, 2H), 8.13 (s, 1H), 7.52 (m, 1H), 6.97 (m, 1H), 7.41 (d, 2H), 7.19 (m, 2H), 6.25 (m, 2H), 5.75 (m, 1H), 5.24 (m, 1H), 4.21

(d, 2H), 4.03 (d, 2H), 2.72 (m, 2H), 2.25 (m, 2H). HPLC PURITY: 99%, MS: m/z=430[M+H]+

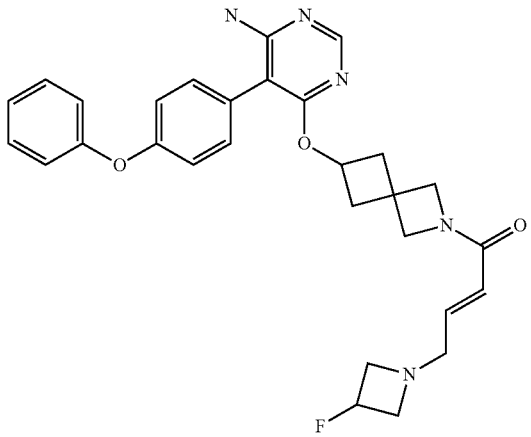 [SMILES: Nc1ncnc(OC2CC3(C2)CN(C(=O)/C=C/CN2CC(F)C2)C3)c1-c1ccc(Oc2ccccc2)cc1]

(E)-1-(6-(((6-amino-5-(4-phenoxyphenyl)pyrimidin-4-yl)oxy)-2-azaspiro[3.3]heptan-2-yl)-4-(3-fluoro-azetidin-1-yl)but-2-en-1-one (A222)

(E)-1-(6-(((6-amino-5-(4-phenoxyphenyl)pyrimidin-4-yl)oxy)-2-azaspiro[3.3]heptan-2-yl)-4-(3-fluoroazetidin-1-yl)but-2-en-1-one was prepared 5,6-dichloropyrimidin-4-amine, 4-phenoxyphenylboronic acid, tert-butyl 6-hydroxy-2-azaspiro[3.3]heptane-2-carboxylate and (E)-4-(3-fluoroazetidin-1-yl)but-2-enoic acid with method S1, S2, S3, 54A. Yield 1.7%. $^1$H NMR (CD$_3$OD) δ 8.28 (s, 1H), 7.10-7.47 (m, 9H), 6.62 (m, 1H), 6.40 (t, 1H), 5.41 (m, 1H), 5.25 (m, 1H), 4.27 (d, 2H), 4.04 (m, 4H), 2.74 (m, 2H), 2.27 (m, 2H). HPLC PURITY: 99%, MS: m/z=516[M+H]+

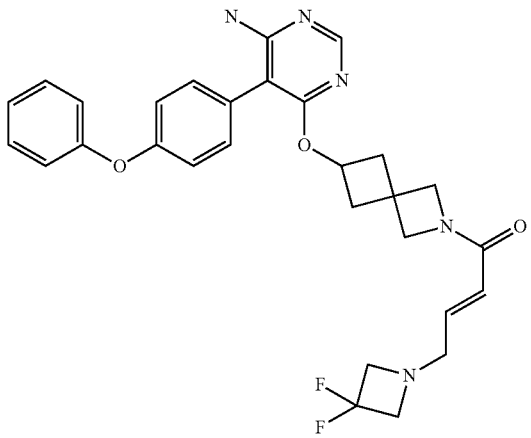 [SMILES: Nc1ncnc(OC2CC3(C2)CN(C(=O)/C=C/CN2CC(F)(F)C2)C3)c1-c1ccc(Oc2ccccc2)cc1]

(E)-1-(6-(((6-amino-5-(4-phenoxyphenyl)pyrimidin-4-yl)oxy)-2-azaspiro[3.3]heptan-2-yl)-4-(3,3-difluoroazetidin-1-yl)but-2-en-1-one (A223)

(E)-1-(6-(((6-amino-5-(4-phenoxyphenyl)pyrimidin-4-yl)oxy)-2-azaspiro[3.3]heptan-2-yl)-4-(3,3-difluoroazetidin-1-yl)but-2-en-1-one was prepared 5,6-dichloropyrimidin-4-amine, 4-phenoxyphenylboronic acid, tert-butyl 6-hydroxy-2-azaspiro[3.3]heptane-2-carboxylate and (E)-4-(3,3-difluoroazetidin-1-yl)but-2-enoic acid with method S1, S2, S3, S4A. Yield 2.7%. $^1$H NMR (CD$_3$OD) δ 8.31 (s, 1H), 7.10-7.47 (m, 9H), 6.60 (m, 1H), 6.40 (t, 1H), 5.25 (m, 1H), 4.54 (qt, 4H), 4.27 (d, 2H), 4.08 (s, 1H), 4.00 (m, 3H), 2.74 (m, 2H), 2.27 (m, 2H). HPLC PURITY: 95%, MS: m/z=534 [M+H]+

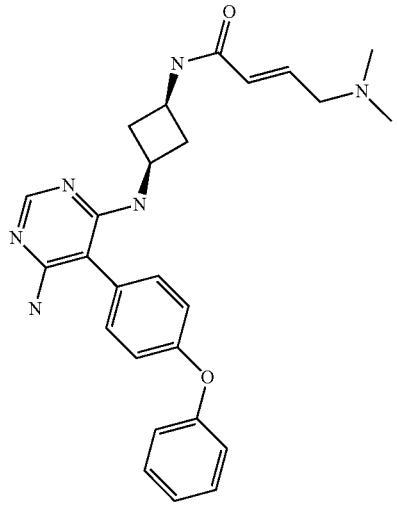 [SMILES: CN(C)C/C=C/C(=O)N[C@H]1C[C@@H](Nc2ncnc(N)c2-c2ccc(Oc3ccccc3)cc2)C1]

(E)-N-(1,3-cis-3-((6-amino-5-(4-phenoxyphenyl)pyrimidin-4-yl)amino)cyclobutyl)-4-(dimethyl-amino)but-2-enamide (A224)

(E)-N-(1,3-cis-3-((6-amino-5-(4-phenoxyphenyl)pyrimidin-4-yl)amino)cyclobutyl)-4-(dimethylamino)but-2-enamide was prepared 5,6-dichloropyrimidin-4-amine, 4-phenoxyphenylboronic acid, tert-butyl(1,3-cis-3-aminocyclobutyl)carbamate and (E)-4-(dimethylamino)but-2-enoic acid hydrochloride with method S1, S2, S3, S4A. Yield 19.4%. $^1$H NMR (CD$_3$OD) δ 8.31 (s, 1H), 7.10-7.47 (m, 9H), 6.60 (m, 1H), 6.40 (t, 1H), 5.25 (m, 1H), 4.54 (qt, 4H), 4.27 (d, 2H), 4.08 (s, 1H), 4.00 (m, 6H), 2.74 (m, 2H), 2.27 (m, 2H) HPLC. PURITY: 99%, MS: m/z=459[M+H]+

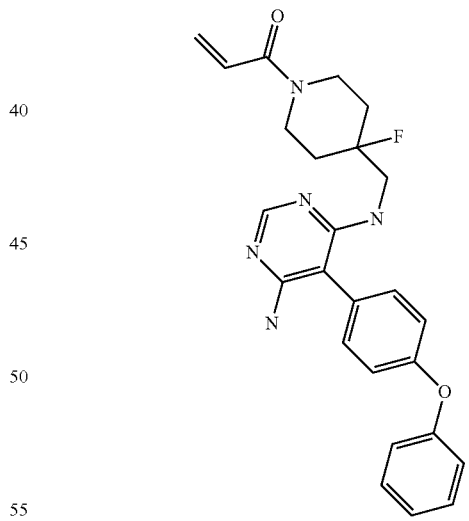

1-(4-(((6-amino-5-(4-phenoxyphenyl)pyrimidin-4-yl)amino)methyl)-4-fluoropiperidin-1-yl)prop-2-en-1-one (A225)

1-(4-(((6-amino-5-(4-phenoxyphenyl)pyrimidin-4-yl)amino)methyl)-4-fluoropiperidin-1-yl)prop-2-en-1-one was prepared 5,6-dichloropyrimidin-4-amine, 4-phenoxyphenylboronic acid, tert-butyl 4-(aminomethyl)-4-fluoropiperidine-1-carboxylate and acrylic acid with method S1, S2, S3, S4A. Yield 16.1%. $^1$H NMR (CD$_3$OD) δ 8.26 (s, 1H), 7.14-7.40 (m, 9H), 6.73 (m, 1H), 6.24 (d, 1H), 5.73 (d, 1H), 4.41 (d, 1H), 4.00 (d, 1H), 3.74 (d, 2H), 3.44 (m, 1H), 3.02 (t, 1H), 1.73 (m, 2H), 1.61 (m, 2H). HPLC PURITY: 94%, MS: m/z=448[M+H]+

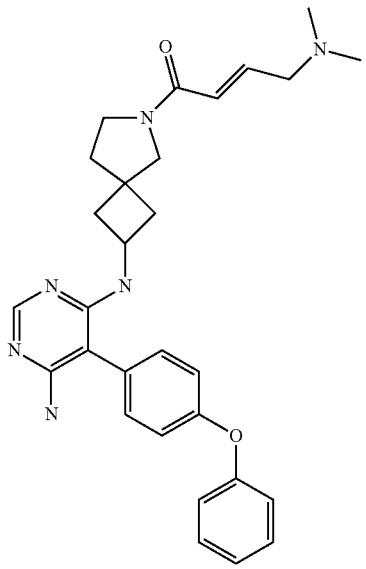 [SMILES: CN(C)C/C=C/C(=O)N1CCC2(CC(Nc3ncnc(N)c3-c3ccc(Oc4ccccc4)cc3)C2)C1]

(E)-1-(2-((6-amino-5-(4-phenoxyphenyl)pyrimidin-4-yl)amino)-6-azaspiro[3.4]octan-6-yl)-4-(dimethylamino)but-2-en-1-one (A226)

(E)-1-(2-((6-amino-5-(4-phenoxyphenyl)pyrimidin-4-yl)amino)-6-azaspiro[3.4]octan-6-yl)-4-(dimethylamino)but-2-en-1-one was prepared 5,6-dichloropyrimidin-4-amine, 4-phenoxyphenylboronic acid, tert-butyl 2-amino-6-azaspiro[3.4]octane-6-carboxylate and (E)-4-(dimethylamino)but-2-enoic acid hydrochloride with method S1, S2, S3, S4A. Yield 5.4%. $^1$H NMR (CD$_3$OD) δ 8.31 (s, 1H), 7.10-7.47 (m, 9H), 6.75 (m, 2H), 3.97 (m, 2H), 3.65 (m, 1H), 3.50 (m, 1H), 2.92 (m, 6H), 2.38 (m, 2H), 2.12 (m, 2H), 2.0 (t, 1H), 1.80 (m, 2H), 1.62 (m, 2H). HPLC PURITY: 98%, MS: m/z=499[M+H]+

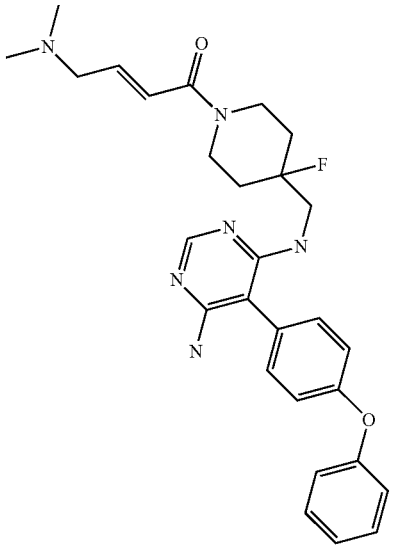 [SMILES: CN(C)C/C=C/C(=O)N1CCC(F)(CNc2ncnc(N)c2-c2ccc(Oc3ccccc3)cc2)CC1]

(E)-1-(4-(((6-amino-5-(4-phenoxyphenyl)pyrimidin-4-yl)amino)methyl)-4-fluoropiperidin-1-yl)-4-(dimethylamino)but-2-en-1-one (A227)

(E)-1-(4-(((6-amino-5-(4-phenoxyphenyl)pyrimidin-4-yl)amino)methyl)-4-fluoropiperidin-1-yl)-4-(dimethylamino)but-2-en-1-one was prepared 5,6-dichloropyrimidin-4-amine, 4-phenoxyphenylboronic acid, tert-butyl 4-(aminomethyl)-4-fluoropiperidine-1-carboxylate and (E)-4-(dimethylamino)but-2-enoic acid hydrochloride with method S1, S2, S3, S4A. Yield 15.9%. $^1$H NMR (CD$_3$OD) δ 8.26 (s, 1H), 7.14-7.40 (m, 9H), 6.93 (d, 1H), 6.74 (m, 1H), 4.47 (d, 1H), 3.98 (m, 3H), 3.75 (d, 2H), 3.41 (t, 1H), 3.03 (t, 1H), 2.97 (m, 6H), 1.81 (m, 2H), 1.62 (m, 2H). HPLC PURITY: 99%, MS: m/z=505[M+H]+

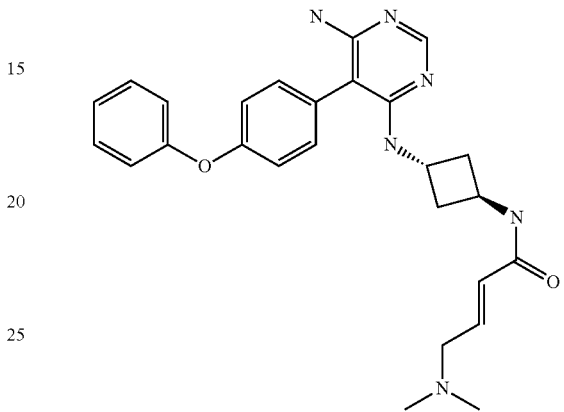

(E)-N-(1,3-trans-3-((6-amino-5-(4-phenoxyphenyl)pyrimidin-4-yl)amino)cyclobutyl)-4-(dimethylamino)but-2-enamide (A228)

(E)-N-((1,3-trans)-3-((6-amino-5-(4-phenoxyphenyl)pyrimidin-4-yl)amino)cyclobutyl)-4-(dimethylamino)but-2-enamide was prepared 5,6-dichloropyrimidin-4-amine, 4-phenoxyphenylboronic acid, tert-butyl(1,3-trans-3-aminocyclobutyl)carbamate and (E)-4-(dimethylamino)but-2-enoic acid hydrochloride with method S1, S2, S3, S4A. Yield 23.6%. $^1$H NMR (CD$_3$OD) δ 8.25 (s, 1H), 7.10-7.47 (m, 9H), 6.73 (m, 1H), 6.40 (d, 1H), 4.26 (m, 1H), 3.92 (m, 2H), 2.96 (s, 6H), 1.79 (m, 2H), 1.67 (m, 2H) HPLC PURITY: 99%, MS: m/z=459[M+H]+

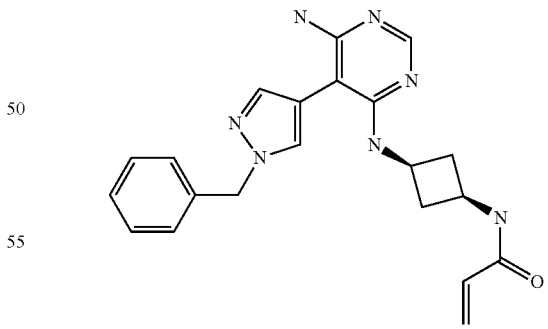

N-(1,3-cis-3-((6-amino-5-(1-benzyl-1H-pyrazol-4-yl)pyrimidin-4-yl)amino)cyclobutyl)acrylamide (A229)

N-(1,3-cis-3-((6-amino-5-(1-benzyl-1H-pyrazol-4-yl)pyrimidin-4-yl)amino)cyclobutyl)acrylamide was prepared 5,6-dichloropyrimidin-4-amine, (1-benzyl-1H-pyrazol-4-yl)boronic acid, tert-butyl(1,3-cis-3-aminocyclobutyl) carbamate and acrylic acid with method S1, S2, S3, S4A. Yield 8.2%. ¹H NMR (CD₃OD) δ 8.25 (s, 1H), 7.80 (s, 1H), 7.59 (s, 1H), 7.38 (m, 5H), 6.24 (m, 2H), 5.61 (d, 1H), 5.45 (s, 2H), 4.37 (m, 1H), 4.03 (m, 1H), 2.74 (m, 2H), 2.02 (m, 2H). HPLC PURITY: 95%, MS: m/z=390[M+H]+

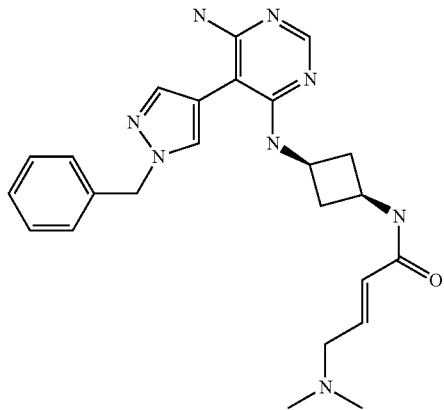 [SMILES: CN(C)C/C=C/C(=O)N[C@H]1C[C@@H](Nc2ncnc(N)c2-c2cnn(Cc3ccccc3)c2)C1]

(E)-N-(1,3-cis-3-(((6-amino-5-(1-benzyl-1H-pyrazol-4-yl)pyrimidin-4-yl)amino)cyclobutyl)-4-(dimethylamino)but-2-enamide (A230)

(E)-N-(1,3-cis-3-(((6-amino-5-(1-benzyl-1H-pyrazol-4-yl)pyrimidin-4-yl)amino)cyclobutyl)-4-(dimethylamino)but-2-enamide was prepared 5,6-dichloropyrimidin-4-amine, (1-benzyl-1H-pyrazol-4-yl)boronic acid, tert-butyl (1,3-cis-3-aminocyclobutyl) carbamate and (E)-4-(dimethylamino)but-2-enoic acid hydrochloride with method S1, S2, S3, S4A. Yield 31.2%. ¹H NMR (CD₃OD) δ 7.95 (s, 1H), 7.77 (s, 1H), 7.38 (m, 5H), 6.74 (m, 1H), 6.01 (d, 1H), 5.45 (s, 2H), 4.25 (m, 1H), 4.08 (m, 1H), 3.09 (d, 2H), 2.74 (m, 2H), 2.27 (m, 2H). HPLC PURITY: 91%, MS: m/z=447[M+H]+

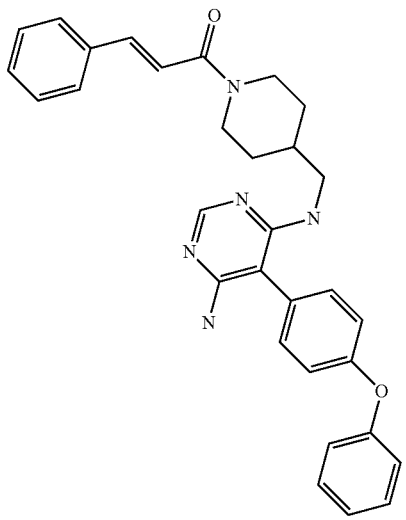 [SMILES: Nc1ncnc(NCC2CCN(C(=O)/C=C/c3ccccc3)CC2)c1-c1ccc(Oc2ccccc2)cc1]

(E)-1-(4-(((6-amino-5-(4-phenoxyphenyl)pyrimidin-4-yl)amino)methyl)piperidin-1-yl)-3-phenylprop-2-en-1-one (A231)

(E)-1-(4-(((6-amino-5-(4-phenoxyphenyl)pyrimidin-4-yl)amino)methyl)piperidin-1-yl)-3-phenylprop-2-en-1-one was prepared 5,6-dichloropyrimidin-4-amine, 4-phenoxyphenylboronic acid, tert-butyl 4-(aminomethyl)piperidine-1-carboxylate and cinnamic acid with method S1, S2, S3, S4A. Yield 45.4%. ¹H NMR (CD₃OD) δ 8.04 (s, 1H), 7.19-7.47 (m, 14H), 4.55 (d, 1H), 4.25 (d, 1H), 3.42 (d, 2H), 3.14 (t, 1H), 2.75 (t, 1H), 2.00 (m, 1H), 1.76 (t, 2H), 1.15 (m, 2H). HPLC PURITY: 98%, MS: m/z=506[M+H]+

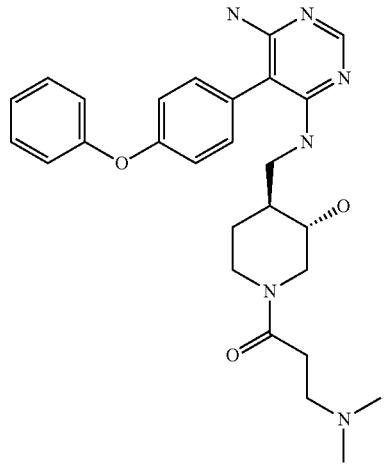 [SMILES: CN(C)CCC(=O)N1CC[C@@H](CNc2ncnc(N)c2-c2ccc(Oc3ccccc3)cc2)[C@H](O)C1]

1-((3S,4S)-4-(((6-amino-5-(4-phenoxyphenyl)pyrimidin-4-yl)amino)methyl)-3-hydroxypiperidin-1-yl)-3-(dimethylamino)propan-1-one (A232)

1-((3S,4S)-4-(((6-amino-5-(4-phenoxyphenyl)pyrimidin-4-yl)amino)methyl)-3-hydroxypiperidin-1-yl)-3-(dimethylamino)propan-1-one was prepared 5,6-dichloropyrimidin-4-amine, 4-phenoxyphenylboronic acid, (3S,4S)-tert-butyl 4-(aminomethyl)-3-hydroxypiperidine-1-carboxylate and 3-(dimethylamino)propanoic acid with method S1, S2, S3, S4A. Yield 17.3%. ¹H NMR (CD₃OD) δ 8.26 (s, 1H), 7.14-7.40 (m, 9H), 4.48 (dd, 1H), 3.89 (m, 1H), 3.66 (m, 1H), 3.28 (m, 1H), 3.01 (m, 1H), 2.61 (m, 4H), 2.44 (t, 1H), 2.25 (s, 6H), 1.75 (m, 2H), 1.20 (m, 1H). HPLC PURITY: 92%, MS: m/z=491[M+H]+

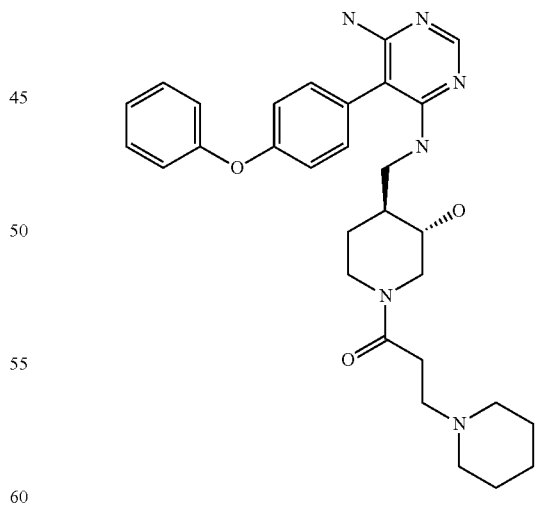

1-((3S,4S)-4-(((6-amino-5-(4-phenoxyphenyl)pyrimidin-4-yl)amino)methyl)-3-hydroxypiperidin-1-yl)-3-(piperidin-1-yl)propan-1-one (A233)

1-((3S,4S)-4-(((6-amino-5-(4-phenoxyphenyl)pyrimidin-4-yl)amino)methyl)-3-hydroxypiperidin-1-yl)-3-(piperidin- 1-yl)propan-1-one was prepared 5,6-dichloropyrimidin-4-amine, 4-phenoxyphenylboronic acid, (3S,4S)-tert-butyl 4-(aminomethyl)-3-hydroxypiperidine-1-carboxylate and 3-(piperidin-1-yl)propanoic acid with method S1, S2, S3, S4A. Yield 24.2%. ¹H NMR (CD₃OD) δ 8.26 (s, 1H), 7.14-7.40 (m, 9H), 4.48 (dd, 1H), 3.89 (t, 1H), 3.67 (t, 1H), 3.28 (m, 1H), 3.00 (m, 1H), 2.31-2.61 (m, 8H), 1.75 (m, 5H), 1.49 (s, 2H), 1.20 (m, 1H). HPLC PURITY: 99%, MS: m/z=530[M+H]+

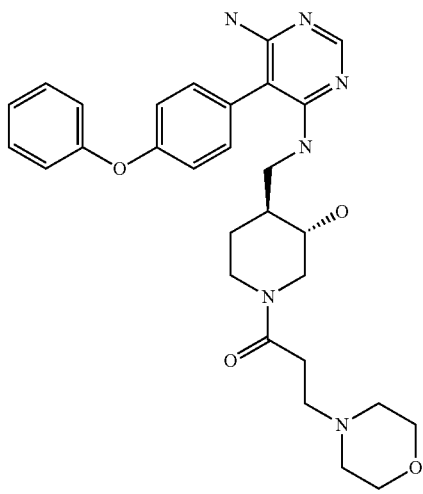 [SMILES: Nc1ncnc(NC[C@@H]2CCN(C(=O)CCN3CCOCC3)C[C@H]2O)c1-c1ccc(Oc2ccccc2)cc1]

1-((3S,4S)-4-(((6-amino-5-(4-phenoxyphenyl)pyrimidin-4-yl)amino)methyl)-3-hydroxypiperidin-1-yl)-3-morpholinopropan-1-one (A234)

1-((3S,4S)-4-(((6-amino-5-(4-phenoxyphenyl)pyrimidin-4-yl)amino)methyl)-3-hydroxypiperidin-1-yl)-3-morpholinopropan-1-one was prepared 5,6-dichloropyrimidin-4-amine, 4-phenoxyphenylboronic acid, (3S,4S)-tert-butyl 4-(aminomethyl)-3-hydroxypiperidine-1-carboxylate and 3-morpholinopropanoic acid with method S1, S2, S3, S4A. Yield 30.5%. ¹H NMR (CD₃OD) δ 8.26 (s, 1H), 7.14-7.40 (m, 9H), 4.48 (dd, 1H), 3.88 (t, 1H), 3.66 (m, 5H), 3.28 (m, 1H), 3.00 (m, 1H), 2.33-2.61 (m, 9H), 1.49 (s, 2H), 1.20 (m, 1H). HPLC PURITY: 99%, MS: m/z=533[M+H]+

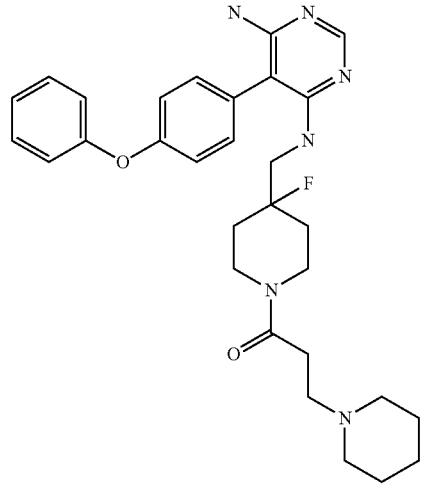 [SMILES: Nc1ncnc(NCC2(F)CCN(C(=O)CCN3CCCCC3)CC2)c1-c1ccc(Oc2ccccc2)cc1]

1-(4-(((6-amino-5-(4-phenoxyphenyl)pyrimidin-4-yl)amino)methyl)-4-fluoropiperidin-1-yl)-3-(piperidin-1-yl)propan-1-one (A235)

1-(4-(((6-amino-5-(4-phenoxyphenyl)pyrimidin-4-yl)amino)methyl)-4-fluoropiperidin-1-yl)-3-(piperidin-1-yl)propan-1-one was prepared 5,6-dichloropyrimidin-4-amine, 4-phenoxyphenylboronic acid, tert-butyl 4-(aminomethyl)-4-fluoropiperidine-1-carboxylate and 3-(piperidin-1-yl)propanoic acid with method S1, S2, S3, S4A. Yield 23.4%. ¹H NMR (CD₃OD) δ 8.26 (s, 1H), 7.14-7.40 (m, 9H), 4.29 (d, 1H), 3.80 (d, 1H), 3.62 (dd, 2H), 3.00 (m, 1H), 2.60-2.77 (m, 7H), 1.78 (m, 2H), 1.69 (m, 5H), 1.52 (m, 2H). HPLC PURITY: 99%, MS: m/z=533[M+H]+

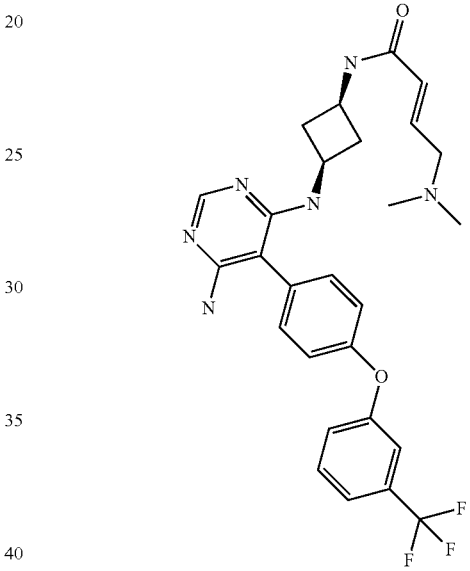

(E)-N-(1,3-cis-3-((6-amino-5-(4-(3-(trifluoromethyl)phenoxy)phenyl)pyrimidin-4-yl)amino)cyclobutyl)-4-(dimethylamino)but-2-enamide (A236)

(E)-N-(1,3-cis-3-((6-amino-5-(4-(3-(trifluoromethyl)phenoxy)phenyl)pyrimidin-4-yl)amino)cyclobutyl)-4-(dimethylamino)but-2-enamide was prepared 5,6-dichloropyrimidin-4-amine, (4-(3-(trifluoromethyl)phenoxy)phenyl)boronic acid, tert-butyl(1,3-cis-3-aminocyclobutyl)carbamate and (E)-4-(dimethylamino)but-2-enoic acid hydrochloride with method S1, S2, S3, S4A. Yield 17.1%. ¹H NMR (CDCl₃) δ 8.26 (s, 1H), 7.18-7.53 (m, 8H), 6.74 (m, 1H), 6.49 (m, 1H), 4.58 (m, 2H), 4.26 (m, 1H), 4.13 (m, 1H), 3.58 (m, 2H), 2.69 (m, 6H), 1.74 (m, 2H). HPLC PURITY: 99%, MS: m/z=527[M+H]+

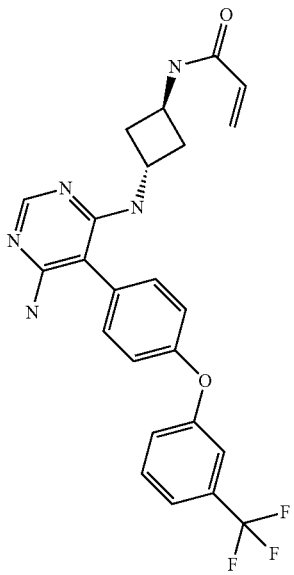 [SMILES: C=CC(=O)N[C@H]1C[C@H](Nc2ncnc(N)c2-c2ccc(Oc3cccc(C(F)(F)F)c3)cc2)C1]

N-(1,3-trans-3-((6-amino-5-(4-(3-(trifluoromethyl)
phenoxy)phenyl)pyrimidin-4-yl)amino)cyclobutyl)
acrylamide (A237)

N-(1,3-trans-3-((6-amino-5-(4-(3-(trifluoromethyl)phenoxy)phenyl)pyrimidin-4-yl)amino)cyclobutyl)acrylamide was prepared 5,6-dichloropyrimidin-4-amine, (4-(3-(trifluoromethyl)phenoxy)phenyl)boronic acid, tert-butyl (1,3-trans-3-aminocyclobutyl)carbamate and acrylic acid with method S1, S2, S3, S4A. Yield 22.8%. $^1$H NMR (CDCl$_3$) δ 8.26 (s, 1H), 7.18-7.53 (m, 8H), 6.74 (d, 1H), 6.27 (m, 1H), 5.71 (d, 1H), 5.25 (m, 1H), 4.50 (m, 1H), 2.50 (m, 2H), 2.28 (m, 2H). HPLC PURITY: 99%, MS: m/z=470[M+H]+

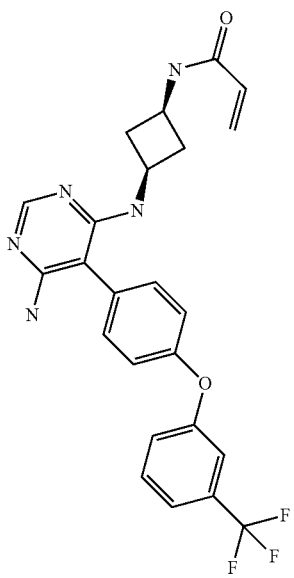 [SMILES: C=CC(=O)N[C@H]1C[C@@H](Nc2ncnc(N)c2-c2ccc(Oc3cccc(C(F)(F)F)c3)cc2)C1]

N-(1,3-cis-3-((6-amino-5-(4-(3-(trifluoromethyl)
phenoxy)phenyl)pyrimidin-4-yl)amino)cyclobutyl)
acrylamide (A238)

N-(1,3-cis-3-((6-amino-5-(4-(3-(trifluoromethyl)phenoxy)phenyl)pyrimidin-4-yl)amino)cyclobutyl)acrylamide was prepared 5,6-dichloropyrimidin-4-amine, (4-(3-(trifluoromethyl)phenoxy)phenyl)boronic acid, tert-butyl(1,3-cis-3-aminocyclobutyl)carbamate and acrylic acid with method S1, S2, S3, S4A. Yield 22.1%. $^1$H NMR (CDCl$_3$) δ 8.23 (s, 1H), 7.18-7.53 (m, 8H), 6.25 (d, 1H), 6.04 (m, 1H), 5.66 (d, 1H), 4.42 (m, 1H), 4.03 (m, 1H), 2.81 (m, 2H), 2.02 (m, 2H). HPLC PURITY: 98%, MS: m/z=470[M+H]+

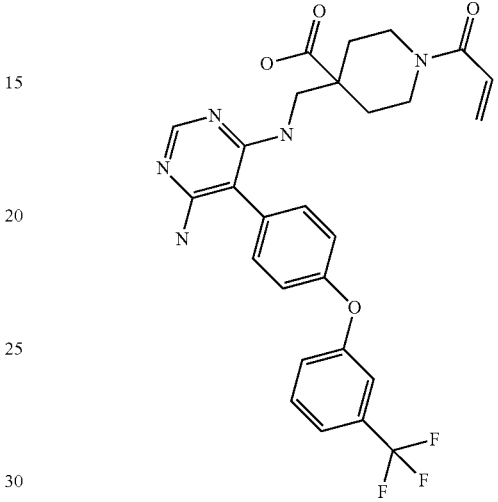

1-acryloyl-4-(((6-amino-5-(4-(3-(trifluoromethyl)
phenoxy)phenyl)pyrimidin-4-yl)amino)methyl)piperidine-4-carboxylic acid (A239)

1-acryloyl-4-(((6-amino-5-(4-(3-(trifluoromethyl)phenoxy)phenyl)pyrimidin-4-yl)amino)methyl)piperidine-4-carboxylic acid was prepared 5,6-dichloropyrimidin-4-amine, (4-(3-(trifluoromethyl)phenoxy)phenyl)boronic acid, 4-(aminomethyl)-1-(tert-butoxycarbonyl)piperidine-4-carboxylic acid and acrylic acid with method S1, S2, S3, S4A. Yield 11.2%. $^1$H NMR (DMSO-d$_6$) δ 8.31 (s, 1H), 7.25-7.75 (m, 8H), 7.03 (br., 2H), 6.77 (m, 1H), 6.62 (s, 1H), 6.04 (d, 1H), 5.60 (d, 1H), 4.12 (m, 1H), 3.83 (m, 1H), 2.75 (m, 1H), 1.91 (m, 2H), 1.28 (m, 2H). HPLC PURITY: 98%, MS: m/z=542[M+H]+

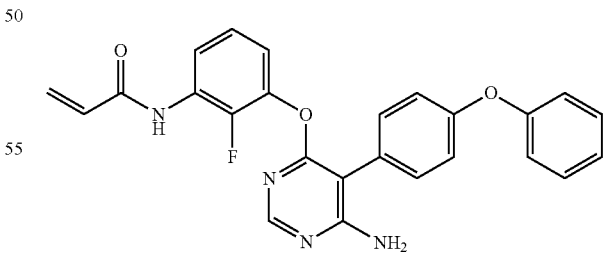

N-(3-((6-amino-5-(4-phenoxyphenyl)pyrimidin-4-yl)
oxy)-2-fluorophenyl)acrylamide (A240)

N-(3-((6-amino-5-(4-phenoxyphenyl)pyrimidin-4-yl)oxy)-2-fluorophenyl)acrylamide was prepared from 6-(3-amino-2-fluorophenoxy)-5-(4-phenoxyphenyl)pyrimidin-4- amine using Method F (82% yield). HPLC: 99%, RT=4.434 min. MS: m/z=433 [M+H]⁺, RT=2.36 min. ¹H-NMR (DMSO-d₆) δ 10.02 (s, 1H), 8.04 (s, 1H), 7.80 (t, 1H), 7.43-7.38 (m, 4H), 7.15 (q, 2H), 7.15 (q, 2H), 7.09 (d, 4H), 7.03 (t, 1H), 6.69 (broad s, 1.5H), 6.57 (dd, 1H), 6.26 (d, 1H), 5.77 (d, 1H).

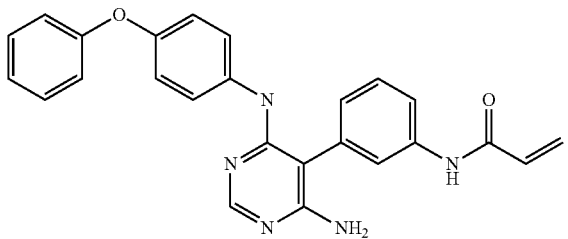 [SMILES: C=CC(=O)Nc1cccc(-c2c(N)ncnc2Nc2ccc(Oc3ccccc3)cc2)c1]

N-(3-(4-amino-6-((4-phenoxyphenyl)amino)pyrimidin-5-yl)phenyl)acrylamide (A241)

N-(3-(4-amino-6-((4-phenoxyphenyl)amino)pyrimidin-5-yl)phenyl)acrylamide was prepared from 5-(3-aminophenyl)-N4-(4-phenoxyphenyl)pyrimidine-4,6-diamine using Method E (21% yield). HPLC: 98%, RT=3.975 min. MS: m/z=424 [M+H]⁺, RT=2.51 min. ¹H-NMR (DMSO-d₆) δ 10.26 (s, 1H), 8.42 (s, 1H), 8.20 (s, 1H), 7.77 (d, 1H), 7.60 (s, 1H), 7.45 (t, 1H), 7.32 (t, 2H), 7.25 (d, 2H), 7.06 (t, 1H), 7.00 (d, 1H), 6.92-6.88 (m, 5H), 6.40 (dd, 1H), 6.21 (d, 1H), 5.71 (d, 1H).

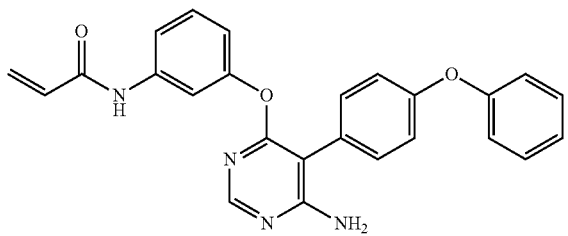

N-(3-((6-amino-5-(4-phenoxyphenyl)pyrimidin-4-yl)oxy)phenyl)acrylamide (A242)

N-(3-((6-amino-5-(4-phenoxyphenyl)pyrimidin-4-yl)oxy)phenyl)acrylamide was prepared from 6-(3-aminophenoxy)-5-(4-phenoxyphenyl)pyrimidin-4-amine using Method E (20% yield). HPLC: 97%, RT=4.264 min. MS: m/z=425 [M+H]⁺, RT=4.22 min. ¹H-NMR (DMSO-d₆) δ 10.14 (s, 1H), 8.00 (s, 1H), 7.41 (s, 1H), 7.36-7.30 (m, 5H), 7.22 (t, 1H), 7.09 (t, 1H), 7.03-7.01 (m, 4H), 6.71 (d, 1H), 6.53 (broad s, 2H), 6.34 (dd, 1H), 6.18 (d, 1H), 5.69 (d, 1H).

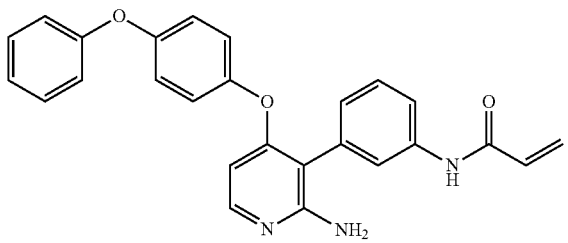

N-(3-(2-amino-4-(4-phenoxyphenoxy)pyridin-3-yl)phenyl)acrylamide (A243)

N-(3-(2-amino-4-(4-phenoxyphenoxy)pyridin-3-yl)phenyl)acrylamide was prepared from 3-(3-aminophenyl)-4-(4-phenoxyphenoxy)pyridin-2-amine using Method F (56% yield). HPLC: 99%, RT=4.196 min. MS: m/z=424 [M+H]⁺, RT=2.09 min. ¹H-NMR (DMSO-d₆) δ 10.24 (s, 1H), 7.89 (d, 1H), 7.75 (s, 1H), 7.65 (d, 1H), 7.43 (t, 1H), 7.33 (t, 2H), 7.15-7.08 (m, 6H), 7.02 (d, 2H), 6.96 (d, 2H), 6.40 (dd, 1H), 6.30 (d, 1H), 6.20 (d, 1H), 5.71 (d, 1H).

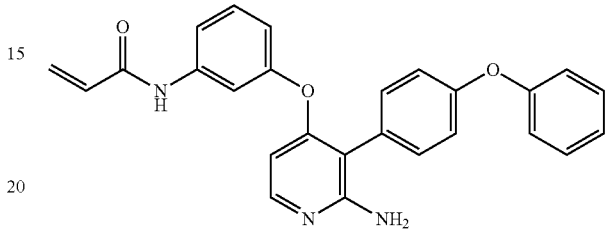

N-(3-((2-amino-3-(4-phenoxyphenyl)pyridin-4-yl)oxy)phenyl)acrylamide (A244)

N-(3-((2-amino-3-(4-phenoxyphenyl)pyridin-4-yl)oxy)phenyl)acrylamide was prepared from 4-(3-aminophenoxy)-3-(4-phenoxyphenyl)pyridin-2-amine using Method F (52% yield). HPLC: 99%, RT=4.182 min. MS: m/z=424 [M+H]⁺, RT=2.08 min. ¹H-NMR (DMSO-d₆) 10.35 (s, 1H), 7.93 (d, 1H), 7.65 (s, 1H), 7.43-7.37 (m, 6H), 7.28 (s, 2H), 7.18 (t, 1H), 7.12-7.08 (m, 4H), 6.86 (d, 1H), 6.40 (dd, 1H), 6.33 (d, 1H), 6.24 (d, 1H), 5.77 (d, 1H).

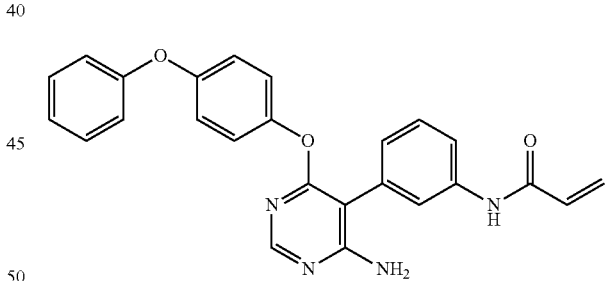

N-(3-(4-amino-6-(4-phenoxyphenoxy)pyrimidin-5-yl)phenyl)acrylamide (A245)

N-(3-(4-amino-6-(4-phenoxyphenoxy)pyrimidin-5-yl)phenyl)acrylamide was prepared from 5-(3-aminophenyl)-6-(4-phenoxyphenoxy)pyrimidin-4-amine using Method E (24 yield). HPLC: 94%, RT=4.298 min. MS: m/z=425 [M+H]⁺, RT=2.16 min. ¹H-NMR (DMSO-d₆) δ 10.10 (s, 1H), 8.08 (s, 1H), 7.71 (s, 2H), 7.41 (t, 1H), 7.37 (t, 2H), 7.13-6.97 (m, 8H), 6.53 (broad s, 2H), 6.44 (dd, 1H), 6.25 (d, 1H), 5.75 (d, 1H).

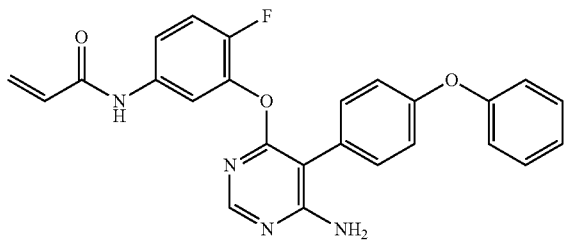 [SMILES: C=CC(=O)Nc1ccc(F)c(Oc2ncnc(N)c2-c2ccc(Oc3ccccc3)cc2)c1]

N-(3-((6-amino-5-(4-phenoxyphenyl)pyrimidin-4-yl)oxy)-4-fluorophenyl)acrylamide (A246)

N-(3-((6-amino-5-(4-phenoxyphenyl)pyrimidin-4-yl)oxy)-4-fluorophenyl)acrylamide was prepared from 6-(5-amino-2-fluorophenoxy)-5-(4-phenoxyphenyl)pyrimidin-4-amine using Method F (6% yield). HPLC: 99%, RT=4.470 min. MS: m/z=443 [M+H]$^+$, RT=2.38 min. $^1$H-NMR (DMSO-d$_6$) δ 10.18 (s, 1H), 7.96 (s, 1H), 7.58 (d, 1H), 7.36-7.32 (m, 5H), 7.20 (t, 1H), 7.10 (t, 1H), 7.05-7.03 (m, 4H), 6.51 (broad s, 2H), 6.32 (dd, 1H), 6.18 (d, 1H), 5.70 (d, 1H).

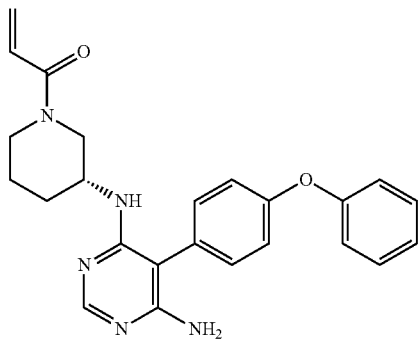

(R)-1-(3-((6-amino-5-(4-phenoxyphenyl)pyrimidin-4-yl)amino)piperidin-1-yl)prop-2-en-1-one (A247)

(R)-1-(3-((6-amino-5-(4-phenoxyphenyl)pyrimidin-4-yl)amino)piperidin-1-yl)prop-2-en-1-one was prepared from (R)-5-(4-phenoxyphenyl)-N4-(piperidin-3-yl)pyrimidine-4,6-diamine using Method F (42% yield). HPLC: 97%, RT=3.713 min. MS: m/z=416 [M+H]$^+$, RT=1.76 min.

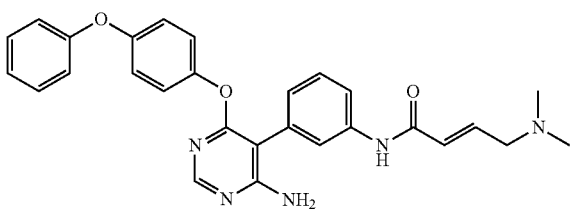 [SMILES: CN(C)C/C=C/C(=O)Nc1cccc(-c2c(N)ncnc2Oc2ccc(Oc3ccccc3)cc2)c1]

(E)-N-(3-(4-amino-6-(4-phenoxyphenoxy)pyrimidin-5-yl)phenyl)-4-(dimethylamino)but-2-enamide (A248)

(E)-N-(3-(4-amino-6-(4-phenoxyphenoxy)pyrimidin-5-yl)phenyl)-4-(dimethylamino)but-2-enamide was prepared from 5-(3-aminophenyl)-6-(4-phenoxyphenoxy)pyrimidin-4-amine and (E)-4-(dimethylamino)but-2-enoic acid hydrochloride using Method E (26% yield). HPLC: 97%, RT=3.608 min. MS: m/z=482 [M+H]$^+$, RT=3.57 min. $^1$H-NMR (DMSO-d$_6$), δ 10.33 (s, 1H), 9.66 (s, 1H), 8.01 (s, 1H), 7.66-7.64 (m, 2H), 7.38 (t, 1H), 7.32 (t, 2H), 7.11-6.92 (m, 8H), 6.68 (m, 1H), 6.41 (m, 3H), 3.88 (m, 2H), 2.73 (s, 6H).

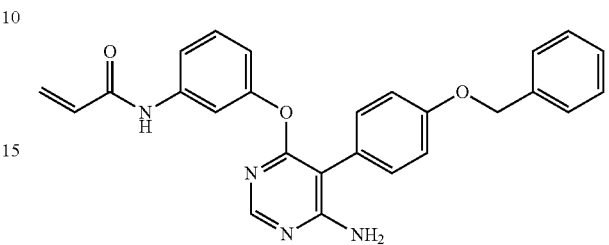

N-(3-((6-amino-5-(4-(benzyloxy)phenyl)pyrimidin-4-yl)oxy)phenyl)acrylamide (A249)

N-(3-((6-amino-5-(4-(benzyloxy)phenyl)pyrimidin-4-yl)oxy)phenyl)acrylamide was prepared from 6-(3-aminophenoxy)-5-(4-(benzyloxy)phenyl)pyrimidin-4-amine using Method E (16% yield). HPLC: 100%, RT=4.251 min. MS: m/z=439 [M+H]$^+$, RT=2.12 min. $^1$H-NMR (DMSO-d$_6$), δ 10.18 (s, 1H), 8.04 (d, 1H), 7.47-7.25 (m, 10H), 7.10 (d, 2H), 6.74 (d, 1H), 6.49 (broad s, 2H), 6.39 (dd, 1H), 6.23 (d, 1H), 5.75 (d, 1H), 5.11 (s, 2H).

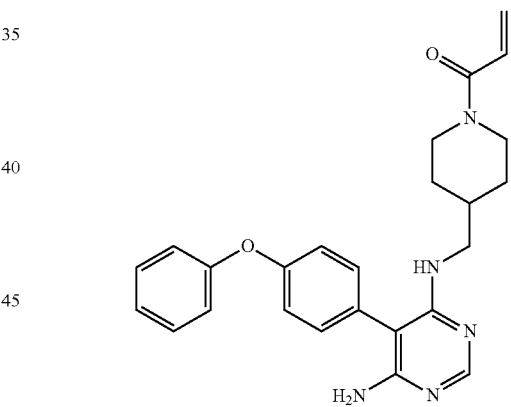

1-(4-(((6-amino-5-(4-phenoxyphenyl)pyrimidin-4-yl)amino)methyl)piperidin-1-yl)prop-2-en-1-one (A250)

1-(4-(((6-amino-5-(4-phenoxyphenyl)pyrimidin-4-yl)amino)methyl)piperidin-1-yl)prop-2-en-1-one was prepared from 5,6-dichloropyrimidin-4-amine, tert-butyl 4-(aminomethyl)piperidine-1-carboxylate, (4-phenoxyphenyl)boronic acid and acryloyl chloride in four steps according to Scheme 2 (using Method B/I, Method C, Method D, and Method F). HPLC purity 97%, RT=3.665 min; MS: m/z=430 [M+H]$^+$, RT=1.53 min. $^1$H-NMR (DMSO-d$_6$) δ 7.93 (s, 1H), 7.40 (t, 2H), 7.21-7.08 (m, 8H), 6.76 (dd, 1H), 6.04 (d, 1H), 5.61 (d, 1H), 5.43 (s, 2H), 4.34 (d, 1H), 3.98 (d, 1H), 3.12 (t, 2H), 2.95 (t, 1H), 2.56 (t, 1H), 1.81 (m, 1H), 1.59 (m, 2H), 0.92 (m, 2H).

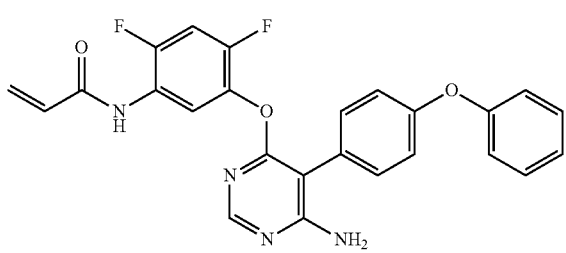

N-(5-((6-amino-5-(4-phenoxyphenyl)pyrimidin-4-yl)oxy)-2,4-difluorophenyl)acrylamide (A251)

N-(5-((6-amino-5-(4-phenoxyphenyl)pyrimidin-4-yl)oxy)-2,4-difluorophenyl)acrylamide was prepared from 6-(5-amino-2,4-difluorophenoxy)-5-(4-phenoxyphenyl)pyrimidin-4-amine using Method F (10% yield). HPLC: 99%, RT=4.569 min. MS: m/z=461 [M+H]+, RT=2.42 min. $^1$H-NMR (DMSO-$d_6$), δ 10.02 (s, 1H), 8.01 (s, 1H), 7.87 (t, 1H), 7.48 (t, 1H), 7.42-7.38 (m, 4H), 7.15 (t, 1H), 7.10-7.07 (m, 4H), 6.56 (dd, 1H), 6.55 (broad s, 2H), 6.24 (d, 1H), 5.77 (d, 1H).

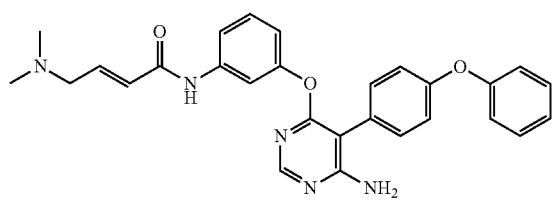 [SMILES: CN(C)C/C=C/C(=O)Nc1cccc(Oc2ncnc(N)c2-c2ccc(Oc3ccccc3)cc2)c1]

(E)-N-(3-((6-amino-5-(4-phenoxyphenyl)pyrimidin-4-yl)oxy)phenyl)-4-(dimethylamino)but-2-enamide (A252)

(E)-N-(3-((6-amino-5-(4-phenoxyphenyl)pyrimidin-4-yl)oxy)phenyl)-4-(dimethylamino)but-2-enamide was prepared from 6-(3-aminophenoxy)-5-(4-phenoxyphenyl)pyrimidin-4-amine and (E)-4-(dimethylamino)but-2-enoic acid hydrochloride using Method E (22% yield). HPLC: 98%, RT=3.556 min. MS: m/z=482 [M+H]+, RT=3.53 min. $^1$H-NMR (DMSO-$d_6$) δ 10.34 (s, 1H), 9.73 (s, 1H), 8.04 (s, 1H), 7.45 (s, 1H), 7.41-7.36 (m, 5H), 7.29 (t, 1H), 7.15 (t, 1H), 7.09-7.06 (m, 4H), 6.78 (d, 1H), 6.74-6.68 (m, 1H), 6.50 (broad s, 2H), 6.41 (d, 1H), 3.93-3.92 (m, 2H), 2.78 (s, 6H).

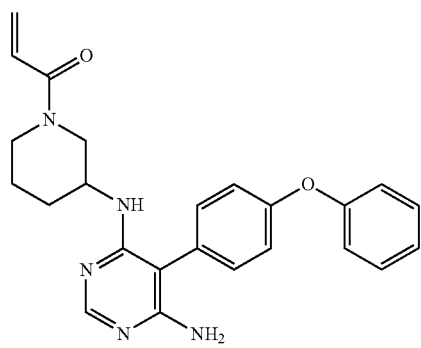

1-(3-((6-amino-5-(4-phenoxyphenyl)pyrimidin-4-yl)amino)piperidin-1-yl)prop-2-en-1-one (A253)

1-(3-((6-amino-5-(4-phenoxyphenyl)pyrimidin-4-yl)amino)piperidin-1-yl)prop-2-en-1-one was prepared from 5-(4-phenoxyphenyl)-N4-(piperidin-3-yl)pyrimidine-4,6-diamine using Method F (27% yield). HPLC: 99%, RT=3.737 min. MS: m/z=416 [M+H]+, RT=1.88 min.

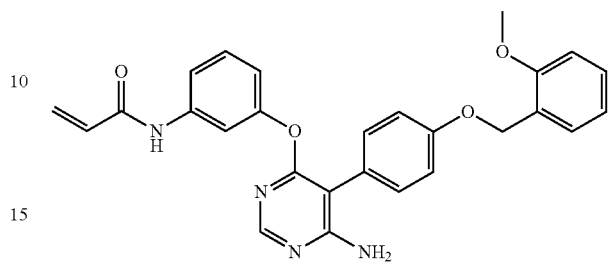

N-(3-((6-amino-5-(4-((2-methoxybenzyl)oxy)phenyl)pyrimidin-4-yl)oxy)phenyl)acrylamide (A254)

N-(3-((6-amino-5-(4-((2-methoxybenzyl)oxy)phenyl)pyrimidin-4-yl)oxy)phenyl)acrylamide was prepared from 6-(3-aminophenoxy)-5-(4-((2-methoxybenzyl)oxy)phenyl)pyrimidin-4-amine using Method F (58% yield). HPLC: 99%, RT=4.290 min. MS: m/z=469 [M+H]+, RT=2.32 min. $^1$H-NMR (DMSO-$d_6$) 1H), 8.14 (s, 1H), 7.50 (s, 1H), 7.44-7.30 (m, 6H), 7.13 (d, 2H), 7.08 (d, 1H), 6.99 (t, 1H), 6.79 (m, 3H), 6.42 (dd, 1H), 6.27 (d, 1H), 5.78 (d, 1H), 5.10 (s, 2H), 3.84 (s, 3H).

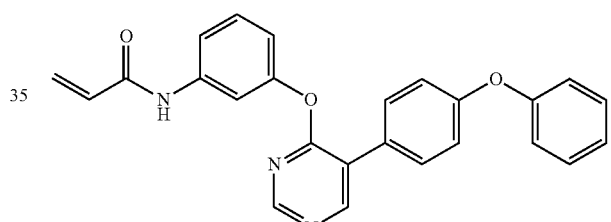

N-(3-((5-(4-phenoxyphenyl)pyrimidin-4-yl)oxy)phenyl)acrylamide (A255)

N-(3-((5-(4-phenoxyphenyl)pyrimidin-4-yl)oxy)phenyl)acrylamide was prepared from 3-((5-(4-phenoxyphenyl)pyrimidin-4-yl)oxy)aniline using Method F (86% yield). HPLC: 97%, RT=5.029 min. MS: m/z=410 [M+H]+, RT=2.57 min. $^1$H-NMR (DMSO-$d_6$) 1H), 8.78 (s, 1H), 8.69 (s, 1H), 7.76 (d, 2H), 7.66 (s, 1H), 7.45-7.36 (m, 4H), 7.18 (t, 1H), 7.13-7.08 (m, 4H), 6.96 (d, 1H), 6.41 (dd, 1H), 6.24 (d, 1H), 5.76 (d, 1H).

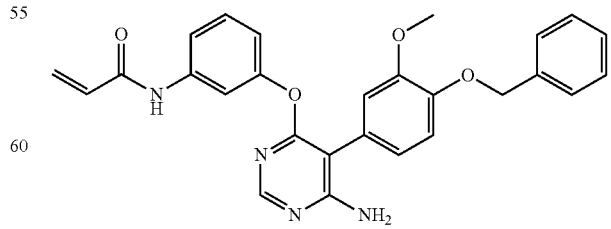

N-(3-((6-amino-5-(4-(benzyloxy)-3-methoxyphenyl)pyrimidin-4-yl)oxy)phenyl)acrylamide (A256)

N-(3-((6-amino-5-(4-(benzyloxy)-3-methoxyphenyl)pyrimidin-4-yl)oxy)phenyl)acrylamide was prepared from 6-(3-aminophenoxy)-5-(4-(benzyloxy)-3-methoxyphenyl)pyrimidin-4-amine using Method F (53% yield). HPLC: 100%, RT=4.133 min. MS: m/z=469 [M+H]⁺, RT=2.19 min. ¹H-NMR (DMSO-d₆) δ 10.13 (s, 1H), 7.99 (s, 1H), 7.41-7.20 (m, 8H), 7.07 (d, 1H), 6.93 (s, 1H), 6.85 (d, 1H), 6.71 (d, 1H), 6.50 (broad s, 2H), 6.34 (dd, 1H), 6.17 (d, 1H), 5.69 (d, 1H), 5.03 (s, 2H), 3.71 (s, 3H).

N-(3-((6-amino-5-(6-(benzyloxy)pyridin-3-yl)pyrimidin-4-yl)oxy)phenyl)acrylamide was prepared from 6-(3-aminophenoxy)-5-(6-(benzyloxy)pyridin-3-yl)pyrimidin-4-amine using Method F (38% yield). HPLC: 99%, RT=4.138 min. MS: m/z=440 [M+H]⁺, RT=2.20 min. ¹H-NMR (DMSO-d₆) δ 10.19 (s, 1H), 8.19 (s, 1H), 8.06 (s, 1H), 7.74 (d, 1H), 7.46-7.26 (m, 8H), 6.97 (d, 1H), 6.77 (d, 1H), 6.69 (broad s, 2H), 6.39 (dd, 1H), 6.23 (d, 1H), 5.74 (d, 1H), 5.36 (s, 2H).

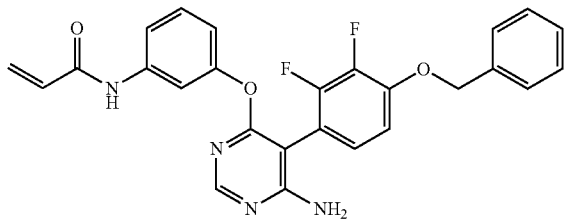 [SMILES: C=CC(=O)Nc1cccc(Oc2ncnc(N)c2-c2ccc(OCc3ccccc3)c(F)c2F)c1]

N-(3-((6-amino-5-(4-(benzyloxy)-2,3-difluorophenyl)pyrimidin-4-yl)oxy)phenyl)acrylamide (A257)

N-(3-((6-amino-5-(4-(benzyloxy)-2,3-difluorophenyl)pyrimidin-4-yl)oxy)phenyl)acrylamide was prepared from 6-(3-aminophenoxy)-5-(4-(benzyloxy)-2,3-difluorophenyl)pyrimidin-4-amine using Method F (37% yield). HPLC: 100%, RT=4.611 min. MS: m/z=475 [M+H]⁺, RT=2.39 min. ¹H-NMR (DMSO-d₆ 1H), δ 10.14 (s, 1H), 8.02 (s, 1H), 7.43-7.28 (m, 7H), 7.22 (t, 1H), 7.12 (quintet, 2H), 6.68 (m, 3H), 6.34 (dd, 1H), 6.18 (d, 1H), 5.69 (d, 1H), 5.18 (s, 2H).

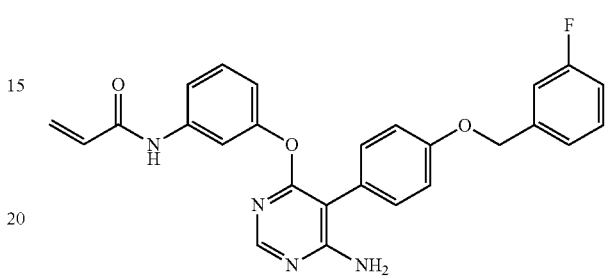

N-(3-((6-amino-5-(4-((3-fluorobenzyl)oxy)phenyl)pyrimidin-4-yl)oxy)phenyl)acrylamide (A260)

N-(3-((6-amino-5-(4-((3-fluorobenzyl)oxy)phenyl)pyrimidin-4-yl)oxy)phenyl)acrylamide was prepared from 6-(3-aminophenoxy)-5-(4-((3-fluorobenzyl)oxy)phenyl)pyrimidin-4-amine using Method E (13% yield). HPLC: 99%, RT=4.334 min. MS: m/z=457 [M+H]⁺, RT=2.17 min. ¹H-NMR (DMSO-d₆), δ 10.18 (s, 1H), 8.04 (s, 1H), 7.46-7.41 (m, 2H), 7.36-7.25 (m, 6H), 7.15 (t, 1H), 7.10 (d, 2H), 6.75 (d, 1H), 6.50 (broad s, 2H), 6.39 (dd, 1H), 6.23 (d, 1H), 5.74 (d, 1H), 5.14 (s, 2H).

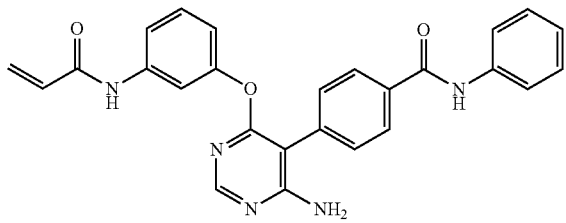 [SMILES: C=CC(=O)Nc1cccc(Oc2ncnc(N)c2-c2ccc(C(=O)Nc3ccccc3)cc2)c1]

4-(4-(3-acrylamidophenoxy)-6-aminopyrimidin-5-yl)-N-phenylbenzamide (A258)

4-(4-(3-acrylamidophenoxy)-6-aminopyrimidin-5-yl)-N-phenylbenzamide was prepared from 4-(4-amino-6-(3-aminophenoxy)pyrimidin-5-yl)-N-phenylbenzamide using Method F (29% yield). HPLC: 98%, RT=3.775 min. MS: m/z=452 [M+H]⁺, RT=1.96 min. ¹H-NMR (DMSO-d₆) δ 10.22 (s, 1H), 10.16 (s, 1H), 8.04 (s, 1H), 7.98 (d, 2H), 7.72 (d, 2H), 7.52 (d, 2H), 7.44 (s, 1H), 7.30-7.22 (m, 4H), 7.04 (t, 1H), 6.73 (d, 1H), 6.63 (broad s, 2H), 6.34 (dd, 1H), 6.18 (d, 1H), 5.70 (d, 1H).

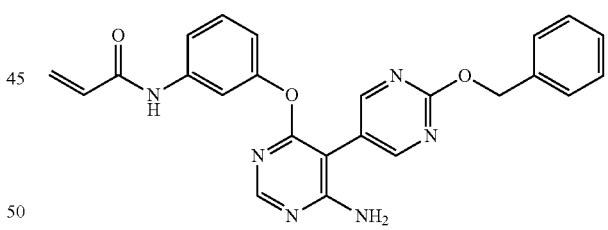

N-(3-((6-amino-2'-(benzyloxy)-[5,5'-bipyrimidin]-4-yl)oxy)phenyl)acrylamide (A261)

N-(3-((6-amino-2'-(benzyloxy)-[5,5'-bipyrimidin]-4-yl)oxy)phenyl)acrylamide was prepared from 6-(3-aminophenoxy)-2'-(benzyloxy)-[5,5'-bipyrimidin]-4-amine using Method F (46% yield). HPLC: 99%, RT=3.953 min. MS: m/z=441 [M+H]⁺, RT=2.04 min. ¹H-NMR (DMSO-d₆ 1H), 8.64 (s, 2H), 8.08 (s, 1H), 7.48-7.26 (m, 8H), 6.88 (broad s, 2H), 6.79 (d, 1H), 6.39 (dd, 1H), 6.23 (d, 1H), 5.74 (d, 1H), 5.42 (s, 2H).

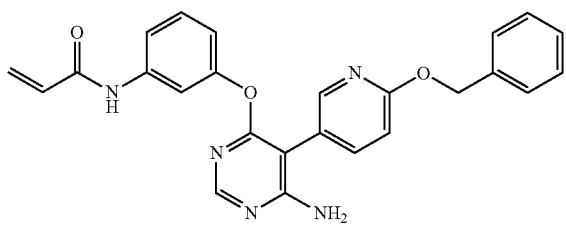 [SMILES: C=CC(=O)Nc1cccc(Oc2ncnc(N)c2-c2ccc(OCc3ccccc3)nc2)c1]

N-(3-((6-amino-5-(6-(benzyloxy)pyridin-3-yl)pyrimidin-4-yl)oxy)phenyl)acrylamide (A259)

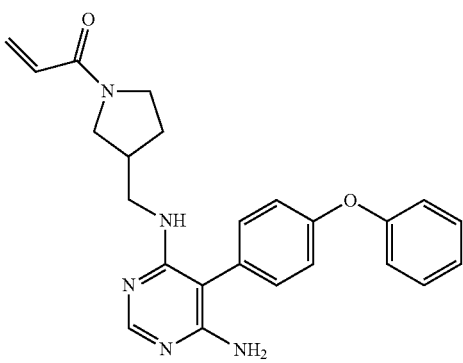 [SMILES: C=CC(=O)N1CCC(CNc2ncnc(N)c2-c2ccc(Oc3ccccc3)cc2)C1]

1-(3-(((6-amino-5-(4-phenoxyphenyl)pyrimidin-4-yl)amino)methyl)pyrrolidin-1-yl)prop-2-en-1-one (A262)

1-(3-(((6-amino-5-(4-phenoxyphenyl)pyrimidin-4-yl)amino)methyl)pyrrolidin-1-yl)prop-2-en-1-one was prepared from 5-(4-phenoxyphenyl)-N4-(pyrrolidin-3-ylmethyl)pyrimidine-4,6-diamine using Method F (26% yield). HPLC: 97%, RT=3.570 min. MS: m/z=416 [M+H]$^+$, RT=1.77 min.

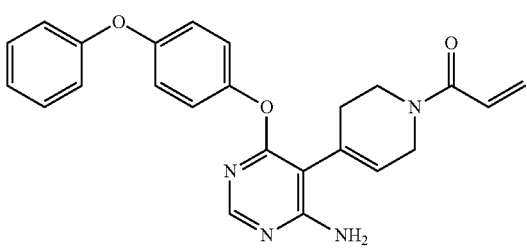 [SMILES: C=CC(=O)N1CC=C(c2c(N)ncnc2Oc2ccc(Oc3ccccc3)cc2)CC1]

1-(4-(4-amino-6-(4-phenoxyphenoxy)pyrimidin-5-yl)-5,6-dihydropyridin-1(2H)-yl)prop-2-en-1-one (A263)

1-(4-(4-amino-6-(4-phenoxyphenoxy)pyrimidin-5-yl)-5,6-dihydropyridin-1(2H)-yl)prop-2-en-1-one was prepared from 6-(4-phenoxyphenoxy)-5-(1,2,3,6-tetrahydropyridin-4-yl)pyrimidin-4-amine using Method F (41% yield). HPLC: 91%, RT=3.997 min. MS: m/z=415 [M+H]$^+$, RT=2.00 min. $^1$H-NMR (DMSO-d$_6$) δ 7.94 (s, 1H), 7.33 (t, 2H), 7.08-6.93 (m, 7H), 6.82-6.68 (m, 3H), 6.07 (dd, 1H), 5.73 (d, 1H), 5.63 (t, 1H), 4.15 (s, 1H), 4.07 (s, 1H), 3.71 (m, 2H), 2.25 (m, 2H).

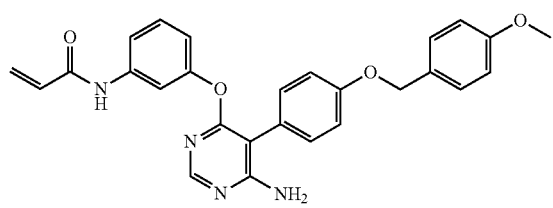 [SMILES: C=CC(=O)Nc1cccc(Oc2ncnc(N)c2-c2ccc(OCc3ccc(OC)cc3)cc2)c1]

N-(3-((6-amino-5-(4-((4-methoxybenzyl)oxy)phenyl)pyrimidin-4-yl)oxy)phenyl)acrylamide (A264)

N-(3-((6-amino-5-(4-((4-methoxybenzyl)oxy)phenyl)pyrimidin-4-yl)oxy)phenyl)acrylamide was prepared from 6-(3-aminophenoxy)-5-(4-((4-methoxybenzyl)oxy)phenyl)pyrimidin-4-amine using Method F (35% yield). HPLC: 98%, RT=4.188 min. MS: m/z=469 [M+H]$^+$, RT=2.25 min. $^1$H-NMR (DMSO-d$_6$), δ 10.21 (s, 1H), 8.07 (s, 1H), 7.47 (s, 1H), 7.42-7.28 (m, 6H), 7.12 (d, 2H), 6.97 (d, 2H), 6.78 (d, 1H), 6.50 (broad s, 2H), 6.42 (dd, 1H), 6.26 (d, 1H), 5.77 (d, 1H), 5.05 (s, 2H), 3.77 (s 3H).

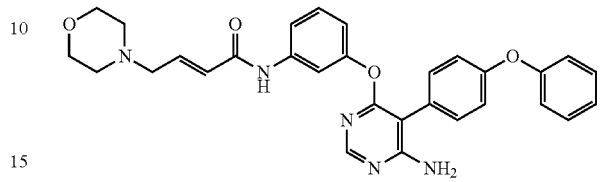

(E)-N-(3-((6-amino-5-(4-phenoxyphenyl)pyrimidin-4-yl)oxy)phenyl)-4-morpholinobut-2-enamide (A265)

(E)-N-(3-((6-amino-5-(4-phenoxyphenyl)pyrimidin-4-yl)oxy)phenyl)-4-morpholinobut-2-enamide was prepared from 6-(3-aminophenoxy)-5-(4-phenoxyphenyl)pyrimidin-4-amine and (E)-4-morpholinobut-2-enoic acid using Method E (19% yield). HPLC: 100%, RT=3.605 min. MS: m/z=524 [M+H]$^+$, RT=3.59 min.

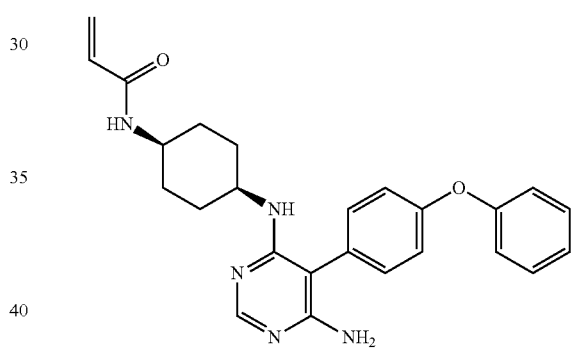

N-((1s,4s)-4-((6-amino-5-(4-phenoxyphenyl)pyrimidin-4-yl)amino)cyclohexyl)acrylamide (A266)

N-((1s,4s)-4-((6-amino-5-(4-phenoxyphenyl)pyrimidin-4-yl)amino)cyclohexyl)acrylamide was prepared from N4-((1s,4s)-4-aminocyclohexyl)-5-(4-phenoxyphenyl)pyrimidine-4,6-diamine using Method F (20% yield). HPLC: 100%, RT=3.712 min. MS: m/z=430 [M+H]$^+$, RT=1.80 min.

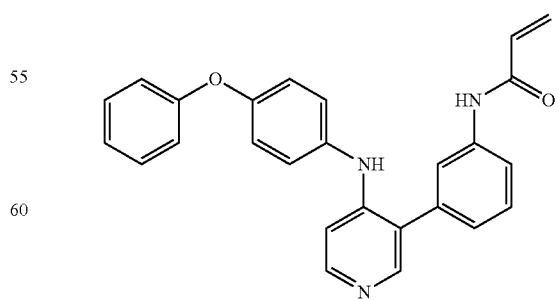

N-(3-(4((4-phenoxyphenyl)amino)pyridin-3-yl)phenyl)acrylamide (A267)

N-(3-(4-((4-phenoxyphenyl)amino)pyridin-3-yl)phenyl)acrylamide was prepared from 3-(3-aminophenyl)-N-(4-phenoxyphenyl)pyridin-4-amine using Method E (13% yield). HPLC: 97%, RT=4.075 min. MS: m/z=408 [M+H]$^+$, RT=2.04 min. $^1$H-NMR (DMSO-d$_6$) δ 10.32 (s, 1H), 9.31 (s, 1H), 8.27 (s, 1H), 8.23 (d, 1H), 7.89 (s, 1H), 7.77 (d, 1H), 7.50 (t, 1H), 7.41 (t, 2H), 7.30 (d, 2H), 7.24 (d, 1H), 7.16 (t, 1H), 7.05 (dd, 4H), 6.98 (d, 1H), 6.45 (dd, 1H), 6.27 (d, 1H), 5.77 (d, 1H).

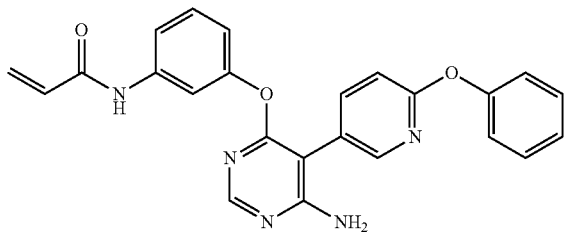

N-(3-((6-amino-5-(6-phenoxypyridin-3-yl)pyrimidin-4-yl)oxy)phenyl)acrylamide (A268)

N-(3-((6-amino-5-(6-phenoxypyridin-3-yl)pyrimidin-4-yl)oxy)phenyl)acrylamide was prepared from 6-(3-aminophenoxy)-5-(6-phenoxypyridin-3-yl)pyrimidin-4-amine using Method F (70% yield). HPLC: 97%, RT=3.880 min. MS: m/z=426 [M+H]$^+$, RT=2.03 min. $^1$H-NMR (DMSO-d$_6$) δ 10.22 (s, 1H), 8.15 (s, 1H), 8.10 (s, 1H), 7.87 (d, 1H), 7.48 (s, 1H), 7.40 (t, 2H), 7.36 (d, 1H), 7.28 (t, 1H), 7.21 (t, 1H), 7.16 (d, 2H), 7.11 (d, 1H), 6.85 (broad s, 1H), 6.78 (d, 1H), 6.39 (dd, 1H), 6.23 (d, 1H), 5.75 (d, 1H).

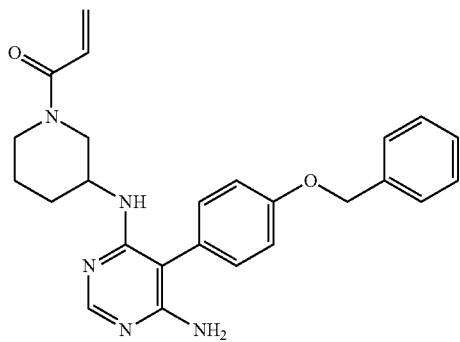 [SMILES: C=CC(=O)N1CCCC(Nc2ncnc(N)c2-c2ccc(OCc3ccccc3)cc2)C1]

1-(3-((6-amino-5-(4-(benzyloxy)phenyl)pyrimidin-4-yl)amino)piperidin-1-yl)prop-2-en-1-one (A269)

1-(3-((6-amino-5-(4-(benzyloxy)phenyl)pyrimidin-4-yl)amino)piperidin-1-yl)prop-2-en-1-one was prepared from 5-(4-(benzyloxy)phenyl)-N4-(piperidin-3-yl)pyrimidine-4,6-diamine using Method F (26% yield). HPLC: 100%, RT=3.701 min. MS: m/z=430 [M+H]$^+$, RT=1.63 min.

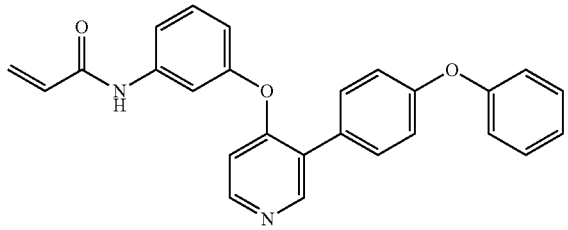 [SMILES: C=CC(=O)Nc1cccc(Oc2ccncc2-c2ccc(Oc3ccccc3)cc2)c1]

N-(3-((3-(4-phenoxyphenyl)pyridin-4-yl)oxy)phenyl)acrylamide (A270)

N-(3-((3-(4-phenoxyphenyl)pyridin-4-yl)oxy)phenyl)acrylamide was prepared from 3-((3-(4-phenoxyphenyl)pyridin-4-yl)oxy)aniline using Method E (36% yield). HPLC: 96%, RT=4.161 min. MS: m/z=409 [M+H]$^+$, RT=4.15 min. $^1$H-NMR (DMSO-d$_6$) δ 10.37 (s, 1H), 8.78 (s, 1H), 8.55 (d, 1H), 7.72-7.70 (m, 3H), 7.46-7.40 (m, 4H), 7.18 (t, 1H), 7.10 (dd, 4H), 7.03 (d, 1H), 6.97 (m, 1H), 6.41 (dd, 1H), 6.24 (d, 1H), 5.77 (d, 1H).

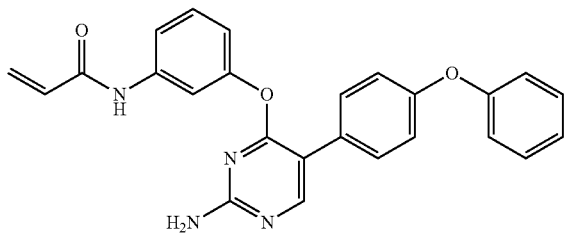 [SMILES: C=CC(=O)Nc1cccc(Oc2nc(N)ncc2-c2ccc(Oc3ccccc3)cc2)c1]

N-(3-((2-amino-5-(4-phenoxyphenyl)pyrimidin-4-yl)oxy)phenyl)acrylamide (A271)

N-(3-((2-amino-5-(4-phenoxyphenyl)pyrimidin-4-yl)oxy)phenyl)acrylamide was prepared from 4-(3-aminophenoxy)-5-(4-phenoxyphenyl)pyrimidin-2-amine using Method E (11% yield). HPLC: 99%, RT=4.256 min. MS: m/z=425 [M+H]$^+$, RT=2.16 min. $^1$H-NMR (DMSO-d$_6$) δ 10.27 (s, 1H), 8.28 (s, 1H), 7.62-7.60 (m, 3H), 7.45-7.35 (m, 4H), 7.20 (broad s, 2H), 7.15 (t, 1H), 7.05 (t, 4H), 6.96 (d, 1H), 6.41 (dd, 1H), 6.25 (d, 1H), 5.76 (d, 1H).

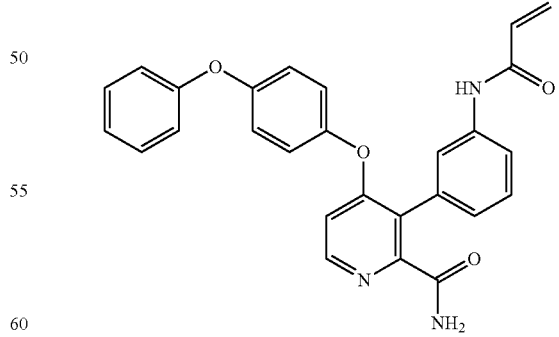

3-(3-acrylamidophenyl)-4-(4-phenoxyphenoxy)picolinamide (A272)

3-(3-acrylamidophenyl)-4-(4-phenoxyphenoxy)picolinamide was prepared from 3-(3-aminophenyl)-4-(4-phenoxyphenoxy)picolinamide using Method E (29% yield). HPLC: 98%, RT=4.218 min. MS: m/z=452 [M+H]⁺, RT=2.15 min.

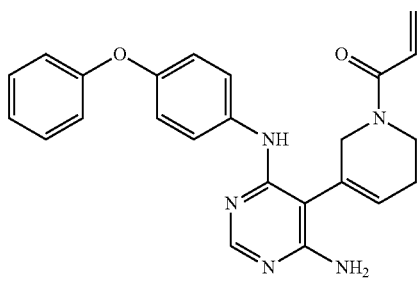

1-(3-(4-amino-6-((4-phenoxyphenyl)amino)pyrimidin-5-yl)-5,6-dihydropyridin-1(2H)-yl)prop-2-en-1-one (A273)

1-(3-(4-amino-6-((4-phenoxyphenyl)amino)pyrimidin-5-yl)-5,6-dihydropyridin-1(2H)-yl)prop-2-en-1-one was prepared from N4-(4-phenoxyphenyl)-5-(1,2,5,6-tetrahydropyridin-3-yl)pyrimidine-4,6-diamine using Method E (20% yield). HPLC: 97%, RT=3.813 min. MS: m/z=414 [M+H]⁺, RT=1.94 min.

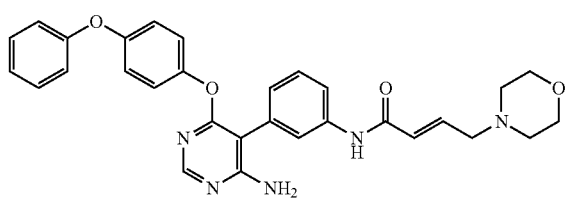 [SMILES: Nc1ncnc(Oc2ccc(Oc3ccccc3)cc2)c1-c1cccc(NC(=O)/C=C/CN2CCOCC2)c1]

(E)-N-(3-(4-amino-6-(4-phenoxyphenoxy)pyrimidin-5-yl)phenyl)-4-morpholinobut-2-enamide (A274)

(E)-N-(3-(4-amino-6-(4-phenoxyphenoxy)pyrimidin-5-yl)phenyl)-4-morpholinobut-2-enamide was prepared from 5-(3-aminophenyl)-6-(4-phenoxyphenoxy)pyrimidin-4-amine and (E)-4-morpholinobut-2-enoic acid using Method E (15% yield). HPLC: 100%, RT=3.662 min. MS: m/z=524 [M+H]⁺, RT=3.66 min.

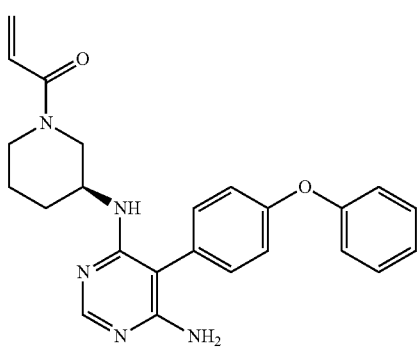 [SMILES: C=CC(=O)N1CCC[C@H](Nc2ncnc(N)c2-c2ccc(Oc3ccccc3)cc2)C1]

(S)-1-(3-((6-amino-5-(4-phenoxyphenyl)pyrimidin-4-yl)amino)piperidin-1-yl)prop-2-en-1-one (A275)

(S)-1-(3-((6-amino-5-(4-phenoxyphenyl)pyrimidin-4-yl)amino)piperidin-1-yl)prop-2-en-1-one was prepared from (S)-5-(4-phenoxyphenyl)-N4-(piperidin-3-yl)pyrimidine-4,6-diamine using Method F (42% yield). HPLC: 99%, RT=3.701 min. MS: m/z=416 [M+H]⁺, RT=1.75 min.

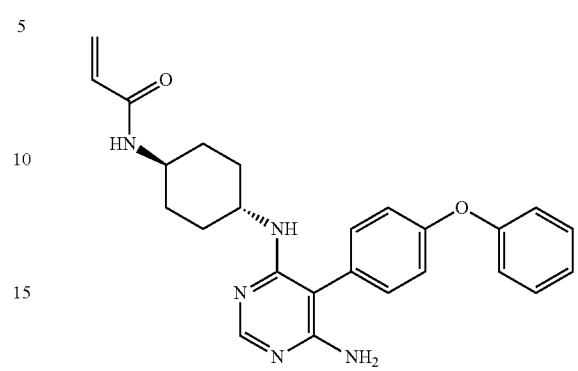

N-((1r,4r)-4-((6-amino-5-(4-phenoxyphenyl)pyrimidin-4-yl)amino)cyclohexyl)acrylamide (A276)

N-((1r,4r)-4-((6-amino-5-(4-phenoxyphenyl)pyrimidin-4-yl)amino)cyclohexyl)acrylamide was prepared from N4-((1r,4r)-4-aminocyclohexyl)-5-(4-phenoxyphenyl)pyrimidine-4,6-diamine using Method F (13% yield). HPLC: 100%, RT=3.690 min. MS: m/z=430 [M+H]⁺, RT=1.58 min.

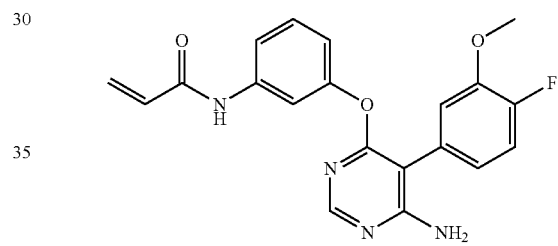

N-(3-((6-amino-5-(4-fluoro-3-methoxyphenyl)pyrimidin-4-yl)oxy)phenyl)acrylamide (A277)

N-(3-((6-amino-5-(4-fluoro-3-methoxyphenyl)pyrimidin-4-yl)oxy)phenyl)acrylamide was prepared from 6-(3-aminophenoxy)-5-(4-fluoro-3-methoxyphenyl)pyrimidin-4-amine using Method E (13% yield). HPLC: 97%, RT=3.519 min. MS: m/z=381 [M+H]⁺, RT=1.77 min. ¹H-NMR (DMSO-d₆) δ 10.19 (s, 1H), 8.06 (s, 1H), 7.47 (s, 1H), 7.35 (d, 1H), 7.29-7.25 (m, 2H), 7.17 (d, 1H), 6.94 (m, 1H), 6.77 (d, 1H), 6.61 (broad s, 2H), 6.39 (dd, 1H), 6.23 (d, 1H), 5.74 (d, 1H), 3.83 (s, 3H).

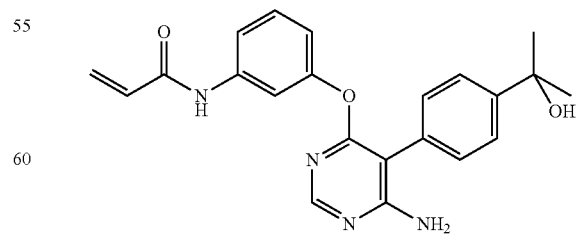

N-(3-((6-amino-5-(4-(2-hydroxypropan-2-yl)phenyl)pyrimidin-4-yl)oxy)phenyl)acrylamide (A278)

N-(3-(((6-amino-5-(4-(2-hydroxypropan-2-yl)phenyl)pyrimidin-4-yl)oxy)phenyl)acrylamide was prepared from 2-(4-(4-amino-6-(3-aminophenoxy)pyrimidin-5-yl)phenyl)propan-2-ol using Method E (22% yield). HPLC: 97%, RT=3.038 min. MS: m/z=391 [M+H]$^+$, RT=1.53 min. $^1$H-NMR (DMSO-d$_6$) δ 10.19 (s, 1H), 8.06 (s, 1H), 7.55 (d, 2H), 7.45 (s, 1H), 7.36-7.33 (m, 3H), 7.27 (t, 1H), 6.75 (d, 1H), 6.50 (broad s, 2H), 6.39 (dd, 1H), 6.23 (d, 1H), 5.74 (d, 1H), 1.44 (s, 6H).

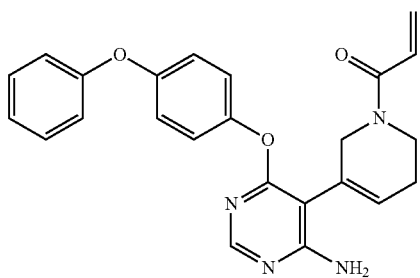 [SMILES: C=CC(=O)N1CCC=C(c2c(N)ncnc2Oc2ccc(Oc3ccccc3)cc2)C1]

1-(3-(4-amino-6-(4-phenoxyphenoxy)pyrimidin-5-yl)-5,6-dihydropyridin-1(2H)-yl)prop-2-en-1-one (A279)

1-(3-(4-amino-6-(4-phenoxyphenoxy)pyrimidin-5-yl)-5,6-dihydropyridin-1(2H)-yl)prop-2-en-1-one was prepared from 6-(4-phenoxyphenoxy)-5-(1,2,5,6-tetrahydropyridin-3-yl)pyrimidin-4-amine using Method E (17% yield). HPLC: 100%, RT=4.065 min. MS: m/z=415 [M+H]$^+$, RT=2.07 min. $^1$H-NMR (DMSO-D6) δ 8.00 (s, 1H), 7.38 (t, 2H), 7.14-7.08 (m, 3H), 7.00 (d, 4H), 6.88-6.70 (m, 3H), 6.09 (dd, 1H), 5.90 (m, 1H), 5.68 (d, 0.5H), 5.58 (d, 0.5H), 8.16 (d, 2H), 3.73 (dt, 2H), 2.25 (d, 2H).

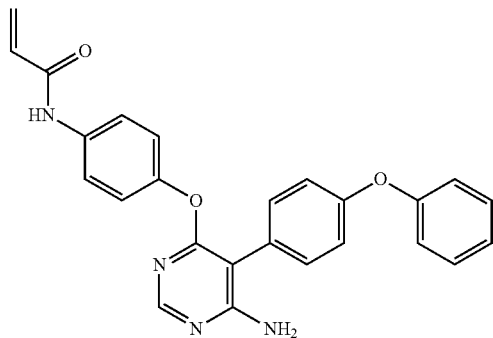 [SMILES: C=CC(=O)Nc1ccc(Oc2ncnc(N)c2-c2ccc(Oc3ccccc3)cc2)cc1]

N-(4-(((6-amino-5-(4-phenoxyphenyl)pyrimidin-4-yl)oxy)phenyl)acrylamide (A280)

N-(4-(((6-amino-5-(4-phenoxyphenyl)pyrimidin-4-yl)oxy)phenyl)acrylamide was prepared from 6-(4-aminophenoxy)-5-(4-phenoxyphenyl)pyrimidin-4-amine using Method E (23% yield). HPLC: 97%, RT=4.191 min. MS: m/z=425 [M+H]$^+$, RT=4.12 min. $^1$H-NMR (DMSO-d$_6$) δ 10.14 (s, 1H), 8.04 (s, 1H), 7.62 (d, 2H), 7.42-7.38 (m, 4H), 7.15 (t, 1H), 7.08 (t, 4H), 7.02 (d, 2H), 6.54 (broad s, 2H), 6.41 (dd, 1H), 6.24 (d, 1H), 5.74 (d, 1H).

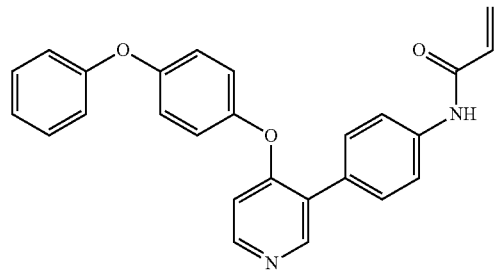

N-(4-(4-(4-phenoxyphenoxy)pyridin-3-yl)phenyl)acrylamide (A281)

N-(4-(4-(4-phenoxyphenoxy)pyridin-3-yl)phenyl)acrylamide was prepared from 4-(4-(4-phenoxyphenoxy)pyridin-3-yl)aniline using Method G (17% yield). HPLC: 100%, RT=4.216 min. MS: m/z=409 [M+H]$^+$, RT=3.29 min. $^1$H-NMR (DMSO-d$_6$) δ 9.89 (s, 1H), 9.01 (s, 1H), 8.85 (d, 1H), 8.30 (d, 2H), 8.10 (d, 2H), 7.84 (t, 2H), 7.64 (d, 2H), 7.58 (t, 1H), 7.55 (d, 2H), 7.48 (d, 2H), 7.25 (d, 1H), 6.92 (dd, 1H), 6.82 (d, 1H), 6.17 (d, 1H).

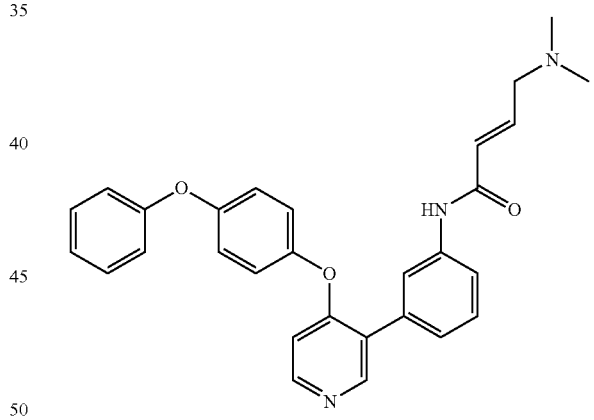

(E)-4-(dimethylamino)-N-(3-(4-(4-phenoxyphenoxy)pyridin-3-yl)phenyl)but-2-enamide (A282)

(E)-4-(dimethylamino)-N-(3-(4-(4-phenoxyphenoxy)pyridin-3-yl)phenyl)but-2-enamide was prepared from 3-(4-(4-phenoxyphenoxy)pyridin-3-yl)aniline and (E)-4-(dimethylamino)but-2-enoic acid using Method E (35% yield). HPLC: 99%, RT=3.399 min. MS: m/z=466 [M+H]$^+$, RT=3.37 min. $^1$H-NMR (DMSO-d$_6$) δ 10.52 (s, 1H), 8.70 (s, 1H), 8.56 (d, 1H), 8.04 (s, 1H), 7.74 (d, 1H), 7.48 (t, 1H), 7.43-7.38 (m, 3H), 7.29-7.26 (d, 2H), 7.17-7.12 (m, 3H), 7.05-6.99 (m, 3H), 6.74 (m, 1H), 6.48 (d, 1H), 3.94 (d, 2H), 2.79 (s, 6H).

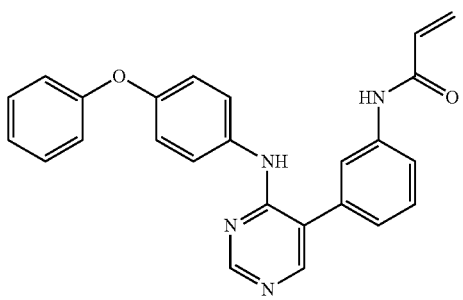 [SMILES: C=CC(=O)Nc1cccc(-c2cncnc2Nc2ccc(Oc3ccccc3)cc2)c1]

N-(3-(4-((4-phenoxyphenyl)amino)pyrimidin-5-yl)phenyl)acrylamide (A283)

N-(3-(4-((4-phenoxyphenyl)amino)pyrimidin-5-yl)phenyl)acrylamide was prepared from 5-(3-aminophenyl)-N-(4-phenoxyphenyl)pyrimidin-4-amine using Method E (19 yield). HPLC: 98%, RT=3.938 min. MS: m/z=409 [M+H]$^+$, RT=1.93 min. $^1$H-NMR (DMSO-d$_6$) δ 10.31 (s, 1H), 9.45 (s, 1H), 8.73 (s, 1H), 8.29 (s, 1H), 7.87 (s, 1H), 7.80 (d, 1H), 7.51-7.49 (m, 3H), 7.38 (t, 2H), 7.25 (d, 1H), 7.13 (t, 1H), 7.01-6.99 (m, 4H), 6.45 (dd, 1H), 6.27 (d, 1H), 5.77 (d, 1H).

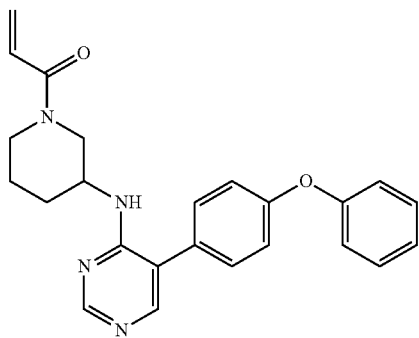 [SMILES: C=CC(=O)N1CCCC(Nc2ncncc2-c2ccc(Oc3ccccc3)cc2)C1]

1-(3-((5-(4-phenoxyphenyl)pyrimidin-4-yl)amino)piperidin-1-yl)prop-2-en-1-one (A284)

1-(3-((5-(4-phenoxyphenyl)pyrimidin-4-yl)amino)piperidin-1-yl)prop-2-en-1-one was prepared from 5-(4-phenoxyphenyl)-N-(piperidin-3-yl)pyrimidin-4-amine using Method F (19% yield). HPLC: 98%, RT=3.632 min. MS: m/z=401 [M+H]$^+$, RT=1.52 min.

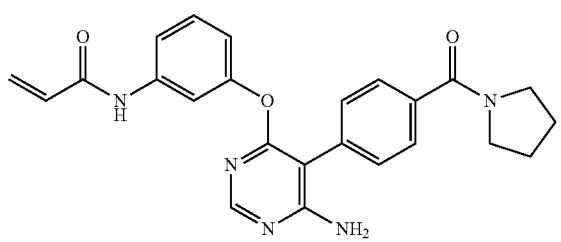 [SMILES: C=CC(=O)Nc1cccc(Oc2ncnc(N)c2-c2ccc(C(=O)N3CCCC3)cc2)c1]

N-(3-((6-amino-5-(4-(pyrrolidine-1-carbonyl)phenyl)pyrimidin-4-yl)oxy)phenyl)acrylamide (A285)

N-(3-((6-amino-5-(4-(pyrrolidine-1-carbonyl)phenyl)pyrimidin-4-yl)oxy)phenyl)acrylamide was prepared from (4-amino-6-(3-aminophenoxy)pyrimidin-5-yl)phenyl)(pyrrolidin-1-yl)methanone using Method F (86 yield). HPLC: 99%, RT=3.121 min. MS: m/z=430 [M+H]$^+$, RT=1.62 min. $^1$H-NMR (DMSO-d$_6$) δ 10.15 (s, 1H), 8.04 (s, 1H), 7.53 (d, 2H), 7.43-7.39 (m, 3H), 7.30 (d, 1H), 7.22 (t, 1H), 6.72 (d, 1H), 6.60 (broad s, 2H), 6.34 (dd, 1H), 6.18 (d, 1H), 5.69 (d, 1H), 3.42-3.37 (m, 4H), 1.77 (doublet of quintet, 4H).

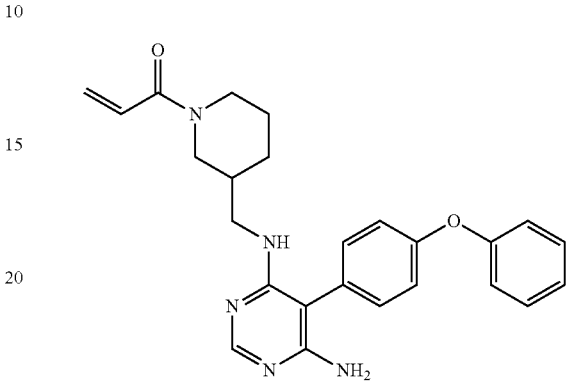

1-(3-(((6-amino-5-(4-phenoxyphenyl)pyrimidin-4-yl)amino)methyl)piperidin-1-yl)prop-2-en-1-one (A286)

1-(3-(((6-amino-5-(4-phenoxyphenyl)pyrimidin-4-yl)amino)methyl)piperidin-1-yl)prop-2-en-1-one was prepared from 5-(4-phenoxyphenyl)-N4-(piperidin-3-ylmethyl)pyrimidine-4,6-diamine using Method F (40% yield).). HPLC: 99%, RT=3.733 min. MS: m/z=430 [M+H]$^+$, RT=1.72 min.

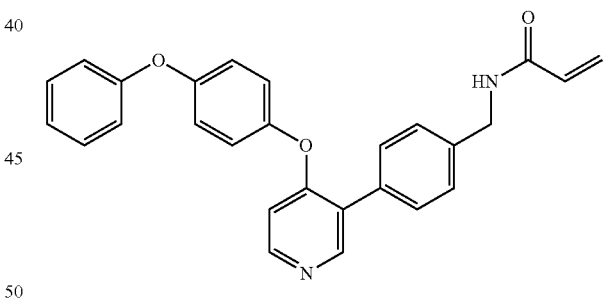

N-(4-(4-(4-phenoxyphenoxy)pyridin-3-yl)benzyl)acrylamide (A287)

N-(4-(4-(4-phenoxyphenoxy)pyridin-3-yl)benzyl)acrylamide was prepared from (4-(4-(4-phenoxyphenoxy)pyridin-3-yl)phenyl)methanamine, triethylamine instead of N,N-diethylethanamine, THF instead of methylpyrrolidin-2-one and dichloromethane using Method G (23% yield). HPLC: 93%, RT=4.014 min. MS: m/z=423 [M+H]$^+$, RT=3.16 min. $^1$H-NMR (DMSO-d$_6$) δ 8.99 (s, 1H), 8.36 (d, 1H), 8.18 (s, 1H), 8.08 (d, 2H), 7.89-7.83 (m, 4H), 7.65-7.48 (m, 7H), 7.25 (d, 1H), 6.80 (dd, 1H), 6.69 (d, 1H), 6.05 (d, 1H), 4.98 (d, 2H).

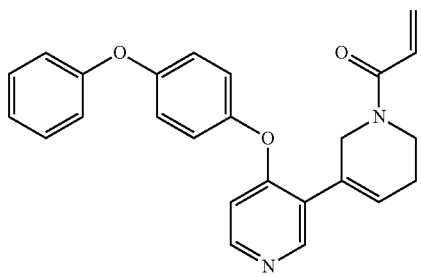 [SMILES: C=CC(=O)N1CCC=C(c2cnccc2Oc2ccc(Oc3ccccc3)cc2)C1]

1-(4'-(4-phenoxyphenoxy)-5,6-dihydro-[3,3'-bipyridin]-1(2H)-yl)prop-2-en-1-one (A288)

1-(4'-(4-phenoxyphenoxy)-5,6-dihydro-[3,3'-bipyridin]-1(2H)-yl)prop-2-en-1-one was prepared from 4'-(4-phenoxyphenoxy)-1,2,5,6-tetrahydro-3,3'-bipyridine using Method E (24% yield). HPLC: 98%, RT=3.872 min. MS: m/z=399 [M+H]+, RT=1.97 min.

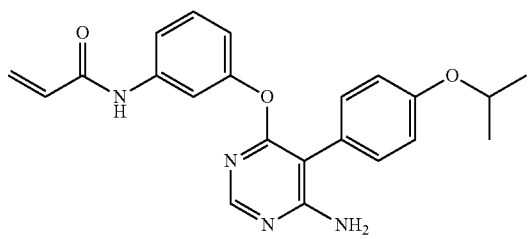 [SMILES: C=CC(=O)Nc1cccc(Oc2ncnc(N)c2-c2ccc(OC(C)C)cc2)c1]

N-(3-((6-amino-5-(4-isopropoxyphenyl)pyrimidin-4-yl)oxy)phenyl)acrylamide (A289)

N-(3-((6-amino-5-(4-isopropoxyphenyl)pyrimidin-4-yl)oxy)phenyl)acrylamide was prepared from 6-(3-aminophenoxy)-5-(4-isopropoxyphenyl)pyrimidin-4-amine using Method F (79% yield). HPLC: 100%, RT=3.826 min. MS: m/z=391 [M+H]+, RT=2.03 min. $^1$H-NMR (DMSO-d$_6$) δ 10.22 (s, 1H), 8.11 (s, 1H), 7.48 (s, 1H), 7.36-7.26 (m, 4H), 6.76 (m, 3H), 6.39 (dd, 1H), 6.23 (d, 1H), 5.75 (d, 1H), 4.63 (septet, 1H), 1.28 (d, 6H).

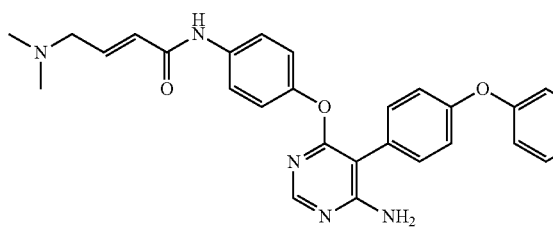

(E)-N-(4-((6-amino-5-(4-phenoxyphenyl)pyrimidin-4-yl)oxy)phenyl)-4-(dimethylamino)but-2-enamide (A290)

(E)-N-(4-((6-amino-5-(4-phenoxyphenyl)pyrimidin-4-yl)oxy)phenyl)-4-(dimethylamino)but-2-enamide was prepared from 6-(4-aminophenoxy)-5-(4-phenoxyphenyl)pyrimidin-4-amine and (E)-4-(dimethylamino)but-2-enoic acid using Method E (29% yield). HPLC: 99%, RT=3.448 min. MS: m/z=482 [M+H]+, RT=3.40 min. $^1$H-NMR (DMSO-d$_6$) δ 10.30 (s, 1H), 8.02 (s, 1H), 7.62 (d, 2H), 7.43-7.38 (m, 4H), 7.15 (tt, 1H), 7.10-7.01 (m, 6H), 6.73 (m, 1H), 6.49 (broad s, 2H), 6.44 (d, 1H), 3.93 (m, 2H), 2.80 (s, 6H).

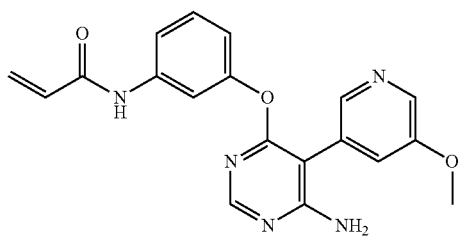 [SMILES: C=CC(=O)Nc1cccc(Oc2ncnc(N)c2-c2cncc(OC)c2)c1]

N-(3-((6-amino-5-(5-methoxypyridin-3-yl)pyrimidin-4-yl)oxy)phenyl)acrylamide (A291)

N-(3-((6-amino-5-(5-methoxypyridin-3-yl)pyrimidin-4-yl)oxy)phenyl)acrylamide was prepared from 6-(3-aminophenoxy)-5-(5-methoxypyridin-3-yl)pyrimidin-4-amine using Method E (13% yield). HPLC: 99%, RT=2.429 min. MS: m/z=364 [M+H]+, RT=1.17 min. $^1$H-NMR (DMSO-d$_6$) δ 10.15 (s, 1H), 8.32 (s, 1H), 8.26 (s, 1H), 8.04 (s, 1H), 7.60 (s, 1H), 7.45 (s, 1H), 7.39 (d, 1H), 7.23 (t, 1H), 6.74 (m, 3H), 6.34 (dd, 1H), 6.18 (d, 1H), 5.69 (d, 1H), 3.83 (s, 3H).

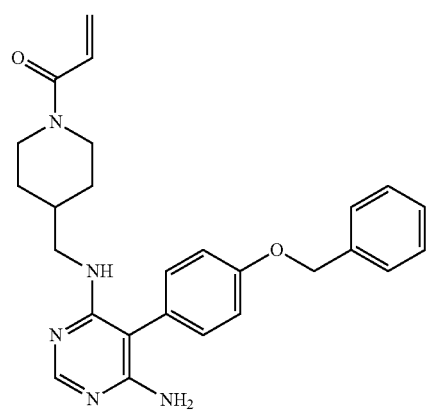 [SMILES: C=CC(=O)N1CCC(CNc2ncnc(N)c2-c2ccc(OCc3ccccc3)cc2)CC1]

1-(4-(((6-amino-5-(4-(benzyloxy)phenyl)pyrimidin-4-yl)amino)methyl)piperidin-1-yl)prop-2-en-1-one (A292)

1-(4-(((6-amino-5-(4-(benzyloxy)phenyl)pyrimidin-4-yl)amino)methyl)piperidin-1-yl)prop-2-en-1-one was prepared from 5-(4-(benzyloxy)phenyl)-N4-(piperidin-4-ylmethyl)pyrimidine-4,6-diamine using Method F (36% yield). HPLC: 100%, RT=3.678 min. MS: m/z=444 [M+H]+, RT=1.65 min.

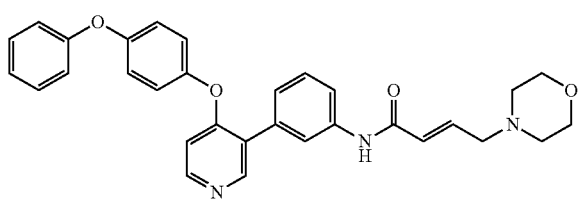 [SMILES: O=C(/C=C/CN1CCOCC1)Nc1cccc(-c2cnccc2Oc2ccc(Oc3ccccc3)cc2)c1]

(E)-4-morpholino-N-(3-(4-(4-phenoxyphenoxy)pyridin-3-yl)phenyl)but-2-enamide (A293)

(E)-4-morpholino-N-(3-(4-(4-phenoxyphenoxy)pyridin-3-yl)phenyl)but-2-enamide was prepared from 3-(4-(4-phenoxyphenoxy)pyridin-3-yl)aniline and (E)-4-morpholinobut-2-enoic acid using Method E (34% yield). HPLC: 100%, RT=3.493 min. MS: m/z=508 [M+H]$^+$, RT=2.27 min.

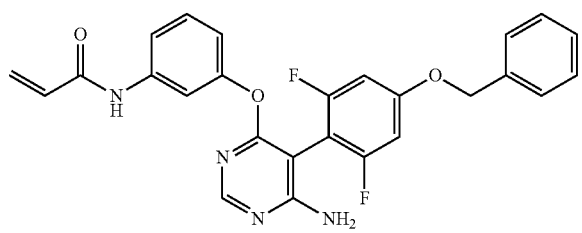 [SMILES: C=CC(=O)Nc1cccc(Oc2ncnc(N)c2-c2c(F)cc(OCc3ccccc3)cc2F)c1]

N-(3-((6-amino-5-(4-(benzyloxy)-2,6-difluorophenyl)pyrimidin-4-yl)oxy)phenyl)acrylamide (A294)

N-(3-((6-amino-5-(4-(benzyloxy)-2,6-difluorophenyl)pyrimidin-4-yl)oxy)phenyl)acrylamide was prepared from 6-(3-aminophenoxy)-5-(4-(benzyloxy)-2,6-difluorophenyl)pyrimidin-4-amine using Method F (14% yield). HPLC: 99%, RT=4.662 min. MS: m/z=475 [M+H]$^+$, RT=2.40 min. $^1$H-NMR (DMSO-D$_6$) δ 10.19 (s, 1H), 8.08 (s, 1H), 7.47-7.33 (m, 7H), 7.28 (t, 1H), 6.92 (d, 2H), 6.81 (broad s, 2H), 6.70 (d, 1H), 6.39 (dd, 1H), 6.23 (d, 1H), 5.74 (d, 1H), 5.14 (s, 2H).

(E)-N-(3-((6-amino-5-(4-phenoxyphenyl)pyrimidin-4-yl)oxy)phenyl)-4-(4-(5-((4S)-2-oxohexahydro-1H-thieno[3,4-d]imidazol-4-yl)pentanoyl)piperazin-1-yl)but-2-enamide (A295)

((E)-N-(3-((6-amino-5-(4-phenoxyphenyl)pyrimidin-4-yl)oxy)phenyl)-4-(4-(5-((4S)-2-oxohexahydro-1H-thieno[3,4-d]imidazol-4-yl)pentanoyl)piperazin-1-yl)but-2-enamide was prepared from (E)-N-(3-((6-amino-5-(4-phenoxyphenyl)pyrimidin-4-yl)oxy)phenyl)-4-(piperazin-1-yl)but-2-enamide and perfluorophenyl 5-((4S)-2-oxohexahydro-1H-thieno[3,4-d]imidazol-4-yl)pentanoate using Method F (45% yield). HPLC: 100%, RT=3.635 min. MS: m/z=750 [M+H]$^+$, RT=1.84 min.

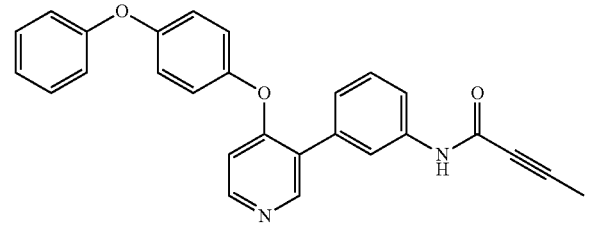 [SMILES: CC#CC(=O)Nc1cccc(-c2cnccc2Oc2ccc(Oc3ccccc3)cc2)c1]

N-(3-(4-(4-phenoxyphenoxy)pyridin-3-yl)phenyl)but-2-ynamide (A296)

N-(3-(4-(4-phenoxyphenoxy)pyridin-3-yl)phenyl)but-2-ynamide was prepared from 3-(4-(4-phenoxyphenoxy)pyridin-3-yl)aniline and but-2-ynoic acid using Method E (63% yield). HPLC: 100%, RT=4.097 min. MS: m/z=421 [M+H]$^+$, RT=4.22 min. $^1$H-NMR (DMSO-d$_6$) δ 10.75 (s, 1H), 8.71 (s, 1H), 8.56 (d, 1H), 7.97 (s, 1H), 7.66 (d, 1H), 7.46 (t, 1H), 7.42-7.39 (m, 3H), 7.28 (d, 2H), 7.17-7.13 (m, 3H), 7.05-7.02 (m, 3H), 2.04 (s, 3H).

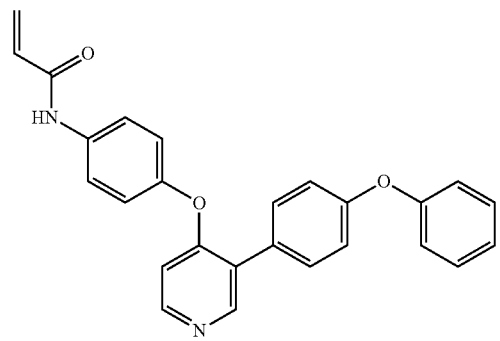 [SMILES: C=CC(=O)Nc1ccc(Oc2ccncc2-c2ccc(Oc3ccccc3)cc2)cc1]

N-(4-((3-(4-phenoxyphenyl)pyridin-4-yl)oxy)phenyl)acrylamide (A297)

N-(4-((3-(4-phenoxyphenyl)pyridin-4-yl)oxy)phenyl)acrylamide was prepared from 4-((3-(4-phenoxyphenyl)pyridin-4-yl)oxy)aniline using Method E (41% yield). HPLC: 87%, RT=4.063 min. MS: m/z=409 [M+H]$^+$, RT=4.05 min. $^1$H-NMR (DMSO-d$_6$) δ 10.16 (s, 1H), 8.48 (s, 1H), 8.33 (d, 1H), 7.68 (d, 2H), 7.60 (d, 2H), 7.35 (t, 2H), 7.12-7.08 (m, 3H), 7.03-7.00 (m, 4H), 6.67 (d, 1H), 6.37 (dd, 1H), 6.20 (d, 1H), 5.70 (d, 1H).

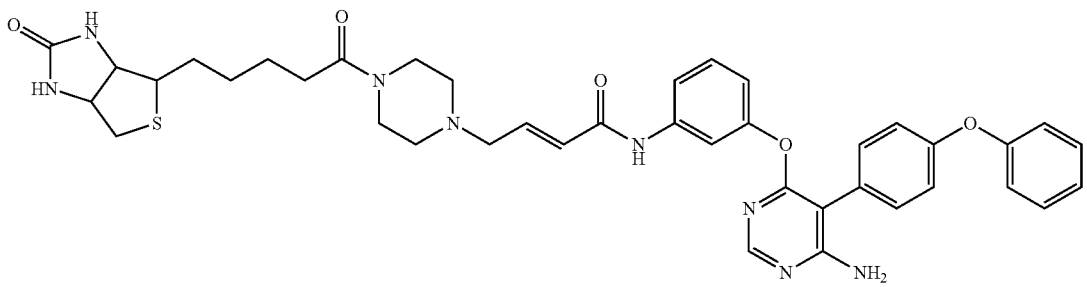

7.13-7.08 (m, 3H), 7.03 (d, 2H), 6.97 (d, 2H), 6.73 (d, 1H), 6.67-6.65 (m, 2H), 6.29 (d, 1H).

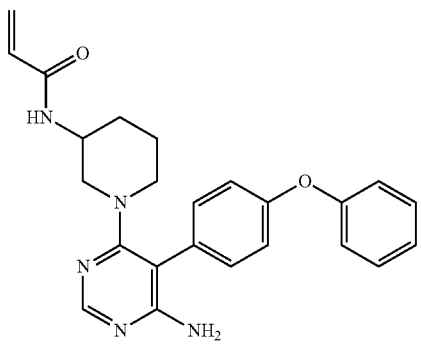 [SMILES: C=CC(=O)NC1CCCN(c2ncnc(N)c2-c2ccc(Oc3ccccc3)cc2)C1]

N-(1-(6-amino-5-(4-phenoxyphenyl)pyrimidin-4-yl)piperidin-3-yl)acrylamide (A298)

N-(1-(6-amino-5-(4-phenoxyphenyl)pyrimidin-4-yl)piperidin-3-yl)acrylamide was prepared from 6-(3-aminopiperidin-1-yl)-5-(4-phenoxyphenyl)pyrimidin-4-amine using Method F (14% yield). HPLC: 99%, RT=3.670 min. MS: m/z=416 [M+H]⁺, RT=1.55 min.

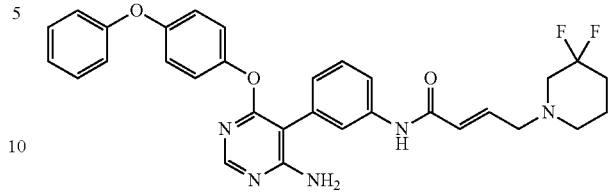

(E)-N-(3-(4-amino-6-(4-phenoxyphenoxy)pyrimidin-5-yl)phenyl)-4-(3,3-difluoropiperidin-1-yl)but-2-enamide (A301)

(E)-N-(3-(4-amino-6-(4-phenoxyphenoxy)pyrimidin-5-yl)phenyl)-4-(3,3-difluoropiperidin-1-yl)but-2-enamide was prepared from 5-(3-aminophenyl)-6-(4-phenoxyphenoxy)pyrimidin-4-amine and (E)-4-(3,3-difluoropiperidin-1-yl)but-2-enoic acid using Method E (48% yield). HPLC: 97%, RT=3.809 min. MS: m/z=558 [M+H]⁺, RT=1.92 min.

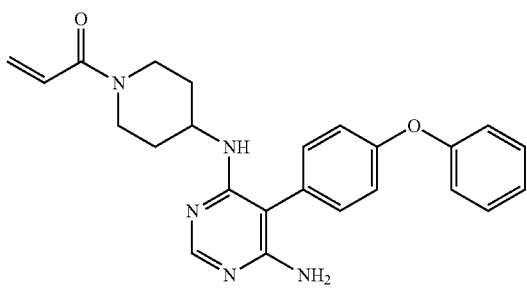 [SMILES: C=CC(=O)N1CCC(Nc2ncnc(N)c2-c2ccc(Oc3ccccc3)cc2)CC1]

1-(4-((6-amino-5-(4-phenoxyphenyl)pyrimidin-4-yl)amino)piperidin-1-yl)prop-2-en-1-one (A299)

1-(4-((6-amino-5-(4-phenoxyphenyl)pyrimidin-4-yl)amino)piperidin-1-yl)prop-2-en-1-one was prepared from 5-(4-phenoxyphenyl)-N4-(piperidin-4-yl)pyrimidine-4,6-diamine using Method F (52% yield). HPLC: 98%, RT=3.574 min. MS: m/z=416 [M+H]⁺, RT=1.74 min.

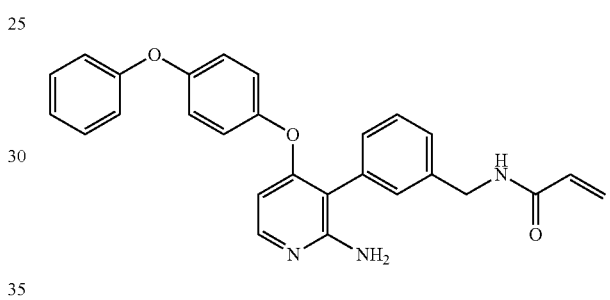

N-(3-(4-(4-phenoxyphenoxy)pyridin-3-yl)benzyl)acrylamide (A302)

N-(3-(4-(4-phenoxyphenoxy)pyridin-3-yl)benzyl)acrylamide was prepared from (3-(4-(4-phenoxyphenoxy)pyridin-3-yl)phenyl)methanamine, triethylamine and tetrahydrofuran using Method G (6% yield). HPLC: 96%, RT=4.127 min. MS: m/z=423 [M+H]⁺, RT=3.22 min. ¹H-NMR (DMSO-d₆) δ 9.14 (s, 1H), 9.02 (d, 1H), 8.23 (s, 1H), 8.16 (s, 1H), 8.09 (d, 1H), 7.93 (t, 1H), 7.87-7.84 (m, 3H), 7.73 (d, 2H), 7.62-7.58 (m, 3H), 7.51-7.50 (m, 3H), 6.77 (dd, 1H), 6.67 (d, 1H), 6.03 (d, 1H), 5.02 (d, 2H).

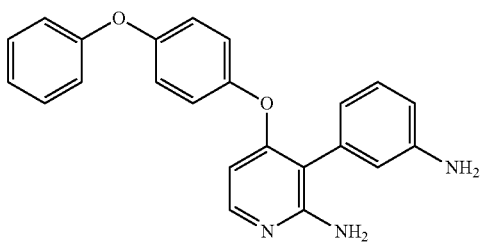 [SMILES: Nc1cccc(-c2c(Oc3ccc(Oc4ccccc4)cc3)ccnc2N)c1]

3-(3-aminophenyl)-4-(4-phenoxyphenoxy)pyridin-2-amine (A300)

3-(4-(4-phenoxyphenoxy)pyridin-3-yl)aniline was prepared from 3-iodo-4-(4-phenoxyphenoxy)pyridin-2-amine using Method C (37% yield). HPLC: 98%, RT=3.369 min. MS: m/z=370 [M+H]⁺, RT=3.37 min. ¹H-NMR (DMSO-d₆) δ 7.88 (d, 1H), 7.34 (t, 2H), 7.28 (s, 2H), 7.19 (t, 1H),

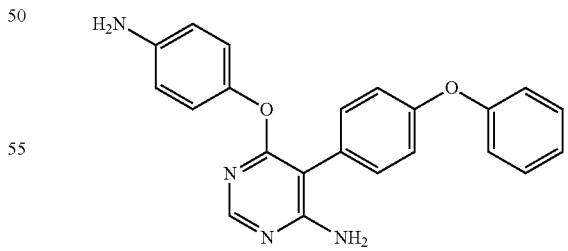

6-(4-aminophenoxy)-5-(4-phenoxyphenyl)pyrimidin-4-amine (A303)

6-(4-aminophenoxy)-5-(4-phenoxyphenyl)pyrimidin-4-amine was prepared from 6-(4-aminophenoxy)-5-bromopyrimidin-4-amine using Method C (78% yield). HPLC: 98%, RT=3.259 min. MS: m/z=371 [M+H]⁺, RT=3.24 min.

¹H-NMR (DMSO-d₆) δ 8.05 (s, 1H), 7.43-7.38 (m, 5H), 7.21 (d, 2H), 7.17-7.06 (m, 8H), 6.64 (broad s, 2H).

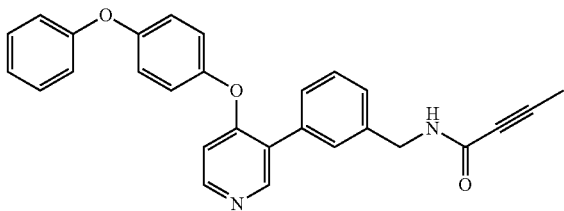 [SMILES: CC#CC(=O)NCc1cccc(-c2cnccc2Oc2ccc(Oc3ccccc3)cc2)c1]

N-(3-(4-(4-phenoxyphenoxy)pyridin-3-yl)benzyl)but-2-ynamide (A304)

N-(3-(4-(4-phenoxyphenoxy)pyridin-3-yl)benzyl)but-2-ynamide was prepared from (3-(4-(4-phenoxyphenoxy)pyridin-3-yl)phenyl)methanamine and but-2-ynoic acid using Method E (64% yield). HPLC: 98%, RT=4.069 min. MS: m/z=435 [M+H]⁺, RT=4.07 min. ¹H-NMR (DMSO-d₆) δ 9.01 (t, 1H), 8.51 (s, 1H), 8.42 (d, 1H), 7.54-7.50 (m, 2H), 7.43-7.37 (m, 3H), 7.27 (d, 1H), 7.22-7.18 (m, 2H), 7.13 (tt, 1H), 7.10-7.07 (m, 2H), 7.04-7.01 (m, 2H), 6.79 (d, 1H), 4.33 (d, 2H), 1.93 (s, 3H).

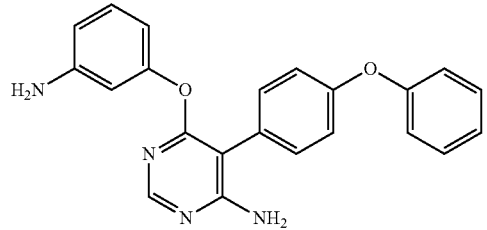

6-(3-aminophenoxy)-5-(4-phenoxyphenyl)pyrimidin-4-amine (A305)

6-(3-aminophenoxy)-5-(4-phenoxyphenyl)pyrimidin-4-amine was prepared from 6-(3-aminophenoxy)-5-bromopyrimidin-4-amine using Method C (74% yield). HPLC: 99%, RT=3.417 min. MS: m/z=371 [M+H]⁺, RT=3.42 min. ¹H-NMR (DMSO-d₆) δ 8.09 (s, 1H), 7.42-7.38 (m, 4H), 7.20 (t, 1H), 7.15 (t, 1H), 7.09-7.06 (m, 4H), 6.75 (d, 1H), 6.64-6.63 (m, 2H).

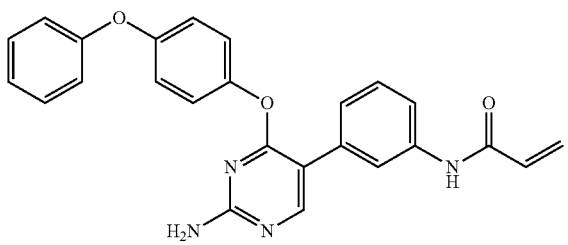 [SMILES: C=CC(=O)Nc1cccc(-c2cnc(N)nc2Oc2ccc(Oc3ccccc3)cc2)c1]

N-(3-(2-amino-4-(4-phenoxyphenoxy)pyrimidin-5-yl)phenyl)acrylamide (A306)

N-(3-(2-amino-4-(4-phenoxyphenoxy)pyrimidin-5-yl)phenyl)acrylamide was prepared from 5-(3-aminophenyl)-4-(4-phenoxyphenoxy)pyrimidin-2-amine using Method E (27% yield). HPLC: 96%, RT=4.208 min. MS: m/z=425 [M+H]⁺, RT=2.13 min. ¹H-NMR (DMSO-d₆) δ 10.22 (s, 1H), 8.27 (s, 1H), 7.93 (s, 1H), 7.66 (d, 1H), 7.42-7.02 (m, 13H), 6.44 (dd, 1H), 6.25 (d, 1H), 5.75 (d, 1H).

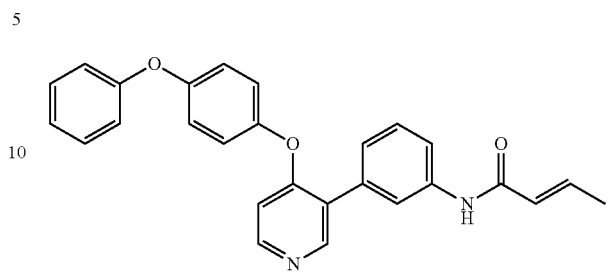

(E)-N-(3-(4-(4-phenoxyphenoxy)pyridin-3-yl)phenyl)but-2-enamide (A307)

(E)-N-(3-(4-(4-phenoxyphenoxy)pyridin-3-yl)phenyl)but-2-enamide was prepared from 3-(4-(4-phenoxyphenoxy)pyridin-3-yl)aniline and (E)-but-2-enoic acid using Method E (56% yield). HPLC: 98%, RT=4.292 min. MS: m/z=423 [M+H]⁺, RT=4.28 min. ¹H-NMR (DMSO-d₆) δ 9.91 (s, 1H), 8.52 (s, 1H), 8.43 (d, 1H), 7.92 (s, 1H), 7.68 (d, 1H), 7.40-7.37 (m, 3H), 7.30 (d, 1H), 7.18-7.12 (m, 3H), 7.08 (d, 2H), 7.02 (d, 2H), 6.83-6.76 (m, 2H), 6.14 (d, 1H), 1.86 (d, 3H).

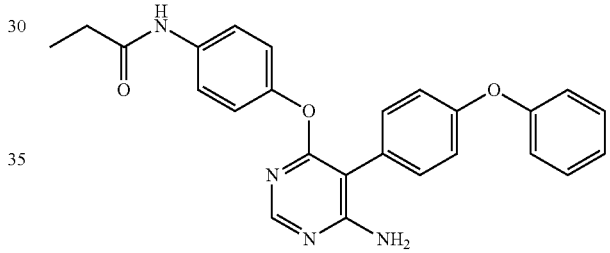

N-(4-((6-amino-5-(4-phenoxyphenyl)pyrimidin-4-yl)oxy)phenyl)propionamide (A308)

N-(4-((6-amino-5-(4-phenoxyphenyl)pyrimidin-4-yl)oxy)phenyl)acrylamide was prepared from 6-(4-aminophenoxy)-5-(4-phenoxyphenyl)pyrimidin-4-amine and propionic acid using Method E (51% yield). HPLC: 96%, RT=4.165 min. MS: m/z=427 [M+H]⁺, RT=4.11 min. ¹H-NMR (DMSO-d₆) δ 9.78 (s, 1H), 7.94 (s, 1H), 7.48 (d, 2H), 7.36-7.32 (m, 4H), 7.09 (t, 1H), 7.02 (t, 4H), 6.91 (d, 2H), 6.39 (broad s, 2H), 2.24 (q, 2H), 1.01 (t, 3H).

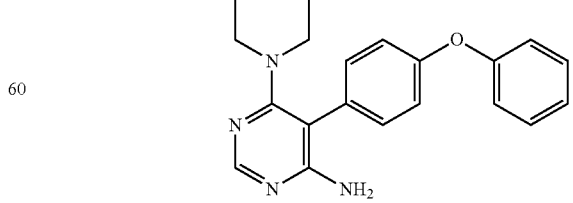

N-((1-(6-amino-5-(4-phenoxyphenyl)pyrimidin-4-yl)piperidin-3-yl)methyl)acrylamide (A309)

N-((1-(6-amino-5-(4-phenoxyphenyl)pyrimidin-4-yl)piperidin-3-yl)methyl)acrylamide was prepared from 6-(3-(aminomethyl)piperidin-1-yl)-5-(4-phenoxyphenyl)pyrimidin-4-amine using Method F (43% yield). HPLC: 100%, RT=3.716 min. MS: m/z=430 [M+H]⁺, RT=1.53 min.

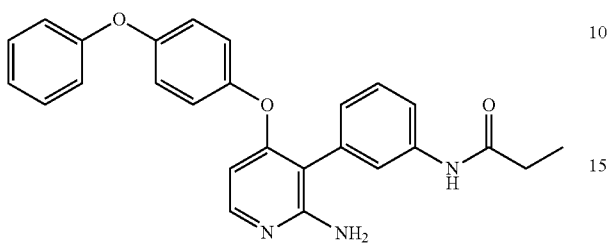

N-(3-(2-amino-4-(4-phenoxyphenoxy)pyridin-3-yl)phenyl)propionamide (A310)

N-(3-(2-amino-4-(4-phenoxyphenoxy)pyridin-3-yl)phenyl)propionamide was prepared from 3-iodo-4-(4-phenoxyphenoxy)pyridin-2-amine and N-(3-(4,4,5,5-tetramethyl-1,3,2-dioxaborolan-2-yl)phenyl)propionamide using Method C (49% yield). HPLC: 98%, RT=4.186 min. MS: m/z=426 [M+H]⁺, RT=4.18 min. ¹H-NMR (DMSO-d₆) δ 10.01 (s, 1H), 7.94 (d, 1H), 7.73 (s, 1H), 7.63 (d, 1H), 7.44 (t, 1H), 7.39 (t, 2H), 7.24 (s, 2H), 7.16-7.01 (m, 8H), 6.35 (d, 1H), 2.32 (q, 2H), 1.07 (t, 3H).

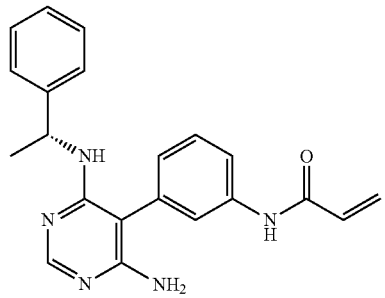 [SMILES: C=CC(=O)Nc1cccc(-c2c(N)ncnc2N[C@H](C)c2ccccc2)c1]

(R)—N-(3-(4-amino-6-((1-phenylethyl)amino)pyrimidin-5-yl)phenyl)acrylamide (A311)

(R)—N-(3-(4-amino-6-((1-phenylethyl)amino)pyrimidin-5-yl)phenyl)acrylamide was prepared from (R)-5-(3-aminophenyl)-N4-(1-phenylethyl)pyrimidine-4,6-diamine using Method F (16% yield). HPLC: 100%, RT=3.515 min. MS: m/z=360 [M+H]⁺, RT=1.73 min. ¹H-NMR (DMSO-d₆), δ 10.33 (s, 1H), 8.28 (s, 1H), 7.82 (s, 1H), 7.64 (d, 1H), 7.52 (t, 1H), 7.29-6.85 (m, 9H), 6.47 (dd, 1H), 6.27 (d, 1H), 5.77 (d, 1H), 5.40 (s, 1H), 1.39 (d, 3H).

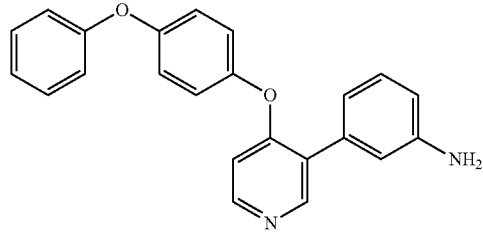 [SMILES: Nc1cccc(-c2cnccc2Oc2ccc(Oc3ccccc3)cc2)c1]

3-(4-(4-phenoxyphenoxy)pyridin-3-yl)aniline (A312)

3-(4-(4-phenoxyphenoxy)pyridin-3-yl)aniline was prepared from 3-bromo-4-(4-phenoxyphenoxy)pyridine using Method C (55% yield). HPLC: 100%, RT=3.396 min. MS: m/z=355 [M+H]⁺, RT=2.88 min.

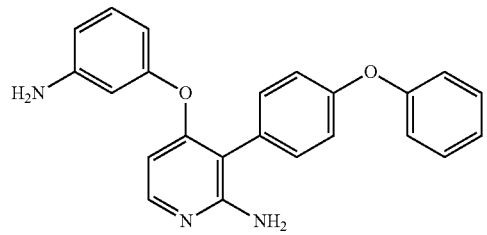 [SMILES: Nc1cccc(Oc2ccnc(N)c2-c2ccc(Oc3ccccc3)cc2)c1]

4-(3-aminophenoxy)-3-(4-phenoxyphenyl)pyridin-2-amine (A313)

4-(3-aminophenoxy)-3-(4-phenoxyphenyl)pyridin-2-amine was prepared from 4-(3-aminophenoxy)-3-iodopyridin-2-amine using Method C (84% yield). HPLC: 98%, RT=3.490 min. MS: m/z=370 [M+H]⁺, RT=3.44 min. ¹H-NMR (DMSO-d₆) δ 8.00 (d, 1H), 7.45-7.41 (m, 6H), 7.18 (t, 1H), 7.13-7.07 (m, 5H), 6.51 (d, 1H), 6.32-6.26 (m, 3H).

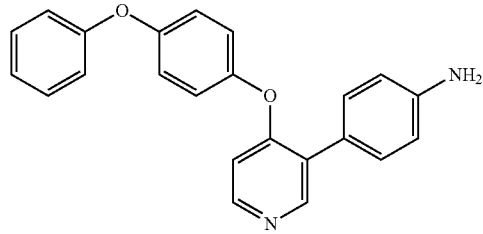 [SMILES: Nc1ccc(-c2cnccc2Oc2ccc(Oc3ccccc3)cc2)cc1]

4-(4-(4-phenoxyphenoxy)pyridin-3-yl)aniline (A314)

4-(4-(4-phenoxyphenoxy)pyridin-3-yl)aniline was prepared from 3-bromo-4-(4-phenoxyphenoxy)pyridine using Method C (74% yield). HPLC: 100%, RT=3.456 min. MS: m/z=355 [M+H]⁺, RT=2.75 min.

191

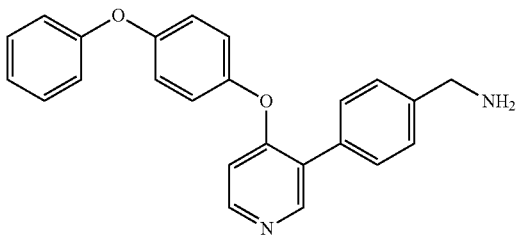 [SMILES: NCc1ccc(-c2cnccc2Oc2ccc(Oc3ccccc3)cc2)cc1]

(4-(4-(4-phenoxyphenoxy)pyridin-3-yl)phenyl)methanamine (A315)

(4-(4-(4-phenoxyphenoxy)pyridin-3-yl)phenyl)methanamine was prepared from 3-bromo-4-(4-phenoxyphenoxy)pyridine using Method C (62% yield). HPLC: 95%, RT=3.286 min. MS: m/z=369 [M+H]$^+$, RT=2.19 min.

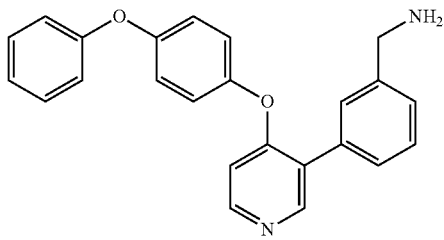 [SMILES: NCc1cccc(-c2cnccc2Oc2ccc(Oc3ccccc3)cc2)c1]

(3-(4-(4-phenoxyphenoxy)pyridin-3-yl)phenyl)methanamine (A316)

(3-(4-(4-phenoxyphenoxy)pyridin-3-yl)phenyl)methanamine was prepared from 3-bromo-4-(4-phenoxyphenoxy)pyridine using Method C (71% yield). HPLC: 95%, RT=3.376 min. MS: m/z=369 [M+H]$^+$, RT=2.29 min.

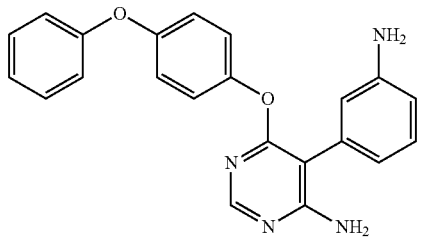 [SMILES: Nc1cccc(-c2c(N)ncnc2Oc2ccc(Oc3ccccc3)cc2)c1]

5-(3-aminophenyl)-6-(4-phenoxyphenoxy)pyrimidin-4-amine (A317)

5-(3-aminophenyl)-6-(4-phenoxyphenoxy)pyrimidin-4-amine was prepared from 5-bromo-6-(4-phenoxyphenoxy)pyrimidin-4-amine using Method C (76% yield). HPLC: 97%, RT=3.433 min. MS: m/z=371 [M+H]$^+$, RT=3.48 min. $^1$H-NMR (DMSO-d$_6$) δ 8.01 (s, 1H), 7.34-7.26 (m, 3H), 7.06 (t, 1H), 7.01-6.87 (m, 9H), 6.41 (broad s, 2H).

192

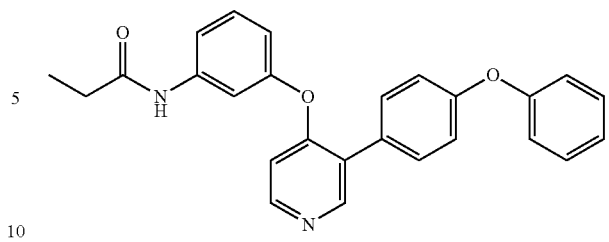

N-(3-((3-(4-phenoxyphenyl)pyridin-4-yl)oxy)phenyl)propionamide (A318)

N-(3-((3-(4-phenoxyphenyl)pyridin-4-yl)oxy)phenyl)propionamide was prepared from 3-((3-(4-phenoxyphenyl)pyridin-4-yl)oxy)aniline using Method E (100% yield). HPLC: 96%, RT=4.161 min. MS: m/z=409 [M+H]$^+$, RT=4.15 min. $^1$H-NMR (DMSO-d$_6$) δ 10.37 (s, 1H), 8.78 (s, 1H), 8.55 (d, 1H), 7.72-7.70 (m, 3H), 7.45-7.40 (m, 4H), 7.18 (t, 1H), 7.13-7.07 (m, 4H), 7.03 (d, 1H), 6.97 (s, 1H), 6.41 (dd, 1H), 6.24 (d, 1H), 5.77 (d, 1H).

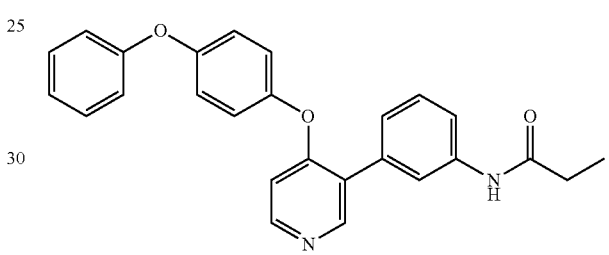

N-(3-(4-(4-phenoxyphenoxy)pyridin-3-yl)phenyl)propionamide (A319)

N-(3-(4-(4-phenoxyphenoxy)pyridin-3-yl)phenyl)propionamide was prepared from 3-(4-(4-phenoxyphenoxy)pyridin-3-yl)aniline and pyridine instead of N,N-diethylethanamine, 1-methylpyrrolidin-2-one, dichloromethane using Method G (65% yield). HPLC: 92%, RT=4.234 min. MS: m/z=411 [M+H]$^+$, RT=3.35 min.

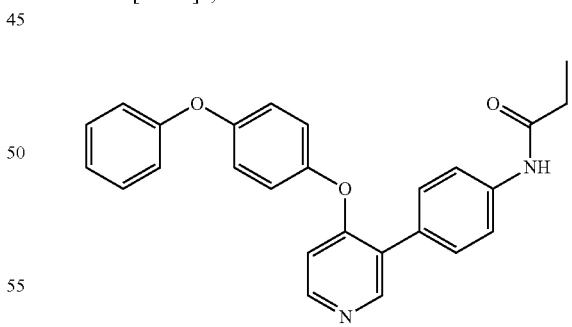

N-(4-(4-(4-phenoxyphenoxy)pyridin-3-yl)phenyl)propionamide (A320)

N-(4-(4-(4-phenoxyphenoxy)pyridin-3-yl)phenyl)propionamide was prepared from 4-(4-(4-phenoxyphenoxy)pyridin-3-yl)aniline and pyridine instead of N,N-diethylethanamine, 1-methylpyrrolidin-2-one, dichloromethane using Method G (77% yield). HPLC: 98%, RT=4.157 min. MS: m/z=411 [M+H]$^+$, RT=3.39 min.

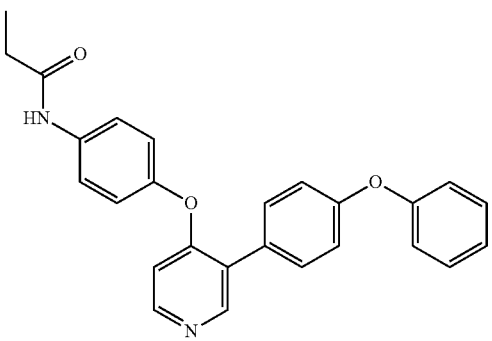 [SMILES: CCC(=O)Nc1ccc(Oc2ccncc2-c2ccc(Oc3ccccc3)cc2)cc1]

N-(4-((3-(4-phenoxyphenyl)pyridin-4-yl)oxy)phenyl)propionamide (A321)

N-(4-((3-(4-phenoxyphenyl)pyridin-4-yl)oxy)phenyl)propionamide was prepared from 4-((3-(4-phenoxyphenyl)pyridin-4-yl)oxy)aniline using Method E (98% yield). HPLC: 96%, RT=4.061 min. MS: m/z=411 [M+H]$^+$, RT=4.01 min. $^1$H-NMR (DMSO-d$_6$) δ 9.93 (s, 1H), 8.53 (s, 1H), 8.37 (d, 1H), 7.67-7.65 (m, 4H), 7.41 (t, 2H), 7.16 (t, 1H), 7.12-7.06 (m, 6H), 6.69 (d, 1H), 2.31 (q, 2H), 1.08 (t, 3H).

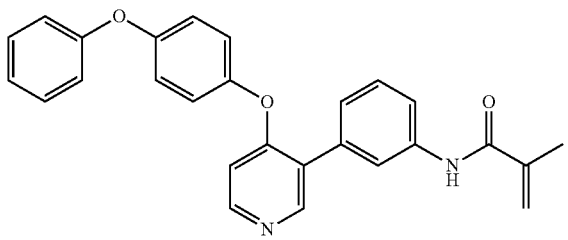 [SMILES: C=C(C)C(=O)Nc1cccc(-c2cnccc2Oc2ccc(Oc3ccccc3)cc2)c1]

N-(3-(4-(4-phenoxyphenoxy)pyridin-3-yl)phenyl)methacrylamide (A322)

N-(3-(4-(4-phenoxyphenoxy)pyridin-3-yl)phenyl)methacrylamide was prepared from 3-(4-(4-phenoxyphenoxy)pyridin-3-yl)aniline and methacrylic acid using Method E (56% yield). HPLC: 98%, RT=4.345 min. MS: m/z=423 [M+H]$^+$, RT=4.33 min. $^1$H-NMR (DMSO-d$_6$), 1H), 8.51 (s, 1H), 8.42 (d, 1H), 7.96 (s, 1H), 7.73 (d, 1H), 7.42-7.33 (m, 4H), 7.19 (d, 2H), 7.13 (t, 1H), 7.09 (d, 2H), 7.02 (d, 2H), 6.79 (d, 1H), 5.80 (s, 1H), 5.51 (s, 1H), 1.94 (s, 3H).

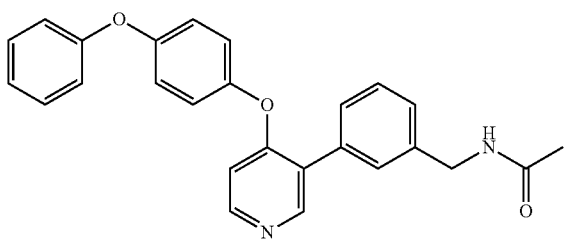 [SMILES: CC(=O)NCc1cccc(-c2cnccc2Oc2ccc(Oc3ccccc3)cc2)c1]

N-(3-(4-(4-phenoxyphenoxy)pyridin-3-yl)benzyl)propionamide (A323)

N-(3-(4-(4-phenoxyphenoxy)pyridin-3-yl)benzyl)propionamide was prepared from (3-(4-(4-phenoxyphenoxy)pyridin-3-yl)phenyl)methanamine and pyridine instead of N,N-diethylethanamine, 1-methylpyrrolidin-2-one, dichloromethane using Method G (58% yield). HPLC: 97%, RT=4.034 min. MS: m/z=425 [M+H]$^+$, RT=3.34 min.

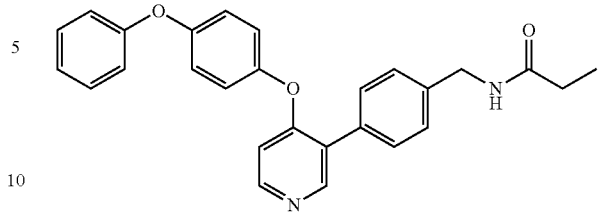

N-(4-(4-(4-phenoxyphenoxy)pyridin-3-yl)benzyl)propionamide (A324)

N-(4-(4-(4-phenoxyphenoxy)pyridin-3-yl)benzyl)propionamide was prepared from (4-(4-(4-phenoxyphenoxy)pyridin-3-yl)phenyl)methanamine and pyridine instead of N,N-diethylethanamine, 1-methylpyrrolidin-2-one, dichloromethane using Method G (43% yield). HPLC: 99%, RT=4.032 min. MS: m/z=425 [M+H]$^+$, RT=3.22 min.

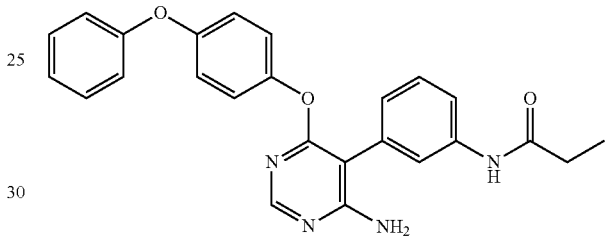

N-(3-(4-amino-6-(4-phenoxyphenoxy)pyrimidin-5-yl)phenyl)propionamide (A325)

N-(3-(4-amino-6-(4-phenoxyphenoxy)pyrimidin-5-yl)phenyl)propionamide was prepared from 5-bromo-6-(4-phenoxyphenoxy)pyrimidin-4-amine and N-(3-(4,4,5,5-tetramethyl-1,3,2-dioxaborolan-2-yl)phenyl)propionamide using Method C (82% yield). HPLC: 99%, RT=4.286 min. MS: m/z=427 [M+H]$^+$, RT=4.25 min. $^1$H-NMR (DMSO-d$_6$) δ 9.93 (s, 1H), 8.10 (s, 1H), 7.64-7.63 (m, 2H), 7.38 (t, 3H), 7.12 (t, 1H), 7.08-7.05 (m, 3H), 6.99 (d, 4H), 6.60 (broad s, 2H), 2.32 (q, 2H), 1.07 (t, 3H).

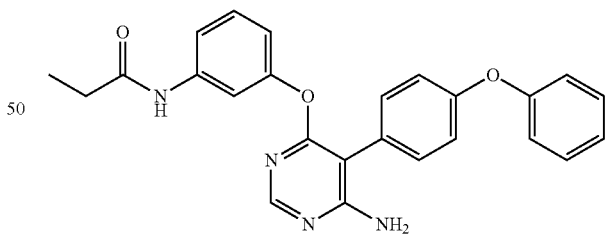

N-(3-((6-amino-5-(4-phenoxyphenyl)pyrimidin-4-yl)oxy)phenyl)propionamide (A326)

N-(3-((6-amino-5-(4-phenoxyphenyl)pyrimidin-4-yl)oxy)phenyl)propionamide was prepared from 6-(3-aminophenoxy)-5-(4-phenoxyphenyl)pyrimidin-4-amine using Method E (61% yield). HPLC: 94%, RT=4.262 min. MS: m/z=427 [M+H]$^+$, RT=4.22 min. $^1$H-NMR (DMSO-d$_6$) δ 9.90 (s, 1H), 8.03 (s, 1H), 7.41-7.38 (m, 5H), 7.29 (d, 1H), 7.23 (t, 1H), 7.15 (t, 1H), 7.07 (t, 4H), 6.70 (d, 1H), 6.49 (broad s, 2H), 2.28 (q, 2H), 1.04 (t, 3H).

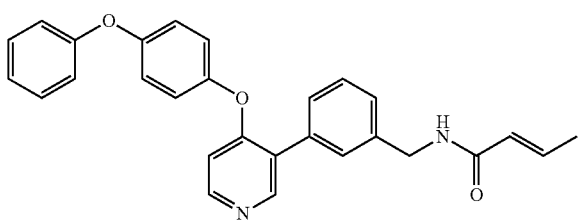 [SMILES: C/C=C/C(=O)NCc1cccc(-c2cnccc2Oc2ccc(Oc3ccccc3)cc2)c1]

(E)-N-(3(4-(4-phenoxyphenoxy)pyridin-3-yl)benzyl)
but-2-enamide (A327)

(E)-N-(3-(4-(4-phenoxyphenoxy)pyridin-3-yl)benzyl)but-2-enamide was prepared from (3-(4-(4-phenoxyphenoxy)pyridin-3-yl)phenyl)methanamine and (E)-but-2-enoic acid using Method E (72% yield). HPLC: 95%, RT=4.079 min. MS: m/z=437 [M+H]$^+$, RT=4.07 min. $^1$H-NMR (DMSO-d$_6$) δ 8.51 (s, 1H), 8.42-8.39 (m, 2H), 7.53-7.52 (m, 2H), 7.43-7.37 (m, 3H), 7.28 (d, 1H), 7.19 (d, 2H), 7.14 (t, 1H), 7.08 (d, 2H), 7.02 (d, 2H), 6.78 (d, 1H), 6.63 (qd, 1H), 5.94 (d, 1H), 4.38 (d, 2H), 1.76 (d, 3H).

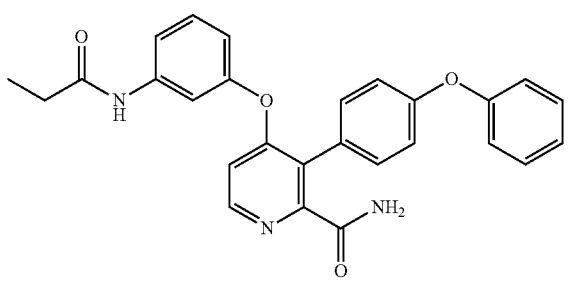 [SMILES: CCC(=O)Nc1cccc(Oc2ccnc(C(N)=O)c2-c2ccc(Oc3ccccc3)cc2)c1]

3-(4-phenoxyphenyl)-4-(3-propionamidophenoxy)
picolinamide (A328)

3-(4-phenoxyphenyl)-4-(3-propionamidophenoxy)picolinamide was prepared from 4-(3-aminophenoxy)-3-(4-phenoxyphenyl)picolinamide using Method F (24% yield). HPLC: 100%, RT=4.113 min. MS: m/z=452 [M+H]$^+$, RT=2.05 min. $^1$H-NMR (DMSO-d$_6$) δ 10.23 (s, 1H), 8.37 (d, 1H), 7.78 (s, 1H), 7.48 (s, 1H), 7.36-7.29 (m, 7H), 7.09 (t, 1H), 6.97 (d, 2H), 6.92 (d, 2H), 6.84 (d, 1H), 6.74 (d, 1H), 6.33 (dd, 1H), 6.18 (d, 1H), 5.70 (d, 1H).

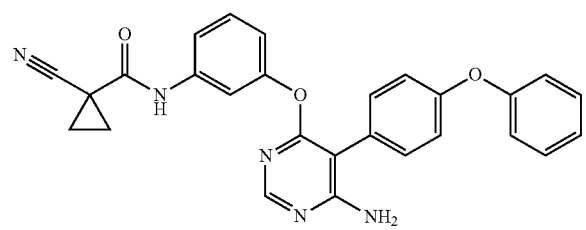 [SMILES: N#CC1(C(=O)Nc2cccc(Oc3ncnc(N)c3-c3ccc(Oc4ccccc4)cc3)c2)CC1]

N-(3-((6-amino-5-(4-phenoxyphenyl)pyrimidin-4-yl)
oxy)phenyl)-1-cyanocyclopropanecarboxamide
(A329)

N-(3-((6-amino-5-(4-phenoxyphenyl)pyrimidin-4-yl)oxy)phenyl)-1-cyanocyclopropanecarboxamide was prepared from 6-(3-aminophenoxy)-5-(4-phenoxyphenyl)pyrimidin-4-amine and 1-cyanocyclopropanecarboxylic acid using Method E (42% yield). HPLC: 96%, RT=4.467 min. MS: m/z=464 [M+H]$^+$, RT=2.24 min. $^1$H-NMR (DMSO-d$_6$) δ 10.85 (s, 1H), 8.91 (s, 1H), 8.22-8.08 (m, 7H), 7.96 (t, 1H), 7.90-7.87 (m, 4H), 7.63 (d, 1H), 7.54 (broad s, 2H), 3.30 (s, 4H).

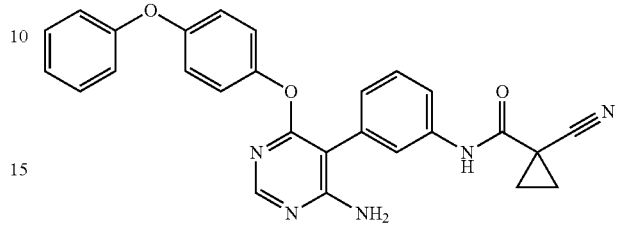

N-(3-(4-amino-6-(4-phenoxyphenoxy)pyrimidin-5-
yl)phenyl)-1-cyanocyclopropanecarboxamide
(A330)

N-(3-(4-amino-6-(4-phenoxyphenoxy)pyrimidin-5-yl)phenyl)-1-cyanocyclopropanecarboxamide was prepared from 5-(3-aminophenyl)-6-(4-phenoxyphenoxy)pyrimidin-4-amine and 1-cyanocyclopropanecarboxylic acid using Method E (66% yield). HPLC: 100%, RT=4.485 min. MS: m/z=465 [M+H]$^+$, RT=2.26 min. $^1$H-NMR (DMSO-d$_6$) δ 10.07 (s, 1H), 8.10 (s, 1H), 7.64-7.61 (m, 2H), 7.43-7.36 (m, 3H), 7.18 (d, 1H), 7.11 (t, 1H), 7.06 (d, 2H), 7.00-6.97 (m, 4H), 6.58 (broad s, 2H), 1.65 (s, 4H).

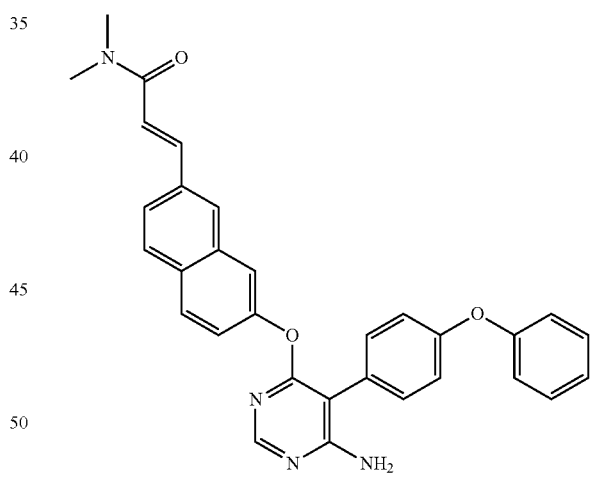

(E)-3-(7-((6-amino-5-(4-phenoxyphenyl)pyrimidin-
4-yl)oxy)naphthalen-2-yl)-N,N-dimethylacrylamide
(A331)

(E)-3-(7-((6-amino-5-(4-phenoxyphenyl)pyrimidin-4-yl)oxy)naphthalen-2-yl)-N,N-dimethylacrylamide was prepared from (E)-3-(7-((6-amino-5-chloropyrimidin-4-yl)oxy)naphthalen-2-yl)-N,N-dimethylacrylamide using Method C (16% yield). HPLC: 93%, RT=4.680 min. MS: m/z=503 [M+H]$^+$, RT=2.54 min. $^1$H-NMR (DMSO-d$_6$) δ 8.09 (d, 2H), 7.94 (d, 2H), 7.66-7.58 (m, 2H), 7.50 (d, 2H), 7.42 (t, 2H), 7.36-7.31 (m, 2H), 7.18 (t, 1H), 7.12-7.10 (m, 5H), 6.70 (broad s, 2H), 3.21 (s, 3H), 2.96 (s, 3H).

197

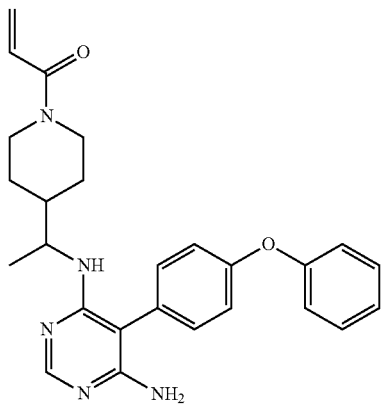 [SMILES: C=CC(=O)N1CCC(C(C)Nc2ncnc(N)c2-c2ccc(Oc3ccccc3)cc2)CC1]

1-(4-(1-((6-amino-5-(4-phenoxyphenyl)pyrimidin-4-yl)amino)ethyl)piperidin-1-yl)prop-2-en-1-one (A332)

1-(4-(1-((6-amino-5-(4-phenoxyphenyl)pyrimidin-4-yl)amino)ethyl)piperidin-1-yl)prop-2-en-1-one was prepared from 5-(4-phenoxyphenyl)-N4-(1-(piperidin-4-yl)ethyl)pyrimidine-4,6-diamine using Method F (30% yield). HPLC: 100%, RT=4.388 min. MS: m/z=444 [M+H]$^+$, RT=1.66 min. $^1$H-NMR (DMSO-d$_6$) (s, 1H), 7.38 (t, 2H), 7.19-7.06 (m, 7H), 6.85 (broad s, 2H), 6.70 (m, 1H), 6.52 (d, 1H), 5.99 (d, 1H), 5.56 (t, 1H), 4.33 (t, 1H), 3.96 (t, 2H), 2.86 (m, 1H), 1.62-1.54 (m, 3H), 1.00 (d, 3H), 0.95-0.84 (m, 2H).

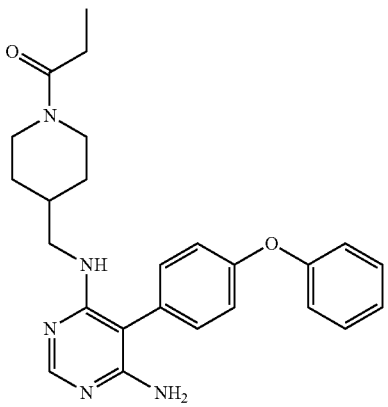 [SMILES: CCC(=O)N1CCC(CNc2ncnc(N)c2-c2ccc(Oc3ccccc3)cc2)CC1]

1-(4-(((6-amino-5-(4-phenoxyphenyl)pyrimidin-4-yl)amino)methyl)piperidin-1-yl)propan-1-one (A333)

1-(4-(((6-amino-5-(4-phenoxyphenyl)pyrimidin-4-yl)amino)methyl)piperidin-1-yl)propan-1-one was prepared from 5-(4-phenoxyphenyl)-N4-(piperidin-4-ylmethyl)pyrimidine-4,6-diamine using Method E (43% yield). HPLC: 99%, RT: 4.412 min. MS: m/z=432 [M+H]$^+$, RT=1.49 min. $^1$H-NMR (DMSO-d$_6$) (s, 1H), 7.38 (t, 2H), 7.20 (d, 2H), 7.15-6.94 (m, 8H), 4.27 (d, 1H), 3.74 (d, 1H), 3.16 (s, 2H), 2.83 (t, 1H), 2.39 (t, 1H), 2.21 (q, 2H), 1.72 (m, 1H), 1.51 (t, 2H), 0.96-0.79 (m, 5H).

198

1-(4-(((5-(4-phenoxyphenyl)pyrimidin-4-yl)amino)methyl)piperidin-1-yl)prop-2-en-1-one (A334)

1-(4-(((5-(4-phenoxyphenyl)pyrimidin-4-yl)amino)methyl)piperidin-1-yl)prop-2-en-1-one was prepared from 5-(4-phenoxyphenyl)-N-(piperidin-4-ylmethyl)pyrimidin-4-amine using Method F (6% yield). HPLC: 99%, RT=4.533 min. MS: m/z=415 [M+H]$^+$, RT=1.67 min.

1-(4-(((6-amino-5-(4-(pyridin-2-yloxy)phenyl)pyrimidin-4-yl)amino)methyl)piperidin-1-yl)prop-2-en-1-one (A335)

1-(4-(((6-amino-5-(4-(pyridin-2-yloxy)phenyl)pyrimidin-4-yl)amino)methyl)piperidin-1-yl)prop-2-en-1-one was prepared from N4-(piperidin-4-ylmethyl)-5-(4-(pyridin-2-yloxy)phenyl)pyrimidine-4,6-diamine using Method F (28% yield). HPLC: 100%, RT: 4.401 min. MS: m/z=431 [M+H]$^+$, RT=1.32 min. $^1$H-NMR (DMSO-d$_6$) □ (s, 1H), 8.18 (d, 1H), 7.84 (t, 1H), 7.23 (s, 4H), 7.14 (t, 1H), 7.03-7.01 (m, 2H), 6.82 (broad s, 2H), 6.71 (dd, 1H), 5.99 (d, 1H), 5.57 (d, 1H), 4.30 (d, 1H), 3.95 (d, 1H), 3.17 (m, 2H), 2.91 (t, 1H), 2.51 (t, 1H), 1.76 (m, 1H), 1.54 (m, 2H), 0.90 (m, 2H).

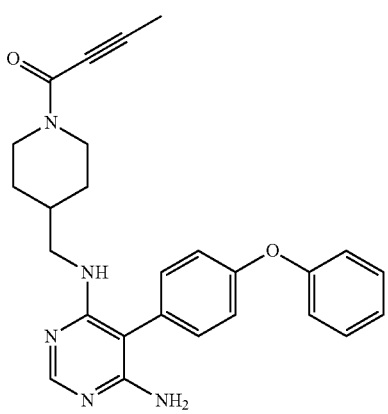 [SMILES: CC#CC(=O)N1CCC(CNc2ncnc(N)c2-c2ccc(Oc3ccccc3)cc2)CC1]

1-(4-(((6-amino-5-(4-phenoxyphenyl)pyrimidin-4-yl)amino)methyl)piperidin-1-yl)but-2-yn-1-one (A336)

1-(4-(((6-amino-5-(4-phenoxyphenyl)pyrimidin-4-yl)amino)methyl)piperidin-1-yl)but-2-yn-1-one was prepared from 5-(4-phenoxyphenyl)-N4-(piperidin-4-ylmethyl)pyrimidine-4,6-diamine using Method E (48% yield). HPLC: 99%, RT: 4.553 min. MS: m/z=442 [M+H]$^+$, RT=1.62 min. $^1$H-NMR (DMSO-d$_6$) ☐ (s, 1H), 7.38 (t, 2H), 7.20 (d, 2H), 7.13 (t, 1H), 7.10-7.05 (dd, 4H), 7.00 (m, 1H), 6.85 (broad s, 2H), 4.15 (t, 2H), 3.16 (m, 2H)m 2.97 (t, 1H), 2.53 (t, 1H), 1.93 (s, 3H), 1.75 (m, 1H), 1.60-1.51 (dd, 2H), 0.98-0.80 (m, 2H).

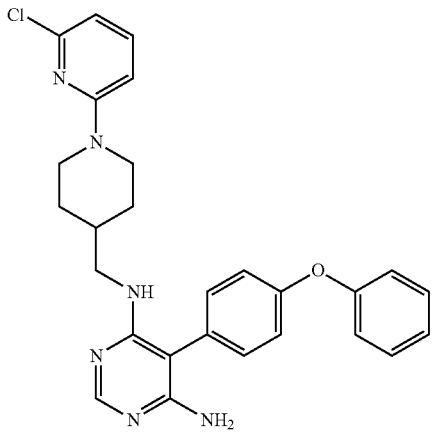 [SMILES: Nc1ncnc(NCC2CCN(c3cccc(Cl)n3)CC2)c1-c1ccc(Oc2ccccc2)cc1]

N4-((1-(6-chloropyridin-2-yl)piperidin-4-yl)methyl)-5-(4-phenoxyphenyl)pyrimidine-4,6-diamine (A337)

N4-((1-(6-chloropyridin-2-yl)piperidin-4-yl)methyl)-5-(4-phenoxyphenyl)pyrimidine-4,6-diamine was prepared from 5-(4-phenoxyphenyl)-N4-(piperidin-4-ylmethyl)pyrimidine-4,6-diamine and 2,6-dichloropyridine using Method B (25% yield). HPLC: 99%, RT: 5.214 min. MS: m/z=487 [M+H]$^+$, RT=2.11 min. $^1$H-NMR (DMSO-d$_6$) ☐ (s, 1H), 7.44-7.36 (m, 3H), 7.20 (d, 2H), 7.15-6.95 (m, 8H), 6.69 (d, 1H), 6.52 (d, 1H), 4.14 (d, 2H), 3.18 (m, 2H), 2.71 (t, 2H), 1.77 (m, 1H), 1.56 (d, 2H), 0.98 (m, 2H).

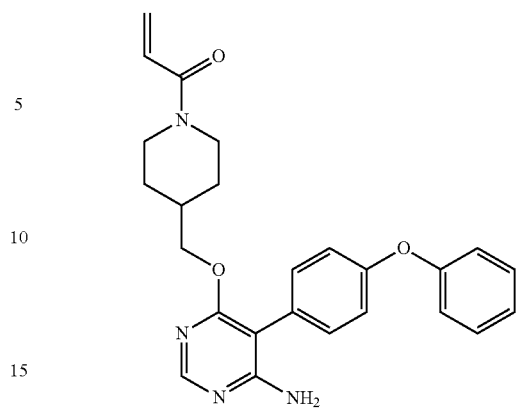

1-(4-(((6-amino-5-(4-phenoxyphenyl)pyrimidin-4-yl)oxy)methyl)piperidin-1-yl)prop-2-en-1-one (A338)

1-(4-(((6-amino-5-(4-phenoxyphenyl)pyrimidin-4-yl)oxy)methyl)piperidin-1-yl)prop-2-en-1-one was prepared from 5-(4-phenoxyphenyl)-6-(piperidin-4-ylmethoxy)pyrimidin-4-amine using Method F (10% yield). HPLC: 100%, RT: 4.366 min. MS: m/z=431 [M+H]$^+$, RT=2.04 min. $^1$H-NMR (DMSO-d$_6$) (s, 1H), 7.35 (t, 2H), 7.21 (d, 2H), 7.10 (t, 1H), 7.02-6.97 (dd, 4H), 6.69 (dd, 1H), 6.40 (broad s, 2H), 6.98 (d, 1H), 5.55 (d, 1H), 4.30 (d, 1H), 4.04 (d, 2H), 3.93 (d, 1H), 2.92 (t, 1H), 2.51 (t, 1H), 1.83 (m, 1H), 1.53 (m, 2H), 0.97 (m, 2H). min.

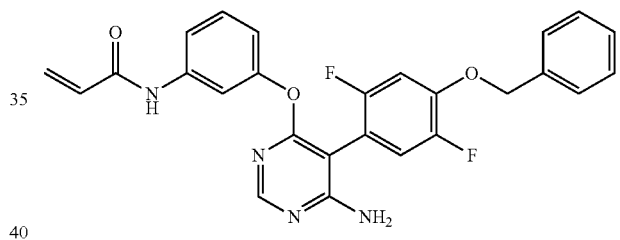

N-(3-((6-amino-5-(4-(benzyloxy)-2,5-difluorophenyl)pyrimidin-4-yl)oxy)phenyl)acrylamide (A339)

N-(3-((6-amino-5-(4-(benzyloxy)-2,5-difluorophenyl)pyrimidin-4-yl)oxy)phenyl)acrylamide was prepared from 6-(3-aminophenoxy)-5-(4-(benzyloxy)-2,5-difluorophenyl)pyrimidin-4-amine using Method F (69% yield). HPLC: 89%, RT: 5.442 min. MS: m/z=475 [M+H]$^+$, RT=2.38 min. $^1$H-NMR (DMSO-d$_6$) ☐ (s, 1H), 8.00 (s, 1H), 7.42-7.20 (m, 11H), 6.67 (m, 3H), 6.34 (dd, 1H), 6.18 (d, 1H), 5.69 (d, 1H), 5.15 (d, 2H).

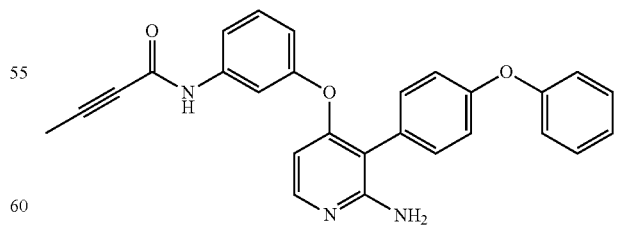

N-(3-((2-amino-3-(4-phenoxyphenyl)pyridin-4-yl)oxy)phenyl)but-2-ynamide (A340)

N-(3-((2-amino-3-(4-phenoxyphenyl)pyridin-4-yl)oxy)phenyl)but-2-ynamide was prepared from 4-(3-aminophenoxy)-3-(4-phenoxyphenyl)pyridin-2-amine using Method E (13% yield). HPLC: 98%, RT: 4.676 min. MS: m/z=436 [M+H]⁺, RT=1.95 min. ¹H-NMR (DMSO-d₆) □ (s, 1H), 7.92 (d, 1H), 7.48 (s, 1H), 7.43-7.34 (m, 6H), 7.28 (broad s, 2H), 7.17 (t, 1H), 7.09 (t, 4H), 6.86 (d, 1H), 6.30 (d, 1H), 2.03 (s, 3H).

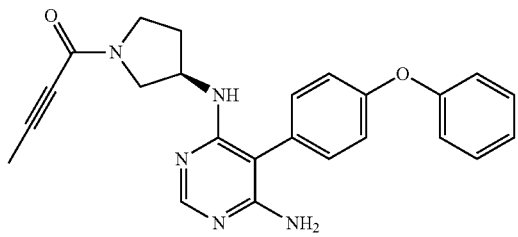 [SMILES: CC#CC(=O)N1CC[C@@H](Nc2ncnc(N)c2-c2ccc(Oc3ccccc3)cc2)C1]

(R)-1-(3-((6-amino-5-(4-phenoxyphenyl)pyrimidin-4-yl)amino)pyrrolidin-1-yl)but-2-yn-1-one (A341)

(R)-1-(3-((6-amino-5-(4-phenoxyphenyl)pyrimidin-4-yl)amino)pyrrolidin-1-yl)but-2-yn-1-one was prepared from (R)-5-(4-phenoxyphenyl)-N4-(pyrrolidin-3-yl)pyrimidine-4,6-diamine using Method E (32% yield). HPLC: 99%, RT: 4.106 min. MS: m/z=414 [M+H]⁺, RT=1.56 min.

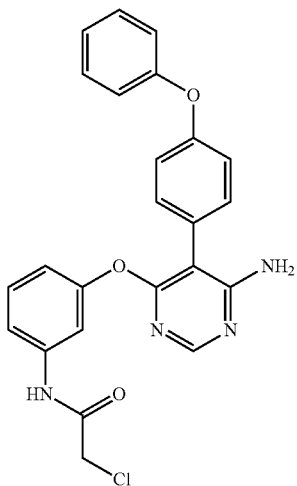 [SMILES: Nc1ncnc(Oc2cccc(NC(=O)CCl)c2)c1-c1ccc(Oc2ccccc2)cc1]

N-{3-[6-Amino-5-(4-phenoxy-phenyl)-pyrimidin-4-yloxy]-phenyl}-2-chloroacetamide (A342)

N-{3-[6-Amino-5-(4-phenoxy-phenyl)-pyrimidin-4-yloxy]-phenyl}-2-chloroacetamide Was prepared using Method E (41.5% yield). HPLC: 97%, RT: 4.26 min. MS: m/z=447 [M+H]⁺, RT=4.24 min. 1H-NMR: 400 MHz, DMSO-d₆: δ 10.45 (s, 1H), 8.05 (s, 1H), 7.40-7.36 (m, 5H), 7.36-7.26 (m, 2H), 7.17-7.12 (m, 1H), 7.09-7.05 (m, 4H), 6.79-6.76 (m, 1H), 6.50 (brs, 2H), 4.23 (s, 2H).

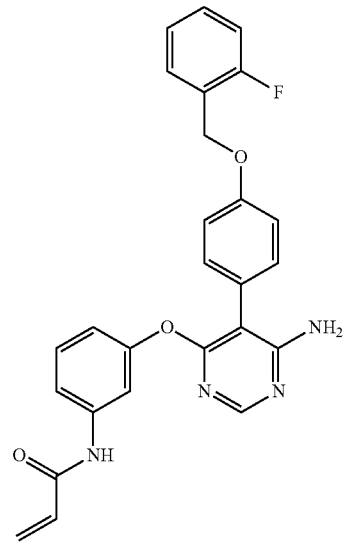 [SMILES: C=CC(=O)Nc1cccc(Oc2ncnc(N)c2-c2ccc(OCc3ccccc3F)cc2)c1]

N-(3-{6-Amino-5-[4-(2-fluoro-benzyloxy)-phenyl]-pyrimidin-4-yloxy}-phenyl)-acrylamide (A343)

N-(3-{6-Amino-5-[4-(2-fluoro-benzyloxy)-phenyl]-pyrimidin-4-yloxy}-phenyl)-acrylamide was prepared using Method E (56.5% yield) HPLC: 94%, RT: 4.22 min. MS: m/z=457 [M+H]⁺, RT=4.22 min. 1H-NMR: 400 MHz, DMSO-d₆: δ 8.19 (s, 1H), 7.71 (s, 1H), 7.52 (t, J=8.00 Hz, 1H), 7.41-7.33 (m, 6H), 7.21-7.10 (m, 6H), 6.84 (d, J=8.00 Hz, 1H), 6.44 (d, J=16.00 Hz, 1H), 6.22 (dd, J=18.00, 12.00 Hz, 1H), 5.81 (d, J=12.00 Hz, 1H), 5.19 (s, 2H).

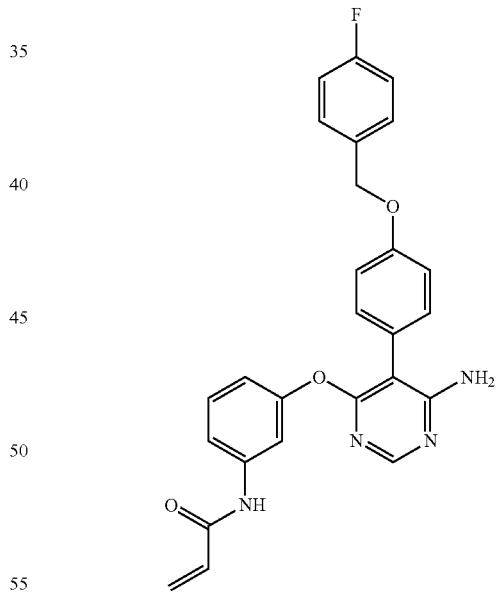

N-(3-{6-Amino-5-[4-(4-fluoro-benzyloxy)-phenyl]-pyrimidin-4-yloxy}-phenyl)-acrylamide (A344)

N-(3-{6-Amino-5-[4-(4-fluoro-benzyloxy)-phenyl]-pyrimidin-4-yloxy}-phenyl)-acrylamide was produced according to Method E (5.1% yield) HPLC: 92%, RT: 4.22 min. MS: m/z=457 [M+H]⁺, RT=4.22 min. 1H-NMR: 400 MHz, DMSO-d₆: δ 10.20 (s, 1H), 8.06 (s, 1H), 7.53-7.49 (m, 2H), 7.46-7.45 (m, 1H), 7.37-7.20 (m, 6H), 7.10 (d, J=8.00 Hz, 2H), 6.76-6.74 (m, 1H), 6.60 (brs, 2H), 6.39 (dd, J=18.00, 12.00 Hz, 1H), 6.25-6.21 (m, 1H), 5.75 (d, J=8.00 Hz, 1H), 5.15 (s, 2H).

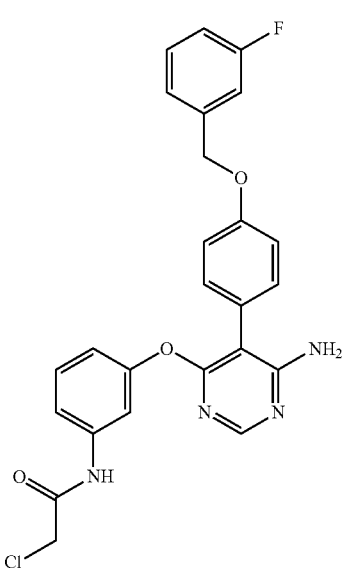 [SMILES: Nc1ncnc(Oc2cccc(NC(=O)CCl)c2)c1-c1ccc(OCc2cccc(F)c2)cc1]

N-(3-{6-Amino-5-[4-(3-fluoro-benzyloxy)-phenyl]-pyrimidin-4-yloxy}-phenyl)-2-chloro-acetamide (A345)

N-(3-{6-Amino-5-[4-(3-fluoro-benzyloxy)-phenyl]-pyrimidin-4-yloxy}-phenyl)-2-chloro-acetamide was produced according to Method E (14.3% Yield). HPLC: 98%, RT: 4.35 min. MS: m/z=479 [M+H]$^+$, RT=4.41 min. 1H-NMR: 400 MHz, DMSO-d$_6$: δ 10.35 (s, 1H), 8.02 (s, 1H), 7.47-7.42 (m, 1H), 7.35-7.26 (m, 7H), 7.18-7.16 (m, 1H), 7.10 (d, J=8.00 Hz, 2H), 6.78-6.75 (m, 1H), 6.43 (brs, 2H), 5.15 (s, 2H), 4.23 (s, 2H).

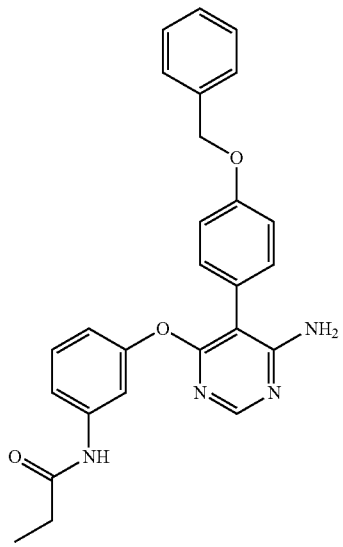 [SMILES: CCC(=O)Nc1cccc(Oc2ncnc(N)c2-c2ccc(OCc3ccccc3)cc2)c1]

N-{3-[6-Amino-5-(4-benzyloxy-phenyl)-pyrimidin-4-yloxy]-phenyl}-propionamide (A346)

N-{3-[6-Amino-5-(4-benzyloxy-phenyl)-pyrimidin-4-yloxy]-phenyl}-propionamide was produced according to Method E (6.8% Yield). HPLC: 91%, RT: 4.18 min. MS: m/z=441 [M+H]$^+$, RT=4.23 min. 1H-NMR: 400 MHz, DMSO-d$_6$: δ 9.90 (s, 1H), 8.01 (s, 1H), 7.46 (d, J=8.00 Hz, 2H), 7.41-7.27 (m, 7H), 7.22 (t, J=8.00 Hz, 1H), 7.10 (d, J=8.00 Hz, 2H), 6.70-6.67 (m, 1H), 6.45 (brs, 2H), 5.11 (s, 2H), 2.28 (q, J=8.00 Hz, 2H), 1.05 (t, J=4.00 Hz, 3H).

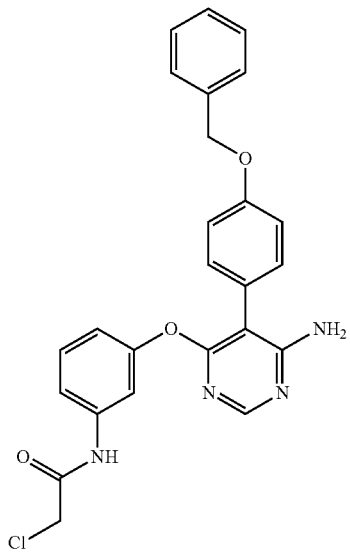 [SMILES: Nc1ncnc(Oc2cccc(NC(=O)CCl)c2)c1-c1ccc(OCc2ccccc2)cc1]

N-{3-[6-Amino-5-(4-benzyloxy-phenyl)-pyrimidin-4-yloxy]-phenyl}-2-chloro-acetamide (A347)

N-{3-[6-Amino-5-(4-benzyloxy-phenyl)-pyrimidin-4-yloxy]-phenyl}-2-chloro-acetamide was produced according to Method E (27.6% yield) HPLC: 95%, RT: 4.31 min. MS: m/z=461 [M+H]$^+$, RT=4.29 min. 1H-NMR: 400 MHz, DMSO-d$_6$: δ 10.35 (s, 1H), 8.02 (s, 1H), 7.46 (d, J=8.00 Hz, 2H), 7.39 (t, J=4.00 Hz, 2H), 7.35-7.26 (m, 6H), 7.10 (d, J=8.00 Hz, 2H), 6.78-6.75 (m, 1H), 6.48 (brs, 2H), 5.11 (s, 2H), 4.22 (s, 2H).

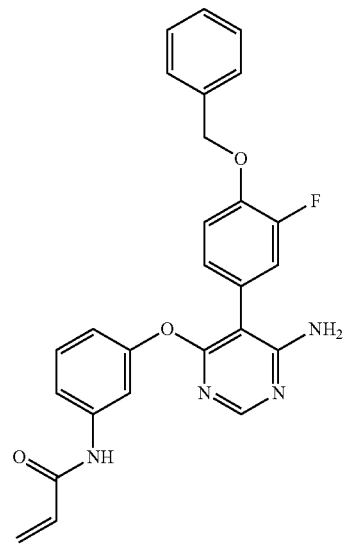 [SMILES: C=CC(=O)Nc1cccc(Oc2ncnc(N)c2-c2ccc(OCc3ccccc3)c(F)c2)c1]

N-{3-[6-Amino-5-(4-benzyloxy-3-fluoro-phenyl)-pyrimidin-4-yloxy]-phenyl}-acrylamide (A348)

N-{3-[6-Amino-5-(4-benzyloxy-3-fluoro-phenyl)-pyrimidin-4-yloxy]-phenyl}-acrylamide was produced according to Method E (23.2% Yield) HPLC: 98%, RT: 4.30 min. MS: m/z=457 [M+H]+, RT=4.35 min. 1H-NMR: 400 MHz, DMSO-$d_6$: δ 10.20 (s, 1H), 8.03 (s, 1H), 7.48-7.45 (m, 3H), 7.41 (t, J=8.00 Hz, 2H), 7.38-7.25 (m, 5H), 7.15 (d, J=8.00 Hz, 1H), 6.77-6.75 (m, 1H), 6.56 (brs, 2H), 6.40 (dd, J=16.00, 12.00 Hz, 1H), 6.26-6.21 (m, 1H), 5.75 (d, J=8.00 Hz, 1H), 5.19 (s, 2H).

N-{3-(6-Amino-5-(4-benzyloxy-2-fluoro-phenyl)-pyrimidin-4-yloxy}-phenyl)-2-chloro-acetamide was produced according to Method E. HPLC: 95%, RT: 4.52 min. MS: m/z=479 [M+H]+, RT=4.41 min. 1H-NMR: 400 MHz, DMSO-$d_6$: δ 10.37 (s, 1H), 8.06 (s, 1H), 7.48-7.27 (m, 9H), 7.03 (d, J=12.00 Hz, 1H), 6.95 (d, J=8.00 Hz, 1H), 6.75 (d, J=4.00 Hz, 1H), 6.59 (brs, 2H), 5.14 (s, 2H), 4.23 (s, 2H).

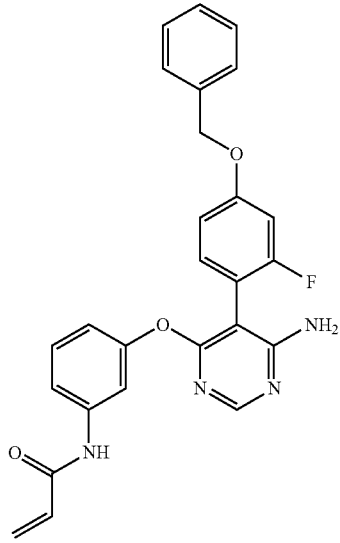 [SMILES: C=CC(=O)Nc1cccc(Oc2ncnc(N)c2-c2ccc(OCc3ccccc3)cc2F)c1]

N-{3-[6-Amino-5-(4-benzyloxy-2-fluoro-phenyl)-pyrimidin-4-yloxy]-phenyl}-acrylamide (A349)

N-{3-[6-Amino-5-(4-benzyloxy-2-fluoro-phenyl)-pyrimidin-4-yloxy]-phenyl}-acrylamide was produced according to Method E (11.8% yield). HPLC: 97%, RT: 4.35 min. MS: m/z=457 [M+H]+, RT=4.39 min. 1H-NMR: 400 MHz, DMSO-$d_6$: δ 10.20 (s, 1H), 8.05 (s, 1H), 7.47-7.25 (m, 9H), 7.02 (d, J=12.00 Hz, 1H), 6.95 (d, J=8.00 Hz, 1H), 6.73-6.70 (m, 1H), 6.60 (brs, 2H), 6.38-6.36 (m, 1H), 6.26-6.21 (m, 1H), 5.75 (d, J=8.00 Hz, 1H), 5.13 (s, 2H).

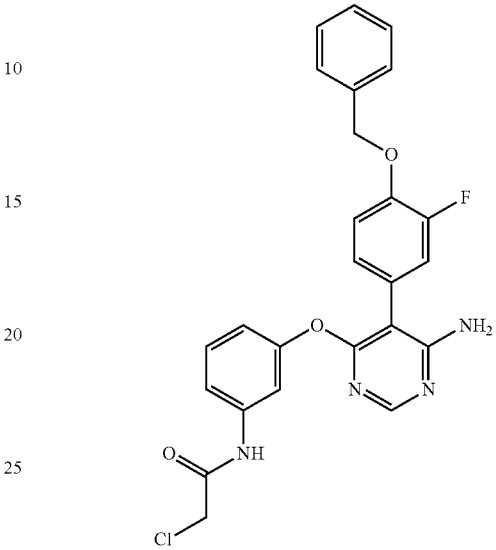

N-{3-[6-Amino-5-(4-benzyloxy-3-fluoro-phenyl)-pyrimidin-4-yloxy]-phenyl}-2-chloro-acetamide (A351)

N-{3-[6-Amino-5-(4-benzyloxy-3-fluoro-phenyl)-pyrimidin-4-yloxy]-phenyl}-2-chloro-acetamide was produced according to Method (27.6% yield). HPLC: 98%, RT: 4.39 min. MS: m/z=479 [M+H]+, RT=4.37 min. 1H-NMR: 400 MHz, DMSO-$d_6$: δ 10.35 (s, 1H), 8.02 (s, 1H), 7.48-7.47 (m, 2H), 7.41 (t, J=8.00 Hz, 2H), 7.36-7.25 (m, 6H), 7.15 (d, J=8.00 Hz, 1H), 6.80-6.77 (m, 1H), 6.51 (brs, 2H), 5.19 (s, 2H), 4.23 (s, 2H).

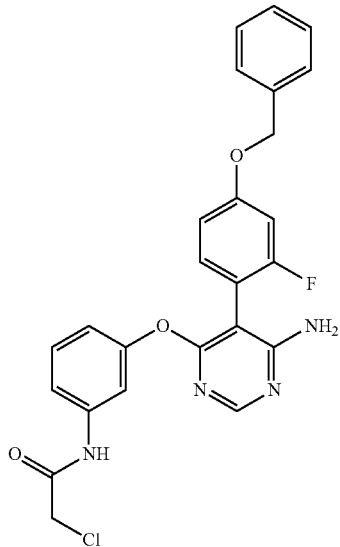 [SMILES: Nc1ncnc(Oc2cccc(NC(=O)CCl)c2)c1-c1ccc(OCc2ccccc2)cc1F]

N-{3-(6-Amino-5-(4-benzyloxy-2-fluoro-phenyl)-pyrimidin-4-yloxy}-phenyl)-2-chloro-acetamide (A350)

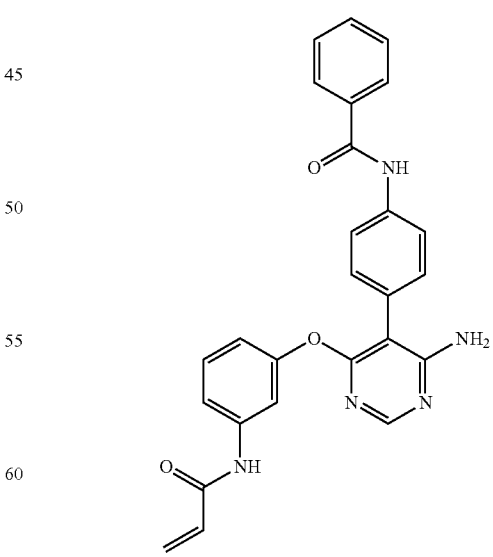

N-{4-[4-(3-Acryloylamino-phenoxy)-6-amino-pyrimidin-5-yl]-phenyl}-benzamide (A352)

N-{4-[4-(3-Acryloylamino-phenoxy)-6-amino-pyrimidin-5-yl]-phenyl}-benzamide was produced according to Method E (8.8% yield). HPLC: 92%, RT: 3.48 min. MS: m/z=452 [M+H]$^+$, RT=3.53 min. 1H-NMR: 400 MHz, DMSO-d$_6$: δ 10.36 (s, 1H), 10.20 (s, 1H), 8.04 (s, 1H), 7.95 (d, J=8.00 Hz, 2H), 7.89 (d, J=8.00 Hz, 2H), 7.60-7.52 (m, 3H), 7.46 (s, 1H), 7.39-7.37 (m, 3H), 7.28 (t, J=8.00 Hz, 1H), 6.77 (d, J=8.00 Hz, 1H), 6.50 (brs, 2H), 6.40 (dd, J=16.00, 12.00 Hz, 1H), 6.24 (d, J=16.00 Hz, 1H), 6.75 (d, J=8.00 Hz, 1H).

Biological Activity

Description of In Vitro Assays

BTK IC50 Enzyme Assay

The following describes a microfluidic, off-chip mobility shift kinase assay used to measure inherent potency of compounds against BTK enzyme. Compounds described by embodiments of the present invention were assayed using this protocol and the data from the same is recorded in Table 2 within the column labeled: "Time Dependent BTK Enzyme Assay IC$_{60}$". These IC$_{60}$ values are reported in ranges wherein: A<100 nM, B<1 uM, and C>1 uM.

2.5× stocks of full-length human BTK (08-080) from CarnaBio USA, Inc., Natick, Mass., 1.6×ATP and appropriate kinKDR peptide substrate (FITC-AHA-EEPLYWSF-PAKKK-NH$_2$) were prepared in kinase reaction buffer consisting of 25 mM MgCl2, 0.015% Brij-35 (30%), 100 mM Hepes, pH 7.5, and 10 mM DTT.

5 uL of enzyme buffer and 7.5 uL of ATP/kinKDR peptide substrate mix were added to Matrix (#115304) 384-well, sterile, polypropylene plates (Thermo Fisher Scientific, Hudson, N.H.) with 125 nL of serially diluted compounds prepared in 100% DMSO, and incubated for 90 min. at 27 C. Following the incubation period, reactions were stopped by adding 60 uL stop buffer consisting of 100 mM Hepes, pH 7.5, 0.015% Brij-35 (30%), 0.277% Coating Reagent #3 (Caliper Life Sciences, Mountain View, Calif.), 5% DMSO. Stopped reactions were monitored at −2 PSI, −3000 V/−700 V in a LabChip 3000 plate reader from Caliper Life Sciences, a PerkinElmer Company (Hopkinton, Mass.), and the activity was measured by off-chip mobility shift assay measuring the charge/mass difference between substrate and product resulting from peptide phosphorilation. IC50 and efficacy were determined by plotting log [Inhibitor] vs. % Activity in GeneData Screener (Basel, Switzerland). Compounds described by embodiments of the present invention were assayed using this protocol and the data from the same is recorded in Table 2 within the column labeled: "Time Dependent PBMC BTK Enzyme Assay IC50." These IC$_{50}$ values are reported in ranges wherein: A<100 nM, B<1 uM, and C>1 uM. I<1 uM and II>1 uM.

Time Dependent Human Whole Blood IC50 Assay

Compounds described by embodiments of the present invention were assayed using a human whole blood assay. The data from the same is recorded in Table 2 within the column labeled: "Time Dependent Human Whole Blood BTK Enzyme Assay IC$_{50}$". These IC$_{50}$ values are reported in ranges wherein: I<1 uM and II>1 uM.

Time Dependent PMBC IC50 Assay

Compounds described by embodiments of the present invention were assayed using a time dependent PMBC assay. The data from the same is recorded in Table 2 within the column labeled: "Time Dependent PBMC Assay IC50." These IC$_{50}$ values are reported in ranges wherein: I<1 uM and II>1 uM.

Table 2 presents IC$_{50}$ values, derived from the in vitro assays detailed above, for selected compounds described by embodiments of the present invention.

TABLE 2

| Compound No. | Time Dependent BTK Enzyme Assay IC$_{50}$ | Time Dependent Human Whole Blood BTK Enzyme Assay IC$_{50}$ | Time Dependent PBMC Assay IC$_{50}$ |
| --- | --- | --- | --- |
| "A1" | A | I | I |
| "A2" | — | — | — |
| "A3" | A | I | I |
| "A4" | A | I | I |
| "A5" | — | — | — |
| "A6" | A | — | I |
| "A7" | C | — | — |
| "A8" | — | — | — |
| "A9" | A | — | — |
| "A10" | A | — | I |
| "A11" | C | — | — |
| "A12" | — | — | — |
| "A13" | C | — | — |
| "A14" | — | — | — |
| "A15" | — | — | — |
| "A16" | C | — | — |
| "A17" | A | — | — |
| "A18" | B | — | — |
| "A19" | A | — | — |
| "A20" | C | — | — |
| "A21" | A | — | — |
| "A22" | — | — | — |
| "A23" | — | — | — |
| "A24" | C | — | — |
| "A25" | C | — | — |
| "A26" | A | — | I |
| "A27" | C | — | — |
| "A28" | A | — | — |
| "A29" | — | — | — |
| "A30" | — | — | — |
| "A31" | — | — | — |
| "A32" | — | — | — |
| "A33" | C | — | — |
| "A34" | A | — | I |
| "A35" | C | — | — |
| "A36" | C | — | — |
| "A37" | A | I | I |
| "A38" | A | — | I |
| "A39" | B | — | — |
| "A40" | B | — | — |
| "A41" | A | — | — |
| "A42" | B | — | — |
| "A43" | B | — | — |
| "A44" | C | — | — |
| "A45" | A | — | I |
| "A46" | A | — | — |
| "A47" | B | — | — |
| "A48" | A | II | I |
| "A49" | B | II | I |
| "A50" | B | — | — |
| "A51" | A | — | I |
| "A52" | A | — | I |
| "A53" | B | — | — |
| "A54" | — | — | — |
| "A55" | — | — | — |
| "A56" | C | — | — |
| "A57" | — | — | — |
| "A58" | A | — | — |
| "A59" | B | — | — |
| "A60" | A | — | — |
| "A61" | A | — | — |
| "A62" | B | — | — |
| "A63" | B | — | — |
| "A64" | A | — | I |
| "A65" | A | — | — |
| "A66" | A | — | — |
| "A67" | A | — | I |
| "A68" | A | — | — |
| "A69" | B | — | — |
| "A70" | A | — | I |
| "A71" | B | — | — |
| "A72" | A | — | — |
| "A73" | B | — | — |

TABLE 2-continued

| Compound No. | Time Dependent BTK Enzyme Assay IC$_{50}$ | Time Dependent Human Whole Blood BTK Enzyme Assay IC$_{50}$ | Time Dependent PBMC Assay IC$_{50}$ |
|---|---|---|---|
| "A74" | B | — | — |
| "A75" | A | — | I |
| "A76" | B | — | — |
| "A77" | C | — | — |
| "A78" | C | — | — |
| "A79" | B | — | — |
| "A80" | B | — | — |
| "A81" | C | — | — |
| "A82" | C | — | — |
| "A83" | B | — | — |
| "A84" | C | — | — |
| "A85" | C | — | — |
| "A86" | B | — | — |
| "A87" | B | — | — |
| "A88" | A | — | — |
| "A89" | — | — | — |
| "A90" | — | — | — |
| "A91" | — | — | — |
| "A92" | B | — | — |
| "A93" | B | — | — |
| "A94" | C | — | — |
| "A95" | A | — | — |
| "A96" | B | — | — |
| "A97" | B | — | — |
| "A98" | A | — | — |
| "A99" | B | — | — |
| "A100" | — | — | — |
| "A101" | — | — | — |
| "A102" | C | — | — |
| "A103" | B | — | — |
| "A104" | A | — | — |
| "A105" | A | — | I |
| "A106" | A | — | II |
| "A107" | B | — | — |
| "A108" | A | — | — |
| "A109" | A | — | — |
| "A110" | A | — | — |
| "A111" | A | — | — |
| "A112" | A | — | — |
| "A113" | A | — | I |
| "A114" | A | — | II |
| "A115" | A | — | II |
| "A116" | C | — | — |
| "A117" | A | — | I |
| "A118" | A | — | I |
| "A119" | A | — | — |
| "A120" | A | I | I |
| "A121" | A | — | I |
| "A122" | C | — | — |
| "A123" | C | — | — |
| "A124" | A | — | I |
| "A125" | C | — | — |
| "A126" | A | — | I |
| "A127" | A | — | I |
| "A128" | — | — | — |
| "A129" | — | — | — |
| "A130" | — | — | — |
| "A131" | — | — | — |
| "A132" | — | — | — |
| "A133" | — | — | — |
| "A134" | — | — | — |
| "A135" | — | — | — |
| "A136" | — | — | — |
| "A137" | — | — | — |
| "A138" | — | — | — |
| "A139" | — | — | — |
| "A140" | — | — | — |
| "A141" | B | — | — |
| "A142" | A | — | — |
| "A143" | A | — | — |
| "A144" | A | — | — |
| "A145" | A | — | — |
| "A146" | A | — | — |
| "A147" | A | — | — |
| "A148" | B | — | — |
| "A149" | B | — | — |
| "A150" | B | — | — |
| "A151" | A | — | II |
| "A152" | B | — | — |
| "A153" | B | — | — |
| "A154" | C | — | — |
| "A155" | C | — | — |
| "A156" | B | — | — |
| "A157" | C | — | — |
| "A158" | A | — | — |
| "A159" | C | — | — |
| "A160" | B | — | — |
| "A161" | A | — | — |
| "A162" | A | — | — |
| "A163" | C | — | — |
| "A164" | C | — | — |
| "A165" | A | — | — |
| "A166" | B | — | — |
| "A167" | A | — | — |
| "A168" | C | — | II |
| "A169" | A | — | — |
| "A170" | A | — | — |
| "A171" | — | I | I |
| "A172" | A | I | I |
| "A173" | A | — | — |
| "A174" | C | — | — |
| "A175" | B | — | — |
| "A176" | C | — | — |
| "A177" | A | — | — |
| "A178" | A | — | — |
| "A179" | B | — | — |
| "A180" | B | — | — |
| "A181" | A | — | — |
| "A182" | A | — | — |
| "A183" | A | — | — |
| "A184" | A | — | — |
| "A185" | A | — | — |
| "A186" | A | — | — |
| "A187" | A | — | — |
| "A188" | B | — | — |
| "A189" | A | — | — |
| "A190" | A | — | — |
| "A191" | A | — | — |
| "A192" | B | — | — |
| "A193" | C | — | — |
| "A194" | A | — | — |
| "A195" | A | — | — |
| "A196" | B | — | — |
| "A197" | B | — | — |
| "A198" | A | — | — |
| "A199" | B | — | — |
| "A200" | B | — | — |
| "A201" | B | — | — |
| "A202" | A | — | — |
| "A203" | A | — | — |
| "A204" | A | — | — |
| "A205" | A | — | — |
| "A206" | A | — | — |
| "A207" | B | — | — |
| "A208" | C | — | — |
| "A209" | B | — | — |
| "A210" | B | — | — |
| "A211" | B | — | — |
| "A212" | A | — | — |
| "A213" | — | — | — |
| "A214" | — | — | — |
| "A215" | A | — | — |
| "A216" | A | — | — |
| "A217" | B | — | — |
| "A218" | B | — | — |
| "A219" | C | — | — |

TABLE 2-continued

| Compound No. | Time Dependent BTK Enzyme Assay IC$_{50}$ | Time Dependent Human Whole Blood BTK Enzyme Assay IC$_{50}$ | Time Dependent PBMC Assay IC$_{50}$ |
|---|---|---|---|
| "A220" | B | — | — |
| "A221" | C | — | — |
| "A222" | A | — | — |
| "A223" | B | — | — |
| "A224" | A | — | — |
| "A225" | A | — | — |
| "A226" | B | — | — |
| "A227" | A | — | — |
| "A228" | B | — | — |
| "A229" | — | — | — |
| "A230" | — | — | — |
| "A231" | — | — | — |
| "A232" | — | — | — |
| "A233" | — | — | — |
| "A234" | — | — | — |
| "A235" | C | — | — |
| "A236" | — | — | — |
| "A237" | — | — | — |
| "A238" | — | — | — |
| "A239" | — | — | — |
| "A240" | A | — | — |
| "A241" | A | — | — |
| "A242" | A | — | I |
| "A243" | A | — | — |
| "A244" | A | — | — |
| "A245" | A | — | I |
| "A246" | A | I | I |
| "A247" | A | — | I |
| "A248" | A | — | — |
| "A249" | A | — | — |
| "A250" | A | I | I |
| "A251" | A | I | I |
| "A252" | A | — | I |
| "A253" | A | — | I |
| "A254" | A | — | — |
| "A255" | A | — | I |
| "A256" | A | — | — |
| "A257" | A | — | — |
| "A258" | A | — | II |
| "A259" | A | — | — |
| "A260" | A | — | — |
| "A261" | A | — | — |
| "A262" | A | — | I |
| "A263" | B | — | — |
| "A264" | A | — | — |
| "A265" | A | — | — |
| "A266" | A | — | I |
| "A267" | A | — | — |
| "A268" | A | — | — |
| "A269" | A | — | — |
| "A270" | A | — | — |
| "A271" | A | — | — |
| "A272" | A | — | — |
| "A273" | A | — | — |
| "A274" | A | — | — |
| "A275" | A | — | — |
| "A276" | A | — | — |
| "A277" | A | — | — |
| "A278" | A | — | — |
| "A279" | A | — | — |
| "A280" | A | — | — |
| "A281" | B | — | — |
| "A282" | A | — | — |
| "A283" | B | — | — |
| "A284" | B | — | — |
| "A285" | B | — | — |
| "A286" | B | — | — |
| "A287" | B | — | — |
| "A288" | B | — | — |
| "A289" | B | — | — |
| "A290" | B | — | — |
| "A291" | B | — | — |
| "A292" | B | — | — |
| "A293" | — | — | — |
| "A294" | B | — | — |
| "A295" | — | — | — |
| "A296" | B | — | — |
| "A297" | C | — | — |
| "A298" | C | — | — |
| "A299" | C | — | — |
| "A300" | B | — | — |
| "A301" | C | — | — |
| "A302" | C | — | — |
| "A303" | C | — | — |
| "A304" | C | — | — |
| "A305" | C | — | — |
| "A306" | A | — | I |
| "A307" | C | — | — |
| "A308" | C | — | — |
| "A309" | C | — | — |
| "A310" | C | — | — |
| "A311" | C | — | — |
| "A312" | C | — | — |
| "A313" | C | — | — |
| "A314" | C | — | — |
| "A315" | C | — | — |
| "A316" | C | — | — |
| "A317" | C | — | — |
| "A318" | C | — | — |
| "A319" | C | — | — |
| "A320" | — | — | — |
| "A321" | — | — | — |
| "A322" | C | — | — |
| "A323" | — | — | — |
| "A324" | C | — | — |
| "A325" | C | — | — |
| "A326" | C | — | — |
| "A327" | C | — | — |
| "A328" | C | — | — |
| "A329" | C | — | — |
| "A330" | C | — | — |
| "A331" | — | — | — |
| "A332" | — | — | — |
| "A333" | B | — | — |
| "A334" | A | — | — |
| "A335" | B | — | — |
| "A336" | A | — | I |
| "A337" | C | — | — |
| "A338" | B | — | — |
| "A339" | A | — | — |
| "A340" | A | — | — |
| "A341" | A | — | I |
| "A342" | A | — | — |
| "A343" | — | — | — |
| "A344" | A | — | — |
| "A345" | A | — | — |
| "A346" | A | — | — |
| "A347" | A | — | — |
| "A348" | A | — | — |
| "A349" | A | — | — |
| "A350" | A | — | — |
| "A351" | A | — | — |
| "A352" | A | — | — |

Description of In Vivo Data

Systemic Lupus Erythematosus Mouse Model (SLE)

Figure 2:
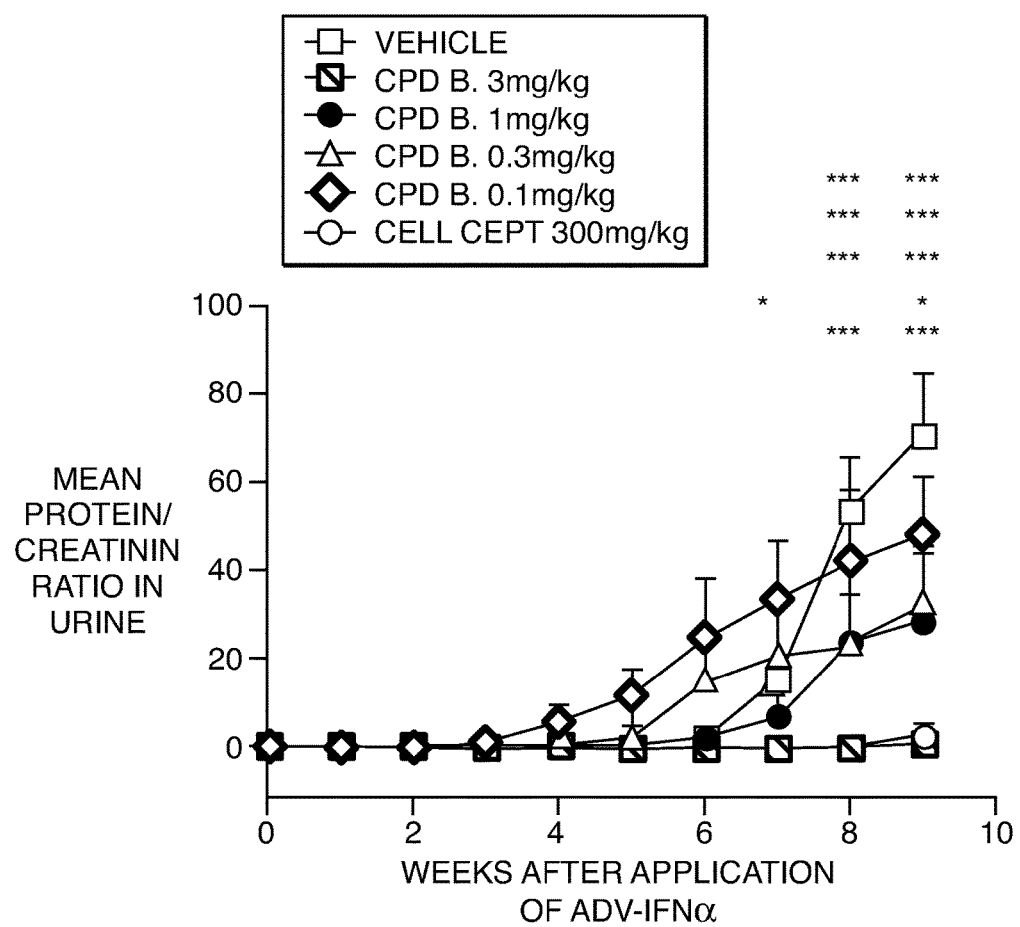
FIG. 2 presents additional data evaluating a compound described by the present invention [1-(4-(((6-amino-5-(4-phenoxyphenyl)pyrimidin-4-yl)amino)methyl)piperidin-1-yl)prop-2-en-1-one, designated as "CPD. B" in the figure] in an interferon-alpha accelerated systemic lupus erythematosus (SLE) mouse model.

1-(4-(((6-amino-5-(4-phenoxyphenyl)pyrimidin-4-yl)amino)methyl)piperidin-1-yl)prop-2-en-1-one, designated as "CPD.B", was evaluated in an interferon-alpha accelerated SLE mouse model. NZB/W F1 mice received i.v. injection at day 0 and day 1 of 10$^8$ infectious units of adenovirus (ADV-IFN-α) to deliver a transient overexpression on interferon alpha. Oral dosing of the different group treatments was initiated on day 14 and continued daily at 24 hour intervals until the end of the study. Treatment groups consisted of 20% Kleptose HPB in Na-citrate buffer (vehicle) or 0.1, 0.3, 1, or 3 mg/kg of Cpd. B. Panel 1A shows the disease activity of each individual animal, calculated by the following Formula: Disease activity=(0.5*(days with proteinuria of individual animal/mean of days with proteinuria of vehicle group)+0.5*(AUC of individual animal/mean AUC of vehicle group))*100. As shown in Panel 1B Cpd. B reduces the disease activity in a dose-dependent manner with the percent reduction of the disease activity for each experimental condition documented. FIG. 2 presents data from another interferon-alpha accelerated SLE experiment in mice. NZB/W F1 mice received i.v. injections at day 0 and day 1 of $10^8$ infectious units of adenovirus (ADV-IFN-α) to deliver a transient overexpression on interferon alpha. Oral dosing of the different group treatments (n=10) was initiated on day 14 and continued daily at 24 hour intervals until the end of the study. Treatment groups consisted of 20% Kleptose HPB in Na-citrate buffer (vehicle), 0.1, 0.3, 1, or 3 mg/kg of Cpd. B or Cell Cept®. FIG. 2 shows the mean protein creatinine ratio +−SEM in the urine, at indicated time points, as a marker of kidney damage. Statiscal analysis was performed using Two way ANOVA with Bonferroni post test with all groups compared to vehicle treated group (*=p<0.05, =p<0.01, *=p<0.001).

Figure 3:
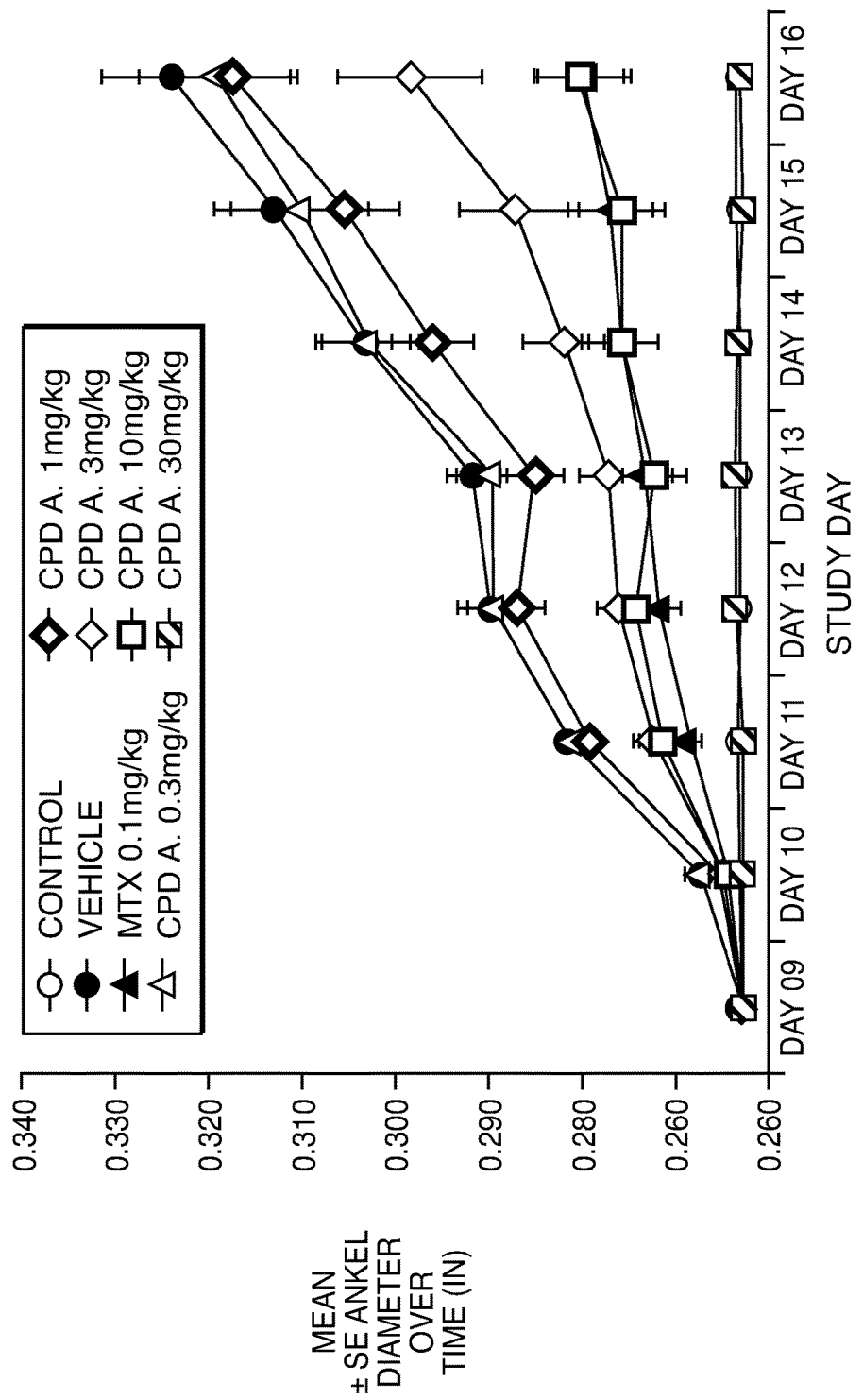
FIG. 3 presents data evaluating a compound described by the present invention [1-(4-(((6-amino-5-(4-phenoxyphenyl)pyrimidin-4-yl)amino)methyl)piperidin-1-yl)prop-2-en-1-one, designated as "CPD. A" in the figure] in a rat collagen-induced arthritis model.

Rat Collagen-Induced Arthritis Model 1-(4-(((6-amino-5-(4-phenoxyphenyl)pyrimidin-4-yl) amino)methyl)piperidin-1-yl)prop-2-en-1-one, designated as "CPD. A", was evaluated in a collagen-induced arthritis model in rats. Anesthetized female Lewis rats received subcutaneous/intradermal injections of 300 μl of Freund's Incomplete Adjuvant containing 4 mg/ml bovine type II collagen, at the base of the tail and 2 sites on the back on days 0 and 6. FIG. 3 presents data from the oral dosing of the different group treatments was initiated on day 6 and continued daily at 24 hour intervals, for 11 days up to day 16. Treatment groups consisted of 20% Hydroxy-Propyl-Beta Cyclodextrin in $H_2O$ (vehicle) or 0.3, 1, 3, or 10 mg/kg of Cpd. A, or methotrexate (MTX) at 0.1 mg/kg. Caliper measurements of ankles were taken every day beginning on day 9 (or day 0 of arthritis). Animals were sacrificed on day 17.

Figure 4:
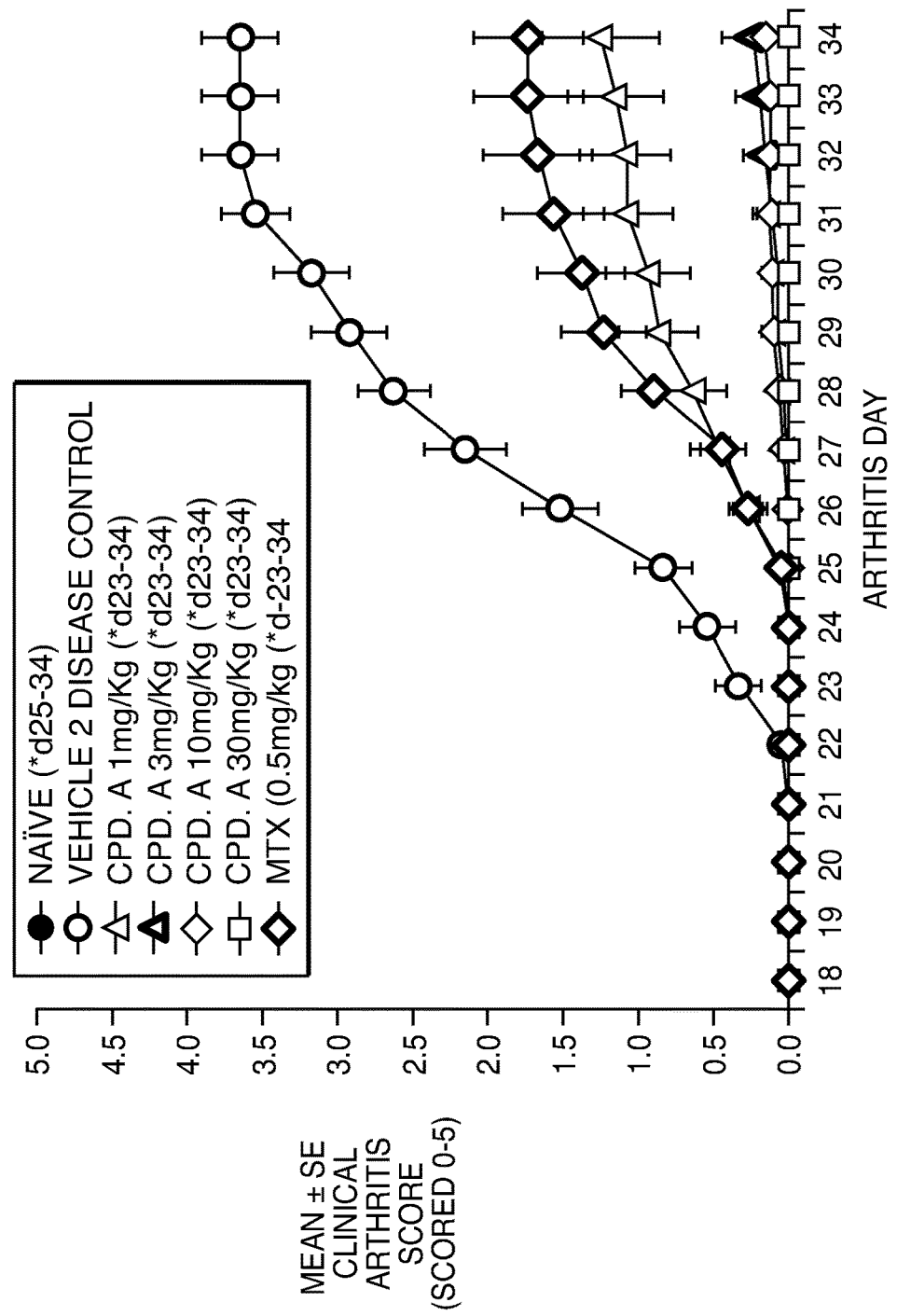
FIG. 4 presents data evaluating a compound described by the present invention [1-(4-(((6-amino-5-(4-phenoxyphenyl)pyrimidin-4-yl)amino)methyl)piperidin-1-yl)prop-2-en-1-one, designated as "CPD. A" in the figure] in an interferon-alpha accelerated systemic lupus erythematosus (SLE) mouse model.

Mouse Collagen-Induced Arthritis Model 1-(4-(((6-amino-5-(4-phenoxyphenyl)pyrimidin-4-yl) amino)methyl)piperidin-1-yl)prop-2-en-1-one, designated as "CPD. A", was evaluated in a collagen-induced arthritis model in mice. Male DBA/1OIaHsd mice were injected intradermally at the base of the tail with 150 μl of Freund's Complete Adjuvant containing bovine type II collagen on day 0 and on day 21. FIG. 4 presents data from this experiment. On day 18, mice were randomized by body weight into treatment groups. Oral treatment was initiated after enrollment on day 18 and continued daily at 24 h intervals up to day 33. Mice were treated with 20% Hydroxy-Propyl-Beta Cyclodextrin in $H_2O$ (vehicle) or Cpd. A at either 1, 3, 10, or 30 mg/kg or with methotrexate (MTX) at 0.5 mg/kg. On study days 22-34 onset of arthritis occurred. Mice were sacrified on day 34. Clinical scores were given for each of the paws (right front, left front, right rear, left rear) on arthritis days 18-34.

Mouse Passive Cutaneous Anaphylaxis (PCA)

Figure 5:
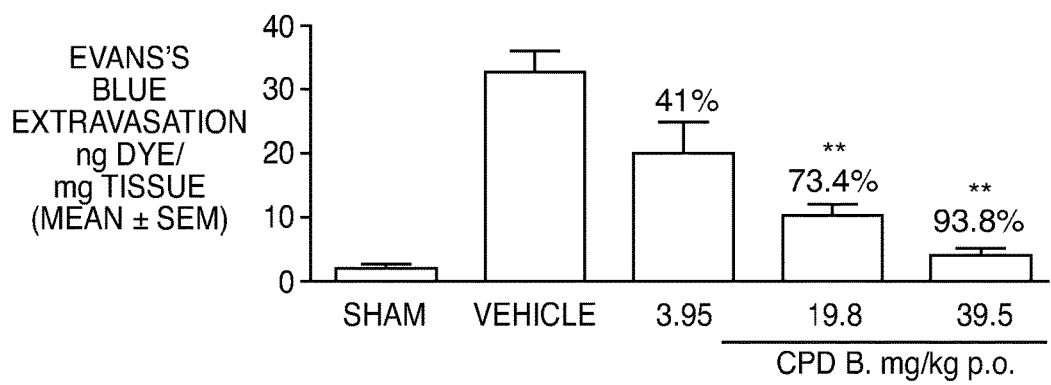
FIG. 5 presents data evaluating a compound described by the present invention [1-(4-(((6-amino-5-(4-phenoxyphenyl)pyrimidin-4-yl)amino)methyl)piperidin-1-yl)prop-2-en-1-one, designated as "CPD. B" in the figure] in a mouse model of passive cutaneous anaphylaxis (PCA).

1-(4-(((6-amino-5-(4-phenoxyphenyl)pyrimidin-4-yl) amino)methyl)piperidin-1-yl)prop-2-en-1-one, designated as "CPD.B", was evaluated in a PCA model in mice. In vivo anaphylaxis mediated through the FcεRI receptor is a mast-cell-dependent allergic response to local or systemic exposure to allergens, which cross-link and activate antigen-specific IgE bound to the FcεRI on the mast cell surface leading to mast cell activation and degranulation. The murine PCA model mimicks these events in vivo and can be used for testing the efficacy of newly developed compounds targeting tyrosine kinases that are downstream of FcεRI like BTK. FIG. 5 presents data from experiments where 10-week old female BALB/c mice were injected intradermally with immunoglobulin E (IgE) directed against the hapten 2,4-dinitrophenyl (DNP). 24 h after sensitization, mice were challenged by systemic administration of DNP coupled to human serum albumin (HSA), together with Evan's blue dye. Mice were dosed orally with three doses of Cpd B. 1 h before challenge. Evan's blue extravasation was measured in the back 30 minutes after the challenge.

Figure 6:
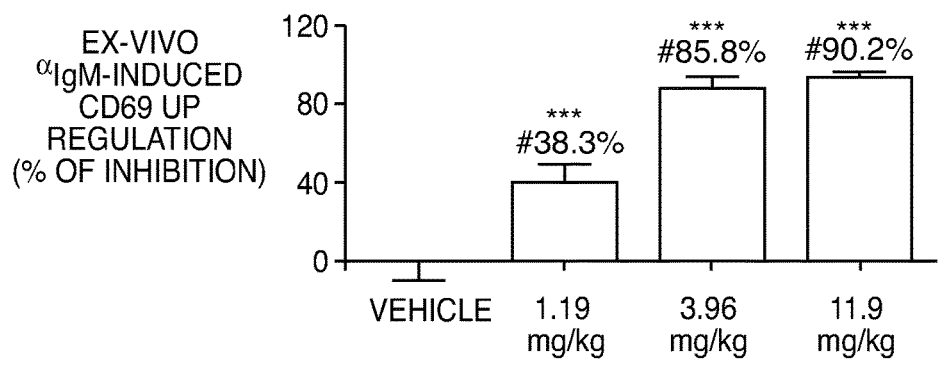
FIG. 6 presents data evaluating a compound described by the present invention [1-(4-(((6-amino-5-(4-phenoxyphenyl)pyrimidin-4-yl)amino)methyl)piperidin-1-yl)prop-2-en-1-one] with regard to the ex vivo anti-IgD-induced CD69 upregulation in mouse whole blood.

Anti-IgD-Induced CD69 Upregulation in Mouse Whole Blood 1-(4-(((6-amino-5-(4-phenoxyphenyl)pyrimidin-4-yl) amino)methyl)piperidin-1-yl)prop-2-en-1-one, designated as "CPD. B", was evaluated anti-IgD-induced CD69 upregulation in mouse whole blood and these data are presented in FIG. 6. BCR activation induces the expression of the surface cluster of differentiation 69 (CD69) which is the earliest inducible cell surface glycoprotein acquired during lymphoid activation and is currently used as a marker for B cell activation both in vitro and ex viva Female C57Bl/6 mice were administered orally with Cyclodextrin or 1.19, 3.96 or 11.9 mg/kg of Cpd. A 1 h before blood collection. Half an hour after intraperitoneal injection of heparin, blood was collected in heparinized tubes and B cells were stimulated with 10 μl of PBS or polyclonal goat anti-mouse IgD antiserum for 4 h. CD69 upregulation in individual cells was determined by flow cytometric analysis using rat anti-mouse B220-PerCP-Cy5.5 and hamster anti-mouse CD69-PE monoclonal antibodies for immunostaining.

What is claimed is:

1. A method of treating rheumatoid arthritis, systemic lupus erythematosus, inflammatory bowel disease, Sjögren's Syndrome, atherosclerosis, psoriatic arthritis, psoriasis, eczema, sclerodema, asthma, diabetes, diabetic retinopathy, retinopathy of prematurity, or age-related macular degeneration, comprising administering to a subject a compound of formula I

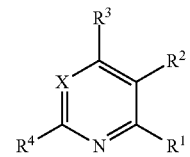

wherein
X denotes CH or N,
$R^1$ denotes $NH_2$, $CONH_2$ or H,
$R^2$ denotes Hal, $Ar^1$ or $Het^1$,
$R^3$ denotes $NR^5[C(R^5)_2]_nHet^2$, $NR^5[C(R^5)_2]_nCyc$, $Het^2$, $O[C(R^5)_2]_nAr^2$, $NR^5[C(R^5)_2]_nAr^2$, $O[C(R^5)_2]_nHet^2$, $NR^5(CH_2)_pNR^5R^6$, $O(CH_2)_pNR^5R^6$ or $NR^5(CH_2)_pCR^7R^8NR^5R^6$,
$R^4$ denotes H, $CH_3$ or $NH_2$,
$R^5$ each independently denotes H or alkyl having 1, 2, 3 or 4 C atoms,
$R^6$ each independently denotes $N(R^5)_2$ $CH_2CH=CHCONH$, $Het^3CH_2CH=CHCONH$, $CH_2=CHCONH(CH_2)_n$, $Het^4(CH_2)_nCOHet^3$-diyl-$CH_2CH=CHCONH$, $HC≡CCO$, $CH_3C≡CCO$, $CH_2$=CH—CO, $CH_2$=C($CH_3$)CONH, $CH_3CH$=CHCONH($CH_2$)$_n$, N≡CCR$^7$R$^8$CONH ($CH_2$)$_n$, Het$^4$NH($CH_2$)$_p$COHet$^3$-diyl-$CH_2$CH=CHCONH, Het$^4$($CH_2$)$_p$CONH($CH_2$$CH_2$O)$_p$ ($CH_2$)$_p$COHet$^3$-diyl-$CH_2$CH=CHCONH, $CH_2$=CHSO$_2$, ACH=CHCO, $CH_3$CH=CHCO, Het$^4$ ($CH_2$)$_p$CONH($CH_2$)$_p$Het$^3$-diyl-$CH_2$CH=CHCONH, Ar$^3$CH=CHSO$_2$, $CH_2$=CHSO$_2$NH or N(R$^5$) $CH_2$CH=CHCO, R$^7$, R$^8$ denote together alkylene having 2, 3, 4, or 5 C atoms, Ar$^1$ denotes phenyl or naphthyl, each of which is unsubstituted or mono-, di- or trisubstituted by R$^6$, Hal, ($CH_2$)$_n$NH$_2$, CONHAr$^3$, ($CH_2$)$_n$NHCOA, O($CH_2$)$_n$Ar$^3$, OCyc, A, COHet$^3$, OA and/or OHet$^3$ ($CH_2$), Ar$^2$ denotes phenyl, naphthyl or pyridyl each of which is unsubstituted or mono-, di- or trisubstituted by R$^6$, Hal, OAr$^3$, ($CH_2$)$_n$NH$_2$, ($CH_2$)$_n$NHCOA and/or Het$^3$, Ar$^3$ denotes phenyl, which is unsubstituted or mono-, di- or trisubstituted by OH, OA, Hal, CN and/or A, Het$^1$ denotes a mono- or bicyclic saturated, unsaturated or aromatic heterocycle having 1 to 4 N, O and/or S atoms, which may be unsubstituted or mono-, di- or trisubstituted by R$^6$, O($CH_2$)$_n$Ar$^3$ and/or ($CH_2$)$_n$Ar$^3$, Het$^2$ each independently denotes a mono- or bicyclic saturated heterocycle having 1 to 4 N, O and/or S atoms, which may be unsubstituted or mono-, di- or trisubstituted by R$^6$, Het$^3$, CycSO$_2$, OH, Hal, COOH, OA, COA, COHet$^3$, CycCO, SO$_2$ and/or =O, Het$^3$ each independently denotes a monocyclic unsaturated, saturated or aromatic heterocycle having 1 to 4 N, O and/or S atoms, which may be unsubstituted or mono-, di- or trisubstituted by Hal, A and/or =O, Het$^4$ each independently denotes a bi- or tricyclic unsaturated, saturated or aromatic heterocycle having 1 to 4 N, O and/or S atoms, which may be unsubstituted or mono-, di-, tri- or tetrasubstituted by A, NO$_2$, Hal and/or =O, Cyc each independently denotes cyclic alkyl having 3, 4, 5 or 6 C atoms, which is unsubstituted, monosubstituted or disubstituted by R$^6$ and/or OH and which may comprise a double bond, A each independently denotes unbranched or branched alkyl having 1-10 C atoms, in which 1-7 H atoms may be replaced by F and/or Cl and/or in which one or two non-adjacent $CH_2$ and/or CH-groups may be replaced by O, NH and/or by N, Hal each independently denotes F, Cl, Br or I, n each independently denotes 0, 1, 2, 3 or 4, p each independently denotes 1, 2, 3, 4, 5 or 6, and pharmaceutically usable salts, tautomers and stereoisomers thereof, including mixtures thereof in all ratios.

2. The method according to claim 1 wherein

Het$^1$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, azabicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by R$^6$, O($CH_2$)$_n$Ar$^3$ and/or ($CH_2$)$_n$Ar$^3$, and pharmaceutically usable salts, tautomers and stereoisomers thereof, including mixtures thereof in all ratios.

3. The method according to claim 2 wherein Het$^1$ denotes pyrazolyl, pyridyl, pyrimidinyl, dihydropyridyl or dihydrobenzodioxinyl, each of which is unsubstituted or mono-, di- or trisubstituted by R$^6$, O($CH_2$)$_n$Ar$^3$ and/or ($CH_2$)$_n$Ar$^3$, and pharmaceutically usable salts, tautomers and stereoisomers thereof, including mixtures thereof in all ratios.

4. The method according to claim 1 wherein

Het$^2$ denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-azaspiro[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by R$^6$, Het$^3$, CycSO$_2$, OH, OA, COA, COHet$^3$, CycCO, SO$_2$ and/or =O, and pharmaceutically usable salts, tautomers and stereoisomers thereof, including mixtures thereof in all ratios.

5. The method according to claim 1 wherein

Het$^3$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O,
and pharmaceutically usable salts, tautomers and stereoisomers thereof, including mixtures thereof in all ratios.

6. The method according to claim 5 wherein

Het$^3$ denotes piperidinyl, pyrrolidinyl, morpholinyl, furyl, thienyl, pyrrolyl, imidazolyl, pyrazolyl, pyridyl, pyrimidinyl, dihydropyrrolyl, dihydropyrazolyl or dihydropyridyl, each of which may be unsubstituted or mono-, di- or trisubstituted by Hal, A and/or =O,
and pharmaceutically usable salts, tautomers and stereoisomers thereof, including mixtures thereof in all ratios.

7. The method according to claim 1 wherein

Het$^4$ denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, NO$_2$, Hal and/or =O, and pharmaceutically usable salts, tautomers and stereoisomers thereof, including mixtures thereof in all ratios.

8. The method according to claim 1 wherein

X denotes CH or N,

R$^1$ denotes NH$_2$, CONH$_2$ or H,

R$^2$ denotes Hal, Ar$^1$ or Het$^1$,

R$^3$ denotes NR$^5$[C(R$^5$)$_2$]$_n$Het$^2$, NR$^5$[C(R$^5$)$_2$]$_n$Cyc, Het$^2$, O[C(R$^5$)$_2$]$_n$Ar$^2$, NR$^5$[C(R$^5$)$_2$]$_n$Ar$^2$, O[C(R$^5$)$_2$]$_n$Het$^2$, NR$^5$(CH$_2$)$_p$NR$^5$R$^6$, O(CH$_2$)$_p$NR$^5$R$^6$ NR$^5$(CH$_2$)$_p$CR$^7$R$^8$NR$^5$R$^6$, R$^4$ denotes H, R$^5$ each independently denotes H or alkyl having 1, 2, 3 or 4 C atoms, R$^6$ each independently denotes N(R$^5$)$_2$ $CH_2$CH=CHCONH, Het$^3$$CH_2$CH=CHCONH, CH$_2$=CHCONH(CH$_2$)$_n$, Het$^4$(CH$_2$)$_n$COHet$^3$-diyl-CH$_2$CH=CHCONH, HC≡CCO, CH$_3$C≡CCO, CH$_2$=CH—CO, CH$_2$=C(CH$_3$)CONH, CH$_3$CH=CHCONH(CH$_2$)$_n$, N≡CCR$^7$R$^8$CONH(CH$_2$)$_n$, Het$^4$NH(CH$_2$)$_p$COHet$^3$-diyl-CH$_2$CH=CHCONH, Het$^4$(CH$_2$)$_p$CONH(CH$_2$CH$_2$O)$_p$(CH$_2$)$_p$COHet$^3$-diyl-CH$_2$CH=CHCONH, CH$_2$=CHSO$_2$, ACH=CHCO, CH$_3$CH=CHCO, Het$^4$(CH$_2$)$_p$CONH(CH$_2$)$_p$Het$^3$-diyl-CH$_2$CH=CHCONH, Ar$^3$CH=CHSO$_2$, CH$_2$=CHSO$_2$NH or N(R$^5$)CH$_2$CH=CHCO, R$^7$, R$^8$ denote together alkylene having 2, 3, 4, or 5 C atoms, Ar$^1$ denotes phenyl or naphthyl, each of which is unsubstituted or mono-, di- or trisubstituted by R$^6$, Hal, (CH$_2$)$_n$NH$_2$, CONHAr$^3$, (CH$_2$)$_n$NHCOA, O(CH$_2$)$_n$Ar$^3$, OCyc, A, COHet$^3$, OA and/or OHet$^3$ (CH$_2$), Ar$^2$ denotes phenyl or naphthyl, each of which is unsubstituted or mono-, di- or trisubstituted by R$^6$, Hal, OAr$^3$, (CH$_2$)$_n$NH$_2$, (CH$_2$)$_n$NHCOA and/or Het$^3$, Ar$^3$ each independently denotes phenyl, which is unsubstituted or mono-, di- or trisubstituted by OH, OA, Hal, CN and/or A, Het$^1$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, indolyl, benzo-1,3-dioxolyl, indazolyl, azabicyclo[3.2.1]octyl, aza-bicyclo[2.2.2]octyl, imidazolidinyl, azetidinyl, azepanyl, benzo-2,1,3-thiadiazolyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl, dihydropyridyl or dihydrobenzodioxinyl, each of which is unsubstituted or mono-, di- or trisubstituted by R$^6$, O(CH$_2$)$_n$Ar$^3$ and/or (CH$_2$)$_n$Ar$^3$, Het$^2$ each independently denotes piperidinyl, piperazinyl, pyrrolidinyl, morpholinyl, azabicyclo[3.2.1]octyl, azabicyclo[2.2.2]octyl, 2,7-diazaspiro[3.5]nonyl, 2,8-diazaspiro[4.5]decyl, 2,7-diazaspiro[4.4]nonyl, 3-azabicylo[3.1.0]hexyl, 2-azaspiro[3.3]heptyl, 6-azaspiro[3.4]octyl, 7-azaspiro[3.5]nonyl, 5-azaspiro[3.5]nonyl, imidazolidinyl, azetidinyl, azepanyl, tetrahydrofuryl, dioxolanyl, tetrahydrothienyl, tetrahydroimidazolyl, tetrahydropyrazolyl, tetrahydropyridyl, each of which is unsubstituted or mono-, di- or trisubstituted by R$^6$, Het$^3$, CycSO$_2$, OH, OA, COA, COHet$^3$, CycCO, SO$_2$ and/or =O, Het$^3$ each independently denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, imidazolidinyl, azetidinyl, azepanyl, tetrahydrofuryl, dioxolanyl, tetrahydrothienyl, dihydropyrrolyl, tetrahydroimidazolyl, dihydropyrazolyl, tetrahydropyrazolyl, tetrahydropyridyl or dihydropyridyl, each of which may be unsubstituted or mono-, di- or trisubstituted by Hal, A and/or =O, Het$^4$ each independently denotes hexahydrothieno[3,4-d]imidazolyl, benzo[c][1,2,5]oxadiazolyl or 5H-dipyrrolo[1,2-c:2',1'-f][1,3,2]diazaborinin-4-ium-uidyl, each of which may be unsubstituted or mono-, di-, tri- or tetrasubstituted by A, NO$_2$, Hal and/or =O, Cyc each independently denotes cyclic alkyl having 3, 4, 5 or 6 C atoms, which is unsubstituted or monosubstituted by R$^6$ and which may comprise a double bond, A each independently denotes unbranched or branched alkyl having 1-10 C atoms, in which 1-7 H atoms may be replaced by F and/or Cl and/or in which one or two non-adjacent CH$_2$ and/or CH-groups may be replaced by O, NH and/or by N, Hal each independently denotes F, Cl, Br or I, n each independently denotes 0, 1, 2, 3 or 4, p each independently denotes 1, 2, 3, 4, 5 or 6, and pharmaceutically usable salts, tautomers and stereoisomers thereof, including mixtures thereof in all ratios.

9. The method according to claim 1, wherein the compound is a compound of formula II

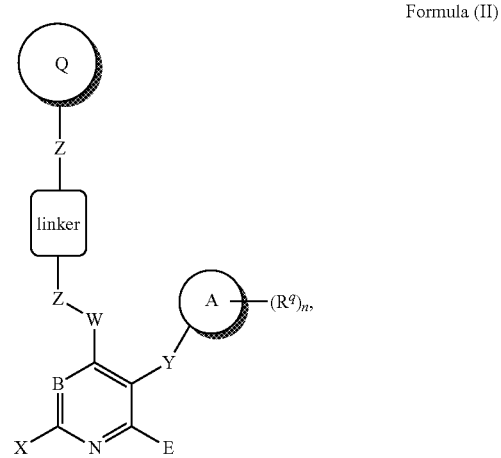

Formula (II)

wherein:

X is H or CH$_3$ or NH$_2$,

Y is H, Hal or is absent,

B is N or CH,

E is NH$_2$ or H,

W is NR, O or a cyclic amine,

Z is, independently, CH$_2$, CH$_3$, CH$_2$—CH$_2$, CH—CH$_2$, H, NH or is absent, "linker" is (CH$_2$)$_n$, wherein: $_n$ is 1, 2 or 3or an optionally substituted group selected from a phenyl ring, an aryl ring, heteroaryl ring, branched or unbranched alkyl group, a 5-6 membered monocyclic heteroaryl ring having 1-4 heteroatoms independently selected from nitrogen, or oxygen, a 4-7 membered saturated or partially unsaturated heterocycle having 1-3 heteroatoms independently selected from nitrogen, or oxygen, or a 7-10 membered bicyclic saturated or partially unsaturated heterocyclic ring having 1-5 heteroatoms independently selected from nitrogen, or oxygen, or a 7-10 membered bicyclic saturated or partially unsaturated heterocyclic ring having 1-5 heteroatoms attached to a hetero saturated ring Linkers may also be cycloalkanes optionally substituted by heteroatoms (independently selected from nitrogen, or oxygen), cycloalkanes optionally substituted with —NH or OH, fused or bridged rings or optionally substituted spirocyclic rings that optionally contain heteroatoms, A is a mono- or bicyclic aromatic homo- or heterocycle having 0, 1, 2, 3 or 4 N, and/or O atoms and 5, 6, 7, 8, 9, or 10 skeleton C atoms, which may be unsubstituted or, independently of one another, mono-, di- or trisubstituted by Hal, OH or OR, Hal is F, Cl, Br or I, R is independently hydrogen, oxygen or an optionally substituted group selected from $C_{1-6}$ linear or cyclic aliphatic, benzyl, phenyl, a phenyl group optionally substituted with 1, 2 or 3 O atoms, a 4-7 membered heterocylic ring having 1-2 heteroatoms independently selected from nitrogen, oxygen, or a 5-6 membered monocyclic heteroaryl ring having 1-4 heteroatoms independently selected from nitrogen, or oxygen or a mono- or bicyclic aromatic homo- or heterocycle having 0, 1, 2, 3 or 4 N, O atoms and 5, 6, 7, or 8 C skeleton atoms, which may be unsubstituted or, independently of one another, mono-, di- or trisubstituted by Hal, A, OH, $NH_2$, nitrile, and/or $CH(Hal)_3$ or is an unbranched or branched linear alkyl having 1, 2, 3, 4, 5, 6, 7 or 8 C atoms, in which one or two $CH_2$ groups may be replaced by an O atom and/or by an —NH—, —CO—, —NHCOO—, —NHCONH—, —CONH—, —NHCO— or —CH=CH— group, and in which 1-3 H atoms may be replaced by Hal, $R^q$ is selected from —R, -A, halogen, —OR, —O(CH$_2$)$_r$OR, —R(NH), —NO$_2$, —C(O)R, —CO$_2$R, —C(O)N(R)$_2$, —NRC(O)R, —NRC(O)NR$_2$, —NRSO$_2$R, or —N(R)$_2$, r is 1-4, n is 0-4, and Q is an electrophilic group.

10. The method according to claim 9, wherein Q is

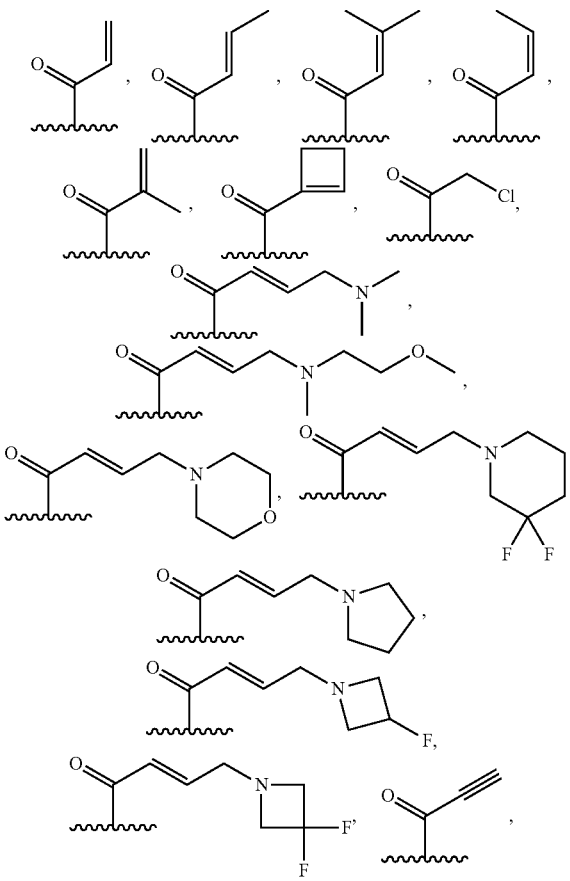

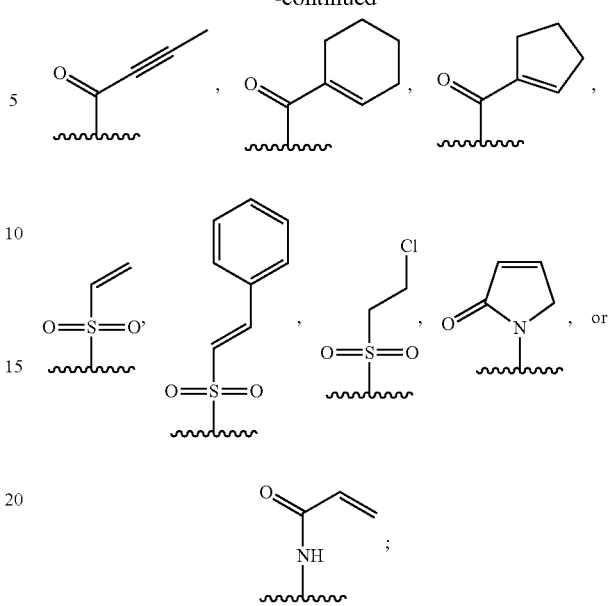

or a pharmaceutically acceptable salt, tautomer or stereoisomer thereof.

11. The method according to claim 10, wherein Q is

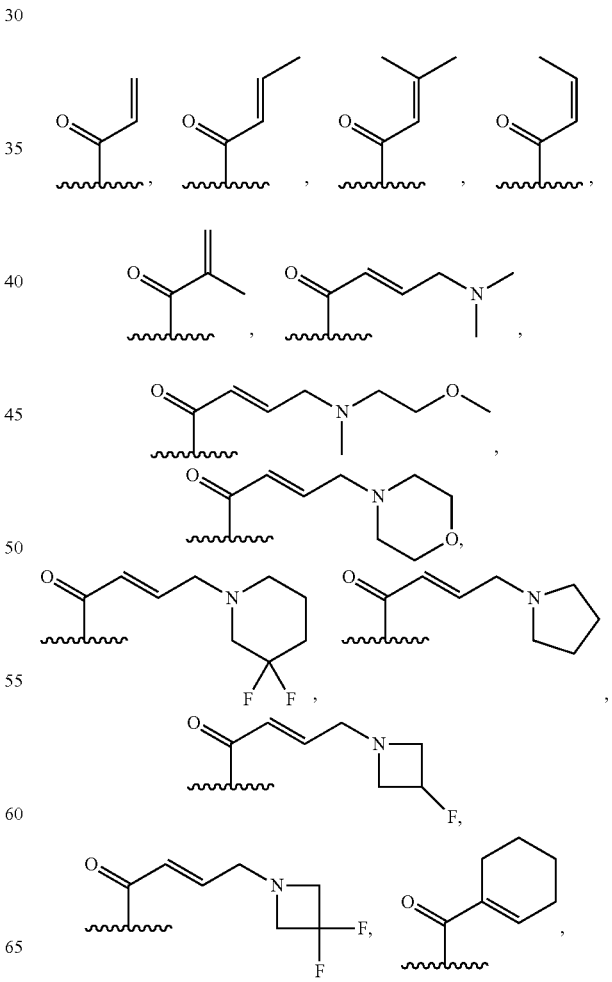

-continued

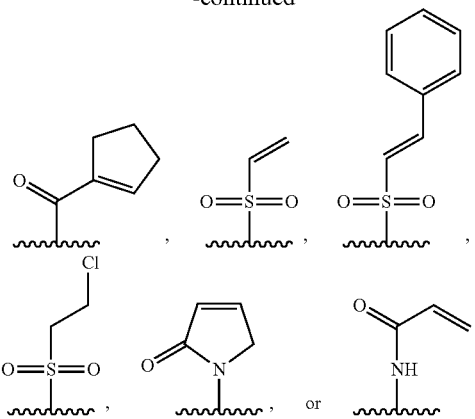

or a pharmaceutically acceptable salt, tautomer or stereoisomer thereof.

12. The method according to claim 10, wherein Q is

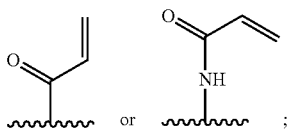

or a pharmaceutically acceptable salt, tautomer or stereoisomer thereof.

13. The method according to claim 9, wherein the compound is a compound of formula IV

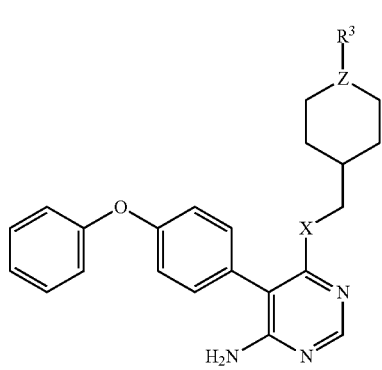

Formula (IV)

wherein:
Z is N or CH,
X is O or NH, and
$R^3$ is

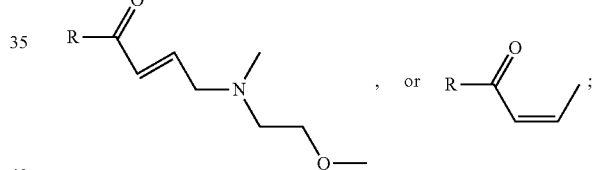

wherein, "R" denotes the bonding point to Z in Formula IV or a pharmaceutically acceptable salt, tautomer or stereoisomer thereof.

14. The method according to claim 1, wherein the compound is selected from the group

| No. | Chemical Name |
|---|---|
| "A1" | (R)-1-(3-(((6-amino-5-(4-phenoxyphenyl)pyrimidin-4-yl)amino)pyrrolidin-1-yl)prop-2-en-1-one |
| "A2" | (R)-1-(3-(((6-amino-5-(4-phenoxyphenyl)pyrimidin-4-yl)oxy)piperidin-1-yl)prop-2-en-1-one |
| "A3" | N-(3-(((6-amino-5-(4-phenoxyphenyl)pyrimidin-4-yl)amino)phenyl)acrylamide |
| "A4" | (R)-1-(3-(((6-amino-5-(4-phenoxyphenyl)pyrimidin-4-yl)amino)methyl)pyrrolidin-1-yl)prop-2-en-1-one |
| "A5" | N-((1-(6-amino-5-(4-phenoxyphenyl)pyrimidin-4-yl)pyrrolidin-3-yl)methyl)acrylamide |
| "A6" | 1-(4-(((5-(4-phenoxyphenyl)pyrimidin-4-yl)oxy)methyl)piperidin-1-yl)prop-2-en-1-one |
| "A7" | N-((1-(6-amino-5-(4-phenoxyphenyl)pyrimidin-4-yl)piperidin-4-yl)methyl)acrylamide |
| "A8" | 4-(4-(((6-amino-5-(4-phenoxyphenyl)pyrimidin-4-yl)amino)methyl)piperidine-1-carbonyl)-1-methylpyridin-2(1H)-one |
| "A9" | 1-(4-(((6-amino-5-(4-phenoxyphenyl)pyrimidin-4-yl)oxy)methyl)piperidin-1-yl)but-2-yn-1-one |

-continued

| No. | Chemical Name |
|---|---|
| "A10" | 5-(4-phenoxyphenyl)-N4-((1-(vinylsulfonyl)piperidin-4-yl)methyl)pyrimidine-4,6-diamine |
| "A11" | (E)-1-(4-(((6-amino-5-(4-phenoxyphenyl)pyrimidin-4-yl)amino)methyl)piperidin-1-yl)-4-((2-methoxyethyl)(methyl)amino)but-2-en-1-one |
| "A12" | (4-(((6-amino-5-(4-phenoxyphenyl)pyrimidin-4-yl)amino)methyl)piperidin-1-yl)(2-fluoropyridin-3-yl)methanone |
| "A13" | (E)-1-(4-(((6-amino-5-(4-phenoxyphenyl)pyrimidin-4-yl)amino)methyl)piperidin-1-yl)but-2-en-1-one |
| "A14" | N4-((1-(cyclopropylsulfonyl)piperidin-4-yl)methyl)-5-(4-phenoxyphenyl)pyrimidine-4,6-diamine |
| "A15" | (Z)-1-(4-(((6-amino-5-(4-phenoxyphenyl)pyrimidin-4-yl)amino)methyl)piperidin-1-yl)but-2-en-1-one |
| "A16" | 1-(4-(2-((6-amino-5-(4-phenoxyphenyl)pyrimidin-4-yl)amino)ethyl)piperidin-1-yl)prop-2-en-1-one |
| "A17" | 1-(3-(((6-amino-5-(4-phenoxyphenyl)pyrimidin-4-yl)oxy)methyl)piperidin-1-yl)prop-2-en-1-one |
| "A18" | N-(2-((6-amino-5-(4-phenoxyphenyl)pyrimidin-4-yl)amino)ethyl)acrylamide |
| "A19" | (R)-1-(3-((6-amino-5-(4-phenoxyphenyl)pyrimidin-4-yl)oxy)pyrrolidin-1-yl)prop-2-en-1-one |
| "A20" | N-(1-(((6-amino-5-(4-phenoxyphenyl)pyrimidin-4-yl)amino)methyl)cyclopentyl)acrylamide |
| "A21" | 1-(3-(((6-amino-5-(4-phenoxyphenyl)pyrimidin-4-yl)oxy)methyl)pyrrolidin-1-yl)prop-2-en-1-one |
| "A22" | 1-(4-(((5-fluoro-3-(4-phenoxyphenyl)pyridin-2-yl)amino)methyl)piperidin-1-yl)prop-2-en-1-one |
| "A23" | 1-(4-(((6-amino-5-(4-phenoxyphenyl)pyrimidin-4-yl)amino)methyl)piperidin-1-yl)ethanone |
| "A24" | (E)-7-(3-(4-(4-((3-((6-amino-5-(4-phenoxyphenyl)pyrimidin-4-yl)oxy)phenyl)amino)-4-oxobut-2-en-1-yl)piperazin-1-yl)-3-oxopropyl)-5,5-difluoro-1,3-dimethyl-5H-dipyrrolo[1,2-c:2',1'-f][1,3,2]diazaborinin-4-ium-5-uide |
| "A25" | 1-(4-(((2-amino-5-(4-phenoxyphenyl)pyrimidin-4-yl)amino)methyl)piperidin-1-yl)prop-2-en-1-one |
| "A26" | (S)-1-(3-(((6-amino-5-(4-phenoxyphenyl)pyrimidin-4-yl)oxy)methyl)pyrrolidin-1-yl)prop-2-en-1-one |
| "A27" | N-(2-((6-amino-5-(4-phenoxyphenyl)pyrimidin-4-yl)oxy)ethyl)acrylamide |
| "A28" | (S)-1-(3-(((6-amino-5-(4-phenoxyphenyl)pyrimidin-4-yl)amino)methyl)pyrrolidin-1-yl)prop-2-en-1-one |
| "A29" | 1-(4-(((6-amino-5-(4-phenoxyphenyl)pyrimidin-4-yl)amino)methyl)piperidin-1-yl)-2-methylprop-2-en-1-one |
| "A30" | (4-(((6-amino-5-(4-phenoxyphenyl)pyrimidin-4-yl)amino)methyl)piperidin-1-yl)(cyclohex-1-en-1-yl)methanone |
| "A31" | 1-(4-(((6-amino-5-(4-phenoxyphenyl)pyrimidin-4-yl)amino)methyl)piperidin-1-yl)-3-methylbut-2-en-1-one |
| "A32" | (4-(((6-amino-5-(4-phenoxyphenyl)pyrimidin-4-yl)amino)methyl)piperidin-1-yl)(cyclopent-1-en-1-yl)methanone |
| "A33" | 1-(4-(((6-amino-5-(1-benzyl-1H-pyrazol-4-yl)pyrimidin-4-yl)amino)methyl)piperidin-1-yl)prop-2-en-1-one |
| "A34" | 1-(4-(((6-amino-5-(4-(3-fluorophenoxy)phenyl)pyrimidin-4-yl)amino)methyl)piperidin-1-yl)prop-2-en-1-one |
| "A35" | (E)-7-(3-((2-(4-(4-((3-((6-amino-5-(4-phenoxyphenyl)pyrimidin-4-yl)oxy)phenyl)amino)-4-oxobut-2-en-1-yl)piperazin-1-yl)ethyl)amino)-3-oxopropyl)-5,5-difluoro-1,3-dimethyl-5H-dipyrrolo[1,2-c:2',1'-f][1,3,2]diazaborinin-4-ium-5-uide |
| "A36" | 1-(4-(((6-amino-2-methyl-5-(4-phenoxyphenyl)pyrimidin-4-yl)amino)methyl)piperidin-1-yl)prop-2-en-1-one |
| "A37" | 1-(4-(((6-amino-5-(4-phenoxyphenyl)pyrimidin-4-yl)amino)methyl)-4-hydroxypiperidin-1-yl)prop-2-en-1-one |
| "A38" | (R)-1-(3-(((6-amino-5-(4-phenoxyphenyl)pyrimidin-4-yl)oxy)methyl)pyrrolidin-1-yl)prop-2-en-1-one |
| "A39" | 1-(4-(((6-amino-5-(4-(phenylamino)phenyl)pyrimidin-4-yl)amino)methyl)piperidin-1-yl)prop-2-en-1-one |
| "A40" | 1-(3-((6-amino-5-(4-phenoxyphenyl)pyrimidin-4-yl)oxy)phenyl)-1H-pyrrol-2(5H)-one |
| "A41" | 1-(4-(((6-amino-5-(4-benzylphenyl)pyrimidin-4-yl)amino)methyl)piperidin-1-yl)prop-2-en-1-one |
| "A42" | (4-(((6-amino-5-(4-phenoxyphenyl)pyrimidin-4-yl)amino)methyl)piperidin-1-yl)(cyclobut-1-en-1-yl)methanone |
| "A43" | (Z)-1-(4-(((6-amino-5-(4-phenoxyphenyl)pyrimidin-4-yl)oxy)methyl)piperidin-1-yl)but-2-en-1-one |
| "A44" | 1-(4-(((6-amino-2-methyl-5-(4-phenoxyphenyl)pyrimidin-4-yl)(methyl)amino)methyl)piperidin-1-yl)prop-2-en-1-one |
| "A45" | 1-(4-(((6-amino-5-(4-phenoxyphenyl)pyrimidin-4-yl)amino)methyl)piperidin-1-yl)-2-chloroethanone |

-continued

| No. | Chemical Name |
|---|---|
| "A46" | 1-(4-(((6-amino-5-(4-phenoxyphenyl)pyrimidin-4-yl)amino)methyl)piperidin-1-yl)prop-2-yn-1-one |
| "A47" | 1-(4-(((6-amino-5-(4-phenoxyphenyl)pyrimidin-4-yl)(methyl)amino)methyl)piperidin-1-yl)prop-2-en-1-one |
| "A48" | 1-(3-(((6-amino-5-(4-phenoxyphenyl)pyrimidin-4-yl)amino)methyl)-8-azabicyclo[3.2.1]octan-8-yl)prop-2-en-1-one |
| "A49" | N-((1S,3S)-3-((6-amino-5-(4-phenoxyphenyl)pyrimidin-4-yl)amino)cyclopentyl)acrylamide |
| "A50" | N-(4-((6-amino-5-(4-phenoxyphenyl)pyrimidin-4-yl)amino)butyl)acrylamide |
| "A51" | N-(cis-3-((6-amino-5-(4-phenoxyphenyl)pyrimidin-4-yl)amino)cyclohexyl)acrylamide |
| "A52" | 1-(3-((6-amino-5-(4-phenoxyphenyl)pyrimidin-4-yl)amino)azepan-1-yl)prop-2-en-1-one |
| "A53" | N-(trans-3-((6-amino-5-(4-phenoxyphenyl)pyrimidin-4-yl)amino)cyclohexyl)acrylamide |
| "A54" | (E)-5-(4-phenoxyphenyl)-N4-((1-(styrylsulfonyl)piperidin-4-yl)methyl)pyrimidine-4,6-diamine |
| "A55" | N4-((1-(methylsulfonyl)piperidin-4-yl)methyl)-5-(4-phenoxyphenyl)pyrimidine-4,6-diamine |
| "A56" | 1-(4-(((6-amino-5-(4-phenoxyphenyl)pyrimidin-4-yl)amino)methyl)piperidin-1-yl)-2,3-dihydroxypropan-1-one |
| "A57" | 4-(((6-amino-5-(4-phenoxyphenyl)pyrimidin-4-yl)amino)methyl)piperidin-2-one |
| "A58" | N-(3-((6-amino-5-(4-phenoxyphenyl)pyrimidin-4-yl)oxy)phenyl)ethenesulfonamide |
| "A59" | N-(3-((6-amino-5-(4-phenoxyphenyl)pyrimidin-4-yl)amino)propyl)acrylamide |
| "A60" | N-(5-((6-amino-5-(4-phenoxyphenyl)pyrimidin-4-yl)oxy)pyridin-3-yl)acrylamide |
| "A61" | (R)-1-(3-(((6-amino-5-(4-phenoxyphenyl)pyrimidin-4-yl)amino)methyl)pyrrolidin-1-yl)prop-2-yn-1-one |
| "A62" | (R,E)-1-(3-(((6-amino-5-(4-phenoxyphenyl)pyrimidin-4-yl)amino)methyl)pyrrolidin-1-yl)-4-(dimethylamino)but-2-en-1-one |
| "A63" | (E)-N-(cis-3-((6-amino-5-(4-phenoxyphenyl)pyrimidin-4-yl)amino)cyclohexyl)-4-(dimethylamino)but-2-enamide |
| "A64" | N-(cis-3-((6-amino-5-(4-phenoxyphenyl)pyrimidin-4-yl)amino)cyclohexyl)propiolamide |
| "A65" | (S)-1-(2-(((6-amino-5-(4-phenoxyphenyl)pyrimidin-4-yl)oxy)methyl)morpholino)prop-2-en-1-one |
| "A66" | (R)-1-(2-(((6-amino-5-(4-phenoxyphenyl)pyrimidin-4-yl)oxy)methyl)morpholino)prop-2-en-1-one |
| "A67" | N-(3-((6-amino-5-(1-(3-fluorobenzyl)-1H-pyrazol-4-yl)pyrimidin-4-yl)oxy)phenyl)acrylamide |
| "A68" | 1-(3-(((6-amino-5-(4-phenoxyphenyl)pyrimidin-4-yl)amino)methyl)-8-azabicyclo[3.2.1]octan-8-yl)prop-2-yn-1-one |
| "A69" | N-(3-((6-amino-5-(1-(4-cyanobenzyl)-1H-pyrazol-4-yl)pyrimidin-4-yl)oxy)phenyl)acrylamide |
| "A70" | N-(3-((6-amino-5-(1-benzyl-1H-pyrazol-4-yl)pyrimidin-4-yl)amino)phenyl)acrylamide |
| "A71" | (E)-1-(3-(((6-amino-5-(4-phenoxyphenyl)pyrimidin-4-yl)amino)methyl)-8-azabicyclo[3.2.1]octan-8-yl)-4-(dimethylamino)but-2-en-1-one |
| "A72" | N-(3-((6-amino-5-(1-(4-methoxybenzyl)-1H-pyrazol-4-yl)pyrimidin-4-yl)oxy)phenyl)acrylamide |
| "A73" | (R,E)-1-(3-((6-amino-5-(4-phenoxyphenyl)pyrimidin-4-yl)amino)pyrrolidin-1-yl)-4-(dimethylamino)but-2-en-1-one |
| "A74" | (R,E)-1-(3-((6-amino-5-(4-phenoxyphenyl)pyrimidin-4-yl)amino)piperidin-1-yl)-4-(dimethylamino)but-2-en-1-one |
| "A75" | 1-(trans-3-((6-amino-5-(4-phenoxyphenyl)pyrimidin-4-yl)amino)-4-hydroxypyrrolidin-1-yl)prop-2-en-1-one |
| "A76" | 1-(4-(((2-amino-3-(4-phenoxyphenyl)pyridin-4-yl)amino)methyl)piperidin-1-yl)prop-2-en-1-one |
| "A77" | 1-(4-(((6-amino-5-(4-fluorophenyl)pyrimidin-4-yl)amino)methyl)piperidin-1-yl)prop-2-en-1-one |
| "A78" | 1-(4-(((6-amino-5-(4-(trifluoromethoxy)phenyl)pyrimidin-4-yl)amino)methyl)piperidin-1-yl)prop-2-en-1-one |
| "A79" | 1-(4-(((6-amino-5-(4-(trifluoromethyl)phenoxy)phenyl)pyrimidin-4-yl)amino)methyl)piperidin-1-yl)prop-2-en-1-one |
| "A80" | 1-(4-(((6-amino-5-(4-(4-(fluorophenoxy)phenyl)pyrimidin-4-yl)amino)methyl)piperidin-1-yl)prop-2-en-1-one |
| "A81" | 1-(4-(((6-amino-5-(4-(trifluoromethyl)phenyl)pyrimidin-4-yl)amino)methyl)piperidin-1-yl)prop-2-en-1-one |
| "A82" | 1-(4-(((6-amino-5-(3,4-dimethoxyphenyl)pyrimidin-4-yl)amino)methyl)piperidin-1-yl)prop-2-en-1-one |
| "A83" | 1-(4-(((6-amino-5-(3,4,5-trimethoxyphenyl)pyrimidin-4-yl)amino)methyl)piperidin-1-yl)prop-2-en-1-one |

| No. | Chemical Name |
|---|---|
| "A84" | 1-(4-(((6-amino-5-(2,3-dihydrobenzo[b][1,4]dioxin-6-yl)pyrimidin-4-yl)amino)methyl)piperidin-1-yl)prop-2-en-1-one |
| "A85" | 1-(4-(((6-amino-5-(4-methoxyphenyl)pyrimidin-4-yl)amino)methyl)piperidin-1-yl)prop-2-en-1-one |
| "A86" | 4-(4-(4-(((1-acryloylpiperidin-4-yl)methyl)amino)-6-aminopyrimidin-5-yl)phenoxy)benzonitrile |
| "A87" | 1-(4-(((6-amino-5-(2,5-difluoro-4-phenoxyphenyl)pyrimidin-4-yl)amino)methyl)piperidin-1-yl)prop-2-en-1-one |
| "A88" | 1-(4-(((6-amino-5-(2,3-difluoro-4-phenoxyphenyl)pyrimidin-4-yl)amino)methyl)piperidin-1-yl)prop-2-en-1-one |
| "A89" | 1-(4-(((6-amino-5-(4-((1-methylpiperidin-4-yl)oxy)phenyl)pyrimidin-4-yl)amino)methyl)piperidin-1-yl)prop-2-en-1-one |
| "A90" | 1-(4-(((6-amino-5-(4-phenoxy-2-(trifluoromethyl)phenyl)pyrimidin-4-yl)amino)methyl)piperidin-1-yl)prop-2-en-1-one |
| "A91" | 1-(2-(6-amino-5-(4-phenoxyphenyl)pyrimidin-4-yl)-2,7-diazaspiro[3.5]nonan-7-yl)prop-2-en-1-one |
| "A92" | 1-(8-(6-amino-5-(4-phenoxyphenyl)pyrimidin-4-yl)-2,8-diazaspiro[4.5]decan-2-yl)prop-2-en-1-one |
| "A93" | 1-(7-(6-amino-5-(4-phenoxyphenyl)pyrimidin-4-yl)-2,7-diazaspiro[4.4]nonan-2-yl)prop-2-en-1-one |
| "A94" | 1-(4-(((6-amino-5-(4-(4-hydroxyphenoxy)phenyl)pyrimidin-4-yl)amino)methyl)piperidin-1-yl)prop-2-en-1-one |
| "A95" | 1-(4-(((6-amino-5-(4-(3-(trifluoromethyl)phenoxy)phenyl)pyrimidin-4-yl)amino)methyl)piperidin-1-yl)prop-2-en-1-one |
| "A96" | 1-(4-(((6-amino-5-(4-(pyridin-3-yloxy)phenyl)pyrimidin-4-yl)amino)methyl)piperidin-1-yl)prop-2-en-1-one |
| "A97" | 1-(4-(((6-amino-5-(4-(pyridin-4-yloxy)phenyl)pyrimidin-4-yl)amino)methyl)piperidin-1-yl)prop-2-en-1-one |
| "A98" | 1-(4-(((6-amino-5-(4-(p-tolyloxy)phenyl)pyrimidin-4-yl)amino)methyl)piperidin-1-yl)prop-2-en-1-one |
| "A99" | 1-(4-(((6-amino-5-(4-(cyclohexyloxy)phenyl)pyrimidin-4-yl)amino)methyl)piperidin-1-yl)prop-2-en-1-one |
| "A100" | N4-((1R,5S,6r)-3-azabicyclo[3.1.0]hexan-6-ylmethyl)-5-(4-phenoxyphenyl)pyrimidine-4,6-diamine hydrochloride |
| "A101" | (3S,4S)-4-(((6-amino-5-(4-phenoxyphenyl)pyrimidin-4-yl)amino)methyl)piperidin-3-ol hydrochloride |
| "A102" | (E)-1-(6-(((6-amino-5-chloropyrimidin-4-yl)oxy)-2-azaspiro[3.3]heptan-2-yl)-4-(dimethylamino)but-2-en-1-one |
| "A103" | 1-(3-(2-((6-amino-5-(4-phenoxyphenyl)pyrimidin-4-yl)amino)ethyl)azetidin-1-yl)prop-2-en-1-one |
| "A104" | 1-(3-(2-((6-amino-5-(4-phenoxyphenyl)pyrimidin-4-yl)amino)ethyl)azetidin-1-yl)prop-2-yn-1-one |
| "A105" | (E)-1-(6-(((6-amino-5-(4-phenoxyphenyl)pyrimidin-4-yl)oxy)-2-azaspiro[3.3]heptan-2-yl)-4-(dimethylamino)but-2-en-1-one |
| "A106" | 1-(6-(((6-amino-5-(1-benzyl-1H-pyrazol-4-yl)pyrimidin-4-yl)oxy)-2-azaspiro[3.3]heptan-2-yl)prop-2-en-1-one |
| "A107" | 1-(6-(((6-amino-5-(1-benzyl-1H-pyrazol-4-yl)pyrimidin-4-yl)amino)-2-azaspiro[3.3]heptan-2-yl)prop-2-en-1-one |
| "A108" | 1-(6-((6-amino-5-(4-phenoxyphenyl)pyrimidin-4-yl)amino)-2-azaspiro[3.3]heptan-2-yl)but-2-yn-1-one |
| "A109" | 1-((3S,4S)-4-(((6-amino-5-(1-benzyl-1H-pyrazol-4-yl)pyrimidin-4-yl)amino)methyl)-3-hydroxypiperidin-1-yl)prop-2-en-1-one |
| "A110" | 1-((3S,4S)-4-(((6-amino-5-(1-benzyl-1H-pyrazol-4-yl)pyrimidin-4-yl)amino)methyl)-3-hydroxypiperidin-1-yl)prop-2-yn-1-one |
| "A111" | 1-(6-(((6-amino-5-(1-benzyl-1H-pyrazol-4-yl)pyrimidin-4-yl)amino)-2-azaspiro[3.3]heptan-2-yl)prop-2-yn-1-one |
| "A112" | 1-(6-(((6-amino-5-(1-benzyl-1H-pyrazol-4-yl)pyrimidin-4-yl)oxy)-2-azaspiro[3.3]heptan-2-yl)prop-2-yn-1-one |
| "A113" | 1-(2-((6-amino-5-(4-phenoxyphenyl)pyrimidin-4-yl)amino)-6-azaspiro[3.4]octan-6-yl)prop-2-en-1-one |
| "A114" | 1-(6-(((6-amino-5-(4-(pyridin-4-yloxy)phenyl)pyrimidin-4-yl)oxy)-2-azaspiro[3.3]heptan-2-yl)prop-2-en-1-one |
| "A115" | 1-(2-((6-amino-5-(4-phenoxyphenyl)pyrimidin-4-yl)amino)-6-azaspiro[3.4]octan-6-yl)prop-2-yn-1-one |
| "A116" | 1-(6-(((6-amino-5-(1-(pyridin-4-ylmethyl)-1H-pyrazol-4-yl)pyrimidin-4-yl)amino)-2-azaspiro[3.3]heptan-2-yl)prop-2-en-1-one |
| "A117" | N-(1,3-trans-3-((6-amino-5-(4-phenoxyphenyl)pyrimidin-4-yl)amino)cyclobutyl)acrylamide |
| "A118" | N-((1,3-cis-3-((6-amino-5-(4-phenoxyphenyl)pyrimidin-4-yl)amino)cyclobutyl)acrylamide |
| "A119" | N4-2-((2-chloroethyl)sulfonyl)-2-azaspiro[3.3]heptan-6-yl)-5-(4-phenoxyphenyl)pyrimidine-4,6-diamine |
| "A120" | 1-(6-(((6-amino-5-(4-phenoxyphenyl)pyrimidin-4-yl)oxy)-2-azaspiro[3.3]heptan-2-yl) prop-2-en-1-one |
| "A121" | 1-(4-(((6-amino-5-(4-phenoxyphenyl)pyrimidin-4-yl)amino)methyl)-4-methoxypiperidin-1-yl)prop-2-en-1-one |

| No. | Chemical Name |
|---|---|
| "A122" | N-(6-((6-amino-5-(4-phenoxyphenyl)pyrimidin-4-yl)amino)spiro[3.3]heptan-2-yl)acrylamide |
| "A123" | 1-(1-((6-amino-5-(4-phenoxyphenyl)pyrimidin-4-yl)amino)-7-azaspiro[3.5]nonan-7-yl)prop-2-en-1-one |
| "A124" | 1-(6-((6-amino-5-(4-phenoxyphenyl)pyrimidin-4-yl)amino)-2-azaspiro[3.3]heptan-2-yl)prop-2-en-1-one |
| "A125" | 1-(8-((6-amino-5-(4-phenoxyphenyl)pyrimidin-4-yl)amino)-5-azaspiro[3.5]nonan-5-yl)prop-2-en-1-one |
| "A126" | (E)-1-((3S,4S)-4-(((6-amino-5-(4-phenoxyphenyl)pyrimidin-4-yl)amino)methyl)-3-hydroxypiperidin-1-yl)-4-(dimethylamino)but-2-en-1-one |
| "A127" | (E)-1-(6-((6-amino-5-(4-phenoxyphenyl)pyrimidin-4-yl)amino)-2-azaspiro[3.3]heptan-2-yl)-4-(dimethylamino)but-2-en-1-one |
| "A128" | 3-((6-Amino-5-chloro-pyrimidin-4-ylamino)-methyl)-benzoic acid methyl ester |
| "A129" | Trans-3-(6-Amino-5-chloro-pyrimidin-4-ylamino)-cyclohexanecarboxylic acid methyl ester |
| "A130" | (1R,3S)-3-(6-Amino-5-chloro-pyrimidin-4-ylamino)-cyclohexanecarboxylic acid methyl ester |
| "A131" | 3-((6-Amino-5-(4-phenoxy-phenyl)-pyrimidin-4-ylamino)-methyl)-benzoic acid methyl ester |
| "A132" | Trans-3-(6-amino-5-(4-phenoxyphenyl)-pyrimidin-4-ylamino)-cyclohexanecarboxylic acid methyl ester |
| "A133" | (1R,3S)-3-(6-Amino-5-(4-phenoxyphenyl)-pyrimidin-4-ylamino)-cyclohexanecarboxylic acid methyl ester |
| "A134" | -((6-Amino-5-(4-phenoxy-phenyl)-pyrimidin-4-ylamino)-methyl)-benzoic acid |
| "A135" | (1S,3S)-3-(6-Amino-5-(4-phenoxyphenyl)-pyrimidin-4-ylamino)-cyclohexanecarboxylic acid |
| "A136" | (1R,3S)-3-(6-Amino-5-(4-phenoxyphenyl)-pyrimidin-4-ylamino)-cyclohexanecarboxylic acid |
| "A137" | (4-(6-Amino-5-(4-phenoxyphenyl)-pyrimidin-4-ylamino)-phenyl)-N-methoxy-N-methyl-acetamide |
| "A138" | 3-((6-Amino-5-(4-phenoxy-phenyl)-pyrimidin-4-ylamino)-methyl)-N-methoxy-N-methyl-benzamide |
| "A139" | (1S,3S)-3-(6-Amino-5-(4-phenoxyphenyl)-pyrimidin-4-ylamino)-cyclohexanecarboxylic acid methoxy-methyl-amide |
| "A140" | (1R,3S)-3-(6-Amino-5-(4-phenoxyphenyl)-pyrimidin-4-ylamino)-cyclohexanecarboxylic acid methoxy-methyl-amide |
| "A141" | 1-(3-((6-Amino-5-(4-phenoxyphenyl)-pyrimidin-4-ylamino)-methyl)-phenyl)-but-2-yn-1-one |
| "A142" | 1-(3-((6-Amino-5-(4-phenoxyphenyl)-pyrimidin-4-ylamino)-methyl)-phenyl)-but-2-en-1-one |
| "A143" | 1-((1S,3S)-3-(6-Amino-5-(4-phenoxyphenyl)-pyrimidin-4-ylamino)-cyclohexyl)-propenone |
| "A144" | 1-((1S,3S)-3-(6-Amino-5-(4-phenoxyphenyl)-pyrimidin-4-ylamino)-cyclohexyl)-but-2-en-1-one |
| "A145" | 1-((1S,3S)-3-(6-Amino-5-(4-phenoxyphenyl)-pyrimidin-4-ylamino)-cyclohexyl)-but-2-yn-1-one |
| "A146" | 1-((1S,3R)-3-(6-Amino-5-(4-phenoxyphenyl)-pyrimidin-4-ylamino)-cyclohexyl)-but-2-en-1-one |
| "A147" | 1-((1S,3R)-3-(6-amino-5-(4-phenoxyphenyl)-pyrimidin-4-ylamino)-cyclohexyl)-but-2-yn-1-one |
| "A148" | (S)-1-(3-((6-amino-5-(4-phenoxyphenyl)pyrimidin-4-yl)amino)pyrrolidin-1-yl)prop-2-en-1-one |
| "A149" | N-(3-((2-amino-3-(4-(benzyloxy)phenyl)pyridin-4-yl)oxy)phenyl)acrylamide |
| "A150" | 1-(3-((2-amino-5-(4-phenoxyphenyl)pyrimidin-4-yl)amino)piperidin-1-yl)prop-2-en-1-one |
| "A151" | (E)-N-(3-((2-amino-3-(4-phenoxyphenyl)pyridin-4-yl)oxy)phenyl)-4-(dimethylamino)but-2-enamide |
| "A152" | (E)-N-(3-((2-amino-3-(4-(benzyloxy)phenyl)pyridin-4-yl)oxy)phenyl)-4-(dimethylamino)but-2-enamide |
| "A153" | (E)-1-(4-(((6-amino-5-(4-phenoxyphenyl)pyrimidin-4-yl)amino)methyl)piperidin-1-yl)-4-(dimethylamino)but-2-en-1-one |
| "A154" | N-cis-4-((6-amino-5-(4-(benzyloxy)phenyl)pyrimidin-4-yl)amino)cyclohexyl)acrylamide |
| "A155" | 4-(4-(((1-acryloylpyrrolidin-3-yl)methyl)amino)-6-aminopyrimidin-5-yl)-N-phenylbenzamide |
| "A156" | 1-(3-(((6-amino-5-(4-(benzyloxy)phenyl)pyrimidin-4-yl)amino)methyl)pyrrolidin-1-yl)prop-2-en-1-one |
| "A157" | 4-(4-(((1-acryloylpiperidin-4-yl)methyl)amino)-6-aminopyrimidin-5-yl)-N-phenylbenzamide |
| "A158" | N-(3-((2-amino-3-(4-phenoxyphenyl)pyridin-4-yl)oxy)-4-fluorophenyl)acrylamide |
| "A159" | 4-(4-((cis-4-acrylamidocyclohexyl)amino)-6-aminopyrimidin-5-yl)-N-phenylbenzamide |

| No. | Chemical Name |
|---|---|
| "A160" | (E)-1-(3-((6-amino-5-(4-phenoxyphenyl)pyrimidin-4-yl)amino)piperidin-1-yl)-4-(dimethylamino)but-2-en-1-one |
| "A161" | N-(3-((6-amino-5-(6-phenoxypyridin-3-yl)pyrimidin-4-yl)oxy)-4-fluorophenyl)acrylamide |
| "A162" | N-(3-((6-amino-5-(4-(pyridin-2-yloxy)phenyl)pyrimidin-4-yl)oxy)phenyl)acrylamide |
| "A163" | N-(3-((6-amino-5-(3-sulfamoylphenyl)pyrimidin-4-yl)oxy)phenyl)acrylamide |
| "A164" | N-(3-((6-amino-5-(3-(trifluoromethoxy)phenyl)pyrimidin-4-yl)oxy)phenyl)acrylamide |
| "A165" | N-(3-((6-amino-5-(6-(2-fluorophenoxy)pyridin-3-yl)pyrimidin-4-yl)oxy)phenyl)acrylamide |
| "A166" | N-(3-((6-amino-5-(6-(4-fluorophenoxy)pyridin-3-yl)pyrimidin-4-yl)oxy)phenyl)acrylamide |
| "A167" | N-(6-((5-(4-phenoxyphenyl)pyrimidin-4-yl)amino)pyridin-2-yl)acrylamide |
| "A168" | 1-(4-(((6-amino-5-(6-phenoxypyridin-3-yl)pyrimidin-4-yl)amino)methyl)piperidin-1-yl)prop-2-en-1-one |
| "A169" | 1-(4-(((6-amino-5-(4-(3-(trifluoromethyl)phenoxy)phenyl)pyrimidin-4-yl)amino)methyl)-4-hydroxypiperidin-1-yl)prop-2-en-1-one |
| "A170" | 1-((3S,4S)-4-(((6-amino-5-(4-(3-(trifluoromethyl)phenoxy)phenyl)pyrimidin-4-yl)amino)methyl)-3-hydroxypiperidin-1-yl)prop-2-en-1-one |
| "A171" | 1-(4-(((6-amino-2'-phenoxy-[5,5'-bipyrimidin]-4-yl)amino)methyl)piperidin-1-yl)prop-2-en-1-one |
| "A172" | N-(3-((6-amino-5-(1-benzyl-1H-pyrazol-4-yl)pyrimidin-4-yl)oxy)phenyl)acrylamide |
| "A173" | N-((1S,3R)-3-((6-amino-5-(4-phenoxyphenyl)pyrimidin-4-yl)amino)cyclohexyl)acrylamide |
| "A174" | N-((1R,3S)-3-((6-amino-5-(4-phenoxyphenyl)pyrimidin-4-yl)amino)cyclohexyl)acrylamide |
| "A175" | N-((1R,3R)-3-((6-amino-5-(4-phenoxyphenyl)pyrimidin-4-yl)amino)cyclohexyl)acrylamide |
| "A176" | N-((1S,3S)-3-((6-amino-5-(4-phenoxyphenyl)pyrimidin-4-yl)amino)cyclohexyl)acrylamide |
| "A177" | N-(4-((6-amino-5-(4-phenoxyphenyl)pyrimidin-4-yl)amino)bicyclo[2.1.1]hexan-1-yl)acrylamide |
| "A178" | (R)-N4-(1-((perfluorophenyl)sulfonyl)pyrrolidin-3-yl)-5-(4-phenoxyphenyl)pyrimidine-4,6-diamine |
| "A179" | (R)-N4-(1-((perfluorophenyl)sulfonyl)piperidin-3-yl)-5-(4-phenoxyphenyl)pyrimidine-4,6-diamine |
| "A180" | (R)-1-(3-((6-amino-5-(1-benzyl-1H-pyrazol-4-yl)pyrimidin-4-yl)amino)piperidin-1-yl)prop-2-en-1-one |
| "A181" | N-(cis-3-((6-amino-5-(4-phenoxyphenyl)pyrimidin-4-yl)amino)cyclopentyl)acrylamide |
| "A182" | N-(3-(((6-amino-5-(4-phenoxyphenyl)pyrimidin-4-yl)amino)methyl)cyclobutyl)acrylamide |
| "A183" | N-(3-((6-amino-5-(1-(3,5-difluorobenzyl)-1H-pyrazol-4-yl)pyrimidin-4-yl)oxy)phenyl)acrylamide |
| "A184" | N-(3-((6-amino-5-(1-(2-fluorobenzyl)-1H-pyrazol-4-yl)pyrimidin-4-yl)oxy)phenyl)acrylamide |
| "A185" | 1-(3-((6-amino-5-(4-phenoxyphenyl)pyrimidin-4-yl)amino)azetidin-1-yl)prop-2-en-1-one |
| "A186" | N-(5-((6-amino-5-(4-phenoxyphenyl)pyrimidin-4-yl)amino)pyridin-3-yl)acrylamide |
| "A187" | N-(3-((6-amino-5-(1-(4-fluorobenzyl)-1H-pyrazol-4-yl)pyrimidin-4-yl)oxy)phenyl)acrylamide |
| "A188" | N-((1R,3S,5R)-3-((6-amino-5-(4-phenoxyphenyl)pyrimidin-4-yl)amino)-5-hydroxycyclohexyl)acrylamide (racemic) |
| "A189" | N-(5-((6-amino-5-(1-benzyl-1H-pyrazol-4-yl)pyrimidin-4-yl)oxy)pyridin-3-yl)acrylamide |
| "A190" | N-(3-((6-amino-5-(1-(3-methylbenzyl)-1H-pyrazol-4-yl)pyrimidin-4-yl)oxy)phenyl)acrylamide |
| "A191" | N-(3-((6-amino-5-(1-(3-chlorobenzyl)-1H-pyrazol-4-yl)pyrimidin-4-yl)oxy)phenyl)acrylamide |
| "A192" | (R)-1-(2-(((6-amino-5-(1-benzyl-1H-pyrazol-4-yl)pyrimidin-4-yl)oxy)methyl)morpholino)prop-2-en-1-one |
| "A193" | (S)-1-(2-(((6-amino-5-(1-benzyl-1H-pyrazol-4-yl)pyrimidin-4-yl)oxy)methyl)morpholino)prop-2-en-1-one |
| "A194" | N-(3-(((6-amino-5-(1-(2-cyanobenzyl)-1H-pyrazol-4-yl)pyrimidin-4-yl)oxy)phenyl)acrylamide |
| "A195" | N-(3-(((6-amino-5-(1-(3-(trifluoromethyl)benzyl)-1H-pyrazol-4-yl)pyrimidin-4-yl)oxy)phenyl)acrylamide |
| "A196" | (R)-1-(3-(((6-amino-5-(1-benzyl-1H-pyrazol-4-yl)pyrimidin-4-yl)oxy)methyl)pyrrolidin-1-yl)prop-2-en-1-one |
| "A197" | N-(5-((6-amino-5-(4-(4-cyanophenoxy)phenyl)pyrimidin-4-yl)oxy)pyridin-3-yl)acrylamide |

| No. | Chemical Name |
|---|---|
| "A198" | N-(3-((6-amino-5-(1-(3-methoxybenzyl)-1H-pyrazol-4-yl)pyrimidin-4-yl)oxy)phenyl)acrylamide |
| "A199" | 4-(4-(4-(((((3S,4S)-1-acryloyl-3-hydroxypiperidin-4-yl)methyl)amino)-6-aminopyrimidin-5-yl)phenoxy)benzonitrile |
| "A200" | (R)-4-(4-(4-((4-acryloylmorpholin-2-yl)methoxy)-6-aminopyrimidin-5-yl)phenoxy)benzonitrile |
| "A201" | (R)-4-(4-(4-((1-acryloylpyrrolidin-3-yl)methoxy)-6-aminopyrimidin-5-yl)phenoxy)benzonitrile |
| "A202" | 4-(4-(4-((2-acryloyl-2-azaspiro[3.3]heptan-6-yl)oxy)-6-aminopyrimidin-5-yl)phenoxy)benzonitrile |
| "A203" | N-(3-((6-amino-5-(1-(3-cyanobenzyl)-1H-pyrazol-4-yl)pyrimidin-4-yl)oxy)phenyl)acrylamide |
| "A204" | 1-((3S,5S)-3-((6-amino-5-(4-phenoxyphenyl)pyrimidin-4-yl)amino)-5-fluoropiperidin-1-yl)prop-2-en-1-one |
| "A205" | 1-((3R,5R)-3-((6-amino-5-(4-phenoxyphenyl)pyrimidin-4-yl)amino)-5-fluoropiperidin-1-yl)prop-2-en-1-one |
| "A206" | methyl 3-((4-(4-(3-acrylamidophenoxy)-6-aminopyrimidin-5-yl)-1H-pyrazol-1-yl)methyl)benzoate |
| "A207" | 4-(4-(4-((2-acryloyl-2-azaspiro[3.3]heptan-6-yl)amino)-6-aminopyrimidin-5-yl)phenoxy)benzonitrile |
| "A208" | 4-(4-(4-(((8-acryloyl-8-azabicyclo[3.2.1]octan-3-yl)methyl)amino)-6-aminopyrimidin-5-yl)phenoxy)benzonitrile |
| "A209" | 1-(3-(((6-amino-5-(1-benzyl-1H-pyrazol-4-yl)pyrimidin-4-yl)amino)methyl)-8-azabicyclo[3.2.1]octan-8-yl)prop-2-en-1-one |
| "A210" | 1-((3R,4R)-3-((6-amino-5-(4-phenoxyphenyl)pyrimidin-4-yl)amino)-4-hydroxypiperidin-1-yl)prop-2-en-1-one (racemic) |
| "A211" | N-(3-((6-amino-5-(1-(3-(methylsulfonyl)benzyl)-1H-pyrazol-4-yl)pyrimidin-4-yl)oxy)phenyl)acrylamide |
| "A212" | N-(3-((6-amino-5-(1-(3-(dimethylamino)benzyl)-1H-pyrazol-4-yl)pyrimidin-4-yl)oxy)phenyl)acrylamide |
| "A213" | N-(3-((6-amino-5-(4-(3-cyanophenoxy)phenyl)pyrimidin-4-yl)oxy)phenyl)acrylamide |
| "A214" | 3-(4-(4-(((1-acryloylpiperidin-4-yl)methyl)amino)-6-aminopyrimidin-5-yl)phenoxy)benzonitrile |
| "A215" | 1-((3S,4S)-4-(((6-amino-5-(4-phenoxyphenyl)pyrimidin-4-yl)amino)methyl)-3-hydroxypiperidin-1-yl)but-2-yn-1-one |
| "A216" | 1-acryloyl-4-(((6-amino-5-(4-phenoxyphenyl)pyrimidin-4-yl)amino)methyl)piperidine-4-carboxylic acid |
| "A217" | (E)-4-(((6-amino-5-(4-phenoxyphenyl)pyrimidin-4-yl)amino)methyl)-1-(4-(dimethylamino)but-2-enoyl)piperidine-4-carboxylic acid |
| "A218" | (E)-1-(4-(((6-amino-5-(4-phenoxyphenyl)pyrimidin-4-yl)amino)methyl)piperidin-1-yl)-4-(3-fluoroazetidin-1-yl)but-2-en-1-one |
| "A219" | (E)-1-(4-(((6-amino-5-(4-phenoxyphenyl)pyrimidin-4-yl)amino)methyl)piperidin-1-yl)-4-(3,3-difluoroazetidin-1-yl)but-2-en-1-one |
| "A220" | (E)-1-(4-(((6-amino-5-(4-phenoxyphenyl)pyrimidin-4-yl)amino)methyl)piperidin-1-yl)-4-(pyrrolidin-1-yl)but-2-en-1-one |
| "A221" | 1-(6-((6-amino-5-(4-(pyridin-3-yloxy)phenyl)pyrimidin-4-yl)oxy)-2-azaspiro[3.3]heptan-2-yl)prop-2-en-1-one |
| "A222" | (E)-1-(6-((6-amino-5-(4-phenoxyphenyl)pyrimidin-4-yl)oxy)-2-azaspiro[3.3]heptan-2-yl)-4-(3-fluoroazetidin-1-yl)but-2-en-1-one |
| "A223" | (E)-1-(6-((6-amino-5-(4-phenoxyphenyl)pyrimidin-4-yl)oxy)-2-azaspiro[3.3]heptan-2-yl)-4-(3-fluoroazetidin-1-yl)but-2-en-1-one |
| "A224" | (E)-N-(1,3-cis-3-((6-amino-5-(4-phenoxyphenyl)pyrimidin-4-yl)amino)cyclobutyl)-4-(dimethylamino)but-2-enamide |
| "A225" | 1-(4-(((6-amino-5-(4-phenoxyphenyl)pyrimidin-4-yl)amino)methyl)-4-fluoropiperidin-1-yl)prop-2-en-1-one |
| "A226" | (E)-1-(2-((6-amino-5-(4-phenoxyphenyl)pyrimidin-4-yl)amino)-6-azaspiro[3.4]octan-6-yl)-4-(dimethylamino)but-2-en-1-one |
| "A227" | (E)-1-(4-(((6-amino-5-(4-phenoxyphenyl)pyrimidin-4-yl)amino)methyl)-4-fluoropiperidin-1-yl)-4-(dimethylamino)but-2-en-1-one |
| "A228" | (E)-N-(1,3-trans-3-((6-amino-5-(4-phenoxyphenyl)pyrimidin-4-yl)amino)cyclobutyl)-4-(dimethylamino)but-2-enamide |
| "A229" | N-(1,3-cis-3-((6-amino-5-(1-benzyl-1H-pyrazol-4-yl)pyrimidin-4-yl)amino)cyclobutyl)acrylamide |
| "A230" | (E)-N-(1,3-cis-3-((6-amino-5-(1-benzyl-1H-pyrazol-4-yl)pyrimidin-4-yl)amino)cyclobutyl)-4-(dimethylamino)but-2-enamide |
| "A231" | (E)-1-(4-(((6-amino-5-(4-phenoxyphenyl)pyrimidin-4-yl)amino)methyl)piperidin-1-yl)-3-phenylprop-2-en-1-one |
| "A232" | 1-((3S,4S)-4-(((6-amino-5-(4-phenoxyphenyl)pyrimidin-4-yl)amino)methyl)-3-hydroxypiperidin-1-yl)-3-(dimethylamino)propan-1-one |
| "A233" | 1-((3S,4S)-4-(((6-amino-5-(4-phenoxyphenyl)pyrimidin-4-yl)amino)methyl)-3-hydroxypiperidin-1-yl)-3-(piperidin-1-yl)propan-1-one |
| "A234" | 1-((3S,4S)-4-(((6-amino-5-(4-phenoxyphenyl)pyrimidin-4-yl)amino)methyl)-3-hydroxypiperidin-1-yl)-3-morpholinopropan-1-one |

| No. | Chemical Name |
|---|---|
| "A235" | 1-(4-(((6-amino-5-(4-phenoxyphenyl)pyrimidin-4-yl)amino)methyl)-4-fluoropiperidin-1-yl)-3-(piperidin-1-yl)propan-1-one |
| "A236" | (E)-N-(1,3-cis-3-((6-amino-5-(4-(3-(trifluoromethyl)phenoxy)phenyl)pyrimidin-4-yl)amino)cyclobutyl)-4-(dimethylamino)but-2-enamide |
| "A237" | N-(1,3-trans-3-((6-amino-5-(4-(3-(trifluoromethyl)phenoxy)phenyl)pyrimidin-4-yl)amino)cyclobutyl)acrylamide |
| "A238" | N-(1,3-cis-3-((6-amino-5-(4-(3-(trifluoromethyl)phenoxy)phenyl)pyrimidin-4-yl)amino)cyclobutyl)acrylamide |
| "A239" | 1-acryloyl-4-(((6-amino-5-(4-(3-(trifluoromethyl)phenoxy)phenyl)pyrimidin-4-yl)amino)methyl)piperidine-4-carboxylic acid |
| "A240" | N-(3-((6-amino-5-(4-phenoxyphenyl)pyrimidin-4-yl)oxy)-2-fluorophenyl)acrylamide |
| "A241" | N-(3-(4-amino-6-((4-phenoxyphenyl)amino)pyrimidin-5-yl)phenyl)acrylamide |
| "A242" | N-(3-((6-amino-5-(4-phenoxyphenyl)pyrimidin-4-yl)oxy)phenyl)acrylamide |
| "A243" | N-(3-(2-amino-4-(4-phenoxyphenoxy)pyridin-3-yl)phenyl)acrylamide |
| "A244" | N-(3-((2-amino-3-(4-phenoxyphenyl)pyridin-4-yl)oxy)phenyl)acrylamide |
| "A245" | N-(3-(4-amino-6-(4-phenoxyphenoxy)pyrimidin-5-yl)phenyl)acrylamide |
| "A246" | N-(3-((6-amino-5-(4-phenoxyphenyl)pyrimidin-4-yl)oxy)-4-fluorophenyl)acrylamide |
| "A247" | (R)-1-(3-((6-amino-5-(4-phenoxyphenyl)pyrimidin-4-yl)amino)piperidin-1-yl)prop-2-en-1-one |
| "A248" | (E)-N-(3-(4-amino-6-(4-phenoxyphenoxy)pyrimidin-5-yl)phenyl)-4-(dimethylamino)but-2-enamide |
| "A249" | N-(3-((6-amino-5-(4-(benzyloxy)phenyl)pyrimidin-4-yl)oxy)phenyl)acrylamide |
| "A250" | 1-(4-(((6-amino-5-(4-phenoxyphenyl)pyrimidin-4-yl)amino)methyl)piperidin-1-yl)prop-2-en-1-one |
| "A251" | N-(5-((6-amino-5-(4-phenoxyphenyl)pyrimidin-4-yl)oxy)-2,4-difluorophenyl)acrylamide |
| "A252" | (E)-N-(3-((6-amino-5-(4-phenoxyphenyl)pyrimidin-4-yl)oxy)phenyl)-4-(dimethylamino)but-2-enamide |
| "A253" | 1-(3-((6-amino-5-(4-phenoxyphenyl)pyrimidin-4-yl)amino)piperidin-1-yl)prop-2-en-1-one |
| "A254" | N-(3-((6-amino-5-(4-((2-methoxybenzyl)oxy)phenyl)pyrimidin-4-yl)oxy)phenyl)acrylamide |
| "A255" | N-(3-((5-(4-phenoxyphenyl)pyrimidin-4-yl)oxy)phenyl)acrylamide |
| "A256" | N-(3-((6-amino-5-(4-(benzyloxy)-3-methoxyphenyl)pyrimidin-4-yl)oxy)phenyl)acrylamide |
| "A257" | N-(3-((6-amino-5-(4-(benzyloxy)-2,3-difluorophenyl)pyrimidin-4-yl)oxy)phenyl)acrylamide |
| "A258" | 4-(4-(3-acrylamidophenoxy)-6-aminopyrimidin-5-yl)-N-phenylbenzamide |
| "A259" | N-(3-((6-amino-5-(6-(benzyloxy)pyridin-3-yl)pyrimidin-4-yl)oxy)phenyl)acrylamide |
| "A260" | N-(3-((6-amino-5-(4-((3-fluorobenzyl)oxy)phenyl)pyrimidin-4-yl)oxy)phenyl)acrylamide |
| "A261" | N-(3-(((6-amino-2'-(benzyloxy)-[5,5'-bipyrimidin]-4-yl)oxy)phenyl)acrylamide |
| "A262" | 1-(3-(((6-amino-5-(4-phenoxyphenyl)pyrimidin-4-yl)amino)methyl)pyrrolidin-1-yl)prop-2-en-1-one |
| "A263" | 1-(4-(4-amino-6-(4-phenoxyphenoxy)pyrimidin-5-yl)-5,6-dihydropyridin-1(2H)-yl)prop-2-en-1-one |
| "A264" | N-(3-((6-amino-5-(4-((4-methoxybenzyl)oxy)phenyl)pyrimidin-4-yl)oxy)phenyl)acrylamide |
| "A265" | (E)-N-(3-((6-amino-5-(4-phenoxyphenyl)pyrimidin-4-yl)oxy)phenyl)-4-morpholinobut-2-enamide |
| "A266" | N-((1s,4s)-4-((6-amino-5-(4-phenoxyphenyl)pyrimidin-4-yl)amino)cyclohexyl)acrylamide |
| "A267" | N-(3-(4-((4-phenoxyphenyl)amino)pyridin-3-yl)phenyl)acrylamide |
| "A268" | N-(3-((6-amino-5-(6-phenoxypyridin-3-yl)pyrimidin-4-yl)oxy)phenyl)acrylamide |
| "A269" | 1-(3-((6-amino-5-(4-(benzyloxy)phenyl)pyrimidin-4-yl)amino)piperidin-1-yl)prop-2-en-1-one |
| "A270" | N-(3-((3-(4-phenoxyphenyl)pyridin-4-yl)oxy)phenyl)acrylamide |
| "A271" | N-(3-((2-amino-5-(4-phenoxyphenyl)pyrimidin-4-yl)oxy)phenyl)acrylamide |
| "A272" | 3-(3-acrylamidophenyl)-4-(4-phenoxyphenoxy)picolinamide |
| "A273" | 1-(3-(4-amino-6-((4-phenoxyphenyl)amino)pyrimidin-5-yl)-5,6-dihydropyridin-1(2H)-yl)prop-2-en-1-one |

| No. | Chemical Name |
|---|---|
| "A274" | (E)-N-(3-(4-amino-6-(4-phenoxyphenoxy)pyrimidin-5-yl)phenyl)-4-morpholinobut-2-enamide |
| "A275" | (S)-1-(3-((6-amino-5-(4-phenoxyphenyl)pyrimidin-4-yl)amino)piperidin-1-yl)prop-2-en-1-one |
| "A276" | N-((1r,4r)-4-((6-amino-5-(4-phenoxyphenyl)pyrimidin-4-yl)amino)cyclohexyl)acrylamide |
| "A277" | N-(3-((6-amino-5-(4-fluoro-3-methoxyphenyl)pyrimidin-4-yl)oxy)phenyl)acrylamide |
| "A278" | N-(3-((6-amino-5-(4-(2-hydroxypropan-2-yl)phenyl)pyrimidin-4-yl)oxy)phenyl)acrylamide |
| "A279" | 1-(3-(4-amino-6-(4-phenoxyphenoxy)pyrimidin-5-yl)-5,6-dihydropyridin-1(2H)-yl)prop-2-en-1-one |
| "A280" | N-(4-((6-amino-5-(4-phenoxyphenyl)pyrimidin-4-yl)oxy)phenyl)acrylamide |
| "A281" | N-(4-(4-(4-phenoxyphenoxy)pyridin-3-yl)phenyl)acrylamide |
| "A282" | (E)-4-(dimethylamino)-N-(3-(4-(4-phenoxyphenoxy)pyridin-3-yl)phenyl)but-2-enamide |
| "A283" | N-(3-(4-((4-phenoxyphenyl)amino)pyrimidin-5-yl)phenyl)acrylamide |
| "A284" | 1-(3-((5-(4-phenoxyphenyl)pyrimidin-4-yl)amino)piperidin-1-yl)prop-2-en-1-one |
| "A285" | N-(3-((6-amino-5-(4-(pyrrolidine-1-carbonyl)phenyl)pyrimidin-4-yl)oxy)phenyl)acrylamide |
| "A286" | 1-(3-(((6-amino-5-(4-phenoxyphenyl)pyrimidin-4-yl)amino)methyl)piperidin-1-yl)prop-2-en-1-one |
| "A287" | N-(4-(4-(4-phenoxyphenoxy)pyridin-3-yl)benzyl)acrylamide |
| "A288" | 1-(4'-(4-phenoxyphenoxy)-5,6-dihydro-[3,3'-bipyridin]-1(2H)-yl)prop-2-en-1-one |
| "A289" | N-(3-((6-amino-5-(4-isopropoxyphenyl)pyrimidin-4-yl)oxy)phenyl)acrylamide |
| "A290" | (E)-N-(4-((6-amino-5-(4-phenoxyphenyl)pyrimidin-4-yl)oxy)phenyl)-4-(dimethylamino)but-2-enamide |
| "A291" | N-(3-((6-amino-5-(5-methoxypyridin-3-yl)pyrimidin-4-yl)oxy)phenyl)acrylamide |
| "A292" | 1-(4-(((6-amino-5-(4-(benzyloxy)phenyl)pyrimidin-4-yl)amino)methyl)piperidin-1-yl)prop-2-en-1-one |
| "A293" | (E)-4-morpholino-N-(3-(4-(4-phenoxyphenoxy)pyridin-3-yl)phenyl)but-2-enamide |
| "A294" | N-(3-((6-amino-5-(4-(benzyloxy)-2,6-difluorophenyl)pyrimidin-4-yl)oxy)phenyl)acrylamide |
| "A295" | (E)-N-(3-((6-amino-5-(4-phenoxyphenyl)pyrimidin-4-yl)oxy)phenyl)-4-(4-(5-((4S)-2-oxohexahydro-1H-thieno[3,4-d]imidazol-4-yl)pentanoyl)piperazin-1-yl)but-2-enamide |
| "A296" | N-(3-(4-(4-phenoxyphenoxy)pyridin-3-yl)phenyl)but-2-ynamide |
| "A297" | N-(4-((3-(4-phenoxyphenyl)pyridin-4-yl)oxy)phenyl)acrylamide |
| "A298" | N-(1-(6-amino-5-(4-phenoxyphenyl)pyrimidin-4-yl)piperidin-3-yl)acrylamide |
| "A299" | 1-(4-((6-amino-5-(4-phenoxyphenyl)pyrimidin-4-yl)amino)piperidin-1-yl)prop-2-en-1-one |
| "A300" | 3-(3-aminophenyl)-4-(4-phenoxyphenoxy)pyridin-2-amine |
| "A301" | (E)-N-(3-(4-amino-6-(4-phenoxyphenoxy)pyrimidin-5-yl)phenyl)-4-(3,3-difluoropiperidin-1-yl)but-2-enamide |
| "A302" | N-(3-(4-(4-phenoxyphenoxy)pyridin-3-yl)benzyl)acrylamide |
| "A303" | 6-(4-aminophenoxy)-5-(4-phenoxyphenyl)pyrimidin-4-amine |
| "A304" | N-(3-(4-(4-phenoxyphenoxy)pyridin-3-yl)benzyl)but-2-ynamide |
| "A305" | 6-(3-aminophenoxy)-5-(4-phenoxyphenyl)pyrimidin-4-amine |
| "A306" | N-(3-(2-amino-4-(4-phenoxyphenoxy)pyrimidin-5-yl)phenyl)acrylamide |
| "A307" | (E)-N-(3-(4-(4-phenoxyphenoxy)pyridin-3-yl)phenyl)but-2-enamide |
| "A308" | N-(4-((6-amino-5-(4-phenoxyphenyl)pyrimidin-4-yl)oxy)phenyl)propionamide |
| "A309" | N-((1-(6-amino-5-(4-phenoxyphenyl)pyrimidin-4-yl)piperidin-3-yl)methyl)acrylamide |
| "A310" | N-(3-(2-amino-4-(4-phenoxyphenoxy)pyridin-3-yl)phenyl)propionamide |
| "A311" | (R)-N-(3-(4-amino-6-((1-phenylethyl)amino)pyrimidin-5-yl)phenyl)acrylamide |
| "A312" | 3-(4-(4-phenoxyphenoxy)pyridin-3-yl)aniline |
| "A313" | 4-(3-aminophenoxy)-3-(4-phenoxyphenyl)pyridin-2-amine |
| "A314" | 4-(4-(4-phenoxyphenoxy)pyridin-3-yl)aniline |
| "A315" | (4-(4-(4-phenoxyphenoxy)pyridin-3-yl)phenyl)methanamine |
| "A316" | (3-(4-(4-phenoxyphenoxy)pyridin-3-yl)phenyl)methanamine |
| "A317" | 5-(3-aminophenyl)-6-(4-phenoxyphenoxy)pyrimidin-4-amine |
| "A318" | N-(3-((3-(4-phenoxyphenyl)pyridin-4-yl)oxy)phenyl)propionamide |
| "A319" | N-(3-(4-(4-phenoxyphenoxy)pyridin-3-yl)phenyl)propionamide |
| "A320" | N-(4-(4-(4-phenoxyphenoxy)pyridin-3-yl)phenyl)propionamide |
| "A321" | N-(4-((3-(4-phenoxyphenyl)pyridin-4-yl)oxy)phenyl)propionamide |
| "A322" | N-(3-(4-(4-phenoxyphenoxy)pyridin-3-yl)phenyl)methacrylamide |
| "A323" | N-(3-(4-(4-phenoxyphenoxy)pyridin-3-yl)benzyl)propionamide |
| "A324" | N-(4-(4-(4-phenoxyphenoxy)pyridin-3-yl)benzyl)propionamide |

| No. | Chemical Name |
|---|---|
| "A325" | N-(3-(4-amino-6-(4-phenoxyphenoxy)pyrimidin-5-yl)phenyl)propionamide |
| "A326" | N-(3-((6-amino-5-(4-phenoxyphenyl)pyrimidin-4-yl)oxy)phenyl)propionamide |
| "A327" | (E)-N-(3-(4-(4-phenoxyphenoxy)pyridin-3-yl)benzyl)but-2-enamide |
| "A328" | 3-(4-phenoxyphenyl)-4-(3-propionamidophenoxy)picolinamide |
| "A329" | N-(3-((6-amino-5-(4-phenoxyphenyl)pyrimidin-4-yl)oxy)phenyl)-1-cyanocyclopropanecarboxamide |
| "A330" | N-(3-(4-amino-6-(4-phenoxyphenoxy)pyrimidin-5-yl)phenyl)-1-cyanocyclopropanecarboxamide |
| "A331" | (E)-3-(7-((6-amino-5-(4-phenoxyphenyl)pyrimidin-4-yl)oxy)naphthalen-2-yl)-N,N-dimethylacrylamide |
| "A332" | 1-(4-(1-((6-amino-5-(4-phenoxyphenyl)pyrimidin-4-yl)amino)ethyl)piperidin-1-yl)prop-2-en-1-one |
| "A333" | 1-(4-(((6-amino-5-(4-phenoxyphenyl)pyrimidin-4-yl)amino)methyl)piperidin-1-yl)propan-1-one |
| "A334" | 1-(4-(((5-(4-phenoxyphenyl)pyrimidin-4-yl)amino)methyl)piperidin-1-yl)prop-2-en-1-one |
| "A335" | 1-(4-(((6-amino-5-(4-(pyridin-2-yloxy)phenyl)pyrimidin-4-yl)amino)methyl)piperidin-1-yl)prop-2-en-1-one |
| "A336" | 1-(4-(((6-amino-5-(4-phenoxyphenyl)pyrimidin-4-yl)amino)methyl)piperidin-1-yl)but-2-yn-1-one |
| "A337" | N4-((1-(6-chloropyridin-2-yl)piperidin-4-yl)methyl)-5-(4-phenoxyphenyl)pyrimidine-4,6-diamine |
| "A338" | 1-(4-(((6-amino-5-(4-phenoxyphenyl)pyrimidin-4-yl)oxy)methyl)piperidin-1-yl)prop-2-en-1-one |
| "A339" | N-(3-((6-amino-5-(4-(benzyloxy)-2,5-difluorophenyl)pyrimidin-4-yl)oxy)phenyl)acrylamide |
| "A340" | N-(3-((2-amino-3-(4-phenoxyphenyl)pyridin-4-yl)oxy)phenyl)but-2-ynamide |
| "A341" | (R)-1-(3-((6-amino-5-(4-phenoxyphenyl)pyrimidin-4-yl)amino)pyrrolidin-1-yl)but-2-yn-1-one |
| "A342" | N-{3-[6-Amino-5-(4-phenoxy-phenyl)-pyrimidin-4-yloxy]-phenyl}-2-chloroacetamide |
| "A343" | N-(3-{6-Amino-5-[4-(2-fluoro-benzyloxy)-phenyl]-pyrimidin-4-yloxy}-phenyl)-acrylamide |
| "A344" | N-(3-{6-Amino-5-[4-(4-fluoro-benzyloxy)-phenyl]-pyrimidin-4-yloxy}-phenyl)-acrylamide |
| "A345" | N-(3-{6-Amino-5-[4-(3-fluoro-benzyloxy)-phenyl]-pyrimidin-4-yloxy}-phenyl)-2-chloro-acetamide |
| "A346" | N-{3-[6-Amino-5-(4-benzyloxy-phenyl)-pyrimidin-4-yloxy]-phenyl}-propionamide |
| "A347" | N-{3-[6-Amino-5-(4-benzyloxy-phenyl)-pyrimidin-4-yloxy]-phenyl}-2-chloro-acetamide |
| "A348" | N-{3-[6-Amino-5-(4-benzyloxy-3-fluoro-phenyl)-pyrimidin-4-yloxy]-phenyl}-acrylamide |
| "A349" | N-{3-[6-Amino-5-(4-benzyloxy-2-fluoro-phenyl)-pyrimidin-4-yloxy]-phenyl}-acrylamide |
| "A350" | N-{3-(6-Amino-5-(4-benzyloxy-2-fluoro-phenyl)-pyrimidin-4-yloxy}-phenyl)-2-chloro-acetamide |
| "A351" | N-{3-[6-Amino-5-(4-benzyloxy-3-fluoro-phenyl)-pyrimidin-4-yloxy]-phenyl}-2-chloro-acetamide |
| "A352" | N-{4-[4-(3-Acryloylamino-phenoxy)-6-amino-pyrimidin-5-yl]-phenyl}-benzamide | and pharmaceutically usable salts, tautomers and stereoisomers thereof, including mixtures thereof in all ratios.

15. The method according to claim 14, wherein the compound is Compound A225: 1-(4-(((6-amino-5-(4-phenoxyphenyl)pyrimidin-4-yl)amino)methyl)-4-fluoropiperidin-1-yl)prop-2-en-1-one.

16. The method according to claim 14, wherein the compound is Compound A250: 1-(4-(((6-amino-5-(4-phenoxyphenyl)pyrimidin-4-yl)amino)methyl)piperidin-1-yl)prop-2-en-1-one.

17. The method of claim 1, wherein the disorder is rheumatoid arthritis.

18. The method of claim 1, wherein the disorder is systemic lupus erythematosus.

* * * * *